US008741373B2

(12) United States Patent
Bromley et al.

(10) Patent No.: US 8,741,373 B2
(45) Date of Patent: Jun. 3, 2014

(54) COMPOSITIONS CONTAINING NON-POLAR COMPOUNDS

(75) Inventors: Philip J. Bromley, Fullerton, CA (US); Chetan S. Rao, Austin, MN (US)

(73) Assignees: Virun, Inc., Walnut, CA (US); Hormel Foods Corporation, Austin, MN (US)

( * ) Notice: Subject to any disclaimer, the term of this patent is extended or adjusted under 35 U.S.C. 154(b) by 0 days.

(21) Appl. No.: 13/134,927

(22) Filed: Jun. 20, 2011

(65) Prior Publication Data

US 2012/0016026 A1    Jan. 19, 2012

Related U.S. Application Data

(60) Provisional application No. 61/398,192, filed on Jun. 21, 2010.

(51) Int. Cl.
| | |
|---|---|
| A61K 31/202 | (2006.01) |
| A61P 39/00 | (2006.01) |
| A23D 7/00 | (2006.01) |
| A23L 1/30 | (2006.01) |
| A23L 2/00 | (2006.01) |
| A23C 9/00 | (2006.01) |
| A23C 19/00 | (2006.01) |
| A23L 1/40 | (2006.01) |
| A23L 1/302 | (2006.01) |
| A23L 1/303 | (2006.01) |
| A23F 3/00 | (2006.01) |

(52) U.S. Cl.
USPC ............ 426/602; 514/560; 426/72; 426/590; 426/585; 426/582; 426/589; 426/597; 426/73

(58) Field of Classification Search
None
See application file for complete search history.

(56) References Cited

U.S. PATENT DOCUMENTS

| | | | |
|---|---|---|---|
| 2,661,349 A | 12/1953 | Caldwell et al. ................. 536/63 |
| 2,680,749 A | 6/1954 | Cawley et al. .................. 549/410 |
| 3,102,078 A | 8/1963 | Robeson et al. ............. 514/458 |
| 3,480,616 A | 11/1969 | Osipow et al. ................. 536/119 |
| 3,538,119 A | 11/1970 | Grant ............................. 549/410 |
| 3,644,333 A | 2/1972 | Osipow et al. ................. 536/119 |
| 3,714,144 A | 1/1973 | Feuge et al. .................... 536/119 |
| 3,917,859 A | 11/1975 | Terada et al. .................. 426/602 |
| 4,035,235 A | 7/1977 | Richards .......................... 435/99 |
| 4,353,365 A | 10/1982 | Hallworth et al. ....... 128/203.15 |
| 4,524,769 A | 6/1985 | Wetterlin ................. 128/203.15 |
| 4,572,915 A | 2/1986 | Crooks .......................... 514/458 |
| 4,665,204 A | 5/1987 | Wirth ............................ 549/410 |
| 4,670,285 A | 6/1987 | Clandinin et al. ............. 426/602 |
| 4,710,567 A | 12/1987 | Kea et al. ...................... 536/119 |
| 4,835,002 A | 5/1989 | Wolf et al. ..................... 426/590 |
| 4,867,986 A | 9/1989 | Desai et al. .................... 424/464 |
| 4,898,935 A | 2/1990 | Nakamura et al. ............ 536/119 |
| 4,916,163 A | 4/1990 | Ni ................................. 514/593 |
| 4,995,911 A | 2/1991 | Matsumoto et al. ............ 127/48 |
| 4,996,309 A | 2/1991 | Matsumoto et al. .......... 536/119 |
| 5,011,922 A | 4/1991 | Matsumoto et al. .......... 536/119 |
| 5,017,697 A | 5/1991 | Matsumoto et al. .......... 536/127 |
| 5,035,237 A | 7/1991 | Newell et al. ............ 128/203.15 |
| 5,167,950 A | 12/1992 | Lins ................................. 424/47 |
| 5,179,122 A | 1/1993 | Greene et al. ................. 514/458 |
| 5,234,695 A | 8/1993 | Hobbs et al. .................. 424/489 |
| 5,239,993 A | 8/1993 | Evans et al. ............. 128/203.15 |
| 5,397,591 A | 3/1995 | Kyle et al. ..................... 426/602 |
| 5,407,957 A | 4/1995 | Kyle et al. ..................... 514/547 |
| 5,415,162 A | 5/1995 | Casper et al. ............ 128/203.12 |
| 5,430,021 A | 7/1995 | Rudnic et al. ................. 514/10.1 |
| 5,492,938 A | 2/1996 | Kyle et al. ..................... 514/786 |
| 5,580,553 A | 12/1996 | Nakajima ................... 424/78.17 |
| 5,583,105 A | 12/1996 | Kovacs et al. ................. 514/20.5 |
| 5,593,682 A | 1/1997 | Papas et al. .................... 424/401 |
| 5,597,595 A | 1/1997 | Dewille et al. .................. 426/74 |
| 5,711,983 A | 1/1998 | Kyle et al. ..................... 426/635 |
| 5,715,810 A | 2/1998 | Armstrong et al. ...... 128/230.15 |
| 5,798,333 A | 8/1998 | Sherman et al. ................ 514/11 |
| 5,891,469 A | 4/1999 | Amselem ....................... 424/451 |
| 5,977,348 A | 11/1999 | Harris ........................ 536/123.1 |
| 6,037,466 A | 3/2000 | Maliczyszyn et al. ......... 536/102 |
| 6,045,826 A | 4/2000 | Borowy-Borowski et al. .............................. 424/451 |
| 6,048,566 A | 4/2000 | Behnam et al. ............... 426/590 |
| 6,056,971 A | 5/2000 | Goldman ....................... 424/439 |
| 6,162,474 A | 12/2000 | Chen et al. ....................... 426/72 |
| 6,180,130 B1 | 1/2001 | Chen et al. ..................... 424/439 |
| 6,184,255 B1 | 2/2001 | Mae et al. ..................... 514/720 |

(Continued)

FOREIGN PATENT DOCUMENTS

| | | |
|---|---|---|
| DE | 10 2005 049664 | 4/2007 |
| DE | 10 2008 015366 | 9/2009 |

(Continued)

OTHER PUBLICATIONS

Letter/Written Disclosure of the Information Disclosure Statement for the above referenced application, mailed on Oct. 20, 2011, 2 pages.
Certified English translation of German patent DE 10 2005 049664, published Apr. 19, 2007, entitled: "Liquid Composition and Method for its Production," Inventor—Haller, 9 pages.
Covington, M., "Omega-3 fatty acids," American Family Physician 70(1):133-140 (2004).
CRC Handbook of Chemistry and Physics, Lide, D., ed., 82nd edition, Cleveland, OH:CRC Press 15(14)-15(18) (2001).
Eastman PCI-102B Publication, "Vitamin E TPGS NF—Applications and Properties," Eastman Chemical Company, Oct. 2005, 24 pages.

(Continued)

*Primary Examiner* — Dennis Heyer
(74) *Attorney, Agent, or Firm* — McKenna Long & Aldridge LLP; Stephanie Seidman

(57) ABSTRACT

Provided are compositions and methods for producing stable foods and beverages that contain high concentrations of additives such as essential fatty acids, including omega-3 fatty acids, omega-6 fatty acids, conjugated fatty acids, and other fatty acids; phytochemicals, including phytosterols and carotenoids; oil soluble vitamins; alpha lipoic acid; other oils; and coenzymes, including Coenzyme Q10, and other oil-based additives.

45 Claims, No Drawings

(56) References Cited

U.S. PATENT DOCUMENTS

| | | | |
|---|---|---|---|
| 6,193,985 B1 | 2/2001 | Sonne et al. | 424/400 |
| 6,200,550 B1 | 3/2001 | Masterson et al. | 424/49 |
| 6,267,985 B1 | 7/2001 | Chen et al. | 424/451 |
| 6,284,268 B1 | 9/2001 | Mishra et al. | 424/455 |
| 6,300,377 B1 | 10/2001 | Chopra | 514/715 |
| 6,335,022 B1 | 1/2002 | Simonnet et al. | 424/401 |
| 6,378,519 B1 | 4/2002 | Davies et al. | 128/203.21 |
| 6,383,471 B1 | 5/2002 | Chen et al. | 424/45 |
| 6,391,370 B1 | 5/2002 | Rogers et al. | 426/611 |
| 6,403,116 B1 | 6/2002 | Anderson et al. | 424/439 |
| 6,441,050 B1 | 8/2002 | Chopra | 514/675 |
| 6,455,512 B1* | 9/2002 | Ward | 514/59 |
| 6,509,044 B2 | 1/2003 | Van Den Braak et al. | 426/2 |
| 6,534,085 B1 | 3/2003 | Zeligs | 424/451 |
| 6,632,443 B2 | 10/2003 | Borowy-Borowski et al. | 424/400 |
| 6,635,293 B2 | 10/2003 | Fullmer et al. | 426/250 |
| 6,761,903 B2 | 7/2004 | Chen et al. | 424/451 |
| 6,870,077 B2 | 3/2005 | Kenaschuk | 800/298 |
| 6,908,626 B2 | 6/2005 | Cooper et al. | 424/489 |
| 6,919,378 B2 | 7/2005 | Jacobs et al. | 514/618 |
| 6,923,988 B2 | 8/2005 | Patel et al. | 424/489 |
| 6,977,166 B1 | 12/2005 | Ratledge et al. | 435/134 |
| 6,982,281 B1 | 1/2006 | Chen et al. | 514/458 |
| 6,982,282 B2 | 1/2006 | Lambert et al. | 424/405 |
| 7,026,361 B2 | 4/2006 | Minemura et al. | 516/75 |
| 7,115,565 B2 | 10/2006 | Gao et al. | 514/9 |
| 7,145,044 B2 | 12/2006 | Ueda et al. | 568/823 |
| 7,182,950 B2 | 2/2007 | Garti et al. | 424/401 |
| 7,374,779 B2 | 5/2008 | Chen et al. | 424/451 |
| 7,906,140 B2 | 3/2011 | Bromley et al. | 424/450 |
| 8,282,977 B2 | 10/2012 | Bromley | 426/72 |
| 8,337,931 B2 | 12/2012 | Bromley | 426/602 |
| 8,414,914 B2 | 4/2013 | Bromley et al. | 424/450 |
| 2001/0025058 A1 | 9/2001 | Borowy-Borowski et al. | 541/772.4 |
| 2003/0072798 A1 | 4/2003 | Schwarz | 424/456 |
| 2003/0165572 A1* | 9/2003 | Auriou | 424/493 |
| 2003/0180352 A1 | 9/2003 | Patel et al. | 424/465 |
| 2004/0033202 A1 | 2/2004 | Cooper et al. | 424/46 |
| 2004/0043043 A1 | 3/2004 | Schlyter et al. | 424/400 |
| 2004/0072330 A1 | 4/2004 | Ratledge et al. | 435/258.1 |
| 2004/0086619 A1 | 5/2004 | Zhong et al. | 426/590 |
| 2004/0105889 A1 | 6/2004 | Ryde et al. | 424/489 |
| 2004/0115287 A1 | 6/2004 | Chen et al. | 424/731 |
| 2004/0121043 A1 | 6/2004 | Behnam | 514/456 |
| 2004/0219274 A1 | 11/2004 | Cook | 426/590 |
| 2005/0008581 A1 | 1/2005 | Parkhideh | 424/46 |
| 2005/0037073 A1 | 2/2005 | Schwarz | 42/464 |
| 2005/0092969 A1 | 5/2005 | Ueda et al. | 252/399 |
| 2005/0208082 A1 | 9/2005 | Papas et al. | 424/400 |
| 2005/0260752 A1 | 11/2005 | Wilding et al. | 435/373 |
| 2005/0281772 A1 | 12/2005 | Bromley et al. | 424/70.14 |
| 2006/0034937 A1 | 2/2006 | Patel et al. | 424/497 |
| 2006/0051462 A1 | 3/2006 | Wang | 426/72 |
| 2006/0088558 A1 | 4/2006 | Jandzinski et al. | 424/400 |
| 2006/0165735 A1* | 7/2006 | Abril et al. | 424/401 |
| 2006/0165769 A1 | 7/2006 | Hyatt et al. | 424/450 |
| 2006/0222716 A1 | 10/2006 | Schwarz et al. | 424/490 |
| 2007/0003614 A1 | 1/2007 | Chen et al. | 424/456 |
| 2007/0087104 A1* | 4/2007 | Chanamai | 426/602 |
| 2007/0104778 A1 | 5/2007 | Zeng et al. | 424/451 |
| 2007/0104780 A1 | 5/2007 | Lipari et al. | 424/456 |
| 2007/0141203 A1 | 6/2007 | Cook et al. | 426/72 |
| 2007/0141224 A1 | 6/2007 | Zawistowski | 426/611 |
| 2007/0160738 A1 | 7/2007 | Van Bokkelen et al. | 426/601 |
| 2007/0166411 A1 | 7/2007 | Anthony et al. | 424/750 |
| 2007/0184117 A1 | 8/2007 | Gregory et al. | 424/489 |
| 2007/0213234 A1 | 9/2007 | Yaghmur | 508/110 |
| 2007/0218138 A1 | 9/2007 | Bittorf et al. | 424/488 |
| 2007/0298083 A1 | 12/2007 | Mehansho et al. | 426/590 |
| 2007/0298099 A1 | 12/2007 | Peresypkin et al. | 424/456 |
| 2008/0058418 A1 | 3/2008 | D'Angelo et al. | 514/560 |
| 2008/0070981 A1 | 3/2008 | Borowy-Borowski et al. | 514/458 |
| 2008/0254188 A1 | 10/2008 | Borowy-Borowski et al. | 426/590 |
| 2009/0018186 A1* | 1/2009 | Chen et al. | 514/458 |
| 2009/0297491 A1 | 12/2009 | Bromley | 424/94.1 |
| 2009/0297665 A1 | 12/2009 | Bromley | 426/72 |
| 2009/0317532 A1 | 12/2009 | Bromley | 426/590 |
| 2010/0041622 A1 | 2/2010 | Bromley et al. | 514/52 |
| 2010/0080785 A1 | 4/2010 | Berl | 424/94.1 |
| 2010/0136175 A1 | 6/2010 | Skiff et al. | 426/72 |
| 2010/0166915 A1 | 7/2010 | Mathisen et al. | 426/477 |
| 2010/0260913 A1 | 10/2010 | Horlacher et al. | 426/546 |
| 2011/0008305 A1 | 1/2011 | Yu et al. | 424/94.1 |
| 2011/0015266 A1 | 1/2011 | Hanefeld et al. | 252/363.5 |
| 2011/0117184 A1 | 5/2011 | Bromley | 424/450 |
| 2011/0118351 A1 | 5/2011 | Berl | 514/560 |
| 2011/0135745 A1 | 6/2011 | Mathisen et al. | 424/522 |
| 2011/0236364 A1 | 9/2011 | Bromley | 424/94.1 |
| 2012/0083530 A1 | 4/2012 | Mai et al. | 514/560 |
| 2012/0308644 A1 | 12/2012 | Bromley et al. | 424/450 |
| 2013/0017183 A1 | 1/2013 | Bromley | 424/94.1 |
| 2013/0017295 A1 | 1/2013 | Bromley | 426/66 |

FOREIGN PATENT DOCUMENTS

| | | |
|---|---|---|
| EP | 1 055 374 | 11/2000 |
| EP | 1972334 | 9/2010 |
| WO | WO 96/36316 | 11/1996 |
| WO | WO 98/08490 | 3/1998 |
| WO | WO 99/59421 | 11/1999 |
| WO | WO 00/23545 | 4/2000 |
| WO | WO 02/17879 | 3/2002 |
| WO | WO 02/069981 | 9/2002 |
| WO | WO 02/076970 | 10/2002 |
| WO | WO 2004/098311 | 11/2004 |
| WO | WO 2005/105290 | 11/2005 |
| WO | WO 2006/009825 | 1/2006 |
| WO | WO 2007/080515 | 7/2007 |
| WO | WO 2007/082149 | 7/2007 |
| WO | WO 2008/039564 | 4/2008 |
| WO | WO 2009/029046 | 3/2009 |
| WO | WO 2009/117151 | 9/2009 |
| WO | WO 2009/117152 | 9/2009 |
| WO | WO 2010/008475 | 1/2010 |
| WO | WO 2010/008762 | 1/2010 |
| WO | WO 2010/019255 | 2/2010 |
| WO | WO 2011/119228 | 9/2011 |

OTHER PUBLICATIONS

Ernst, E., "The risk-benefit profile of commonly used herbal therapies: ginkgo, St. John's Wort, Ginseng, Echinacea, Saw Palmetto, and Kava," Ann Intern Med. 136(1):42-53 (2002).

Fan, Y. and R. Chapkin, "Importance of dietary γ-linolenic acid in human health and nutrition," Journal of Nutrition 1411-1414 (1998).

Giddings et al., "High pressure gas chromatography of nonvolatile species. Compressed gas is used to cause migration of intractable solutes," Science, 162:67-73 (1968).

Goodrum et al., "Gum arabic glycoprotein contains glycomodules of both extensin and arabinogalactan-glycoproteins," Phytochemistry 54(1):99-106 (2000).

Gordon, A. and A. Shaughnessy, "Saw palmetto for prostate disorders," American Family Physician 67(6):1281-1283 (2003).

Griffin, W., "Classification of surface-reactive agents by HLB," J. Soc. Cos. Chem. 1:311-326 (1949).

Gutmann, V., "Solvent effects on the reactivities of organometallic compounds," Coord. Chem. Rev. 18:225-255 (1976).

Idris et al., "Characterisation of gum from Acacia senegal trees of different age and location using multidetection gel permeation chromatography," Food Hydrocolloids 12(4):379-388 (1998).

Islam et al., "A review of recent developments on the regulatory, structural and functional aspects of gum arabic," Food Hydrocolloids 11(4):493-505 (1997).

Kosower, E., "2.6 Solvent polarity: empirical measures," found in *An Introduction to Physical Organic Chemistry*, New York: Wiley, p. 293 (1969).

Lands, W., "Biochemistry and physiology of n-3 fatty acids," The FASEB Journal, 6(8):2530-2536 (1992).

(56) References Cited

OTHER PUBLICATIONS

Lowery et al., "2.4 Solutions," found in Mechanism and Theory in Organic Chemistry, HarperCollins Publishers, 3rd ed., p. 177 (1987).
Miyashita, K., "Effects of chemical properties of Oil in Water Emulsion on Lipid Peroxidation," Foods Food Ingredients J. Jpn., 209(11):1-2 (2004).
Offer for Sale, "Kaneka Liquid CoQ10" formulation, to Kaneka Nutrients L.P., Pasadena, TX, on Jun. 22-27, 2007, 2 pages.
Okamoto et al., "Effect of sucrose fatty acid esters on transdermal permeation of lidocaine and Ketoprofen," Biol. Pharm. Bull., 28(9):1689-1694 (2005).
Perry, R. and D. Green, *Perry's Chemical Engineers' Handbook*, Sixth Edition, New York: McGraw-Hill, pp. 20-54 to 20-57 (1984).
Randall et al., "The role of the proteinaceous component on the emulsifying properties of gum arabic," Food Hydrocolloids 2(2):131-140 (1988).
Ross et al., "Omega-3 fatty acids as treatments for mental illness: which disorder and which fatty acid?," Lipids in Health and Disease 6:21 pp. 1-19 (2007).
Snyder, L., "Classification of the solvent properties of common liquids," J. Chromatography A 92:223-230 (1974).
Starling, S., "Virun debuts shelf-stable, H20 soluble, nanotech omega-3," Retrieved from the Internet:<URL: beveragedaily.com/Products/Virun-debuts-shelf-stable-H20-soluble-nanotech-omega-3, Beveragedaily.com News Release Mar. 12, 2009. 1 pg.
Virun Clear Water Soluble Omega-3 DHA, EPA & ALA for Foods & Beverages Retrieved from the Internet:<URL: slideshare.net/virun/virun-food-beverage-division-v2 [accessed on May 11, 2009] 6 pages.
Virun home Webpage found at www.virun.com [ accessed on Mar. 24, 2011], 59 pages.
Virun Improving Life Through Safe & Effective Oral Delivery found at: www.slideshare.net/virun/virun-improving-life-through-safe-effective-oral-delivery [accessed on May 11, 2009], 15 pages.
Virun Intricate Science; found at www.slideshare.net/virun/virun-intricate-science [accessed May 25, 2011], 22 pages.
Virun on slideshare.net, Philip Bromley's Presentations on SlideShare found at: www.slideshare.net/virun [accessed on Jul. 2, 2009], 2 pages.
Virun Pharmaceutical & Food Beverage Divisions: www.slideshare.net/virun/virun-food-beverage-divisions [accessed on Aug. 12, 2009], 9 pages.
Virun Product Sheet "Clear oils for water based beverages," Jan. 16, 2009, 4 pages.
Wright, R., "Companies to watch-Nutraceuticals World," located at: www.nutraceuticalsworld.com/articles/2009/06/companies-to-watch, (2009) [accessed on Jun. 4, 2009], 7 pages.
Youan et al., "Evaluation of Sucrose Esters as Alternative Surfactants in Microencapsulation of Proteins by the Solvent Evaporation Method," AAPS PharmSci., 5(2):1-9 (2003).
International Search Report/Written Opinion, issued Jul. 3, 2009, in connection with related International Application No. PCT/US2009/001775, 15 pages.
Response to Written Opinion, issued Jul. 3, 2009, in connection with related International Patent Application No. PCT/US2009/001775, 26 pages.
International Search Report/Written Opinion, issued Mar. 2, 2010, in connection with related International Application No. PCT/US2009/003761, 13 pages.
Response to Written Opinion, issued Feb. 4, 2010, in connection with related International Application No. PCT/US2009/003761, 19 pages.
International Search Report/Written Opinion, issued Apr. 7, 2010, in connection with related International Patent Application No. PCT/US2009/001774, 15 pages.
Response to Written Opinion, issued Apr. 1, 2010, in connection with related International Patent Application No. PCT/US2009/001774, 27 pages.
International Preliminary Report on Patentability, issued Jun. 11, 2010, in connection with related International Patent Application No. PCT/US2009/001775, 18 pages.
International Preliminary Report on Patentability, issued Jul. 27, 2010, in connection with related International Patent Application No. PCT/US2009/003761, 13 pages.
International Preliminary Report on Patentability, issued Sep. 3, 2010, in connection with related International Patent Application No. PCT/US2009/001774, 15 pages.
Examination Report, issued Mar. 7, 2011, in connection with related Eurpoean Patent Application No. 09722985.0, 6 pages.
Response to Examination Report, issued Mar. 7, 2011, in connection with related Eurpoean Patent Application No. 09722985.0, 8 pages.
International Search Report and Written Opinion, issued Jul. 22, 2011, for related International Application No. PCT/US2011/000538, 10 pages.
U.S. Appl. No. 60/887,754, filed Feb. 1, 2007, Borowy-Borowski et al.
Letter/Written Disclosure of the Supplemental Information Disclosure Statement for the above-referenced application, mailed on Jan. 16, 2013, 2 pages.
Press Release: "OmegaH2O® Clear Shelf Stable Omega-3, CoQ10 and other non polar compounds U.S. Appl. No. 12/383,244 Approved in Europe and notice of allowance in U.S." Published on Jun. 4, 2012 [online] Retrieved from:<URL:pr.com/press-release/417599 [4 pages].
Press Release: "VIRUN® closes $2.1 million series-A funding to bolster innovation and world-wide expansion," Published on Aug. 2, 2012 [online] Retrieved from:<URL: pr.com/press-release/431579 [4 pages].
Swern, D., *Bailey's Industrial Oil and Fat Products*, vol. 1, 4th edition. John Wiley & Sons, New York, pp. 387-391 and then 424-428 (1979).
Tadros, T., "Emulsion science and technology: a general introduction," *Emulsion Science and Technology*, Ed. T. Tadros., Wienheim: Wiley-VCH, pp. 1-56 (2009).
Restriction Requirement, issued Sep. 6, 2011, in connection with U.S. Appl. No. 12/383,241, 6 pages.
Itention to Grant European patent, issued Nov. 8, 2011, in connection with European Patent Application No. 09723157.5, 5 pages.
Examination Report, issued Dec. 19, 2011, in connection with European Patent Application No. 09722985.0, 4 pages.
Translation of Office Action, received Feb. 8, 2012, in connection with Chinese patent Application No. 200980118257.4, 2 pages.
Response to Restriction Requirement, issued Sep. 6, 2011, in connection with U.S. Appl. No. 12/383,241, 11 pages.
Examiner's Report, issued Mar. 28, 2012, in connection with Canadian Patent Application No. 2,715,018, 2 pages.
Examiner's Report, issued Mar. 28, 2012, in connection with Canadian Patent Application No. 2,718,231, 3 pages.
Response to Examination Report, issued Dec. 19, 2011, in connection with European Patent Application No. 09722985.0, 60 pages.
Response to Examiner's Report, issued Mar. 28, 2012, in connection with Canadian Patent Application No. 2,715,018, 7 pages.
Decision to Grant, issued Apr. 19, 2012, in connection with European Patent Application No. 09723157.5, 1 page.
PCT Communication, mailed Apr. 25, 2012, in connection with International Patent Application No. PCT/US2011/000538, 4 pages.
Notice of Allowance, issued May 17, 2012 in connection with Canadian Patent Application No. 2,715,018, 1 page.
Notice of Allowance, mailed May 30, 2012, in connection with U.S. Appl. No. 12/383,244, 5 pages.
Translation of Office Action, issued May 31, 2012, in connection with Chinese Patent Application No. 200980118258.9, 1 page.
Second Written Opinion, issued Jun. 1, 2012 in connection with corresponding International Patent Application No. PCT/US2011/001099, 5 pages.
Response to Examiner's Report, issued Mar. 28, 2012, in connection with Canadian Patent Application No. 2,718,231, 18 pages.
Itention to Grant European patent, issued Jun. 15, 2012, in connection with European Patent Application No. 09722985.0, 5 pages.

(56) References Cited

OTHER PUBLICATIONS

Response to PCT Communication, mailed Apr. 25, 2012, in connection with International Patent Application No. PCT/US2011/000538, 5 pages.
Office Action and Search Report, issued Jun. 25, 2012, in connection with Chinese Patent Application No. 200980132984.6, 13 pages.
International Preliminary Report on Patentability, mailed Jul. 16, 2012 in connection with International Patent Application No. PCT/US2011/000538, 12 pages.
Response to Office Action, received Feb. 8, 2012, and Instructions for Response to Office Action, in connection with Chinese patent Application No. 200980118257.4, 27 pages.
Response to Office Action, issued Apr. 4, 2012, in connection with U.S. Appl. No. 12/383,241, 16 pages.
Response to Written Opinion, issued Jun. 1, 2012 in connection with corresponding International Patent Application No. PCT/US2011/001099, 5 pages.
Amendment after Final Office Action of Jun. 19, 2012, submitted Aug. 6, 2012, in connection with U.S. Appl. No. 12/456,926, 13 pages.
Supplemental Notice of Allowance, mailed Aug. 17, 2012, in connection with U.S. Appl. No. 12/383,244, 1 page.
Examination Report, issued Aug. 17, 2012, in connection with Canadian Patent Application No. 2,718,231, 2 pages.
Examiner's Amendment Communication, issued Aug. 20, 2012, in connection with U.S. Appl. No. 12/456,926, 5 pages.
International Preliminary Report on Patentability, issued Aug. 20, 2012, in connection with corresponding International Patent Application No. PCT/US2011/001099, 16 pages.
Notice of Allowance, mailed Aug. 21, 2012, in connection with U.S. Appl. No. 12/456,926, 10 pages.
Final Office Action, mailed Aug. 21, 2012, in connection with U.S. Appl. No. 12/383,241, 18 pages.
Response to Examination Report, issued Aug. 17, 2012, in connection with Canadian Patent Application No. 2,718,231, 11 pages.
Office Action, issued Sep. 6, 2012, in connection with U.S. Appl. No. 13/065,510, 22 pages.
Third Party Reexamination Request, submitted Oct. 9, 2012, in connection with U.S. Patent No. 8,282,977, 148 pages.
Response to Office Action, issued May 31, 2012 in connection with Chinese Patent Application No. 200980118258.9, 17 pages.
Supplemental Notice of Allowability, mailed Nov. 6, 2012, in connection with U.S. Appl. No. 12/456,926, 10 pages.
Notice of Allowance, issued Nov. 7, 2012, in connection with Canadian Patent Application No. 2,718,231, 3 pages.
Decision to Grant, issued Nov. 8, 2012, in connection with European Patent Application No. 09722985.0, 2 pages.
Office communication, issued Nov. 14, 2012, in connection with U.S. Appl. No. 90/012,700, 3 pages.
Translation of Office Action, issued Nov. 25, 2012, in connection with Israeli Patent Application No. 208133, 3 pages.
Extended European Search Report, issued Dec. 5, 2012, in connection with European Patent Application No. 12188577.6, 7 pages.
Order Granting Request for Ex Parte Reexamination, issued Dec. 10, 2012, in connection with U.S. Appl. No. 90/012,700, 27 pages.
Response to Office Action, submitted Jan. 10, 2013, in connection with Chinese Patent Application No. 200980132984.6, 22 pages.
Letter/Written Disclosure of the Supplemental Information Disclosure Statement for the above-referenced application, mailed on Jun. 27, 2012, 2 pages.
Response of Jan. 23, 2012 to Written Opinion issued for related International Application No. PCT/US2011/000538, 9 pages.
Office Action, issued Oct. 4, 2011, in connection with U.S. Appl. No. 12/383,244, 13 pages.
Response to Office Action, issued Oct. 4, 2011, in connection with U.S. Appl. No. 12/383,244, 16 pages.
International Search Report and Written Opinion, issued Sep. 26, 2011, in connection with corresponding International Application No. PCT/US2011/001099, 9 pages.

Response to Written Opinion, issued Sep. 26, 2011, in connection with corresponding International Application No. PCT/US2011/001099, 10 pages.
Office Action, issued Nov. 4, 2011, in connection with U.S. Appl. No. 12/456,926, 9 pages.
Response, dated May 4, 2012, to Office Action issued Sep. 9, 2011 in connection with U.S. Appl. No. 12/456,926, 27 pages.
Office Action, issued Apr. 4, 2012, in connection with U.S. Appl. No. 12/383,241, 12 pages.
Final Office Action, mailed Jun. 19, 2012, in connection with U.S. Appl. No. 12/456,926, 8 pages.
Letter/Written Disclosure of the Supplemental Information Disclosure Statement for the above-referenced application, mailed on Sep. 26, 2013, 2 pages.
"Alpha-Tocopherol Polyethylene glycol Succinate (TPGS)," Pure Matters website [online][retrieved on Feb. 26, 2013] Retrieved from:<URL:resources.purematters.com/herbs-supplements/a/alpha-tocopherol-polyethylene-glycol-succinate-tpgs, 2 pages.
Boukley, B. "'Next Generation' Omega-3 sports drink set to hydrate America" Beveragedaily.com Aug. 1, 2013 [online] Retrieved from:<URL:beveragedaily.com/content/view/print/804977] [accessed on Aug. 16, 2013], 2 pages.
Boukley, B. "Runaway Omega-3 beverage demand 'can be scary'— Virun CEO" Beveragedaily.com Dec. 20, 2013 [online] Retrieved from:<URL:beveragedaily.com/content/view/print/711158] [accessed on Aug. 16, 2013], 2 pages.
Boukley, B. "Searching for the Holy Grail: Science-backed functional beverages" Beveragedaily.com Mar. 3, 2013 [online] [retrieved at Retrieved from:<URL:beveragedaily.com/content/view/print/749075] [accessed on Aug. 16, 2013], 2 pages.
Boukley, B. "Stepan Lipid Nutrition and Virun paint bold brushstrokes on clear beverage 'canvas'," Beveragedaily.com Apr. 11, 2013 [online] Retrieved from:<URL:beveragedaily.com/content/view/print/761692] [accessed on Aug. 16, 2013], 2 pages.
Boukley, B. "Time for a Change . . . Cola? US firm heralds healthy cola revolution'," Beveragedaily.com Apr. 30, 2013 [online] [retrieved at Retrieved from:<URL:beveragedaily.com/content/view/print/769020] [accessed on Aug. 16, 2013], 2 pages.
Bromley, P., "Nanotechnology and nonpolar active compounds in functional foods: An application note," Chapter 39, *Bio-Nanotechnology: A Revolution in Food, Biomedical and Health* Sciences (eds., Bagchi et al.), Blackwell Publishing Ltd., Oxford, UK., 7 pages (2013).
Compass Foods Website, Food emulsification products, Retrieved from:<URL:compassfoods.com [accessed Sep. 25, 2008], 1 page.
DK Ester Sucrose Esters Applications, Montello Inc [online][retrieved on Mar. 24, 2008] Retrieved from:<URL:montelloinc.com/dk_ester2.htm , 1 page.
DK Ester Sucrose Esters Properties Montello Inc [online][retrieved on Mar. 24, 2008] Retrieved from:<URL:montelloinc.com/dk_ester.htm, 2 pages.
DK Ester Sucrose Esters Specifications, Montello Inc [online][retrieved on Mar. 24, 2008] Retrieved from:<URL:montelloinc.com/dk_ester3.htm, 1 page.
IPEC—Americas News "IPEC—Americas Gains Four New Members in May," pp. 1-12 (May 2008).
Schultz, H. "PQQ set to make splash in sports nutrition beverages," nutraingredients-usa.com Aug. 6, 2013 [online] [retrieved at http://www.nutraingredients-usa.com/content/view/print/807624] [accessed on Aug. 16, 2013], 2 pages.
Stojkovic et al., "Coenzyme Q10 in submicron-sized dispersion improws development, hatching, cell proliferation, and adenosine triphosphate content of in vitro-produced bovine embryos," 61:541-547 (1999).
Surfhope SE Pharma, Mitsubishi-Kagaku Foods Corporation, Copyright 2002 [online] Retrieved from:<URL:mfc.co.jp/english/se_pharma/sepharma.htm [accessed on Sep. 25, 2008] 3 pages.
Virun Facebook Page, [online] Retrieved from:<URL:facebook.com/pages/Virun/168007462662 [accessed on Aug. 16, 2013] 3 pages.
Office Action, issued Jan. 5, 2013, and translation, in connection with Chinese Patent Application No. 200980118257.4, 8 pages.

(56) References Cited

OTHER PUBLICATIONS

Office Action, issued Mar. 4, 2013, in connection with U.S. Appl. No. 90/012,700, 40 pages.
Office Action, issued Mar. 4, 2013, and translation, in connection with Chinese Patent Application No. 200980118258.9, 11 pages.
Response to Office Action, submitted Mar. 6, 2013, in connection with U.S. Appl. No. 13/065,510, 25 pages.
Office Action, issued Mar. 7, 2013, in connection with U.S. Appl. No. 13/573,424, 11 pages.
Response to Office Action, submitted Mar. 20, 2013, and instructions for response, in connection with Chinese Patent Application No. 200980118257.4, 17 pages.
Office Action, issued Mar. 27, 2013, in connection with Mexican Patent Application No. MX/a/2010/010050, 9 pages.
Response to Office Action, submitted May 6, 2013, in connection with U.S. Appl. No. 90/012,700, 89 pages.
Response to Office Action, submitted May 15, 2013, and instructions for response, in connection with Mexican Patent Application No. MX/a/2010/010050, 16 pages.
Office Action and Search Report, issued May 15, 2013, and translation, in connection with Chinese Patent Application No. 200980132984.6, 15 pages.
International Search Report and Written Opinion, issued May 29, 2013, in connection with International Patent Application No. PCT/US2013/025445, 11 pages.
Request for Continued Examination and Preliminary Amendment filed in response to Final Office Action, submitted Jun. 19, 2013, in connection with U.S. Appl. No. 12/383,241, 31 pages.
Final Office Action, issued Jun. 28, 2013, in connection with in connection with U.S. Appl. No. 13/065,510, 22 pages.
Office Action, issued Jul. 4, 2013, in connection with Australian Patent Application No. 2009226019, 2 pages.
Response to Office Action, submitted Jul. 19, 2013, and instructions for response, in connection with Chinese patent Application No. 200980118258.9, 25 pages.
Response to Office Action, submitted Jul. 22, 2013, in connection with Australian Patent Application No. 2009226019, 18 pages.
Response to Rule 70(2) and 70a(2) communication, submitted Jul. 23, 2013, in conneciton with European Patent Application No. 12188577.6, 9 pages.
Supplemental Response to Office Action, submitted Jul. 26, 2013, in connection with Australian Patent Application No. 2009226019, 19 pages.
Office Action, issued Jul. 30, 2013, and translation, in connection with Chinese Patent Application No. 200980118257.4, 6 pages.
Notice of Acceptance, issued Aug. 15, 2013, in connection with Australian Patent Application No. 2009226019, 2 pages.
Final Office Action, issued Sep. 23, 2013, in connection with U.S. Appl. No. 90/012,700, 46 pages.

* cited by examiner

COMPOSITIONS CONTAINING NON-POLAR COMPOUNDS

RELATED APPLICATIONS

Benefit of priority is claimed to U.S. Provisional Application Ser. No. 61/398,192, filed Jun. 21, 2010, entitled "COMPOSITIONS CONTAINING NON-POLAR COMPOUNDS," to Philip J. Bromley and Chetan S. Rao.

This application is related to International PCT Application No. PCT/US2011/001099, filed Jun. 20, 2011, entitled "COMPOSITIONS CONTAINING NON-POLAR COMPOUNDS," which also claims priority to U.S. Provisional Application Ser. No. 61/398,192.

This application is related to U.S. application Ser. No. 12/383,244, filed Mar. 20, 2009, published as US-2009-0297665-A1, and entitled "COMPOSITIONS CONTAINING NON-POLAR COMPOUNDS," and International Application No. PCT/US2009/001775, filed Mar. 20, 2009, published as International PCT Application No. WO 2009/117152 and entitled "EMULSIONS INCLUDING A PEG-DERIVATIVE OF TOCOPHEROL," all of which claim priority to U.S. Provisional Application Ser. No. 61/070,381, filed Mar. 20, 2008, entitled "COMPOSITIONS CONTAINING NON-POLAR COMPOUNDS" and U.S. Provisional Application Ser. No. 61/132,424, filed Jun. 16, 2008, entitled "COMPOSITIONS CONTAINING NON-POLAR COMPOUNDS," each to Philip Bromley.

This application also is related to U.S. patent application Ser. No. 12/383,241, filed Mar. 20, 2009, published as US-2009-0297491-A1 entitled "COMPOSITIONS CONTAINING NON-POLAR COMPOUNDS" and International Application No. PCT/US2009/001774, filed Mar. 20, 2009, published as International PCT Application No. WO 2009/117151 and entitled "VITAMIN E DERIVATIVES AND THEIR USES," all of which claim priority to U.S. Provisional Application Ser. No. 61/070,392, filed Mar. 20, 2008, entitled "COMPOSITIONS CONTAINING NON-POLAR COMPOUNDS" and U.S. Provisional Application Ser. No. 61/132,409, filed Jun. 16, 2008, entitled "COMPOSITIONS CONTAINING NON-POLAR COMPOUNDS," each to Philip Bromley.

This application also is related to U.S. patent application Ser. No. 13/065,510, filed Mar. 22, 2011, entitled "COMPOSITIONS CONTAINING NON-POLAR COMPOUNDS" and International Application No. PCT/US2011/000538, filed Mar. 22, 2011, entitled "COMPOSITIONS CONTAINING NON-POLAR COMPOUNDS," all of which claim priority to U.S. Provisional Application Ser. No. 61/340,944, filed Mar. 23, 2010, entitled "COMPOSITIONS CONTAINING NON-POLAR COMPOUNDS," each to Philip Bromley.

The subject matter of each of the above-referenced applications is incorporated by reference in its entirety.

FIELD OF THE INVENTION

Provided are compositions and methods for preparing foods and beverages that contain additives, such as nutraceuticals, pharmaceuticals and supplements.

BACKGROUND

Non-polar compounds are not easily dissolved in aqueous solutions, such as water or other polar solvent. A number of non-polar compounds are used in compositions for human ingestion, for example, pharmaceuticals, nutraceuticals and/or dietary supplements. Exemplary of non-polar compounds used in such compositions are vitamins and minerals, fatty acids, and other non-polar compounds, non-polar active agents, and non-polar active ingredients.

Because of poor water solubility, inclusion of non-polar compounds in products for human consumption, for example, supplements, foods and beverages, is often challenging. Available compositions containing non-polar compounds, particularly food or beverage compositions containing non-polar compounds, and methods for formulating such compositions, are limited. Thus, there is a need to develop compositions containing non-polar compounds and methods for making the compositions. Accordingly, it is among the objects herein to provide compositions, including food and beverage compositions, containing non-polar compounds, and methods for making the compositions.

SUMMARY

Provided are first compositions (concentrates) that contain non-polar compounds, including liquid emulsion concentrates. Also provided are methods that use such first compositions to prepare other compositions, such as water-based finished food and beverages, into which the first compositions are diluted to form food and beverage dilution compositions. Also provided are foods and beverage dilution compositions containing the food or beverage and the diluted concentrate. The concentrates contain dispersions, and/or can be used to prepare dispersions, of effective amounts of additives, such as non-polar compounds, including non-polar active ingredients, such as nutraceuticals, pharmaceuticals, and supplements, such as essential fatty acids, including polyunsaturated fatty acids, such as omega-3 fatty acids, omega-6 fatty acids, omega-9 fatty acids, conjugated fatty acids, and other fatty acids; oil soluble vitamins, including vitamin D3 and vitamin A palmitate; alpha lipoic acid; other oils; phytochemicals, including phytosterols and resveratrol; coenzymes, including Coenzyme Q10; and carotenoids, including lycopene, lutein, zeaxanthin, and a mixture of lutein and zeaxanthin; and other oil-based additives. The amounts in the resulting diluted compositions are effective to supplement the diet. The compositions provided herein are stable dispersions without phase separation or other changes.

For example, the provided compositions include concentrates containing non-polar compounds containing non-polar active ingredients, surfactants, and emulsion stabilizers at amounts whereby dilution of the concentrate in a water-based finished food or beverage at a particular amount (e.g., any of the specified amounts, concentrations, and dilutions of the concentrates and any of the amounts of the non-polar active ingredients described herein below), yields a liquid dilution composition containing effective amounts of the non-polar active ingredient and having one or more desired properties. The provided compositions further include food and beverage dilution compositions, including the food and beverage dilution compositions made from the concentrates, containing the water-based finished food or beverage, non-polar active ingredients at effective amounts that have the desired properties. The desired properties include stability of the food or beverage dilution compositions, such as compositions that are as stable or about as stable as the food or beverages in the absence of the concentrate and/or in the absence of the non-polar active ingredient; for example, the compositions are free from phase separation, flocculation, creaming, precipitation, and/or ringing; and/or are substantially free of oxidation. The desired properties of a liquid dilution composition include clarity, such as compositions that are clear or about as clear as the aqueous medium in the absence of the concentrate and/or in the absence of the non-polar active ingredient; particle size, such as particle size of less than 200 nm or less than about 200 nm, less than 100 nm or less than about 100 nm, less than 50 nm or less than about 50 nm, or less than 25 nm or less than about 25 nm, at most or on average; turbidity, such as a Nephelometric Turbidity Units (NTU) value of less than 200 or about 200, less than 100 or about 100, less than 50 or about 50, less than 30 or about 30, less than 25 or about 25, or less than 10 or about 10; and the lack of visible particles, visible crystals, phase separation, and/or ringing.

The provided compositions typically are liquid emulsion concentrates, that contain surfactants (typically a surfactant that is a sugar fatty acid ester or mixture of sugar fatty acids esters, such as, for example a sucrose fatty acid ester or a mixture of sucrose fatty acids esters, a PEG-derivative of Vitamin E, or a polysorbate or a polysorbate analog; or mixtures of two or more surfactants, such as, for example, a mixture of one or more sucrose fatty acid esters and a PEG-derivative of Vitamin E; or a mixture of one or more sucrose fatty acid esters and a polysorbate 80 or polysorbate 80 analog; or a PEG-derivative of Vitamin E and a polysorbate 80 or polysorbate 80 analog; or a mixture of one or more sucrose fatty acid esters, a PEG-derivative of Vitamin E and a polysorbate 80 or polysorbate 80 analog), non-polar compound(s) (which typically is/are a non-polar active ingredient that differs from the surfactant, such as for example, polyunsaturated fatty acids, omega-3 fatty acids, omega-6 fatty acids, omega-9 fatty acids, conjugated fatty acids, coenzyme Q-containing active ingredients, oil soluble vitamins other than a vitamin E, alpha lipoic acid, carotenoid-containing active ingredients and phytochemicals) and an emulsion stabilizer (e.g., a fatty-acid modified carbohydrate-based macromolecule).

The amount of the non-polar compound(s) in the concentrate is typically between 20% or about 20% and 50% or about 50%, inclusive, by weight, of the concentrate, e.g., between 20% or about 20% and 50% or about 50%, inclusive; or between 20% or about 20% and 45% or about 45%, inclusive; or between 20% or about 20% and 40% or about 40%, inclusive; or between 30% or about 30% and 50% or about 50%, inclusive; or between 30% or about 30% and 45% or about 45%, inclusive; or between 30% or about 30% and 40% or about 40%, inclusive, by weight, of the concentrate; or between 35% or about 35% and 50% or about 50%, inclusive; or between 35% or about 35% and 45% or about 45%, inclusive; or between 35% or about 35% and 40% or about 40%, inclusive, by weight, of the concentrate.

The surfactants in the provided concentrates typically have a Hydrophilic Lipophilic Balance (HLB) value of between 12 or about 12 and 20 or about 20, such as between 13 or about 13 and 20 or about 20, or between 14 or about 14 and 20 or about 20, or between 12 or about 12 and 15 or about 15, or between 12 or about 12 and 18 or about 18, or between 12 or about 12 and 16 or about 16, or between 14 or about 14 and 18 or about 18, or between 15 or about 15 and 18 or about 18, e.g., at or about 12, 13, 14, 15, 16, 17, 18, 19 or 20. Exemplary surfactants for use in the compositions provided include non-ionic surfactants, such as sugar ester surfactants, such as sugar fatty acid ester surfactants, typically, sucrose fatty acid ester surfactants, which typically contain sucrose fatty acid monoesters (e.g., sucrose fatty acid ester surfactants); PEG-derivatives of vitamin E, typically a tocopherol polyethylene glycol diester (TPGD), such as, for example, a tocopherol polyethylene glycol succinate (TPGS); and/or polysorbates or polysorbate analogs, such as, polysorbate 80 or polysorbate 80 analogs, such as polysorbate 60, polysorbate 40 or polysorbate 20. The amount of each surfactant in the concentrate typically is between 3% or about 3% and 16% or about 16%, inclusive, by weight, of the concentrate, e.g., between 3% or about 3% and 16% or about 16%, or between 6% or about 6% and 14% or about 14%, or between 8% or about 8% and 11% or about 11%; or 3% or about 3%; or 4% or about 4%; or 5% or about 5%; or 6% or about 6%; or 7% or about 7%; or 8% or about 8%; or 9% or about 9%; or 10% or about 10%; or 11% or about 11%; or 12% or about 12%; or 13% or about 13%; or 14% or about 14%; or 15% or about 15%; or 16% or about 16%, by weight, of the concentrate.

When one or more surfactants are present, the total amount of surfactants, excluding the fatty acid-modified carbohydrate-based macromolecule, is between 16% or about 16% and 30% or about 30%, inclusive, by weight of the concentrate, e.g., between 16% or about 16% and 30% or about 30%; or between 16% or about 16% and 25% or about 25%; or between 17% or about 17% and 22% or about 22%.

The amount of emulsion stabilizer in the concentrate typically is in a range greater than 1%, up to and including 3%, 4% or 5% or in an amount up to and including at or about 1.5%, 2%, 3%, 4%, 5%, 6%, 7%, 8%, 9%, 10%, 11%, 12%, 13%, 14% or 15%, by weight, of the concentrate. The amount of emulsion stabilizer in the concentrate typically is between 1% or about 1% and 15% or about 15%; or between 1% or about 1% and 5% or about 5%; or 1% or about 1%; or 1.5% or about 1.5%; or 2% or about 2%; or 2.2% or about 2.2%; or 2.5% or about 2.5%; or 3% or about 3%; or 4% or about 4%; or 5% or about 5%; or 6% or about 6%; or 7% or about 7%; or 8% or about 8%; or 9% or about 9%; or 10% or about 10%; or 11% or about 11%; or 12% or about 12%; or 13% or about 13%; or 14% or about 14%; or 15% or about 15%, by weight, of the concentrate composition.

Among the sugar ester surfactants are sugar fatty acid ester surfactants, typically sucrose fatty acid ester surfactants. The sugar fatty acid ester surfactants can be blends of different esters, such as sugar fatty acid monoesters, diesters, triesters, and polyesters. The sucrose fatty acid ester surfactants typically contain sucrose fatty acid monoesters. The sucrose fatty acid esters containing monoesters further can contain one or more of sucrose fatty acid diesters, triesters, and/or polyesters. In one example, the sucrose fatty acid ester contains one or more of sucrose stearate, sucrose laurate, sucrose palmitate, sucrose oleate, sucrose caprylate, sucrose decanoate, sucrose myristate, sucrose pelargonate, sucrose undecanoate, sucrose tridecanoate, sucrose pentadeconoate, sucrose heptadecanoate, and homologs thereof, including mono-, di-, tri-, and poly-ester forms of these sucrose fatty acid esters.

The sucrose fatty acid ester surfactants include surfactants that are blends of sucrose fatty acid esters, containing a plurality of different sucrose fatty acid esters. The different sucrose fatty acid esters in the blend can vary in the length and/or saturation of the carbon chain of the fatty acid portion of the ester, or in the degree of esterification (e.g., whether the ester is a monoester, diester, triester, or polyester). Typically, the sucrose fatty acid ester surfactant contains proportionally more monoesters than other types of esters (e.g., diesters, triesters, and polyesters).

The relative amount of monoester in the sucrose fatty acid ester surfactant can be specified as a percentage of the total esters. For example, among the sucrose fatty acid ester surfactants are surfactants containing at least at or about 50%, at least at or about 60%, at least at or about 70%, at least at or about 80%, or at least at or about 90%, by weight or by molecule, sucrose fatty acid monoesters. In one aspect, the sucrose fatty acid ester surfactant is a blend of sucrose fatty acid esters containing at or about 72% monoesters, at or about 23% diesters, and at or about 5% triesters, by weight or by molecule. In another aspect, the sucrose fatty acid ester surfactant is a blend of sucrose fatty acid esters containing at or about 61%, monoesters, at or about 30% diesters, at or about 7%, triesters, and at or about 2%, polyesters, by weight or by molecule. In another aspect, the sucrose fatty acid ester surfactant is a blend of sucrose fatty acid esters containing at or about 52%, monoesters, at or about 36%, diesters, at or about 10% triesters, and at or about 2% polyesters, by weight or by molecule.

The sucrose fatty acid ester(s) of the sucrose fatty acid ester surfactants can contain a fatty acid chain of any length, and typically have between 4 or about 4 and 28 or about 28 carbon atoms, typically between 8 or about 8 and 22 or about 22 carbon atoms (e.g., 8, 9, 10, 11, 12, 13, 14, 15, 16, 17, 18, 19, 20, 21, or 22 carbon atoms), and more typically between 12 or about 12 and 18 or about 18 carbon atoms (e.g., 12, 13, 14, 15, 16, 17, or 18 carbon atoms), such as fatty acids having carbon chains that contain 12, 14, 16 or 18 carbon atoms, such as stearic acid, lauric acid, oleic acid, and palmitic acid. Such sucrose fatty acid esters include sucrose stearate (e.g., sucrose monostearate), sucrose laurate (e.g., sucrose monolaurate), sucrose oleate (e.g., sucrose monooleate), sucrose palmitate (e.g., sucrose monopalmitate), and combinations thereof, including homologs thereof. The sucrose fatty acid ester surfactants include any of those described herein, and typically those having an HLB value of between 14 or about 14 and 20 or about 20, and more typically between 15 or about 15 and 18 or about 18 (e.g., at or about 15, 16, 17, or 18). In one example, the sucrose fatty acid ester surfactant contains any one or more of sucrose monostearate, sucrose monolaurate, sucrose monooleate, and sucrose monopalmitate. Exemplary sucrose fatty acid esters are described herein, and include those having a structure according to Scheme I, provided herein below.

In one example, the concentrates contain one or more surfactants, selected from among a mixture of one or more sucrose fatty acid esters and a PEG-derivative of Vitamin E. The PEG-derivative of vitamin E surfactants typically have an HLB value of between 12 or about 12 and 20 or about 20, for example, between 12 or about 12 and 20 or about 20, or between 14 or about 14 and 20 or about 20 or between 15 or about 15 and 18 or about 18 or between 15 or about 15 and 20 or about 20. In one example, the PEG-derivative of Vitamin E that is a tocopherol polyethylene glycol diester (TPGD), for example, a tocopherol polyethylene glycol succinate (TPGS), tocopherol sebacate polyethylene glycol, tocopherol dodecanodioate polyethylene glycol, tocopherol suberate polyethylene glycol, tocopherol azelaate polyethylene glycol, tocopherol citraconate polyethylene glycol, tocopherol methylcitraconate polyethylene glycol, tocopherol itaconate polyethylene glycol, tocopherol maleate polyethylene glycol, tocopherol glutarate polyethylene glycol, tocopherol glutaconate polyethylene glycol and tocopherol phthalate polyethylene glycol, or a TPGS analog. In another example, the PEG-derivative of vitamin E is a TPGS that is a TPGS-1000 or D-α TPGS.

In another example, the concentrates contain one or more surfactants, selected from among a mixture of one or more sucrose fatty acid esters and a polysorbate 80 or polysorbate 80 analog. Typically, a polysorbate 80 or polysorbate 80 analog has an HLB value of between 12 or about 12 and 20 or about 20, for example, between 12 or about 12 and 20 or about 20, or between 14 or about 14 and 20 or about 20, or between 14 or about 14 and 20 or about 20, or between 15 or about 15 and 20 or about 20. In one example, the polysorbate 80 analog is a polysorbate 80 homolog, for example, a polysorbate 80 homolog differs from polysorbate 80 by one or more methylene unit(s), for example, a polysorbate 60, polysorbate 40 or polysorbate 20.

Exemplary non-polar compounds in the provided compositions (including the liquid emulsion concentrates) are non-polar active ingredients, which include, but are not limited to, omega-3 fatty acids, omega-6 fatty acids, omega-9 fatty acids, conjugated fatty acids, coenzyme Q-containing active ingredients, oil soluble vitamins other than a vitamin E, alpha lipoic acid, carotenoid-containing active ingredients and phytochemicals. The non-polar active ingredients include, for example, non-polar compounds containing Docosahexaenoic acid (DHA) and/or Eicosapentaenoic acid (EPA), Alpha-Linolenic acid (α-Linolenic acid; ALA), conjugated linoleic acid (CLA), and gamma-linolenic acid (GLA), including, but not limited to, fish oil, algae oil, flaxseed oil, borage oil, oleic acid, saw palmetto extract, lipoic acid, phytosterols, resveratrol, coenzyme Q10, vitamin D3, vitamin A palmitate, lycopene, lutein, zeaxanthin, and mixtures of lutein and zeaxanthin.

The non-polar active ingredients include, but are not limited to, compounds containing any fat-soluble nutraceutical or pharmaceutical and/or oil, such as, for example, drugs, hormones, vitamins, nutrients, including any and other lipophilic compounds containing essential fatty acids, for example, polyunsaturated fatty acids (PUFAs), including, for example, omega-3 fatty acids, for example, natural and synthetic omega-3 fatty acids, for example, compounds containing omega-3 polyunsaturated long-chain fatty acids, including Eicosapentaenoic acid (EPA) (20:5ω3), Docosahexaenoic acid (DHA) (22:6ω3), Eicosatetraenoic acid (24:4ω3); Docosapentaenoic acid (DPA, Clupanodonic acid) (22:5ω3), 16:3 ω3; 24:5 ω3, and/or nisinic acid (24:6ω3), which can include, for example, fish oil, algae oil, krill oil, canola oil, flaxseed oil, soybean oil, and walnut oil; compounds containing short-chain omega-3 fatty acids, for example, Alpha-Linolenic acid (α-Linolenic acid; ALA) (18:3ω3) (e.g., flaxseed oil) and Stearidonic acid (18:4ω3); esters of an omega-3 fatty acid and glycerol, for example, monoglycerides, diglycerides and triglycerides; esters of omega-3 fatty acid and a primary alcohol, for example, fatty acid methyl esters and fatty acid esters; precursors of omega-3 fatty acid oils, for example, EPA precursor, DHA precursor; derivatives such as polyglycolized derivatives or polyoxyethylene derivatives; oils containing the omega-3 fatty acids, for example, fish oil (e.g., marine oil), including, for example, highly purified fish oil concentrates, *perilla* oil, krill oil, and algae oil (e.g., microalgae oil); compounds containing omega-6 fatty acids, for example, compounds containing Linoleic acid (18:2(06) (a short-chain fatty acid), Gamma-linolenic acid (GLA) (18:3ω6), Dihomo gamma linolenic acid (DGLA) (20:3ω6), Eicosadienoic acid (20:2ω6), Arachidonic acid (AA) (20:4ω6), Docosadienoic acid (22:2ω6), Adrenic acid (22:4ω6), and/or Docosapentaenoic acid (22:5ω6), for example, borage oil, corn oil, cottonseed oil, grape seed oil, peanut oil, primrose oil, for example, evening primrose (*Oenothera biennis*) oil, blackcurrant seed oil, hemp seed oil, spirulina extract, safflower oil, sesame oil and soybean oil;

compounds containing other fatty acids, for example, triglycerides, including medium chain triglycerides; polar lipids, for example, ether lipids, phosphoric acid, choline, fatty acids, glycerol, glycolipids, triglycerides, and phospholipids (e.g., phosphatidylcholine (lecithin), phosphatidylethanolamine, and phosphatidylinositol); saw palmetto extract; ethyl linoleate; herb oils, for example, garlic oils and scordinin; short-chain saturated fatty acids (4:0-10:0); Laurie acid (12:

0); Myristic acid (14:0); Pentadecanoic acid (15:0); Palmitic acid (16:0); Palmitoleic acid (16:1 ω7); Heptadecanoic acid (17:0); Stearic acid (18:0); Oleic acid (18:1 ω9); and/or Arachidic acid (20:0);

compounds containing micronutrients, for example, vitamins, minerals, co-factors, for example, coenzymes, such as coenzyme Q, e.g., Coenzyme Q10 (CoQ10, also called ubiquinone, e.g., ubidecarenone or a reduced form of CoQ10, e.g., ubiquinol), turmeric extract (e.g., cucuminoids), saw palmetto lipid extract (e.g., saw palmetto oil), echinacea extract, hawthorn berry extract, ginseng extract, lipoic acid (e.g., thioctic acid), ascorbyl palmitate, kava extract, St. John's Wort (e.g., hypericum, Klamath weed, goat weed), extract of quercitin, dehydroepiandrosterone, indol-3-carbinol;

compounds containing carotenoids, including hydrocarbons and oxygenated, alcoholic derivatives of hydrocarbons, for example, beta carotene, mixed carotenoids complex, lutein, lycopene, Zeaxanthin, Cryptoxanthin, for example, beta-cryptoxanthin, beta carotene, mixed carotenoids complex, astaxanthin, bixin, canthaxanthin, capsanthin, capsorubin, apo-carotenal, beta-12'-apo-carotenal, "Carotene" (mixture of alpha and beta-carotene), gamma carotene, ciolerythrin, zeaxanthin, esters of hydroxyl- or carboxyl-containing members thereof;

compounds containing fat-soluble vitamins, for example, Vitamins A, D, E and K, and corresponding provitamins and vitamin derivatives such as esters with an action resembling that of vitamin A, D, E or K for example; retinol (vitamin A) and pharmaceutically acceptable derivatives thereof, for example, palmitate ester of retinol and other esters of retinol, and calciferol (vitamin D, including vitamin D3 ergocalciferol and/or vitamin D3 cholecalciferol) and pharmaceutically acceptable derivatives thereof and precursors of vitamin D, d-alpha tocopherol (vitamin E) and derivatives thereof, including pharmaceutical derivatives thereof, for example, Tocotrienols, d-alpha tocopherol acetate and other esters of d-alpha tocopherol, and ascorbyl palmitate, a fat-soluble version of vitamin C;

compounds containing phytochemicals, including phytoestrogens, for example, genistein and daidzein, for example, isoflavones, for example, soy isoflavones, flavonoids, phytoalexins, for example, Resveratrol (3,5,4'-trihydroxystilbene), red clover extract, and phytosterols;

compounds containing lipid-soluble drugs, including natural and synthetic forms of immunosuppressive drugs, such as Cyclosporine, protease inhibitors such as Ritonavir, macrolide antibiotics and oil soluble anesthetics such as Propofol, natural and synthetic forms of steroidal hormones, for example, estrogens, estradiols, progesterone, testosterone, cortisone, phytoestrogens, dehydroepiandrosterone (DHEA), growth hormones and other hormones;

compounds containing oil-soluble acids and alcohols, for example, tartaric acid, lactylic acid butylated hydroxyanisole, butylated hydroxytoluene, lignin, sterols, polyphenolic compounds, oryzanol, cholesterol, phytosterols, flavonoids, such as, but not limited to, quercetin and resveratrol, and diallyl disulfides.

The non-polar active ingredients include ingredients containing polyunsaturated fatty acids, such as compounds containing any one or more of omega-3 fatty acids, including docosahexaenoic acid (DHA), eicosapentaenoic acid (EPA), and alpha-linolenic acid (ALA) (e.g., fish oils, krill oils, algae oils, and/or flaxseed oils), omega-6 fatty acids, such as gamma-linolenic acid (GLA) (e.g., borage oils); omega-9 fatty acids, such as oleic acid, conjugated fatty acids (e.g., conjugated linoleic acid (CLA)), and saw palmetto extracts; ingredients containing phytochemicals (e.g., phytosterols and/or resveratrol); ingredients containing carotenoids (e.g., lycopene, lutein, zeaxanthin, and mixtures of lutein and zeaxanthin); ingredients containing coenzymes such as coenzyme Q, for example Coenzyme Q10 (e.g., ubidecarenone); and ingredients containing oil soluble vitamins (vitamin D3 and vitamin A palmitate), and combinations thereof.

In one example, the non-polar active ingredient contains eicosapentaenoic acid (EPA), docosahexaenoic acid (DHA), or a combination thereof. In one example, the non-polar active ingredient contains DHA at an amount between 10% or about 10% and 90% or about 90% or between 25% or about 25% and 85% or about 85%; or between 35% or about 35% and 70% or about 70%, or between 10% or about 10% and 40% or about 40%, by weight (w/w), of the non-polar active ingredient. In another aspect, the non-polar active ingredient contains EPA at an amount between 5% or about 5% and 20% or about 20%, between 5% or about 5% and FT % or about 17%, or between 5% or about 5% and 13% or about 13% by weight (w/w), of the non-polar active ingredient. In one aspect, the amount of EPA is not more than 10% or about 10%, or not more than 13% or about 13%, by weight (w/w), of the non-polar active ingredient. For example, the non-polar active ingredients include fish oil and algae oil containing any such percentage of EPA and/or DHA.

In another example, the non-polar active ingredient contains alpha-linolenic acid (ALA). In one example, the non-polar active ingredient contains ALA at an amount of at least 45% or about 45%, by weight (w/w), of the non-polar active ingredient, such as between 45% or about 45% and 80% or about 80%, or between 65% or about 65% and 75% or about 75%, by weight (w/w), of the non-polar active ingredient. For example, the non-polar active ingredients include flaxseed oils containing any such percentage of ALA.

In another example, the non-polar active ingredient contains gamma-linolenic acid (GLA). In one example, the non-polar active ingredient contains GLA at an amount of at least 22% or about 22%, by weight (w/w), of the non-polar active ingredient. For example, the non-polar active ingredients include a borage oil containing GLA at an amount of at least 22% or about 22%, by weight (w/w), of the borage oil.

In some examples, the concentrate contains more than one non-polar active ingredient, for example, two or more non-polar active ingredients, such as any of the non-polar compounds described herein. In one example, the total amount of non-polar active ingredient(s) is between at or about 20% and 50% of the weight of the concentrate, for example, where the combined weight of the non-polar active ingredient and additional non-polar active ingredient(s) is not more than at or about 50%, by weight (w/w), of the concentrate. In one example, the concentrate contains a polyunsaturated fatty acid and an oil-soluble vitamin. In another example, the concentrate contains a polyunsaturated fatty acid, a phytochemical-containing active ingredient and an oil-soluble vitamin. In yet another example, the concentrate contains a polyunsaturated fatty acid, a carotenoid-containing active ingredient and an oil-soluble vitamin. In one example, the concentrate contains a polyunsaturated fatty acid, a coenzyme Q-containing active ingredient and an oil-soluble vitamin. In another example, the concentrate contains a polyunsaturated fatty acid, a coenzyme Q-containing active ingredient, an oil-soluble vitamin and a non-polar solvent.

The emulsion stabilizers contained in the provided concentrates include fatty-acid modified carbohydrate-based macromolecules, typically a fatty acid modified gum, a fatty acid modified starch or a fatty acid modified cellulose, such as a fatty acid modified gum that is an n-octenylsuccinic anhydride (OSAn-) modified gum acacia or a fatty acid modified starch that is an n-octenylsuccinic anhydride (OSAn-) modified corn starch. Typically, the emulsion stabilizer contains the reaction product of at least one hydrocolloid having a viscosity of at or about from 2 to 500 cP in 10% aqueous solution at 20° C. and at or about from 2 to 15%, by weight, based on the hydrocolloid, of at least one dicarboxylic acid anhydride selected from alkane- and alkene-substituted dicarboxylic acid anhydrides of the formula:

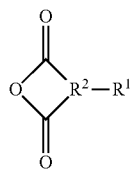

wherein $R^1$ is an alkyl radical or ethylenically-unsaturated alkyl radical having 3-18 carbon atoms and $R^2$ is at least a divalent radical and has 2-3 carbon atoms, such as for example, an acid anhydrides with an $R^1$ that has 6-10 carbon atoms and an $R^2$ that has 2 carbon atoms. Typically, the acid anhydride consists essentially of n-octenylsuccinic anhydride. In one example, the at least one hydrocolloid comprises at least about or at least 10%, by weight, of the hydrocolloid, of each of gum acacia and guar gum. In another example, the at least one hydrocolloid has a viscosity of about or at 2-250 cP, 2-100 cP, 50-100 cP, 50-200 cP or 2-150 cP in 10% aqueous solution at 20° C. In yet another example, the hydrocolloid further contains up to 95% or up to about 95%, by weight, of the total solids in the emulsion stabilizer, of at least one carbohydrate bulking agent, selected from, for example, hydrolyzed polysaccharides, oligosaccharides and monosaccharides, for example, dextrose. In one example, the bulking agent is present in a quantity of up to 95%, by weight, of the emulsion stabilizer solids.

The provided concentrates can further contain one or more additional ingredients. In one example, the concentrate further contains a polar solvent, such as polar protic solvents, such as polar solvents having a dielectric constant of greater than at or about 15, or a dielectric constant of between at or about 20 and at or about 80; and polar solvents having a polarity index of between at or about 3 and at or about 9 or a dipole moment between at or about 1.8 and at or about 2.8. The polar solvents include water and alcohols, such as monohydric, dihydric, trihydric and other alcohols, and typically alcohols other than monohydric alcohols, alcohols having two or more hydroxyl groups, such as dihydric (two hydroxy groups) and trihydric (three hydroxyl groups) alcohols. The polar solvents include, but are not limited to, glycerin, ethylene glycols, such as propylene glycol, ethylene glycol, tetraethylene glycol, triethylene glycol, and trimethylene glycol. Polar solvents can further include low molecular weight polyethylene glycols (PEGs), such as PEGs with molecular weights at or about, or less than at or about, 600, 400 or 200 kDa. In some examples, the polar solvent is water, glycerin, or propylene glycol. In one example, the amount of the polar solvent, e.g., water, is between at or about 30% and at or about 70%, or between at or about 40% and at or about 60%, by weight, of the concentrate. In another example, the concentrates contain one or more polar solvents selected from among water, glycerin, propylene glycol, ethylene glycol, tetraethylene glycol, triethylene glycol and trimethylene glycol.

In another example, the concentrates further contain a soluble fiber, such as but not limited to fructo-oligosaccharides or fructans, for example, an inulin. In one example, the amount of the soluble fiber is between 0.5% or about 0.5% and 10% or about 10%, inclusive, by weight, of the concentrate or between 0.5% or about 0.5% and 5% or about 5%, by weight, inclusive, of the concentrate, or between 1% or about 1% and 10% or about 10%, inclusive, by weight, of the concentrate or between 1% or about 1% and 5% or about 5%, by weight, inclusive, of the concentrate.

In another example, the concentrates further contain a preservative, in amount sufficient to preserve the concentrate, compared to the absence of the preservative. Exemplary preservatives in the compositions provided are natural preservatives, such as benzyl alcohol and preservatives containing benzyl alcohol. In one example, the amount of preservative is between 0.1% or about 0.1% and 1% or about 1%, by weight (w/w), of the concentrate, for example, at or about 0.1, 0.2, 0.3, 0.4, 0.5, 0.6, 0.7, 0.8, 0.9, or 1%, by weight of the concentrate. In one example, the amount of benzyl alcohol is between 0.1% or about 0.1% and 1% or about 1%, by weight (w/w), of the concentrate, for example, at or about 0.1, 0.2, 0.3, 0.4, 0.5, 0.6, 0.7, 0.8, 0.9, or 1%, by weight of the concentrate.

In another example, the concentrate contains a non-polar solvent, for example, a non-polar solvent that dissolves the non-polar active ingredient and differs therefrom. Typically, the amount of non-polar solvent is sufficient to dissolve the non-polar active ingredient, and can be, for example, between 1% or about 1% and 6% or about 6%, for example, at or about 1, 2, 3, 4, 5, or 6%, by weight (w/w), of the concentrate. The non-polar solvent typically is an oil, such as any oil suitable for dissolving the non-polar ingredient. Exemplary non-polar solvents in the compositions provided are Vitamin E oil, flaxseed oil, sunflower oil, any vegetable oils, and other oils.

In another example, the concentrates contain pH adjusters. Typically, the pH adjuster contains an acid or a base at an amount sufficient to affect the pH of the concentrate compared to the absence of the pH adjuster. The pH adjusters include, but are not limited to, citric acid, phosphoric acid and combinations thereof.

In some examples, the concentrate is formulated based on the desired properties of resulting dilution compositions generated by diluting the concentrate in a water-based finished food or beverage. Typically, the concentrate is formed so that it can be diluted in a food or beverage to produce a dilution composition having one, more than one, all, or any combination of, of the following properties:

In one example, the concentrate is formulated such that dilution of a certain amount of the concentrate in a certain amount of a food or beverage yields a dilution composition that is stable, for example, that does not exhibit phase separation, does not exhibit flocculation, does not exhibit creaming, does not contain precipitate, and/or does not exhibit ringing; or is substantially free of oxidation. For example, the concentrate can be formulated such that dilution of at or about 0.5 grams (g) to at or about 10 g of the concentrate into a serving of a food or beverage; or dilution of the concentrate in a food or beverage at up to 1:10 or about 1:10, 1:25 or about 1:25, 1:50 or about 1:50, 1:100 or about 1:100 or 1:250 or about 1:250; or dilution of the concentrate into a food or beverage of about or at 25 milligrams (mg) to at or about 500 mg, or up to at about 25 mg, 35 mg, 50 mg, 100 mg, 250 mg or 500 mg of the non-polar active ingredient per serving of the food or beverage, yields a dilution composition that is at least as stable or at least about as stable as, the food or beverage in the absence of the concentrate; does not exhibit phase separation, does not exhibit flocculation, does not exhibit creaming, does not contain precipitate, and/or does not exhibit ringing; or is substantially free of oxidation.

In one example, the concentrate is formulated such that dilution of a certain amount of the concentrate in a certain amount of aqueous medium yields a liquid dilution composition having a desired particle size, typically a particle size that is not greater than a particular particle size or is less than a particular particle size. The specified particle size can be expressed as the average particle size, or the largest particle size in the aqueous medium. For example, it can be desired that the liquid dilution composition contains less than a particular particle size on average or at most. For example, the concentrate can be formulated such that dilution of at least 0.5 grams (g) or about 0.5 g, at least 1 g or about 1 g, at least 2 g or about 2 g, at least 5 g or about 5 g, or at least 10 g or about 10 g of the concentrate into at or about 8 fluid ounces (0.236588 liters) of an aqueous medium; or dilution of the concentrate in an aqueous medium, at a dilution not more than 1:10 or about 1:10, not more than 1:25 or about 1:25, not more than 1:50 or about 1:50, not more than 1:100 or about 1:100, not more than 1:250 or about 1:250 or, at most, not more than 1:500 or about 1:500; or dilution of the concentrate in an aqueous medium to form a liquid dilution composition containing at least 25 mg or about 25 mg, at least 35 mg or about 35 mg, at least 50 mg or about 50 mg, at least 100 mg or about 100 mg, at least 250 mg or about 250 mg, or at least 500 mg or about 500 mg of the non-polar active ingredient per 8 fluid ounces of the liquid dilution composition, yields a liquid dilution composition having a particle size of less than 500 nm or less than about 500 nm, less than 200 nm or less than about 200 nm, less than 100 nm or less than about 100 nm, less than 50 nm or less than about 50 nm or less than 25 nm or less than about 25 nm, at most or on average.

In another example, the concentrate is formulated such that dilution of a certain amount of the concentrate in an amount of aqueous medium yields a liquid dilution composition having a desired clarity, such as by yielding a dilution composition having a desired NTU value, typically an NTU value that is not greater than or is less than a given NTU value, or by yielding a liquid dilution composition that is as clear, or about as clear, as the aqueous medium prior to the addition of the concentrate (i.e., in the absence of the concentrate). For example, the concentrate can be formulated such that dilution of at least 0.5 grams (g) or about 0.5 g, at least 1 g or about 1 g, at least 2 g or about 2 g, at least 5 g or about 5 g, or at least 10 g or about 10 g of the concentrate into at or about 8 fluid ounces (0.236588 liters) of an aqueous medium; or dilution of the concentrate in an aqueous medium, at a dilution not more than 1:10 or about 1:10, not more than 1:25 or about 1:25, not more than 1:50 or about 1:50, not more than 1:100 or about 1:100, not more than 1:250 or about 1:250 or, at most, not more than 1:500 or about 1:500; or dilution of the concentrate in an aqueous medium to form a liquid dilution composition containing at least 25 mg or about 25 mg, at least 35 mg or about 35 mg, at least 50 mg or about 50 mg, at least 100 mg or about 100 mg, at least 250 mg or about 250 mg, or at least 500 mg or about 500 mg of the non-polar active ingredient per 8 fluid ounces of the liquid dilution composition, yields a liquid dilution composition having a Nephelometric Turbidity Units (NTU) value of less than 200 or about 200, less than 100 or about 100, less than 50 or about 50, less than 30 or about 30, less than 25 or about 25, or less than 10 or about 10, or yields a liquid dilution composition that is at least as clear or at least about as clear as, the aqueous medium in the absence of the concentrate (i.e., compared to the clarity of the aqueous medium prior to addition of the concentrate).

In another example, the concentrate is formulated such that, upon dilution, it yields a stable liquid dilution composition, for example a composition that does not contain visible particles, does not contain visible crystals, does not exhibit ringing, or a combination thereof. The stability can be for a specified period of time, and/or when the concentrate or liquid dilution composition is kept at a particular temperature. For example, the concentrate can be formulated such that dilution of at least 0.5 g or about 0.5 g, at least 1 g or about 1 g, at least 2 g or about 2 g, at least 5 g or about 5 g, or at least 10 g or about 10 g of the concentrate into 8 fluid ounces (0.236588 liters), or about 8 fluid ounces, of an aqueous medium; dilution of the concentrate in an aqueous medium, at a dilution of not more than 1:10 or about 1:10, not more than 1:25 or about 1:25, not more than 1:50 or about 1:50, not more than 1:100 or about 1:100, not more than 1:250 or about 1:250, or, at most, not more than 1:500 or about 1:500; and/or dilution of the concentrate into an aqueous medium to form a liquid dilution composition containing at least 25 mg or about 25 mg, at least 35 mg or about 35 mg, at least 50 mg or about 50 mg, at least 100 mg or about 100 mg, at least 250 mg or about 250 mg, or at least 500 mg or about 500 mg of the non-polar active ingredient per 8 fluid ounces of the liquid dilution composition, yields a liquid dilution composition that does not contain visible particles, does not contain visible crystals, does not exhibit phase separation, and/or does not exhibit ringing, and/or is pleasant tasting and/or smelling. The concentrate can be formulated such that the food or beverage dilution composition remains stable; remains free from visible particles, remains free from visible crystals, remains free from phase separation, remains free from floc, remains free from creaming, remains free from precipitation, remains free from ringing and/or is pleasant tasting and smelling, when the concentrate and/or the food or beverage dilution composition is stored at room temperature, or at a refrigerated temperature, or at a frozen temperature. The storage can be, for example, for at least one day, at least one week, at least thirty days, or at least one year.

The food or beverage provided herein can be, for example, a water-based finished food or beverage, such as, for example, tomato-paste based products, dairy-based products, sauces, dressings, creams, salsa, queso cheese, syrups, soups, juices, including fruit juice, energy drinks, sports drinks, nutritional beverages, vitamin-fortified beverages, milk, tea, soda, flavored water and water. A serving of a food or beverage, for example, is or is about 1 teaspoon (0.166667 ounce, 4.7249 g), 1 tablespoon (0.5 fluid ounce, 14.1747 g), 2 tablespoons (1 fluid ounce, 28.3495 g), 0.25 cup (2 fluid ounces, 56.6990 g), 0.5 cup (4 fluid ounces, 113.398 g), 0.75 cup (6 fluid ounces, 170.097 g) or 1 cup (8 fluid ounces, 226.796 g).

In one example, the concentrate is formulated such that the food or beverage dilution composition contains one or more of polyunsaturated fatty acids, omega-3 fatty acids, omega-6 fatty acids, omega-9 fatty acids, conjugated fatty acids, coenzyme Q-containing active ingredients, oil soluble vitamins, alpha lipoic acid, carotenoid-containing active ingredients and phytochemical-containing active ingredients in an amount of at least 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 325, 350, 375, 400, 425, 450, 475, 500, 550, 600, 700, 800, 900, 1000, 1500, 2000, 2500 or 3000 mg per serving of the food or beverage.

In another example, the concentrate is formulated such that when diluted 1:250 in a food or beverage, the food or beverage dilution composition is as about as stable as the same food or beverage in the absence of the concentrate.

In one example, a serving of the food or beverage containing the concentrate provides at least 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 325, 350, 375, 400, 425, 450, 475, 500, 550, 600, 700, 800, 900, 1000, 1500, 2000, 2500 or 3000 mg of the non-polar active ingredient. In this example, the food or beverage is or is about as stable as the same food or beverage in the absence of the concentrate.

In another example, a serving of the food or beverage containing the concentrate provides a single dosage of the non-polar active ingredient. For example, the food or beverage can contain one or more of 1.5 to 3.0 g omega-6 CLA, 30 to 220 mg omega-3 DHA/EPA or 220 mg DHA/EPA, 400 to 800 IU vitamin D3, 40 to 400 mcg vitamin A palmitate, 50 to 200 mg CoQ10, 100 to 500 mg phytosterols and 1 to 200 mg carotenoids per serving of the food or beverage and the food or beverage is stable.

Also provided are methods for making the concentrates and methods for making the liquid dilution compositions. Generally, the methods for making the concentrates are carried out by generating, separately, an oil phase and a water phase, and mixing the two phases, typically by emulsification, to form the concentrate, which is a liquid nanoemulsion concentrate. Oil phase ingredients are added to form the oil phase and water phase ingredients are added to form the water phase. The ingredients are selected from ingredients of the concentrates, as described herein, which typically include a non-polar compound, a surfactant and an emulsion stabilizer, as described herein. Typically, the oil phase ingredients include the non-polar compound(s), typically a non-polar active ingredient(s), of the concentrate, and the water phase ingredients include the polar solvent. The ingredients are added at amounts within the appropriate concentration range for the provided concentrates as described herein. In one example, the water phase ingredients include the surfactant. In another example, the oil phase ingredients contain the surfactant. In one example, the water phase ingredients and the oil phase ingredients contain the surfactant. In one example, the water phase ingredients include the emulsion stabilizer. In another example, the oil phase ingredients contain the emulsion stabilizer. In one example, the water phase ingredients and the oil phase ingredients contain the emulsion stabilizer.

The amounts of the surfactant(s), non-polar active ingredient(s) and emulsion stabilizer(s) are selected based on the appropriate concentration ranges of these ingredients in the resulting concentrate. For example, the non-polar compound is included at an amount that is between 20% or about 20% and 50% or about 50%, by weight, of the concentrate; the surfactant is included at an amount that is between 3% or about 3% and 16% or about 16%, by weight, of the concentrate, such that when one or more surfactants are contained in the concentrate, the total amount of surfactants is included at an amount between 16% or about 16% and 30% or about 30%, by weight, of the concentrate; and the emulsion stabilizer is included at an amount of at least 1%, by weight, of the concentrate.

In one example, the oil phase ingredients further include the non-polar solvent(s). In one example, the concentrate is made with first and second oil phase ingredients and the first oil phase ingredients include the non-polar active ingredient and the solvent. In one example, the solvent contains an oil, other than the non-polar active ingredient, such as, for example, Vitamin E, flaxseed oil and/or safflower oil. In one example, the solvent is Vitamin E oil that is present in an amount between 1% or about 1% and 6% or about 6%, by weight, of the concentrate.

In one example, the oil phase ingredients and/or the water phase ingredients further contain a soluble fiber, such as a fructo-oligosaccharide or fructan, for example, an inulin, at an amount between 0.5% or about 0.5% and 5% or about 5%, by weight, of the concentrate. In another example, the oil phase ingredients and/or the water phase ingredients further contain the at least one preservative in amount sufficient to preserve the concentrate, such as, for example, a preservative containing benzyl alcohol. In one example, the amount of preservative and/or the benzyl alcohol is between 0.1% or about 0.1% and 1% or about 1%, by weight (w/w), of the concentrate.

In another example, the oil phase ingredients and/or the water phase ingredients further contain an additional emulsion stabilizer, at an amount sufficient to stabilize the concentrate, such as an emulsion stabilizer containing a fatty-acid modified carbohydrate based macromolecule, an ester gum or a blend of gums. In another example, the oil phase ingredients and/or the water phase ingredients further contain an a pH adjuster that is an acid or base in an amount sufficient to affect the pH of the concentrate.

In an exemplary provided method for making the concentrate, an oil phase is generated by mixing the oil phase ingredients in a first vessel and heating the oil phase ingredients; a water phase is generated by mixing one or more water phase ingredients in a second vessel and heating the water phase ingredients; and the oil and water phases are emulsified to generate the concentrate.

In another exemplary provided method, an oil phase is generated by mixing one or more first oil phase ingredients in a first vessel and heating the first oil phase ingredients at least until the first oil phase ingredients dissolve; then adding one or more additional oil phase ingredients to the first vessel; and mixing and heating the first and the additional oil phase ingredients; a water phase is generated by mixing one or more water phase ingredients in a second vessel and heating the water phase ingredient(s); and the water and oil phases are emulsified, to generate the concentrate.

The heating and mixing of the water and oil phases can be carried out simultaneously or sequentially, in any order.

In any of the provided methods for making the concentrates, the mixing steps (e.g., mixing the oil and/or water phases) can be carried out with a standard mixer, such as any of the standard mixers listed herein, or with any of the other mixers described herein, such as with a homogenizer. In any of the provided methods, the heating can be carried out using one or more heating apparatuses, such as, for example, a hot plate, a water jacket, or any of the heating apparatuses listed herein. In one example, the oil phase ingredients are heated with a first heating apparatus and the water phase ingredients are heated with a second heating apparatus. In one example, heating involves heating the ingredients to 60° C. or about 60° C., or to at or about 70° C. or at or about 71° C. In one example, the oil phase and/or water phase ingredients are heated to between about between 45° C. or about 45° C. and 85° C. or about 85° C., for example, at or about 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84 or 85° C.

In any of the provided methods, the emulsifying can be carried out using a homogenizer, such as any homogenizer described herein. In one example, the emulsifying is performed at between 850 rpm or about 850 rpm and 1200 rpm or about 1200 rpm. In another example, the emulsifying is performed at a speed lower than 850 rpm, such as, for example, between 25 or about 25 rpm and 50 rpm or about 50 rpm, for example at or about 30 rpm.

Any of the provided methods for producing the concentrates can be used to make any of the provided concentrates, as described herein.

Also provided are methods for producing the provided liquid dilution compositions containing the concentrates, such as beverages containing the concentrates. These methods include methods for providing oil-based additives, for example, in a food or beverage. These methods include adding any of the provided concentrates, e.g., liquid nanoemulsion concentrates, to an aqueous medium, such as a beverage. Typically, the concentrate is added to the medium, e.g., food or beverage, such that the medium contains an effective amount of the additive (e.g., the non-polar active ingredient).

The effective amount of the additive, such as the non-polar active ingredient is the quantity and/or concentration of the additive necessary for preventing, curing, ameliorating, arresting or partially arresting a symptom of a disease or disorder, or the quantity and/or concentration desired by an individual for intake, such as daily intake, and/or nutritional supplementation, for example, an amount sufficient to enhance the nutritional, pharmaceutical, nutraceutical, health or energy property of a food, beverage, or other consumable. In some examples, the concentrate is added to the aqueous medium such that the resulting liquid dilution composition contains an effective amount of a particular non-polar compound, for example, a particular amount per volume or weight of the composition, such as, for example, at least 25 mg or about 25 mg, at least 35 mg or about 35 mg, at least 50 mg or about 50 mg, at least 100 mg or about 100 mg, at least 250 mg or about 250 mg, or at least 500 mg or about 500 mg of the non-polar active ingredient per serving, for example, at or about 1 teaspoon (0.166667 ounce, 4.7249 g), 1 tablespoon (0.5 fluid ounce, 14.1747 g), 2 tablespoons (1 fluid ounce, 28.3495 g), 0.25 cup (2 fluid ounces, 56.6990 g), 0.5 cup (4 fluid ounces, 113.398 g), 0.75 cup (6 fluid ounces, 170.097 g) or 1 cup (8 fluid ounces, 226.796 g), of the food or beverage dilution composition. The food or beverage can be, for example, a water-based finished food or beverage, such as, for example, tomato-paste based products, dairy-based products, sauces, dressings, creams, salsa, queso cheese, syrups, soups, juices, including fruit juice, energy drinks, sports drinks, nutritional beverages, vitamin-fortified beverages, milk, tea, soda, flavored water and water.

In one example, an effective amount is a concentration or amount of the liquid nanoemulsion where at least 25 mg or about 25 mg, typically at least 35 mg, for example, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 325, 350, 375, 400, 425, 450, 475, 500, 550, 600, 700, 800, 900, 1000, 1500, 2000 mg, or more, of the non-polar active ingredient, is contained in at least a serving of the food or beverage.

Also provided herein are food or beverage dilution compositions containing at least 25 mg or about 25 mg, at least 35 mg or about 35 mg, at least 50 mg or about 50 mg, at least 100 mg or about 100 mg, at least 250 mg or about 250 mg, or at least 500 mg or about 500 mg or at least 25 mg, 35 mg, 50 mg, 100 mg to 250 mg or 500 mg, of the non-polar active ingredient per serving of the food or beverage.

Also provided herein, are powders formulated from the liquid emulsion concentrates that provide at least 25 mg or about 25 mg, at least 35 mg or about 35 mg, at least 50 mg or about 50 mg, at least 100 mg or about 100 mg, at least 250 mg or about 250 mg, or at least 500 mg or about 500 mg or at least 25 mg, 35 mg, 50 mg, 100 mg to 250 mg or 500 mg, of the non-polar active ingredient when dissolved in a serving of a food or beverage. The powders can be prepared from the liquid emulsion concentrates by any method, for example, by spray drying or freeze drying the liquid emulsion concentrates provided herein.

Related nanoemulsion concentrates and preparations thereof are described, for example, in co-pending U.S. application Ser. No. 12/383,244, published as US-2009-0297665, U.S. patent application Ser. No. 12/383,241, published as US-2009-0297491, U.S. patent application Ser. No. 12/456,926, published as US-2009-0317532 and U.S. patent application Ser. No. 13/065,510, the subject matter of each of the above-referenced applications is incorporated herewith by reference in its entirety.

DETAILED DESCRIPTION

Outline
A. DEFINITIONS
B. COMPOSITIONS CONTAINING NON-POLAR COMPOUNDS
  1. Liquid emulsion concentrates containing the non-polar compounds
    a. Formulating the liquid concentrates
      i. Ingredients and typical concentration ranges
      i. Evaluation of the initial concentrate
        1. Stability
        2. Clarity
        3. Empirical evaluation
        4. Oxidative Stability
        5. Particle size
        6. Turbidity measurement
      ii. Selecting a formulation and modifying formulations
    b. Emulsion stabilizers (co-emulsifier)
    c. Non-Polar Compounds
      i. Polyunsaturated Fatty Acid (PUFA)-containing active ingredients
        1. Omega-3 fatty acid compounds
          a. DHA/EPA
          i. Fish Oils
          ii. Algae oil
          b. Flax Seed Oil—omega 3 (ALA)
        2. Omega-6 compounds
          a. Borage oil (Gamma-Linolenic Acid (GLA))
        3. Saw Palmetto extract
        4. Conjugated Linoleic Acid (CLA)
      ii. Coenzyme Q Active Ingredients
        1. Coenzyme Q10
      iii. Phytochemical-Containing Active Ingredients
        1. Phytosterols
        2. Resveratrol
      iv. Carotenoid-Containing Active Ingredients
        1. Carotenes
        2. Xanthophylls
      v. Micronutrient-Containing Active Ingredients
        1. Vitamins
        2. Alpha Lipoic Acid (Thioctic Acid)
    d. Surfactants
      i. Sucrose Fatty Acid Ester surfactants
        1. Production of Sucrose Esters
      ii. Vitamin E derived surfactants
        1. PEG-Derivatives of Vitamin E
          a. Tocopherols and Tocotrienols
          b. PEG moieties
          c. Linkers d. Tocopherol polyethylene glycol and Tocotrienol polyethylene glycol diesters (dicarboxylic acid esters of Vitamin E linked to PEG)
    e. Other Vitamin E PEG Esters
      f. TPGS Surfactants
   iii. PEG-derived surfactants
   iv. Concentration of the surfactant
   v. HLB
  e. Polar solvents
  f. Soluble Fiber
  g. Co-surfactants (emulsifiers)
    i. Phospholipids
  h. Preservatives and Sterilizers
  i. Non-polar solvents
  j. Flavors
  k. pH adjusters
  l. Antifoaming agents
 2. Powder forms of the compositions
 3. Compositions containing the liquid emulsion concentrates
  a. Stability
    i. Stability determined by empirical evaluation
    ii. Oxidative stability
  b. Clarity
    i. Clarity determined by empirical evaluation
    ii. Clarity determined by particle size or number of particles
    iii. Turbidity
  c. Desirable characteristics for human consumption
  d. Safety
  e. Oral bioavailability
C. METHODS FOR MAKING LIQUID EMULSION CONCENTRATES CONTAINING NON-POLAR COMPOUNDS
 1. Equipment for making the concentrates
  a. Scales
  b. Purifiers, including filters
  c. Vessels for mixing the ingredients
  d. Mixers
  e. Heating apparatuses
  f. Cooling apparatuses
  g. Transfer means
  h. Evaluation equipment
 2. General methods for making the liquid emulsion concentrates
  a. Generating the water phase
    i. Water phase ingredients
  b. Generating the oil phase
    i. Oil phase ingredients
  c. Combining and emulsifying the oil phase and the water phase
    i. Combining the oil and water phases
    ii. Emulsifying the oil and water phases
    iii. Cooling
  d. Additional steps
    i. Additional ingredients
    ii. Evaluation of the concentrate
    iii. Filtering the concentrate
 3. Bench-top process
 4. Scaled-up manufacturing processes
  a. Water purification
  b. Generation of the water phase and oil phase
  c. Combining and emulsifying the phases
  d. Cooling
  e. Additional steps D. METHODS FOR MAKING FOOD AND BEVERAGE DILUTION COMPOSITIONS CONTAINING THE CONCENTRATES
 1. Dilutions
 2. Analyzing the dilution compositions containing the liquid emulsion concentrates
  a. Stability
    i. Stability determined by empirical evaluation
    ii. Oxidative stability
  b. Clarity/turbidity
    i. Empirical evaluation
    ii. Particle size
    iii. Turbidity measurement
E. EXAMPLES

A. DEFINITIONS

Unless defined otherwise, all technical and scientific terms used herein have the same meaning as is commonly understood by one of skill in the art to which the invention(s) belong. All patents, patent applications, published applications and publications, GENBANK sequences, websites and other published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information.

As used herein, colloid refers to a mixture containing two phases, a dispersed phase and a continuous phase, the dispersed phase containing particles (droplets) distributed throughout the continuous phase. Colloidal mixtures include aerosols, foams and dispersions, for example, emulsions. A liquid colloid, for example, an emulsion, can have a similar appearance, for example, clarity, to a solution, in which there is no dispersed phase.

As used herein, emulsion refers to a colloidal dispersion of two immiscible liquids, for example, an oil and water (or other aqueous liquid, e.g., a polar solvent), one of which is part of a continuous phase and the other of which is part of a dispersed phase. The provided compositions include emulsions, typically oil-in-water emulsions (which include any oil soluble phase dispersed in any aqueous phase, also called the water phase), in which the oil phase is the dispersed phase and the water phase is the continuous phase. Emulsions typically are stabilized by one or more surfactants and/or co-surfactants and/or emulsion stabilizers. Surfactants form an interfacial film between the oil and water phase of the emulsion, providing stability. Typically, the emulsions of the provided compositions contain micelles, containing one or more surfactants surrounding a non-polar active ingredient, which are dispersed in the water phase. Exemplary of the provided emulsions are the provided liquid emulsion concentrates and compositions made by diluting the concentrates.

As used herein, a nanoemulsion is an emulsion in which the dispersed droplets, for example, the micelles, have a diameter (particle size) less than 1000 nm or less than about 1000 nm, typically, less than 500 nm or less than about 500 nm, typically less than 300 nm or about 300 nm, for example, less than 250 nm or about 250 nm, for example, less than 200 nm or less than about 200 nm, for example, less than or less than about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm.

As used herein, "micelle" refers to aggregates formed by surfactants that typically form when the surfactant is present in an aqueous composition, typically when the surfactant is used at a concentration above the critical micelle concentration (CMC). In micelles, the hydrophilic portions of the surfactant molecules contact the aqueous or the water phase, while the hydrophobic portions form the core of the micelle, which can encapsulate non-polar ingredient(s), for example, the non-polar compounds in the provided compositions. Typically, the surfactants and/or co-surfactants in the provided compositions aggregate in the emulsions and the aqueous liquids to form micelles, which contain the non-polar compound(s). The hydrophilic portion(s) of the surfactant molecules are oriented toward the outside of the micelle, in contact with the aqueous medium, while the hydrophobic portion(s) of the surfactant molecules are oriented toward the center of the micelle, in contact with the non-polar compound(s), which is contained in the center of the micelle. The micelles can contain more than one surfactant. Typically, the micelles in the provided compositions have a particle size of about 1000 nm, typically, less than 500 nm or less than about 500 nm, typically less than 300 or about 300 nm, for example, less than 250 nm or about 250 nm, for example, less than 200 nm or less than about 200 nm, for example, less than or less than about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm.

As used herein, "inverse micelles" are surfactant aggregates that typically form in lipophilic solutions, with the hydrophilic portions forming the core. When the cross sectional area of the hydrophobic region of the surfactant molecule is greater than that of the hydrophilic part of the molecule, the formation of micelles, which can be hexagonal phase structures, is favored.

As used herein, "liposomes" are surfactant aggregates composed of lipid bilayers, typically having an aqueous core. Liposomes typically are formed by lipid surfactants, typically, phospholipids, which are amphipathic, phosphate-containing lipids, for example, molecules containing one phosphate, a glycerol and one or more fatty acids, and similar surfactants. Alternatively, phospholipid surfactants can be used as co-surfactants, which can be incorporated into aggregates of other surfactant(s), for example, micelles. Lipid bilayers are two dimensional sheets in which all of the hydrophobic portions, e.g., acyl side chains, are shielded from interaction with aqueous liquid, except those at the ends of the sheet. An energetically unfavorable interaction of the acyl chains with water results in the folding of the bilayers to form liposomes, three-dimensional lipid bilayer vesicles. In one example, the liposome is formed as a single bilayer enclosing a single aqueous space (small unilamellar vesicles; SUVS). In another example, the liposome is composed of concentric bilayers with many aqueous spaces alternating with the bilayers (multilamellar vesicles; MLVS). Liposomes can be used to encapsulate hydrophobic and hydrophilic active ingredients. In liposomes, non-polar active ingredients typically are partitioned within the bilayers whereas hydrophilic active ingredients typically are trapped within the aqueous compartments. In one example, liposomes can be advantageous as a carrier/encapsulation system because they are stable and can protect the active ingredients from degradation, e.g., by oxygen and digestive enzymes.

As used herein, "surfactant" and "surface active agent" refer synonymously to synthetic and naturally occurring amphiphilic molecules that have hydrophobic portion(s) and hydrophilic portion(s). Due to their amphiphilic (amphipathic) nature, surfactants and co-surfactants typically can reduce the surface tension between two immiscible liquids, for example, the oil and water phases in an emulsion, stabilizing the emulsion. Any known surfactant or co-surfactant can be used with the provided compositions (see, e.g., U.S. Pat. No. 6,267,985). The surfactant(s) contained in the provided compositions typically have an HLB value between 12 and 20, inclusive, such as 12 or about 12 and 18, 19 or 20 or about 18, 19 or 20, 13 or about 13 and 20 or about 20, for example, 13 or about 13, 14 or about 14, 15 or about 15, 16 or about 16, 17 or about 17, 18 or about 18, 19 or about 19, and 20 or about 20, and typically between at or about 13 and at or about 18, more typically between at or about 15 and at or about 18. Exemplary of the surfactants include, but are not limited to, non-ionic surfactants, such as sugar ester surfactants and polyethylene glycol (PEG)-derived surfactants, such as sucrose fatty acid ester (SFAE) surfactants, PEG-derivatives of Vitamin E, and (PEG)-sorbitan fatty acid esters, which typically include sucrose fatty acid monoesters, such as sucrose monolaurate, sucrose monopalmitate, sucrose monostearate, and sucrose monooleate, tocotrienol or tocopherol PEG diesters, such as TPGS (e.g., TPGS 1000) and TPGS analogs, and PEG-sorbitan monooleates, such as Polyoxyethylene (20) sorbitan monooleate (also called polysorbate 80), as well as polysorbate 80 analogs, such as polysorbate 80 homologs and polysorbate 80 derivatives. Typically, the surfactant is a natural surfactant, for example, a surfactant that is G.R.A.S. (generally recognized as safe) by the FDA and/or Kosher certified.

As used herein, "hydrophilic-lipophilic balance," "hydrophile-lipophile balance" or "HLB" refer synonymously to a value that is used to index and describe a surfactant according to its relative hydrophobicity/hydrophilicity, relative to other surfactants. A surfactant's HLB value is an indication of the molecular balance of the hydrophobic and lipophilic portions of the surfactant, which is an amphipathic molecule. Each surfactant and mixture of surfactants (and/or co-surfactants) has an HLB value that is a numerical representation of the relative weight percent of hydrophobic and hydrophilic portions of the surfactant molecule(s). HLB values are derived from a semi-empirical formula. The relative weight percentages of the hydrophobic and hydrophilic groups are indicative of surfactant properties, including the molecular structure, for example, the types of aggregates the surfactant will form and the solubility of the surfactant. See, for example, Griffin, W. C. J. Soc. Cos. Chem. 1:311 (1949). HLB values have been determined and are available for a plurality of surfactants (e.g., see U.S. Pat. No. 6,267,985) and can be determined using routine methods. It should be appreciated that HLB values for a surfactant or co-surfactant can vary, depending upon the empirical method used to determine the value. HLB values also are influenced by factors such as temperature and pH, such that accepted values vary as much as ±10% (see, e.g., Nonionic Surfactants: Physical Chemistry, Surfactant Science Series, Volume 23, Martin J. Schick, ed., 1987). Thus, HLB values of surfactants and co-surfactants provide a rough guide for formulating compositions based on relative hydrophobicity/hydrophilicity.

Surfactant HLB values range from 1-45, while the range for non-ionic surfactants typically is from 1-20 and the general range of interest herein is 12-20 or about 12- about 20, inclusive. The more lipophilic a surfactant is, the lower its HLB value. Conversely, the more hydrophilic a surfactant is, the higher its HLB value. In general, surfactants with HLB values greater than 10 or greater than about 10 are more soluble in aqueous compositions, for example, water, and are called "hydrophilic surfactants," while surfactants having HLB values less than 10 or less than about 10 are more soluble in fats, oils and waxes, and are referred to as "hydrophobic surfactants" or "lipophilic surfactants." Relatively amphiphilic surfactants are soluble in oil and water based liquids and typically have HLB values close to 10 or about 10. A surfactant typically is selected from among surfactants having HLB values within a particular range of the surfactant or co-surfactant that can be used to guide formulations. Table 1A lists HLB values of exemplary surfactants and co-surfactants. Table 1B (see section B(1)(c) for exemplary sucrose fatty acid ester surfactants and their HLB values).

TABLE 1A reported HLB Values of Exemplary Surfactants and Co-Surfactants

| Surfactant/co-surfactant | HLB |
|---|---|
| PEG-2 Hydrogenated Castor Oil | 1.7 |
| Sorbitan Trioleate | 1.8 |
| Sorbitan Tristearate | 2.1 |
| Glyceryl Stearate | 3.5 |
| Sorbitan Sesquioleate | 3.7 |
| Labrafil | 4 |
| Sorbitan Oleate | 4.3 |
| Sorbitan monostearate | 4.7 |
| PEG-2 oleyl ether | 4.9 |
| PEG-2 stearyl ether | 4.9 |
| PEG-7 Hydrogenated Castor Oil | 5 |
| PEG-2 cetyl ether | 5.3 |
| PEG-4 Sorbitan Stearate | 5.5 |
| PEG-2 Sorbitan Isostearate | 6 |
| Sorbitan Palmitate | 6.7 |
| Triton SP-135 | 8 |
| Sorbitan monolaurate | 8.6 |
| PEG-40 Sorbitan Peroleate | 9.5 |
| PEG-4 lauryl ether | 9.7 |
| Polysorbate 81 | 10 |
| PEG-40 Sorbitan Hexaoleate | 10 |
| PEG-40 Sorbitan Perisostearate | 10 |
| PEG-10 Olive Glycerides | 10 |
| PEG sorbitol hexaoleate | 10.2 |
| Polysorbate 65 | 10.5 |
| PEG-25 Hydrogenated Castor Oil | 10.8 |
| Polysorbate 85 | 11 |
| PEG-7 Glyceryl Cocoate | 11 |
| PEG-8 Stearate | 11.1 |
| PEG sorbitan tetraoleate | 11.4 |
| PEG-15 Glyceryl Isostearate | 12 |
| PEG-35 Almond Glycerides | 12 |
| Tocopherol polyethylene glycol succinate (TPGS) | 12-18 |
| PEG-10 oleyl ether | 12.4 |
| PEG-8 isooctylphenyl ether | 12.4 |
| PEG-10 stearyl ether | 12.4 |
| PEG-35 Castor Oil | 12.5 |
| PEG-10 cetyl ether | 12.9 |
| Nonoxynol-9 | 12.9 |
| PEG-40 Castor Oil | 13 |
| PEG-10 isooctylphenyl ether | 13.5 |
| PEG-40 Hydrogenated Castor Oil | 14 |
| Labrasol | 14 |
| Nonoxynol-15 | 14.2 |
| PEG-12 tridecyl ether | 14.5 |
| PEG-18 tridecyl ether | 14.5 |
| Polysorbate 60 | 14.9 |
| Polysorbate 80 | 15 |
| PEG-20 Glyceryl Stearate | 15 |
| PEG-20 Stearate | 15 |
| PEG-20 stearyl ether | 15.3 |
| PEG-20 oleyl ether | 15.3 |
| Polysorbate 40 | 15.6 |

TABLE 1A-continued reported HLB Values of Exemplary Surfactants and Co-Surfactants

| Surfactant/co-surfactant | HLB |
|---|---|
| PEG20 cetyl ether | 15.7 |
| PEG(20) hexadecyl ether | 15.7 |
| PEG-60 Hydrogenated Castor Oil | 16 |
| PEG-30 Stearate | 16.5 |
| Polysorbate 20 | 16.7 |
| PEG-75 Lanolin | 16.7 |
| PEG23 lauryl ether | 16.9 |
| PEG-40 Stearate | 17.3 |
| PEG-50 Stearate | 17.7 |
| PEG40 isooctylphenyl ether | 17.9 |
| PEG-100 Stearate | 18.8 |
| Pluronic F68 | 29 |
| Phosphatidylcholine | 7.6 |

As used herein, a "sucrose fatty acid ester" is a compound having the formula shown in Scheme I, below.

Scheme I

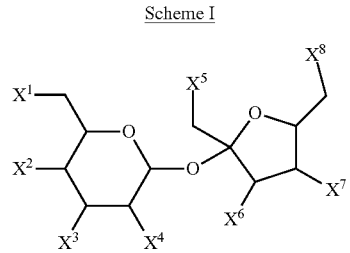

where each of $X^1$, $X^2$, $X^3$, $X^4$, $X^5$, $X^6$, $X^7$ and $X^8$ independently is:

an hydroxyl (—OH) group, or

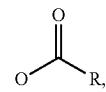

where:

each R is an alkyl group having 3-27 carbon atoms; and when more than one of $X^1$, $X^2$, $X^3$, $X^4$, $X^5$, $X^6$, $X^7$ and $X^8$ is

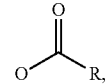

each R can be a different alkyl group (e.g., having different number of carbon atoms and/or different saturation), or can be the same alkyl group.

A sucrose fatty acid monoester has the structure set forth in Scheme I, where one of $X^1$, $X^2$, $X^3$, $X^4$, $X^5$, $X^6$, $X^7$ and $X^8$ (typically $X^1$) is:

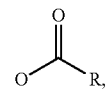

and the other seven of $X^1$, $X^2$, $X^3$, $X^4$, $X^5$, $X^6$, $X^7$ and $X^8$ are each, independently, —OH. Sucrose fatty acid diesters, sucrose fatty acid triesters, and sucrose fatty acid polyesters, respectively, are sucrose fatty acid esters having structures according to Scheme I, above, where two (diesters), three (triesters) or more (polyesters) of $X^1$, $X^2$, $X^3$, $X^4$, $X^5$, $X^6$, $X^7$ and $X^8$, (and typically $X^1$ and $X^8$) independently, are

The sucrose fatty acid ester surfactants include mixtures, or blends, of sucrose fatty acid esters, which typically include monoesters, and can also include diesters, triesters and polyesters. Typically, the sucrose fatty acid ester surfactants contain sucrose fatty acid monoesters. The sucrose fatty acid ester surfactants include single fatty acid esters and also include homogeneous mixtures of sucrose esters, containing two or more sucrose fatty acid esters with different lengths of fatty acid carbon chains and/or members with different degrees of esterification. The sucrose fatty acid ester mixtures can include one or more sucrose fatty acid esters, such as, but not limited to, sucrose stearate, sucrose laurate, sucrose palmitate, sucrose oleate, sucrose caprylate, sucrose decanoate, sucrose myristate, sucrose pelargonate, sucrose undecanoate, sucrose tridecanoate, sucrose pentadecanoate and sucrose heptadecanoate, and homologs thereof.

An exemplary sucrose fatty acid monoester has the following structure:

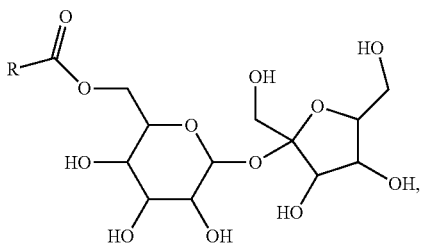

where R is an alkyl group having 3-27 carbons.

As used herein, a "PEG derivative of Vitamin E" is a compound containing one or more Vitamin E moieties (e.g., a tocopherol or tocotrienol) joined, for example by an ester, ether, amide or thioester bond, with one or more polyethylene glycol (PEG) moieties, via a linker, for example, a dicarboxylic or tricarboxylic acid. Exemplary of PEG derivatives of Vitamin E are tocopherol polyethylene glycol succinate (TPGS), TPGS analogs, TPGS homologs and TPGS derivatives.

As used herein, a "tocopherol polyethylene glycol diester" and "TPGD" refer to a PEG-derivative of tocopherol where the linker is a dicarboxylic acid (a carboxylic acid having two carboxy groups, e.g., succinic acid), such as succinic acid. Exemplary of dicarboxylic acids that can be used as linkers in these tocopherol and tocotrienol PEG diester surfactants are succinic acid, sebacic acid, dodecanedioic acid, suberic acid, or azelaic acid, citraconic acid, methylcitraconic acid, itaconic acid, maleic acid, glutaric acid, glutaconic acid, fumaric acids and phthalic acids. Exemplary of TPGDs are tocopherol succinate polyethylene glycol (TPGS), tocopherol sebacate polyethylene glycol, tocopherol dodecanodioate polyethylene glycol, tocopherol suberate polyethylene glycol, tocopherol azelaate polyethylene glycol, tocopherol citraconate polyethylene glycol, tocopherol methylcitraconate polyethylene glycol, tocopherol itaconate polyethylene glycol, tocopherol maleate polyethylene glycol, tocopherol glutarate polyethylene glycol, tocopherol glutaconate polyethylene glycol, and tocopherol phthalate polyethylene glycol, among others.

As used herein, "tocopherol polyethylene glycol succinate", "TPGS", "tocopheryl polyethylene glycol succinate surfactant" and "TPGS surfactant" refer to tocopherol polyethylene glycol (PEG) diesters, that are formed by joining, via esterification, tocopherol succinate, which itself is an ester made by esterification of tocopherol and succinic acid. The term tocopherol refers to any naturally occurring or synthetic form of vitamin E, and can refer to a single compound or a mixture. Examples of tocopherols include, for example, α-tocopherol, D-α-tocopherol, β-tocopherol, γ-tocopherol and δ-tocopherol. The PEG moiety of the TPGS surfactant can be any PEG moiety, for example, PEG moieties between 200 kDa or about 200 kDa and 20,000 kDa or about 20,000 kDa, typically between 200 kDa or about 200 kDa and 6000 kDa or about 6000 kDa, for example, between 600 kDa or about 600 kDa and 6000 kDa or about 6000 kDa, typically between 200 kDa or about 200 kDa and 2000 kDa or about 2000 kDa, between 600 kDa or about 600 kDa and 1500 kDa or about 1500 kDa, or between 600 kDa or about 600 kDa and 1000 kDa or about 1000 kDa, for example, 200 kDa or about 200 kDa, 300 kDa or about 300 kDa, 400 kDa or about 400 kDa, 500 kDa or about 500 kDa, 600 kDa or about 600 kDa, 800 kDa or about 800 kDa, and 1000 kDa or about 1000 kDa; and PEG moieties that are modified, for example, methylated PEG (m-PEG) and/or PEG moieties including other PEG analogs, e.g., PEG-NHS, PEG-aldehyde, PEG-SH, PEG-NH$_2$, PEG-CO$_2$H, and branched PEGs. Typically, the TPGS surfactant is GRAS (Generally Recognized As Safe) and Kosher certified.

Exemplary of the TPGS surfactants is TPGS-1000, which has a PEG moiety of 1000 kDa. The TPGS can be any natural, water-soluble, tocopherol polyethylene glycol succinate, for example, the food grade TPGS sold under the name Eastman Vitamin E TPGS®, food grade, by Eastman Chemical Company, Kingsport, Tenn. This TPGS is water-soluble form of natural-source vitamin E, which is prepared by esterifying the carboxyl group of crystalline d-alpha-tocopheryl acid succinate with polyethylene glycol 1000 (PEG 1000), and contains between 260 and 300 mg/g total tocopherol. TPGS typically has a reported HLB value of between 12 or 13 or about 12 or 13 and 18 or about 18.

As used herein, "tocopherol polyethylene glycol succinate analog", "TPGS analog", and "TPGS analog surfactant" refer to compounds, other than TPGS, that are similar to a parent TPGS compound, but differ slightly in composition, for example, by the variation, addition or removal of an atom, one or more units (e.g., methylene unit(s)—$(CH_2)_n$) or one or more functional groups. TPGS analogs include Vitamin E derived surfactants, including PEG derivatives of Vitamin E, including vitamin E PEG diesters, such as, but not limited to, tocopherol polyethylene glycol sebacate (PTS), tocopherol polyethylene glycol dodecanodioate (PTD), tocopherol polyethylene glycol suberate (PTSr), tocopherol polyethylene glycol azelaate (PTAz), and polyoxyethanyl tocotrienyl sebacate (PTrienS) as well as other PEG derivatives of Vitamin E.

Exemplary of TPGS analogs are compounds, other than TPGS compounds, having the formula shown in Scheme II:

Scheme II

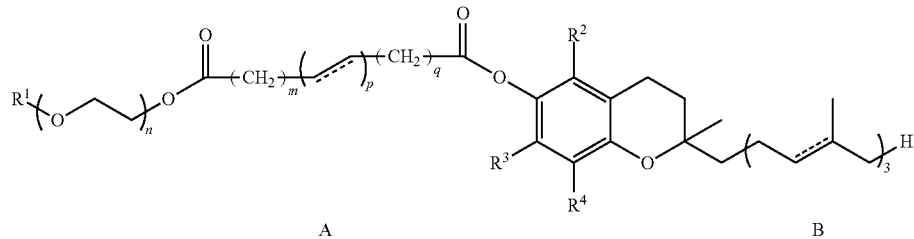

where $R^1$, $R^2$, $R^3$ and $R^4$ each independently is hydrogen (H) or methyl ($CH_3$); each dashed line is, independently, a single or double bond; n is an integer from 1 to 5000; m and q each independently are 0 or 1; and p is an integer from 1 to 20. For example, TPGS analogs include, but are not limited to, compounds having the formula in Scheme II, where, when the bonds represented by the dashed lines marked by "A" and "B" are single bonds, and m and q each equal 0, p is any integer from 2-20. TPGS analogs also include compounds where the dashed line at B or the dashed line at A, or both the dashed lines, represents at least one double bond. For example, TPGS analogs include a compound as in Scheme II, where when the dashed line in A represents only single bonds, the dashed line in "B" represents one or more double bond, e.g., tocotrienol PEG diesters. TPGS analogs also include compounds as in Scheme II, where when the dashed line marked "B" represents only single bonds, the dashed line marked "A" represents one or more double bonds; or when the dashed line labeled "A" does not represent double bonds, and m and q are each zero, p is greater than 1.

Also exemplary of TPGS analogs are compounds, other than TPGS compounds, having the formula shown in Scheme III:

Scheme III

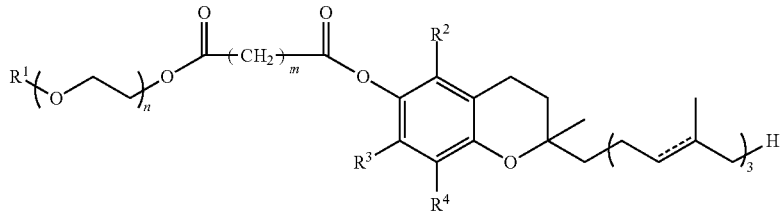

where $R^1$, $R^2$, $R^3$ and $R^4$ each independently is hydrogen (H) or methyl ($CH_3$); the bond represented by the dashed line is either a single or double bond; m is an integer from 1 to 20, and n is an integer from 1 to 5000.

Also exemplary of TPGS analogs include compounds other than TPGS, having PEG moieties that vary in chain length, according to the formula shown in Scheme IV:

Scheme IV

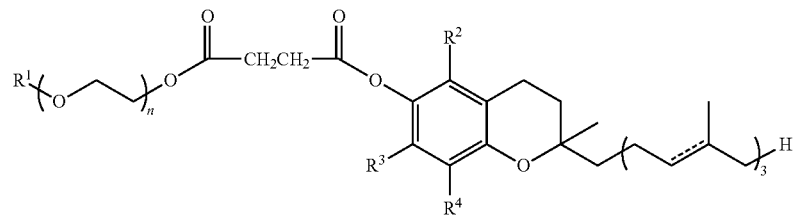

where $R^1$, $R^2$, $R^3$ and $R^4$ each independently is hydrogen (H) or methyl ($CH_3$), and n is an integer from 1 to 5000.

As used herein, "TPGS-1000 analogs" are compounds other than TPGS-1000 that are similar to a parent TPGS-1000 compound, but differ slightly in composition, for example, by the variation, addition or removal of an atom, one or more units (e.g., methylene unit(s)—$(CH_2)_n$) or one or more functional groups. Suitable TPGS-1000 analogs include, but are not limited to, other TPGS compounds, having PEG moiety(ies) that vary in chain length and molecular weight compared to TPGS-1000, including, for example, TPGS compounds having PEG moieties between 200 or about 200 kDa and 20,000 kDa or about 20,000 kDa, typically between 200 kDa or about 200 kDa and 6000 kDa or about 6000 kDa, for example, between 600 kDa or about 600 kDa and 6000 kDa or about 6000 kDa, typically between 200 kDa or about 200 kDa and 2,000 kDa or about 2,000 kDa, between 600 kDa or about 600 kDa and 1500 kDa or about 1500 kDa, such as, but not limited to, 200, 300, 400, 500, 600, 800, and 1000 kDa. Also exemplary of TPGS-1000 analogs are TPGS compounds having PEG moieties that are modified, for example, methylated PEG (m-PEG) and/or PEG moieties including other PEG analogs, e.g., PEG-NHS, PEG-aldehyde, PEG-SH, PEG-$NH_2$, PEG-$CO_2H$, and branched PEGs. Also exemplary of TPGS-1000 analogs are any TPGS analogs, e.g., Vitamin E derived surfactants, including PEG derivatives of Vitamin E, including vitamin E PEG diesters, such as, but not limited to, tocopherol polyethylene glycol sebacate (PTS), tocopherol polyethylene glycol dodecanodioate (PTD), tocopherol polyethylene glycol suberate (PTSr), tocopherol polyethylene glycol azelaate (PTAz) and polyoxyethanyl tocotrienyl sebacate (PTrienS) as well as other PEG derivatives of Vitamin E.

As used herein, "TPGS homologs" are analogs of TPGS that differ from a TPGS parent compound only by the presence or absence of a simple unit, such as a methylene unit, or some multiple of such units, e.g., $—(CH_2)_n—$. Typically, suitable TPGS homologs have similar surfactant properties compared to the parent compound (TPGS), for example, similar HLB values, for example, HLB values between 12 or 13 or about 12 or about 13 and 20 or about 20. Exemplary of TPGS homologs are tocopherol polyethylene glycol sebacate (PTS), tocopherol polyethylene glycol dodecanodioate (PTD), tocopherol polyethylene glycol suberate (PTSr), tocopherol polyethylene glycol azelaate (PTAz). Exemplary of TPGS homologs are compounds having the formula in Scheme II (above), where neither the A or B dashed line represents a double bond and where, when m and q each are 0, p is greater than 1.

As used herein, "TPGS-1000 homologs" are analogs of TPGS-1000 that differ from a TPGS-1000 parent compound only by the presence or absence of a simple unit, such as a methylene unit, or some multiple of such units, e.g., $—(CH_2)_n—$. Exemplary TPGS-1000 homologs have similar surfactant properties compared to the parent compound (TPGS-1000), for example, similar HLB values, for example, HLB values between 12, 13, or 14 or about 12, 13 or 14 and 18, 19 or 20 or about, 18, 19 or 20. Exemplary TPGS-1000 homologs include TPGS-1000 homologs with slight variations in the length of the PEG chain moiety, and me-TPGS-1000, which is a TPGS-1000 having a methyl cap on the PEG moiety.

As used herein, a "polyethylene glycol (PEG)-Sorbitan fatty acid ester" or "polysorbate" refer to esters derived from PEGylated sorbitan (derivative of sorbitol) esterified with one or more fatty acids. Polysorbates include, but are not limited to, PEG-sorbitan monooleates, such as Polyoxyethylene (20) sorbitan monooleate (also called polysorbate 80), as well as polysorbate 80 analogs, such as polysorbate 80 homologs and polysorbate 80 derivatives. Exemplary polysorbate 80 analog surfactants are polysorbate 40 (polyoxyethylene (20) sorbitan monopalmitate) and polysorbate 60 (polyoxyethylene (20) sorbitan monostearate). In one aspect, the surfactant is a polysorbate 80 homolog, such as, for example, a polysorbate 80 homolog that differs from a polysorbate 80 parent compound by the addition or removal of one or more methylene unit(s), e.g., $—(CH_2)_n—$.

As used herein, analog refers to a chemical compound that is structurally similar to another compound (referred to as a parent compound), but differs slightly in composition, for example, by the variation, addition or removal of an atom, one or more units (e.g., methylene unit(s), $—(CH_2)_n—$) or one or more functional groups. The analog can have different chemical or physical properties compared with the original compound and/or can have improved biological and/or chemical activity. Alternatively, the analog can have similar or identical chemical or physical properties compared with the original compound and/or can have similar or identical biological and/or chemical activity. For example, the analog can be more hydrophilic or it can have altered reactivity as compared to the parent compound. The analog can mimic the chemical and/or biologically activity of the parent compound (i.e., it can have similar or identical activity), or, in some cases, can have increased or decreased activity. The analog can be a naturally or non-naturally occurring (e.g., synthetic) variant of the original compound. Other types of analogs include isomers (e.g., enantiomers, diastereomers) and other types of chiral variants of a compound, as well as structural isomers. The analog can be a branched or cyclic variant of a linear compound. For example, a linear compound can have an analog that is branched or otherwise substituted to impart certain desirable properties (e.g., improve hydrophobicity or bioavailability). Exemplary of the analogs used in the provided compositions and methods are sucrose fatty acid ester analogs and TPGS analogs, which can be used as surfactants in place of the sucrose fatty acid ester parent compound surfactants or TPGS in the provided compositions.

As used herein, homolog refers to an analog that differs from the parent compound only by the presence or absence of a simple unit, such as a methylene unit, or some multiple of such units, e.g., $—(CH_2)_n—$. Typically, a homolog has similar chemical and physical properties as the parent compound. Exemplary of the homologs used in the provided compositions and methods are sucrose fatty acid ester homologs and TPGS homologs.

As used herein, $C_1-C_x$ includes $C_1-C_2$, $C_1-C_3$ ... $C_1-C_x$.

As used herein, the term "alkyl" and "alkyl group" refer to straight or branched chain substituted or unsubstituted hydrocarbon groups having any number of carbon atoms; number of carbon atoms can be specified, for example, 1 to 30 carbon atoms, 8 to 28 carbon atoms, 7 to 27 carbon atoms, 8 to 22 carbon atoms, 8 to 20 carbon atoms, 8 to 18 carbon atoms and 12 to 18 carbon atoms. An alkyl group can be a "saturated alkyl," meaning that it does not contain any alkene or alkyne groups or an "unsaturated alkyl," meaning that it contains at least one alkene or alkyne group, and optionally can be substituted. An alkyl group that includes at least one carbon-carbon double bond (C═C) also is referred to by the term "alkenyl;" alkenyl groups optionally can be substituted. An alkyl group that includes at least one carbon-carbon triple bond (C≡C) also is referred to by the term "alkynyl;" alkynyl groups optionally can be substituted.

As used herein, "hydrophilic" and "polar" refer synonymously to ingredients and/or compounds having greater solubility in aqueous liquids, for example, water, than in fats, oils and/or organic solvents (e.g., methanol, ethanol, ethyl ether, acetone and benzene). Exemplary of the polar ingredients in the provided compositions are polar solvents.

As used herein, a "solvent" is an ingredient that can be used to dissolve another ingredient. Solvents include polar and non-polar solvents.

As used herein, "polar solvent" refers to a solvent which is more readily miscible with water and polar ingredients. The polarity of a solvent can be assessed by measuring a number of different parameters according to well known methods as described herein (see, e.g., Prizbytek, "High Purity Solvent Guide," Burdick and Jackson Laboratories, Inc., 1980). Polar solvents generally have high dielectric constants, typically dielectric constants greater than at or about 15, such as at or about 15, 16, 17, 18, 19, 20, 21, 22, 23, 24, 25, 26, 27, 28, 29, 30, 31, 32, 33, 34, 35, 40, 45, 50, 55, 60, 65, 70, 75, 80 85, 90, or greater than 90, and generally have high polarity indices, typically greater than at or about 3, such as at or about 3, 4, 5, 6, 7, 8 or 9 or greater than 9. Polar solvents generally have large dipole moments, typically greater than at or about 1.4 Debye, such as at or about, 1.4, 1.5, 1.6, 1.7, 1.8, 1.9, 2.0, 2.1, 2.2, 2.3, 2.4, 2.5, 2.6, 3.0, 3.5, 4 or greater than 4 Debye. Polar solvents include polar protic solvents and polar aprotic solvents. Exemplary polar solvents include, but are not limited to, water, glycerin, and propylene glycol.

As used herein, a "polar protic solvent" is a polar Solvent containing a hydrogen atom attached to an electronegative atom, such that the hydrogen has a proton-like character and/or the bond between the hydrogen and electronegative atom is polarized. Exemplary polar protic solvents include, but are not limited to water, alcohols, including monohydric, dihydric and trihydric alcohols, including, but not limited to, methanol, ethanol, glycerin and propylene glycol. Dihydric alcohols are alcohols containing two hydroxyl groups. Exemplary dihydric alcohols include, but are not limited to, glycols, e.g., propylene glycol, ethylene glycol, tetraethylene glycol, triethylene glycol and trimethylene glycol. Trihydric alcohols are alcohols containing three hydroxyl groups. Exemplary trihydric alcohols include, but are not limited to glycerin, butane-1,2,3-triol, pentane-1,3,5-triol and 2-amino-2-hydroxymethyl-propane-1,3-diol. Monohydric alcohols are alcohols containing a single hydroxyl group, including but not limited to, methanol, ethanol, propanol, isopropanol, n-butanol and t-butanol.

As used herein, "emulsion stabilizer" refers to compounds that stabilize and/or emulsify and/or change the viscosity of the provided compositions, for example, the liquid emulsion concentrate and/or the aqueous compositions containing the concentrates. For example, the emulsion stabilizer prevents separation of the oil and water phases. Exemplary of emulsion stabilizers that can be used in the provided compositions are fatty acid-modified carbohydrate-based macromolecule emulsion stabilizers, such as fatty-acid modified gums and starches. Exemplary of such emulsion stabilizers are modified gum acacias, for example, the modified gum acacia sold under the name Tic Pretested® Ticamulsion® A-2010 Powder, by Tic Gums, Inc., Belcamp, Md.; ester gums, for example, the ester gum sold under the name Ester Gum 8BG by Pinova/Hercules, Brunswick, Ga. (its preparation is described in U.S. Pat. No. 6,455,512); and modified corn starches, for example, the modified corn starch sold under the name Farmal™ MS 6135, from Corn Products International Inc., Westchester, Ill., available from Cosmetic Specialties, Inc., Haddon Heights, N.J.

As used herein, "modified carbohydrate emulsion stabilizer," "fatty acid-modified carbohydrate emulsion stabilizer" and "fatty acid-modified carbohydrate-based macromolecule emulsion stabilizer" refer synonymously to emulsion stabilizers with balanced hydrophobic and hydrophilic properties, particularly gums and starches that are modified by reaction with fatty acids (see also, discussion below). These are employed as co-emulsifiers with the surfactants, such as sucrose fatty acid esters (SFAE), in the compositions herein.

The modified carbohydrate emulsion stabilizers, include, for example, gums and starches modified by reaction with any fatty acid chain containing from 6-30 carbons, such as an alkyl succinic anhydride, including n-octenyl succinic anhydride (OSAn), whereby the resulting modified gum or starch has hydrophobic (fatty acid chain) and hydrophilic (carbohydrate) properties and is an emulsion stabilizer.

As used herein, "hydrocolloid" refers to water-soluble gums, including starches, gums, celluloses, modified celluloses, carboxymethyl cellulose, dextrans, dextrins, inulin, glycogen, hemicellulose, gum arabic, agar, karaya gum, tragacanth gum, pectin, carrageenan, alginates, tamarind seed gum, xanthan gum, konjac gum, guar gum, gum acacia, and locust bean (or carob seed) gum. These water-soluble gums are reacted with an alkane- or alkene-substituted dicarboxylic acid anhydride to produce a fatty acid-modified carbohydrate-based emulsion stabilizer.

As used herein, "non-polar", "lipophilic" and "lipid-soluble" synonymously refer to compounds (e.g., non-polar compounds) and/or ingredients, for example, non-polar active ingredients, which have greater solubility in organic solvents (e.g., ethanol, methanol, ethyl ether, acetone, and benzene) and in fats and oils, than in aqueous liquids, for example, water.

As used herein, "non-polar compounds" include drugs, hormones, vitamins, nutrients and other lipophilic compounds that contain one or more non-polar active ingredients. Typically, the non-polar compounds used in the provided compositions are poorly water soluble, for example, water insoluble or compounds having low water solubility. Exemplary non-polar compounds contain non-polar active ingredients, for example, lipid-soluble drugs, hormones, essential fatty acids, for example, polyunsaturated fatty acids (PUFA), for example, omega-3, omega-6 and omega-9 fatty acids, vitamins, nutrients, nutraceuticals, minerals and other non-polar active ingredients. Additional exemplary non-polar compounds are described herein. The provided compositions can be formulated with any non-polar compound, for example, containing any non-polar active ingredient.

As used herein, a "non-polar active ingredient" refers to a non-polar ingredient within a non-polar compound, that, when administered to a subject, for example, a human, induces or is proposed to induce a desired response, such as altering body function at the cellular, tissue, organ or other level, and/or altering cosmetic appearance or other property, or a non-polar compound or ingredient that is ingested in order to achieve a desired effect. Non-polar active ingredients can be any synthetic or natural non-polar ingredient or compound, including a pharmaceutical, drug, therapeutic, nutritional supplement, herb, hormone or other ingredient. Non-polar active ingredients can include the non-polar active ingredients listed herein, as well as other pharmaceutically acceptable or food-grade active derivatives of the active ingredients, for example, salts, esters, amides, prodrugs, active metabolites, isomers, fragments and analogs. Active ingredients can include compounds proven to have a desired effect and also compounds thought to produce such effects, for example, compounds typically ingested for nutritional supplementation purposes.

As used herein, "fatty acid" refers to straight-chain hydrocarbon molecules with a carboxyl (COOH) group at one end of the chain.

As used herein, "polyunsaturated fatty acid" and "PUFA" are used synonymously to refer to fatty acids that contain more than one carbon-carbon double bond in the carbon chain of the fatty acid. PUFAs, particularly essential fatty acids, are useful as dietary supplements.

As used herein, "essential fatty acids" are PUFAs that mammals, including humans, cannot synthesize using any known chemical pathway. Thus, essential fatty acids must be obtained from diet or by supplementation. Exemplary of essential PUFA fatty acids are omega-3 ($\omega 3$; n-3) fatty acids and omega-6 ($\omega$-6; n-6) fatty acids.

As used herein, omega-3 ($\omega 3$; n-3) fatty acids are methylene interrupted polyenes, which have two or more cis double bonds, separated by a single methylene group and in which the first double bond appears at the third carbon from the last ($\omega$) carbon. Omega-3 fatty acids are used as dietary supplements, for example, for disease treatment and prevention. In one example, the provided compositions contain non-polar active ingredients that contain at least one omega-3 fatty acid. Exemplary of omega-3 fatty acids are Alpha-Linolenic acid ($\alpha$-Linolenic acid; ALA) (18:3$\omega$3) (a short-chain fatty acid); Stearidonic acid (18:4$\omega$3) (a short-chain fatty acid); Eicosapentaenoic acid (EPA) (20:5$\omega$3); Docosahexaenoic acid (DHA) (22:6$\omega$3); Eicosatetraenoic acid (24:4$\omega$3); Docosapentaenoic acid (DPA, Clupanodonic acid) (22:5$\omega$3); 16:3 $\omega$3; 24:5 $\omega$3 and nisinic acid (24:6$\omega$3). Longer chain omega-3 fatty acids can be synthesized from ALA (the short-chain omega-3 fatty acid). Exemplary of non-polar active ingredients containing omega-3 fatty acids are non-polar active ingredients containing DHA and/or EPA, for example, containing fish oil, krill oil and/or algae oil, for example, microalgae oil, and non-polar active ingredients containing alpha-linolenic acid (ALA), for example, containing flaxseed oil.

As used herein, omega-6 ($\omega$-6; n-6) fatty acids are methylene interrupted polyenes, which have two or more cis double bonds, separated by a single methylene group and in which the first double bond appears at the sixth carbon from the last ($\omega$) carbon. In one example, the provided compositions contain non-polar active ingredients that contain at least one omega-6 fatty acid. Exemplary of omega-6 fatty acids are Linoleic acid (18:2$\omega$6) (a short-chain fatty acid); Gamma-linolenic acid (GLA) (18:3$\omega$6); Dihomo gamma linolenic acid (DGLA) (20:3$\omega$6); Eicosadienoic acid (20:2$\omega$6); Arachidonic acid (AA) (20:4$\omega$6); Docosadienoic acid (22:2$\omega$6); Adrenic acid (22:4$\omega$6); and Docosapentaenoic acid (22:5$\omega$6). Exemplary of non-polar active ingredients containing omega-6 fatty acids are ingredients containing GLA, for example, borage oil. Also exemplary of PUFA-containing non-polar active ingredients are compounds containing conjugated fatty acids, for example, conjugated linoleic acid (CLA) and compounds containing saw palmetto extract.

As used herein, "algae oil" refers to any oil derived from marine dinoflagellates in, for example, microalgae, for example, *Crypthecodinium* sp., particularly, *Crypthecodinium cohnii*. In one example, algae oil is used as a non-polar compound, for example, as an active ingredient, in the provided compositions. The algae oil typically contains DHA. In one example, the algae oil also is a source of EPA.

As used herein, "fish oil" refers to any oil derived from any fish, typically a cold water fish, for example, from fish tissue, for example, from frozen fish tissue, for example, from cod liver. In one example, fish oil is used as a non-polar compound, for example, an active ingredient, in the provided compositions. The fish oil typically contains DHA. In one example, the fish oil also contains EPA.

As used herein, a "non-polar solvent" refers to oils and other non-polar ingredients that dissolve non-polar compounds. Typically, the non-polar solvent is an oil that is included in the composition in addition to the non-polar compound. For example, the non-polar solvent typically is not the non-polar compound itself, e.g., is distinct from the non-polar compound. Certain compounds, for example, flaxseed oil and safflower oil, can be non-polar solvents and non-polar compounds, or non-polar active ingredients. Typically, the non-polar solvent contains one or more oils, typically oils other than the non-polar active ingredient, or oil(s) not contained in the active ingredient. Exemplary non-polar solvents include, but are not limited to, oils (in addition to the non-polar active ingredient), for example, Vitamin E oil, oleic acid, flaxseed oil, CLA, Borage Oil, D-limonene, canola oil, corn oil, MCT oil and oat oil. Other oils also can be used. Exemplary of the Vitamin E oil is the oil sold by ADM Natural Health and Nutrition, Decatur, Ill., under the name Novatol™ 5-67 Vitamin E (D-alpha-Tocopherol; ADM product code 410217). This Vitamin E oil contains at least 67.2% Tocopherol and approximately 32.8% soybean oil. In one example, the non-polar solvent is referred to, synonymously as "non-polar solubilizer." In one example, the non-polar compound is dissolved in a non-polar solvent in practicing the methods of producing the provided compositions. In this example, the provided compositions contain non-polar solvents in amounts sufficient to dissolve the non-polar compound. More than one non-polar solvent can be used.

As used herein, "soluble fiber" refers to any soluble dietary fiber that can be readily fermented in the colon, typically a plant based dietary fiber, for example, a soluble fiber from legumes, vegetables, such as broccoli and carrots, root vegetables, such as potatoes, sweet potatoes and onions, oats, rye, chia, barley and fruits, such as prunes, plums, berries, bananas, apples and pears. Typically, soluble dietary fiber contains non-starch polysaccharides, such as arabinoxylans, cellulose, dextrans, inulin, beta-glucans, fructo-oligosaccharides, oligosaccharides and polysaccharides. For example, soluble fibers include but are not limited to fructo-oligosaccharides, for example, inulins, for example, inulins found in chicory, Jerusalem artichoke, dahlia, garlic, leeks and onions, fructans and water-soluble soybean fiber. Exemplary of a soluble fiber that can be used in the provided concentrates is an inulin, for example, Oliggo-Fiber Instant Inulin (Fibruline® Instant) (supplied by Cosucra-Groupe Warcoing SA, Belgium, sold by Gillco Products, San Marcos, Calif.), containing chicory inulin.

As used herein, "inulin" refers to a mixture of polysaccharides having various molecular weights or degrees of polymerization; in general, inulin contains fructose units with beta 1-2 bonds terminating in a glucose unit. The term "inulin" is used generically herein to refer to raw inulin and fractions of inulin.

As used herein, "preservative" and "preservativer" are used synonymously to refer to ingredients that can improve stability of the provided compositions. Preservatives, particularly food and beverage preservatives, are well known. Any known preservative can be used in the provided compositions. Exemplary of the preservatives that can be used in the provided compositions are oil soluble preservatives, for example, benzyl alcohol, Benzyl Benzoate, Methyl Paraben, Propyl Paraben, antioxidants, for example, Vitamin E, Vitamin A Palmitate and Beta Carotene. Typically, a preservative is selected that is safe for human consumption, for example, in foods and beverages, for example, a GRAS certified and/or Kosher-certified preservative, for example, benzyl alcohol.

As used herein, a "pH adjuster" is any compound, typically an acid or a base, that is capable of changing the pH of the provided compositions, for example, to reduce the pH of the composition or to increase the pH of the composition, typically without altering other properties of the composition, or without substantially altering other properties. pH adjusters are well known. Exemplary of the pH adjusters are acids, for example, citric acid and phosphoric acid, and bases.

As used herein, "flavor" is any ingredient that changes, typically improves, the taste and/or smell of the provided composition, for example, the aqueous liquid dilution compositions, for example, beverages.

As used herein, "co-surfactant" is used to refer to a surfactant, typically a phospholipid, that is used, in the provided compositions, in combination with a surfactant (e.g., a primary surfactant), for example, to improve the emulsification of the provided compositions and/or compounds, for example, to emulsify the ingredients. In one example, the provided compositions contain at least one surfactant and at least one co-surfactant. Typically, the co-surfactant is a lipid, for example, a phospholipid, for example, phosphatidylcholine. In one example, the co-surfactant has an HLB value of between 7 or about 7 and 8 or about 8. Typically, the co-surfactant represents a lower percent, by weight (w/w), of the provided compositions, compared to the surfactant. Thus, the provided compositions typically have a lower concentration of the co-surfactant(s) than of the surfactant.

As used herein, a "phospholipid" is an amphipathic, phosphate-containing lipid, for example, a molecule containing one phosphate, a glycerol and one or more fatty acids. In one example, one or more phospholipids is used as a co-surfactant in the provided compositions. Exemplary of the phospholipids used in the provided compositions are lecithin, including phosphatidylcholine (PC), phosphatidylethanolamine (PE), distearoylphosphatidylcholine (DSPC), phosphatidylserine (PS), phosphatidylglycerol (PG), phosphatidic acid (PA), phosphatidylinositol (PI), sphingomyelin (SPM) or a combination thereof. Typically, the phospholipid is phosphatidylcholine (PC), which sometimes is referred to by the general name "lecithin." Exemplary of the phospholipids that can be used as co-surfactants in the provided compositions are the phospholipids sold by Lipoid, LLC, Newark, N.J., for example, Purified Egg Lecithins, Purified Soybean Lecithins, Hydrogenated Egg, Soybean Lecithins, Egg Phospholipids, Soybean Phospholipids, Hydrogenated Egg and Soybean Phospholipids, Synthetic Phospholipids, PEG-ylated Phospholipids and phospholipid blends sold by Lipoid, LLC. Exemplary of the phosphatidylcholine that can be used as a co-surfactant in the provided compositions is the phosphatidylcholine composition sold by Lipoid, LLC, under the name Lipoid S100, which is derived from soy extract and contains greater than 95% or greater than about 95% phosphatidylcholine.

As used herein, "stability" refers to a desirable property of the provided compositions, for example, the ability of the provided compositions to remain free from one or more changes over a period of time, for example, at least or over 1, 2, 3, 4, 5, 6 or more days, at least or over 1, 2, 3, 4, or more weeks, at least or over 1, 2, 3, 4, 5, 6, 7, 8, 9, 10, 11, 12 or more months, or at least or over 1, 2, 3, 4 or more years. In one example, the composition is stable if it is formulated such that it remains free from oxidation or substantial oxidation over time. In another example, the stable compositions remain clear over time. In another example, the stable compositions remain safe and/or desirable for human consumption over time. In one example, stability refers to the lack of precipitates forming in the compositions over the period of time. In a related example, stability refers to the lack of "ringing" over the period of time. In another example, the composition is stable if it does not exhibit any visible phase separation, flocculation, creaming, coagulation or sedimentation over a period of time, for example, after 24 hours, after one week or after one month. In one example, the compositions are stable if they exhibit one or more of these described characteristics, over time, when kept at a particular temperature. In one example, the compositions remain stable at room temperature, for example, 25° C. or about 25° C. In another example, the compositions remain stable at between 19° C. and 25° C. In another example, the compositions remain stable at refrigerated temperatures, for example, 4° C. or about 4° C., or at frozen temperature, for example, at −20° C. or about −20° C. Typically, stability means that the shelf life of food or beverage that contains the concentrates provided herein is the same or about the same or longer than as it is without the concentrate. Any or all of the above properties, particularly the stability of the emulsion is retained for the shelf-life of the food or beverage without the non-polar active ingredient(s) under conditions in which the food or beverage is normally stored. Generally foods and beverages containing the concentrate will have emulsion active ingredient and flavor retention for at least 6 months unless the food or beverage without the concentrate has a shorter shelf life. The mixture of the food or beverage with the concentrate will be retained without phase separation, flocculation, creaming, coagulation or sedimentation of the concentrate or components thereof for this period of time.

As used herein, "stabilize" means to increase the stability of one of the provided compositions or render such composition stable.

As used herein, "shelf life" refers to a time period within which the provided compositions remain stable, for example, the ability of the provided compositions to remain stable, i.e., free from one or more changes over a period of time, for example, for at least or over 1, 2, 3, 4, 5, 6 or more days, at least or over 1, 2, 3, 4, or more weeks, at least or over 1, 2, 3, 4, 5, 6, 7, 8, 9, 10, 11, 12 or more months, or at least or over 1, 2, 3, 4 or more years. In one example, the compositions are stable if they exhibit one or more of these described characteristics, over time, when kept at a particular temperature. In one example, the compositions remain stable at room temperature, for example, 25° C. or about 25° C. In another example, the compositions remain stable at between 19° C. and 25° C. In another example, the compositions remain stable at refrigerated temperatures, for example, 4° C. or about 4° C., or at frozen temperature, for example, at −20° C. or about −20° C.

As used herein, "oxidative stability" refers to accumulation of by products produced by peroxidation or addition of oxygen atoms to the fatty acids contained within fish oil triglyceride molecules. The accumulation of such oxidative by-products can be measured by a variety of methods known to those skilled in the art, including, for example, organoleptic evaluation methods by which rancidity becomes detectable by taste and/or smell and chemical, as well as chemical analytical methods.

As used herein, "phase separation" refers to the physical separation of a homogenous emulsion, for example, the separation of the oil and water phases of an emulsion, into two separate visible heterogeneous layers.

As used herein, "flocculation" or "floc" refers to the process by which colloids come out of suspension in the form of floc or flakes. For example, flocculation refers to the process by which fine particulates are caused to clump together into floc, which can float to the top or bottom of a liquid and or foodstuff. Generally, floc are visible when viewing the food or beverage with the naked eye (e.g., without magnification). The presence or absence of flocculation typically is determined by empirical observation and can be observed by the artisan formulating the compositions, for example, the concentrates or the compositions containing the concentrates. In one example, the provided compositions do not exhibit flocculation. In another example, the compositions exhibit small amounts of flocculation, for example, no more flocculation than another food or beverage. Flocculation can, in some examples, lead to phase separation.

As used herein, "creaming" and "sedimentation" refer synonymously to the process by which the dispersed phase of an emulsion migrates, under the influence of buoyance to either the top or the bottom of the continuous phase, resulting in visible phase separation. Generally, creaming is visible when viewing the food or beverage with the naked eye (e.g., without magnification).

As used herein, "coagulation" refers to the process by which colloids come out of suspension and is synonymous with flocculation. Generally, coagulation is visible when viewing the food or beverage with the naked eye (e.g., without magnification).

As used herein, "ringing" refers to the formation of a whitish or opaque ring around a container containing a liquid, for example, an aqueous liquid, for example a beverage, for example, a liquid dilution composition containing an emulsion or emulsion. Typically, the ring forms around the perimeter of the container, typically at the surface level of the liquid in the container, for example, at the neck of the container. Ringing can occur over time and, if it occurs over a short period of time, can be a sign of instability. Ringing typically is undesirable, particularly in the case of a liquid for human consumption, for example, a beverage. Typically, the provided compositions do not exhibit "ringing" or are stable, without ringing, for a long period of time, for example, days, weeks, months or years. In one example, the compositions are free from ringing over time, when kept, for example, at room temperature, refrigerated and/or frozen.

As used herein, "free from oxidation" and "oxidative stability" refer synonymously to the ability of a composition containing an oil, for example, a polyunsaturated fatty acid, for example, a fish oil, to remain free from oxidation, or formation of peroxides, for a long period of time, for example, days, weeks, months or years. In one example, the compositions are oxidatively stable over time, when kept, for example, at room temperature, refrigerated and/or frozen.

As used herein, "particle size" and "average particle size" refer synonymously to the average diameter of particles in a provided liquid, for example, the droplet diameter or micelle diameter in an emulsion. Typically, the provided emulsion concentrates, and the food or beverage dilution compositions made from the concentrates, have a particle size of less than about 1000 nm, typically, less than 500 nm or less than about 500 nm, typically less than 300 nm or about 300 nm, for example, less than 250 nm or about 250 nm, for example, less than 200 nm or less than about 200 nm, for example, less than or less than about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm. In one example, the dilution compositions yielded by diluting the liquid emulsion concentrates have a particle size between 10 nm or about 10 nm and 1000 nm or about 1000 nm, for example, between 15 nm or about 15 nm and 500 nm or about 500 nm, for example, between 15 nm or about 15 nm and 300 nm or about 300 nm, for example, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, 200 nm or more. Typically, the provided liquid emulsion concentrates are formulated such that, dilution of the liquid emulsion concentrates in a food or beverage yields a liquid dilution composition having an appropriate particle size, for example, between 15 nm or about 15 nm and 500 nm or about 500 nm.

Information about particles in the compositions, alternatively, can be expressed in terms of particle density, for example, ppm (parts per million) or percent solids, in the liquids.

As used herein, "visible particles" are particles, for example, in a liquid, for example, an emulsion, that are visible when viewing the liquid with the naked eye (e.g., without magnification). In one example, the visible particles are particles that are observed by the artisan formulating the compositions, for example, the concentrates or the compositions containing the concentrates. In one example, the provided compositions contain no visible particles. In another example, the compositions contain few visible particles, for example, no more visible particles than another liquid, for example, a beverage. The presence of visible particles and the number of visible particles is determined by empirical observation.

As used herein, "visible crystals" are crystals that are visible when viewing a liquid with the naked eye (e.g., without magnification). The presence or absence of visible crystals typically is determined by empirical observation and can be observed by the artisan formulating the compositions, for example, the concentrates or the compositions containing the concentrates. In one example, the provided compositions contain no visible crystals. In another example, the compositions contain few visible crystals, for example, no more visible crystals than are contained in another liquid, for example, a beverage.

As used herein, "turbidity" is a measure of the cloudiness or haziness of a liquid, caused by particles in suspension in the liquid. Turbidity can measured optically, for example, using a nephelometer, an instrument with a light and a detector. The nephelometer measures turbidity by detecting scattered light resulting from exposure of the liquid to an incident light. The amount of scattered light correlates to the amount of particulate matter in the liquid. For example, a beam of light will pass through a sample with low turbidity with little disturbance. Other methods for measuring turbidity are well known and can be used with the provided methods and compositions. The units of a turbidity value measured with a nephelometer are Nephelometric Turbidity Units (NTU). In one example, the provided compositions, e.g., the aqueous liquid dilution compositions containing the emulsion concentrates, have low turbidity, for example, a turbidity value (NTU) of 30 or about 30; or an NTU value of less than 30 or about 30, for example, less than 29 or about 29, less than 28 or about 28, less than 27 or about 27, less than 26 or about 26, less than 25 or about 25, less than 24 or about 24, less than 23 or about 23, less than 22 or about 22, less than 21 or about 21, less than 20 or about 20, less than 19 or about 19, less than 18 or about 18, less than 17 or about 17, less than 16 or about 16, less than 15 or about 15, less than 14 or about 14, less than 13 or about 13, less than 12 or about 12, less than 11 or about 11, less than 10 or about 10, less than 9 or about 9, less than 8 or about 8, less than 7 or about 7, less than 6 or about 6, less than 5 or about 5, less than 4 or about 4, less than 3 or about 3, less than 2 or about 2, less than 1 or about 1; or 29 or about 29, 28 or about 28, 27 or about 27, 26 or about 26, 25 or about 25, 24 or about 24, 23 or about 23, 22 or about 22, 21 or about 21, 20 or about 20, 19 or about 19, 18 or about 18, 17 or about 17, 16 or about 16, 15 or about 15, 14 or about 14, 13 or about 13, 12 or about 12, 11 or about 11, 10 or about 10, 9 or about 9, 8 or about 8, 7 or about 7, 6 or about 6, 5 or about 5, 4 or about 4, 3 or about 3, 2 or about 2, 1 or about 1, or 0 or about 0. In another example, the turbidity value of the aqueous liquid dilution composition is less than 1000 or less than about 1000, less than 500 or less than about 500, less than 300 or less than about 300, less than 250 or less than about 250, 200 or less than about 200, for example, 200, 175, 150, 100, 50, 25 or less.

As used herein, a turbid liquid is one that is thick or opaque with visible particles in suspension, for example, a liquid that is cloudy or muddy in appearance.

As used herein, "clear" can be used to describe a composition as provided herein, for example, an aqueous liquid dilution composition containing the emulsion concentrates and/or the emulsion concentrates themselves. In one example, a clear liquid is one that does not appear cloudy by empirical observation (e.g., to the naked eye) and/or does not contain particles or crystals that are visible to the naked eye, or that does not exhibit "ringing." In another example, a clear liquid is one that has a low or relatively low turbidity value, for example an NTU value, that is less than or equal to a desired NTU value. In one example, a clear liquid has an NTU value of less than 300 or less than about 300, typically less than 250 or less than about 250, typically less than 200 or less than about 200, for example, 200, 175, 150, 100, 50, 25 or less. In another example, a liquid is clear if it has a turbidity value (NTU) of 30 or about 30; or an NTU value of less than 30 or about 30, for example, less than 29 or about 29, less than 28 or about 28, less than 27 or about 27, less than 26 or about 26, less than 25 or about 25, less than 24 or about 24, less than 23 or about 23, less than 22 or about 22, less than 21 or about 21, less than 20 or about 20, less than 19 or about 19, less than 18 or about 18, less than 17 or about 17, less than 16 or about 16, less than 15 or about 15, less than 14 or about 14, less than 13 or about 13, less than 12 or about 12, less than 11 or about 11, less than 10 or about 10, less than 9 or about 9, less than 8 or about 8, less than 7 or about 7, less than 6 or about 6, less than 5 or about 5, less than 4 or about 4, less than 3 or about 3, less than 2 or about 2, less than 1 or about 1; or 29 or about 29, 28 or about 28, 27 or about 27, 26 or about 26, 25 or about 25, 24 or about 24, 23 or about 23, 22 or about 22, 21 or about 21, 20 or about 20, 19 or about 19, 18 or about 18, 17 or about 17, 16 or about 16, 15 or about 15, 14 or about 14, 13 or about 13, 12 or about 12, 11 or about 11, 10 or about 10, 9 or about 9, 8 or about 8, 7 or about 7, 6 or about 6, 5 or about 5, 4 or about 4, 3 or about 3, 2 or about 2, 1 or about 1, or 0 or about 0. In another example, a clear liquid is one that has a small or relatively small average particle size (e.g., less than 1000 nm or about 1000 nm, typically less than 500 nm or less than about 500 nm, typically less than 300 nm or about 300 nm, typically less than 250 nm or about 250 nm, typically less than 200 nm or about 200 nm, for example, less than 150 or about 150 nm, less than 100 nm or about 100 nm, less than 75 nm or about 75 nm, less than 50 nm or about 50 nm, less than 25 nm or about 25 nm or less than 10 nm or about 10 nm), for example, less than or less than about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm.

In another example, clarity is expressed relatively. For example, it can be desired that a particular composition is equally as clear, about as clear, or more clear than another composition (as measured empirically, or by measuring turbidity value or particle size). For example, clarity can be assessed relative to another aqueous liquid dilution composition, for example, a beverage. In one example, a liquid is clear if it is similar in appearance to another clear liquid, for example, a beverage, for example, water. For example, it can be desired that a composition has a particle size that is less than or equal to another liquid, for example, a beverage: In another example, it can be desired that a composition has a turbidity value that is less than or equal to another liquid, for example, a beverage. In another example, it can be desired that a composition appears more clear or as clear as another liquid, for example, a beverage, for example, by having no more visible particles, no more crystal formation and/or no more cloudiness than the other liquid. In one example, the provided compositions are clear. In another example, they are relatively clear or as clear as or about as clear as another composition, for example, a beverage that does not contain the non-polar compound or liquid emulsion concentrate.

As used herein, an "additive" includes anything that one can add to a food, beverage, or other human consumable, to enhance one or more of its nutritional, pharmaceutical, dietary, health, nutraceutical, health benefit, energy-providing, treating, holistic, or other properties. For example, provided herein are compositions and methods for preparing foods, beverages and other aqueous human consumables, that include one or more additives, typically oil based additives (e.g., non-polar compounds), such as nutraceuticals, pharmaceuticals, vitamins, typically oil soluble vitamins, for example, Vitamin D, Vitamin E, and Vitamin A, minerals, fatty acids, such as essential fatty acids, e.g., polyunsaturated fatty acids, for example, omega-3 fatty acids, omega-6 fatty acids and omega-9 fatty acids, for example, alpha-linolenic acid (ALA), docosahexaenoic acid (DHA), eicosapentaenoic acid (EPA), gamma-linolenic acid (GLA), conjugated linoleic acid (CLA), oleic acid, saw palmetto extract, flaxseed oil, fish oil, algae oil, phytosterols, resveratrol, lipoic acid, carotenoids, for example lutein, zeaxanthin and lycopene, and coenzymes, for example, Coenzyme Q10 and other additives.

As used herein, an "effective amount" of an additive, such as a non-polar compound, such as a non-polar active ingredient, refers to the quantity and/or concentration of the additive necessary for preventing, curing, ameliorating, arresting or partially arresting a symptom of a disease or disorder, or the quantity and/or concentration desired by an individual for intake, such as daily intake, and/or nutritional supplementation, for example, an amount sufficient to enhance the nutritional, pharmaceutical, nutraceutical, health or energy property of a food, beverage, or other consumable. In some examples, it is desired that the provided compositions, for example, the liquid emulsion concentrates and/or the dilution compositions, contain an effective amount of a particular non-polar compound, for example, a particular amount per volume or weight of the composition.

In one example, an effective amount is an amount of liquid emulsion concentrate that provides between at or about 1.5 to at or about 3.0 grams (g) of omega-6 fatty acids per serving, between at or about 16 to at or about 220 milligrams (mg), for example, between at or about 32 to at our about 220 mg docosahexaenoic acid (DHA) and eicosapentaenoic acid (EPA) per serving, between at or about 100 and at or about 500 mg phytosterols per serving, between at or about 10 and at or about 200 mg, for example, between at or about 50 and at or about 200 mg Coenzyme Q10 per serving, between at or about 40 and at or about 400 micrograms (mcg) Vitamin A per serving, or between at or about 200 and at or about 2000 international units (IU), for example between at or about 400 and at or about 800 IU Vitamin D3 per serving of a food or beverage, for example, per 8 ounces of a beverage.

In one example, an effective amount is a concentration or amount of a liquid emulsion composition where at least 25 mg or about 25 mg, typically at least 35 mg, for example, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 325, 350, 375, 400, 425, 450, 475, 500, 550, 600, 700, 800, 900, 1000, 1500, 2000, 2500, 3000 mg, or more, of the non-polar active ingredient, is contained in at least one serving of a food or beverage, for example, 8 fluid ounces of an aqueous medium, e.g., a beverage.

As used herein, a "serving" of a food or beverage refers to a typical serving or the food or beverage, as determined by the USDA Center for Nutrition Policy and Promotion, typically for example, 1 teaspoon (0.166667 ounce, 4.7249 g), 1 tablespoon (0.5 fluid ounce, 14.1747 g), 2 tablespoons (1 fluid ounce, 28.3495 g), 0.25 cup (2 fluid ounces, 56.6990 g), 0.5 cup (4 fluid ounces, 113.398 g), 0.75 cup (6 fluid ounces, 170.097 g) or 1 cup (8 fluid ounces, 226.796 g), of the food or beverage, for example, 8 fluid ounces of an aqueous medium, 2 tablespoons of a mayonnaise, or 4 ounces of a pasta sauce.

As used herein, "water-based finished food or beverage" refers to any food or beverage that is typically an aqueous based food or beverage, for example, having greater solubility in aqueous liquids, for example, water, than in fats and oils. Exemplary water-based finished foods and beverages, include, but are not limited to, tomato-paste based products, dairy-based products, creams, sauces, soups, pastes, dressings, water, flavored water, soda, milk, juices, including fruit juices, sauces, syrups, sports drinks, fitness drinks, nutritional beverages, nutritional supplement, energy drinks and vitamin-fortified beverages.

As used herein, "water insoluble" refers to a property of a compound, none of which dissolves when the compound is mixed with water, for example, when mixed with water at room temperature, for example, between 19° C. an 25° C. or between about 19° C. and 25° C. In one example, the non-polar compounds are water insoluble. In another example, the non-polar compounds in the provided compositions are slightly soluble in water, for example, having low water solubility.

As used herein, low water solubility refers water solubility of less than 30 or about 30 mg/mL, typically less than 20 mg/mL or about 20 mg/mL, typically, less than 10 mg/mL or about 10 mg/mL, typically less than 1 mg/mL or about 1 mg/mL, for example, solubility in water of 30, 29, 28, 27, 26, 25, 24, 23, 22, 21, 20, 19, 18, 17, 16, 15, 14, 13, 12, 11, 10, 9, 8, 7, 6, 5, 4, 3, 2, 1 mg/mL or less, for example, when mixed with water at room temperature, for example, between 19° C. and 25° C. or between about 19° C. and 25° C. As used herein, poorly water soluble can be used to refer to compounds, for example, non-polar compounds that are water insoluble or have low water solubility.

As used herein, "concentrate", "liquid concentrate" and "liquid emulsion concentrate", are used synonymously to refer to provided compositions that contain the non-polar compounds, are liquid at room temperature, for example at 25° C. or about 25° C., or at a temperature of between 19° C. or about 19° C. and 25° C. or about 25° C., and can be diluted in a food or beverage to form the provided dilution compositions. Typically, the liquid emulsion concentrate is an emulsion concentrate that has a particle (droplet) size (or can be diluted to form a dilution composition having a particle size) that is less than 1000 or about 1000, typically less than 500 or about 500, typically less than 300 or about 300 nm, typically less than 250 or about 250 nm, for example, less than 200 or about 200, for example, less than 150 or about 150 nm, for example, a particle size equal to, less than or less than about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm.

As used herein, "liquid composition" is used to refer to any liquid, for example, a composition that is a liquid at room temperature, for example, at 25° C. or about 25° C., or at a temperature of between 19° C. or about 19° C. and 25° C. or about 25° C. Exemplary of the provided liquid dilution compositions are aqueous liquid dilution compositions into which one or more liquid emulsion concentrate has been diluted, for example, aqueous liquid dilution compositions containing the concentrates. In this example, the non-polar compound and other lipophilic compounds in the concentrate form the dispersion phase within the aqueous liquid, which is an emulsion (e.g., emulsion).

As used herein, "dilution composition" is used to refer to any composition that contains one or more of the provided liquid emulsion concentrates (e.g., the liquid emulsion concentrates containing the non-polar compound(s)), diluted in a food or beverage, for example a water-based finished food or beverage. Exemplary of the provided dilution composition are tomato-paste based products, dairy-based products, creams, sauces, soups, pastes, dressings, water, flavored water, soda, milk, juices, including fruit juices, sauces, syrups, sports drinks, fitness drinks, nutritional beverages, nutritional supplement, energy drinks, vitamin-fortified beverages and other food and beverages containing the concentrates.

As used herein, "liquid dilution composition" and "liquid dilution" are used synonymously to refer to a composition that contains one or more of the provided liquid emulsion concentrates (e.g., the liquid emulsion concentrates containing the non-polar compound(s)), diluted in a liquid, for example, an aqueous medium. Exemplary of the provided liquid dilution compositions are aqueous liquid dilution compositions, for example, beverages or other liquids containing the liquid emulsion concentrates, for example, water, sauces, soups, syrups, soda, juice, for example, fruit juice, milk, coffee, tea, nutritional beverages, sports drinks, energy drinks, vitamin-fortified beverages, flavored water, and other beverages containing the concentrates.

As used herein, "aqueous liquid dilution compositions" are liquid dilution compositions that are primarily aqueous, for example, a composition containing a liquid emulsion concentrate diluted in an aqueous medium, for example, water or other beverage. It is not necessary that the aqueous liquid dilution composition is completely aqueous. For example, the aqueous liquid dilution compositions can contain an aqueous portion, for example, an aqueous continuous phase, as well as an additional portion, for example, a dispersion phase, for example, a lipophilic dispersion phase. Typically, the lipophilic dispersion phase contains one or more lipophilic substances, for example, one or more non-polar compounds, for example, non-polar active ingredients. Exemplary of the provided aqueous liquid dilution compositions are beverages containing the active ingredients, for example, water, soda, juice, for example, fruit juice, milk, coffee, tea, nutritional beverages, sports drinks, energy drinks, vitamin-fortified beverages, flavored water, and other beverages. Typically, the aqueous liquid dilution compositions are beverages including the non-polar compound, for example, beverages containing the concentrates.

As used herein, "oil phase" is used to refer to the portion (or phase) of a composition such as those provided herein that contains one or more lipophilic ingredients and/or amphiphilic ingredients (oil phase ingredients) and is, in general, the lipid-soluble phase. In the provided emulsion compositions (e.g., the emulsion concentrates and the dilution compositions), the oil phase typically represents the dispersion phase. "Oil phase" also can be used to refer to the liquid containing the oil phase ingredients that is generated, typically in an oil phase vessel, while carrying out the methods for making the liquid emulsion concentrates. For example, oil phase can refer to the mixture of the components (oil phase ingredients) that are combined, mixed and heated, for example, in the oil phase vessel (e.g., tank), prior to mixing with the water phase. "Oil phase" can refer to the oil phase mixture that is formed after all the ingredients are dissolved; alternatively, it can refer to the forming mixture, for example, as it is being mixed/heated.

As used herein, oil phase ingredient(s) refers to the components of the provided compositions that are included in the oil phase in the provided methods for making the compositions. Typical oil phase ingredients include non-polar compounds, e.g., non-polar active ingredients; surfactants; co-surfactants; oils, such as non-polar solvents; preservatives; and emulsion stabilizers. Other lipophilic and/or amphiphilic ingredients can be included in the oil phase.

As used herein, "water phase" is used to refer to the portion (phase) of a composition such as those provided herein that contains one or more hydrophilic ingredients and/or amphiphilic ingredients (water phase ingredients) and is, in general, the water-soluble phase. Typically, in the provided emulsion compositions, for example, the emulsion concentrates and the dilution compositions, the water phase is the continuous phase. "Water phase" also is used to refer to the liquid containing the water phase ingredients that is generated while carrying out the methods for making the liquid emulsion concentrates. For example, water phase can refer to the mixture of the components (water phase ingredients) that are combined, mixed and heated, for example, in the water phase tank, prior to mixing with the oil phase. "Water phase" can refer to the water phase mixture that is formed after all the ingredients are dissolved; alternatively "water phase" can refer to the forming mixture, for example, as it is being mixed/heated.

As used herein, water phase ingredient(s) refers to the components of the provided compositions that are included in the water phase (e.g., added to the water phase vessel) in the provided methods for making the compositions. Typical water phase ingredients include, but are not limited to, polar solvents, typically polar protic solvents, such as water and alcohols, typically alcohols having more than one hydroxy group such as dihydroxy and trihydroxy alcohols, e.g., glycerol and propylene glycol; surfactants; co-surfactants; preservatives; soluble fiber; and emulsion stabilizers. Other hydrophilic and/or amphiphilic ingredients can be included in the water phase.

As used herein, an initial concentrate is a concentrate (e.g., liquid emulsion concentrate) that is made in the provided methods of formulating the provided concentrates, typically by selecting ingredients, for example, surfactant(s), non-polar compound(s), polar solvent, and, optionally, other ingredients, and selecting starting concentrations of the ingredients from an appropriate concentration range as described herein.

As used herein, "room temperature" and "ambient temperature" are used to describe a temperature that is common in one or more enclosed spaces in which human beings typically are or reside. Room temperature can vary, but generally refers to temperatures between 19° C. or about 19° C. and 25° C. or about 25° C. When a composition is stored at room temperature, it should be understood it is generally kept at a temperature within this range or about within this range.

As used herein, "refrigerated temperature" refers to a temperature that is common in a refrigerator, for example, a household or restaurant refrigerator, for example, a temperature that is cooler than room temperature, but typically a few degrees above the freezing point of water (32° F. or about 32° F., or 0° C. or about 0° C.). Typically, refrigerated temperatures are between about 10° C. or about 10° C. and 0° C. or about 0° C., for example, 4° C. or about 4° C. When a composition is stored at a refrigerated temperature, it should be understood that it is kept at a temperature common to household or industrial refrigerators.

As used herein, "frozen temperature" refers to a temperature around or below the freezing point of water, e.g., a temperature commonly used in a household freezer, for example, 0° F. or about 0° F., for example, −19° C. or about −19° C. or −20° C. or about −20° C., or colder.

As used herein, "w/w," "weight per weight," "by weight", "% by weight" and "weight percent" are used synonymously used to express the ratio of the mass of one component of a composition compared to the mass of the entire composition. For example, when the amount of a particular ingredient represents 1%, by weight (w/w) of a concentrate, the mass of that ingredient is 1% of the mass of the entire concentrate. Similarly, when the amount of an ingredient is 50% (w/w) of the concentrate, the mass of that ingredient is 50% of the entire mass of the concentrate. Similarly, when a composition and/or a compound contains 10%, by weight of an ingredient, the mass of the ingredient is 10% of the total mass of the composition or compound. When only a concentration, amount, or percentage (without units) is listed, it is to be understood that the concentration or percentage is a concentration or percentage, by weight.

Similarly, as used herein "v/v", "volume per volume", "percent by volume" and "volume percent" are used synonymously to express the ratio of the volume of one component of a composition and the volume of the entire composition.

As used herein, "not more than" and "NMT" refer to a quantity that is less than or equal to the listed quantity. Similarly, "not less than" and "NLT" refer to a quantity that is greater than or equal to the listed quantity.

As used herein, natural is used to refer to a composition, and/or ingredients in the composition, that can be found in nature and is not solely man-made. For example, benzyl alcohol is a natural preservative. In one example, the natural composition/ingredient is GRAS and/or Kosher-certified. Typically, the provided compositions are natural, semi-natural and/or contain one or more natural ingredients.

As used herein, "G.R.A.S." and "GRAS" are used synonymously to refer to compounds, compositions and ingredients that are "Generally Regarded as Safe" by the USDA, FDA for use as additives, for example, in foods, beverages and/or other substance for human consumption, for example, any substance that meets the criteria of sections 201(s) and 409 of the U.S. Federal Food, Drug and Cosmetic Act. Typically, the compositions provided herein are GRAS certified.

As used herein, "kosher" is used to refer to substances that conform to Jewish Kosher dietary laws, for example, substances that do not contain ingredients derived from non-kosher animals or ingredients that were not made following kosher procedures. Typically, the compositions provided herein are Kosher certified.

As used herein, "vessel" refers to any container, for example, tanks, pots, vials, flasks, cylinders and beakers, that can be used to contain the ingredients and/or phases of the provided compositions, during the methods for making the compositions. In one example (e.g., for the provided scaled-up methods), the vessel is a tank, which is used to mix and/or heat one or more ingredients and/or phases of the compositions, for example, water phase tanks and oil phase tanks. Typically, the oil and the water phases are mixed and heated in separate tanks, before combining the phases to form an emulsion. In another example, the tank is a packaging or holding tank, which holds the provided compositions after forming the compositions, for example, the emulsions. A number of tanks are available for mixing ingredients. Typically, the tanks are cleaned, for example, rinsed, soaped and/or sanitized according to known procedures, prior to use and between uses. Typically, the tanks are equipped with one or more mixers, for example, a standard mixer and/or homogenizer, which are used to mix the ingredients added to the tank. In one example, the tank further is equipped with a heating and/or cooling device. For example, the tank can be a water jacketed tank. The temperature of the water-jacketed tank is controlled through the water-jacket, for example, to heat the contents, for example, while mixing.

As used herein, a water phase vessel refers to the vessel used to mix and/or heat the water phase ingredients to generate the water phase of the provided compositions. In one example (e.g., for the scaled-up methods), the water phase vessel is a water phase tank. In one example, the water phase tank is a water-jacketed tank.

As used herein, an oil phase vessel refers to the vessel used to mix and/or heat the oil phase ingredients to generate the oil phase of the provided compositions. Typically, the oil phase vessel is an oil phase tank. In one example, the oil phase tank is a water jacketed tank.

As used herein, transfer means refers to any equipment, combination of equipment and/or system that can be used to transfer liquid, for example, from one tank to another tank, in the provided methods for making the compositions. Exemplary of the transfer means are a transfer pump and appropriate fittings, for example, sanitary fittings, ball valves and transfer hoses, for example, food grade hoses.

As used herein, a "mixer" is any piece of equipment or combination of equipment that can be used to mix ingredients in the provided methods for making the compositions, for example, standard mixers and homogenizers (shears). For example, mixers can be used to mix the ingredients of the water phase, the oil phase, and/or to mix the additional ingredients.

As used herein, "standard mixers" are mixers that are used to combine a group of ingredients, for example, the oil phase ingredients or the water phase ingredients, or to mix one or more ingredients with a liquid, for example, with an emulsion, for example, to mix additional ingredients with the emulsion. Standard mixers can be any mixers that move the material, for example, the ingredients, during heating, for example, to promote dissolving of the ingredients.

As used herein, "homogenizer" and "shear" are used to refer to mixers that typically have high shear, which can be used, for example, to form an emulsion, for example, to emulsify the water phase and the oil phase, in the provided methods. The homogenizers typically are capable of high-shear mixing, which emulsifies the phases.

As used herein, a "cooling apparatus" is any piece of equipment or combination of equipment that can be used with the provided methods to cool the compositions and phases and ingredients thereof, for example, during mixing and/or homogenizing, for example, to chill the mixture while emulsifying the oil and water phases. Exemplary of the cooling apparatuses are coolers (chillers), for example, recirculating coolers which can be attached, for example, to the tanks used in the provided methods, for example, remotely or by a tank mounted in the cooler, to recirculate fluid from the tank, through the chiller and back to the tank, in order to rapidly cool and maintain the temperature of the mixture during mixing. Typically, the cooling apparatus can be used to cool the liquid to between 25° C. or about 25° C. and 45° C. or about 45° C., for example, 25, 26, 27, 28, 29, 30, 31, 32, 33, 34, 35, 36, 37, 38, 39, 40, 41, 42, 43, 44 or 45° C., typically between 25° C. and 43° C., for example, 26.5° C.

As used herein, rapid cooling refers to a process by which a composition, for example, a liquid composition, for example, a forming emulsion, is cooled to a desired temperature, for example, between 25° C. or about 25° C. and 45° C. or about 45° C., typically between 25° C. and 43° C., for example, 26.5° C., in less than 2 hours or about 2 hours, typically less than 1 hour or about 1 hour, for example, in at least between 30 minutes or about 30 minutes and 60 minutes or about 60 minutes, for example, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 minutes.

As used herein, low heat refers to a temperature between 45° C. or about 45° C. and 85° C. or about 85° C., for example, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84 or 85° C., for example, not more than 85° C. or about 85° C., typically not more than 60° C. or about 60° C., typically, 60° C. or about 60° C. In the provided methods for making the liquid emulsion concentrates, the oil phase and water phase ingredients typically are heated, using low heat, in order to preserve the ingredients, for example, in order to prevent oxidation of the ingredients, for example, the non-polar active ingredients, for example, the omega-3 containing compounds, for example, the DHA.

As used herein, unit dose form refers to physically discrete units suitable for human and animal subjects and packaged individually as is known in the art.

As used herein, a "subject" includes an animal, typically a mammal, typically a human.

As used herein, "consisting essentially of," means containing the following list of ingredient(s), and not including any additional active ingredient, for example, not including any additional active drug or pharmaceutical. For example, a composition, for example, a liquid emulsion, consisting essentially of a listed plurality of ingredients contains those particular ingredients and does not contain any additional active drug or pharmaceutical.

As used herein, the singular forms "a", "an" and "the" include plural referents unless the context clearly dictates otherwise. Thus, for example, reference to compound a composition comprising a surfactant includes compositions that contain one surfactant (not including the emulsion stabilizer component) and compositions containing a plurality thereof.

As used herein, ranges and amounts can be expressed as "about" a particular value or range. About also includes the exact amount. Hence "about 5 grams" means "about 5 grams" and also "5 grams.' It also is understood that ranges expressed herein include whole numbers within the ranges and fractions thereof. For example, a range between 5 grams and 20 grams includes whole number values such as 5, 6, 7, 8, 9, 10, 11, 12, 13, 14, 15, 16, 17, 18, 19 and 20 grams, and fractions within the range, for example, but not limited to, 5.25, 6.72, 8.5, and 11.95 grams.

As used herein, "optional" or "optionally" means that the subsequently described event or circumstance does or does not occur and that the description includes instances where said event or circumstance occurs and instances where it does not. For example, an optionally variant portion means that the portion is variant or non-variant. In another example, an optional ligation step means that the process includes a ligation step or it does not include a ligation step.

B. COMPOSITIONS CONTAINING NON-POLAR COMPOUNDS

Provided herein are compositions containing non-polar compounds and methods for making the compositions. Nonpolar compounds are poorly water soluble (e.g., having low water solubility or being water-insoluble). Thus, it generally can be difficult to formulate non-polar compounds into compositions for human consumption, particularly water-based compositions, for example, water-based finished foods and beverages. Poor water solubility of non-polar compounds also can contribute to their poor bioavailability. Improved methods and compositions for formulating non-polar compounds are provided herein.

In general, emulsions (e.g., oil-in-water emulsions) are colloidal dispersions of two immiscible liquids (e.g., oil and water or other aqueous liquid), containing a continuous and a dispersed phase. Emulsions can be used to disperse non-polar compounds in aqueous liquids. In an oil-in-water emulsion, the dispersed phase is an oil phase and the continuous phase is an aqueous (water) phase. There is a need for emulsions (e.g., oil-in-water emulsions) containing non-polar compounds in aqueous liquids and methods and compositions for generating the dilution compositions, such as food and beverages, that are stable and/or clear. In particular, emulsions are needed that are more suitable and desirable for human consumption of the non-polar compounds, for example, in foods and beverages. For example, emulsions having improved stability (e.g., lack of separation, flocculation, creaming), clarity (e.g., small particle size, low turbidity), taste and smell, particularly when diluted into a food or beverage to provide a desired dosage of an active ingredient are needed and are provided herein.

Emulsions that are provided contain the non-polar compounds dispersed in aqueous liquid and have desirable properties, including improved stability, clarity, smell and taste. The provided compositions (and methods for making the compositions) can be used to formulate any non-polar compound in water-based food and beverage compositions, including the non-polar compounds (e.g., non-polar active ingredients) described herein and other known non-polar compounds.

Typically, the provided emulsions containing the non-polar compounds are emulsions, which are emulsions having dispersed droplets (particles) with diameters less than 1000 nm or less than about 1000 nm, typically, less than 500 nm or less than about 500 nm, typically less than 300 nm or about 300 nm, typically less than 250 or less than about 250 nm, typically less than 200 nm or less than about 200 nm, for example, less than or less than about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm. Typically, the provided emulsion compositions are oil-in-water emulsions, containing the non-polar compounds dispersed in aqueous liquid.

The provided emulsion compositions are stabilized by one or more surfactants and/or co-surfactants and also include at more than about or more than 1%, generally up to and including 3, 4, 5, 6, 7, 8, 9, 10, 12, 13, 14 and 15%, of an emulsion stabilizer, which is a fatty acid-modified carbohydrate-based macromolecule emulsion stabilizer. The fatty acid-modified carbohydrate-based macromolecules generally are modified gums and starches or other such suitable carbohydrate-based macromolecules. They are modified by esterification with a fatty acid anhydride, such as an n-octenyl succinic anhydride. Such modified gums and starches act as a co-emulsifier to a surfactant, such as the SFAE, in the compositions provided herein, whereby the resulting solution can include high concentrations (up to 50% or up to at least about 50% or at least 50%) of a non-polar compound into the concentrate. In one example, the fatty acid modified carbohydrate is a modified starch, for example, a modified corn starch obtained through the chemical conversion of a waxy corn starch, such as by modification with an n-octenyl succinic anhydride (OSAn-). Exemplary of an OSAn-modified corn starch is a calcium starch octenyl succinate, sold under the name Farmal® MS 6135, from Corn Products International Inc., Westchester, Ill., available from Cosmetic Specialties, Inc., Haddon Heights, N.J. Modified corn starches and processes for their preparation are disclosed in U.S. Pat. No. 2,661,349.

In another example, the fatty acid-modified carbohydrate is a modified gum acacia, for example, gum acacia, or gum arabic, modified by reaction with a cyclic anhydride, especially a cyclic anhydride that contains a substituent group containing 5 to 18 carbon atoms, such as 1-octenylsuccinic anhydride (OSAn), resulting in gum acacia derivatives with balanced lipophilic and hydrophilic properties, i.e., "lipophilic gum acacia". Exemplary of a modified gum acacia is for example, the modified gum acacia sold under the name Tic Pretested® Ticamulsion A-2010 Powder, by Tic Gums, Inc., Belcamp, Md., which has a reported degree of esterification that is not more than 0.6%. Modified gum acacia and processes for its preparation are disclosed in U.S. Pat. No. 6,455,512, which describes a hydrocolloid system containing the modified gum acacia.

Surfactants form an interfacial film in the emulsion, between the oil and water phase, providing stability. Typically, the emulsions of the provided compositions contain micelles, in which one or more surfactant(s) surround the non-polar active compound. The micelles are dispersed in the water phase.

The provided emulsion compositions include liquid emulsion concentrates containing the non-polar compounds, which can be diluted to provide non-polar compounds in water-based finished foods and beverages. The liquid emulsion concentrates can be diluted into a medium, for example, an aqueous medium, for example, a beverage, to form a liquid dilution composition (e.g., aqueous liquid dilution composition) containing the non-polar compound. Alternatively, the liquid emulsion concentrate can be diluted into a food, for example, a tomato-paste based product, a dairy-based product, a sauce, a cream, a soup or a dressing, to form a dilution composition containing the non-polar compound. Also exemplary of the provided compositions are the dilution compositions (e.g., food or beverage dilution compositions, which can be stable) made by diluting the liquid emulsion concentrates in the food or beverage.

The compositions can be made using any non-polar compound. The non-polar compounds typically are non-polar active ingredients, for example, pharmaceuticals, nutraceuticals, vitamins and minerals. The non-polar active ingredients include, but are not limited to, polyunsaturated fatty acid (PUFA)-containing compounds, for example, omega-3-containing active ingredients, for example, compounds containing ALA, DHA and/or EPA, for example, oils derived from fish and microalgae, krill and/or flaxseed extract, and omega-6-containing non-polar active ingredients, for example, gamma-linolenic acid (GLA)-containing compounds, for example, borage oil; omega-9 containing non-polar active ingredients, for example, oleic acid; saw palmetto oil-containing compounds; conjugated fatty acid containing-ingredients, for example, conjugated linoleic acid (CLA)-containing compounds; coenzyme Q-containing active ingredients, for example, Coenzyme Q10 (CoQ10), typically oxidized CoQ10 (ubidecarenone)-containing compounds; phytochemical-containing compounds, for example, phytosterols (plant sterols), resveratrol, and carotenoids, for example, lycopene, lutein and zeaxanthin; fat-soluble vitamins, for example, Vitamin A palmitate and vitamin D3; and alpha lipoic acid (thioctic acid). Additional exemplary non-polar active ingredients are described herein.

1. Liquid Emulsion Concentrates Containing the Non-Polar Compounds

Provided are liquid emulsion concentrates (also called "concentrates" or "liquid concentrates") containing one or more non-polar compounds (non-polar active ingredients). The concentrates can be diluted into food or beverages to form dilution compositions containing the non-polar compounds. The liquid concentrates are formulated based on one or more desirable properties, for example, stability, for example, lack of phase separation, flocculation, creaming, "ringing" and/or precipitation over time; clarity; safety; taste; smell; and/or bioavailability of the concentrate and/or the dilution compositions containing the concentrate. In one example, the desirable property is stability, such that when the provided concentrate is diluted into a food or beverage, the composition is stable, for example, free from separation, precipitation, flocculation, creaming and/or degradation of the non-polar compound. In another example, the desirable property is the ability of the provided concentrate to yield a clear or partially clear aqueous liquid dilution composition when it is diluted into aqueous medium, for example, a beverage such as water. In another example, the desirable property relates to the safety of the concentrates and/or the desirability of the concentrates for human consumption, for example, in foods and beverages. In another example, it can be desirable that the concentrate provides an effective amount of the non-polar active compound. In another example, it can be desirable that the concentrate contains less than or equal to a particular concentration of one or more ingredients. In another example, it can be desirable that the concentrate contains greater than or equal to a particular concentration of one or more ingredients.

In addition to the non-polar compounds, the concentrates contain at least one surfactant. Typically, the surfactant has an HLB value between 13 or about 13 and 20 or about 20, more typically between 15 or about 15 and 18 or about 18, for example, 13, 14, 15, 16, 17, 18, 19, 20, about 13, about 14, about 15, about 16, about 17, about 18, about 19 or about 20. Exemplary of suitable surfactants are sugar ester surfactants, such as sucrose fatty acid ester (SFAE) surfactants, vitamin E derived surfactants containing a polyethylene glycol (PEG) moiety, such as tocopherol polyethylene glycol succinate (TPGS), and PEG-derived surfactants, such as PEG-sorbitan fatty acid esters, such as polysorbate 80. Typically, the surfactant is a natural surfactant, for example, a surfactant that is GRAS (generally recognized as safe) certified by the FDA and/or Kosher certified.

The liquid concentrates further contain at least one polar solvent, such as water (e.g., filtered water), or other edible aqueous liquid (e.g., propylene glycol or glycerin), or combination thereof.

The liquid concentrates further contain at least one emulsion stabilizer in addition to the surfactants, that is typically a fatty acid-modified carbohydrate-based macromolecule, such as an n-octenyl succinic anhydride modified gum arabic, for example, the modified gum acacia sold under the name Tic Pretested® Ticamulsion A-2010 Powder, by Tic Gums, Inc., Belcamp, Md.

Typically, the concentrates further contain one or more additional ingredients. Exemplary of additional ingredients that can be included in the concentrates are soluble fiber, preservatives, non-polar solvents, co-surfactants, emulsion stabilizers, pH adjusters and flavoring agents.

The non-polar compounds in the concentrates and dilution compositions are contained in micelles. These micelles, containing the non-polar compound surrounded by the one or more surfactants, allow dispersion of the non-polar compound among polar solvents, for example, when the concentrates are diluted to form dilution compositions. The micelles containing the non-polar compounds typically have a small or relatively small particle size, for example, less than 1000 nm or about 1000 nm, less than 500 nm or about 500 nm, typically less than 300 nm or about 300 nm, typically less than 200 nm or about 200 nm, for example, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 125, 150 or 200 nm. Smaller particle size correlates with clarity of the liquid dilution compositions containing the concentrates. For example, a liquid with a smaller particle size is more clear than a liquid with a larger particle size. Small particle size also can contribute to other desirable properties, for example, stability.

A number of factors, including ingredients, their relative concentrations, and methods for making the concentrates, affect the particle size of the compositions, and other desirable properties of the compositions, such as stability. In particular, the nature of the surfactant, particularly the HLB of the surfactant, and the relative concentrations of polar solvent (e.g., water), surfactant, emulsion stabilizer and the non-polar compound, contribute to small particle size, and the stability of the dilution compositions. Typically, several of these parameters and properties are related to one another. For example, several of the parameters contribute to the particle size, typically small particle size, of the compositions. Particle size contributes directly to clarity of liquid dilution compositions, e.g., beverages, containing the concentrates. Particle size also can relate to other properties, for example, stability, lack of "ringing" and/or precipitate formation of food or beverage compositions containing the concentrates.

Accordingly, properties of the ingredients and their relative concentrations in the concentrates are important for the ability of the concentrate to yield desirable dilution compositions. Provided are methods for formulating the liquid emulsion concentrates. Determining the appropriate ingredients, and relative concentrations thereof, that will yield dilution compositions having desirable properties, is performed using provided methods for formulating the liquid concentrates.

a. Formulating the Liquid Concentrates

In the provided formulation methods, the concentrates are formulated by selecting ingredients and concentration ratios of the ingredients that yield compositions having one or more desired properties. When formulating the concentrates, selected ingredients and starting concentrations are used to make initial concentrates, which are evaluated and modified, if necessary.

As a first step in formulating the provided concentrates, one or more initial concentrates are made and evaluated for desired properties. For this step, ingredients are selected, for example, from among the ingredients described herein. The ingredients generally include surfactants, polar solvents, non-polar active ingredients, emulsion stabilizers and other ingredients. A starting concentration (weight percentage) of each selected ingredient is selected from within the appropriate concentration range for that ingredient or category of ingredient, for example, the appropriate concentration range for the surfactant. In some cases, the initial concentrate is formulated based on the ingredients, and concentrations thereof, of an existing concentrate, having one or more desired properties. In other cases, the initial concentrate is formulated based on providing a particular amount of a non-polar active ingredient, such that upon dilution of the concentrate in a food or beverage, a serving of the food or beverage provides a specific amount of non-polar active ingredient. For example, the initial concentrates provided herein are formulated such that upon dilution in a food or beverage, the food or beverage contains between at or about 1.5 to at or about 3.0 grams (g) of omega-6 fatty acids per serving, between at or about 16 to at or about 220 milligrams (mg), for example, between at or about 32 to at or about 220 mg docosahexaenoic acid (DHA) and eicosapentaenoic acid (EPA) per serving, between at or about 100 and at or about 500 mg phytosterols per serving, between at or about 10 and at or about 200 mg, for example, between at or about 50 and at or about 200 mg Coenzyme Q10 per serving, between at or about 40 and at or about 400 micrograms (mcg) Vitamin A per serving, or between at or about 400 and at or about 800 international units (IU) per serving, for example, per a serving of a food or beverage, for example, per 8 ounces of a beverage.

The initial concentrate(s) then is made, using the methods for making the concentrates, provided below, adding each ingredient at its starting concentration at the appropriate step. In one example, more than one initial concentrate, e.g., multiple initial concentrates, each having a different concentration of one or more ingredients, is made, and compared. In one example, multiple initial concentrates are produced to test various representative concentrations within an appropriate concentration range for one or more particular ingredient.

In a typical example, the initial concentrate is made by including at least one surfactant, such as from among the surfactants described herein, that has an HLB value between 13 or about 13 and 20 or about 20, at a starting concentration within the concentration range of between 3% or about 3% and 16% or about 16%, and typically between at or about 6% and at about 14%, by weight (w/w), of the concentrate; at least one non-polar compound, at a starting concentration within the concentration range of between 15% or about 15% and 50% or about 50%, and typically between at or about 20% and at or about 50%; a polar solvent, at a starting concentration of between 30% or about 30% and 70% or about 70%, and typically between at or about 40% and at or about 60%, by weight; and an emulsion stabilizer, at a starting concentration between 0.1% or about 0.1% and 10% or about 10%, and typically between at or about 1% and at or about 3%. In one example, the initial concentrate further includes other ingredients, for example, soluble fiber(s), preservative(s), co-surfactant(s), and/or other ingredients as described herein.

After making the initial concentrate(s), the concentrate(s) is evaluated for one or more desired properties, for example, the ability to form dilution compositions (e.g., stable dilution compositions or dilution compositions having a particular desired property, such as lack of flocculation). The ability to form dilution compositions having one or more properties is determined by diluting the concentrate in a water-based finished food or beverage, for example, diluting the concentrate in the food or beverage at a dilution factor of between 1:10 or about 1:10 and at most 1:1000 or about 1:1000, typically between 1:10 or about 1:10 and 1:500 or about 1:500, for example, at a dilution between 1:10 or about 1:10 and up to 1:250 or about 1:250, for example, diluted between 1:10 or about 1:10, 1:20 or about 1:20, 1:25 or about 1:25, 1:50 or about 1:50, 1:100 or about 1:100, 1:200 or about 1:200, 1:250 or about 1:250, or up to 1:500 or about 1:500, for example, 1:10, 1:20, 1:25, 1:30, 1:35, 1:40, 1:50, 1:55, 1:60, 1:65, 1:70, 1:75, 1:80, 1:85, 1:90, 1:95, 1:100, 1:110, 1:120, 1:130, 1:140, 1:150, 1:160, 1:170, 1:180, 1:190, 1:200, 1:210, 1:220, 1:230, 1:240, 1:250, 1:260, 1:270, 1:280, 1:290, 1:300, 1:350, 1:400, 1:500, or according to other dilutions provided herein, and assessing the stability, presence of flocculation or creaming, "ringing" or forming of precipitates, clarity, turbidity value, particle size, color, smell, taste, safety or other desired property of the resulting dilution composition.

After evaluation, the ingredients, and/or concentrations thereof, can be adjusted in order to generate the desired properties in the final concentrate. Typically, the concentration of the non-polar compound, the surfactant, and/or the polar solvent is the concentration that is adjusted after evaluating the initial concentrate. Similarly, when formulating multiple initial concentrates, one or more of the non-polar compound, surfactant and polar solvent concentration is/are varied among the multiple initial concentrates. In some cases, following evaluation, it can be determined that additional ingredients (not included in the initial formulation) are needed or desirable for achieving the desired properties of a particular concentrate. This process can be repeated until a concentrate having the desired property or properties is generated.

i. Exemplary Ingredients and Concentration Ranges

Each of the provided concentrates contains a non-polar compound, such as, but not limited to, the exemplary non-polar compounds described herein below. More typically, one or more non-polar compounds are included in each of the provided concentrates. Typically, the one or more non-polar compounds are non-polar active ingredients, for example, oil-based active ingredients such as a polyunsaturated fatty acid (PUFA), a coenzyme Q, a phytochemical, a carotenoid or a vitamin. For formulating the initial concentrate, the starting concentration of the total amount of non-polar compounds typically is a concentration chosen from within a concentration range of between 15% or about 15% and 50% or about 50% (w/w) of the concentrate, for example within a range of between 20% or about 20% and 50% or about 50%, for example, typically between at or about 20% and at or about 45%, or between at or about 25% and at or about 45%, or between at or about 20% and at or about 40%, such as a starting concentration of 20% or about 20%, 21% or about 21%, 22% or about 22%, 23% or about 23%, 24% or about 24%, 25% or about 25%, 26% or about 26%, 27% or about 27%, 28% or about 28%, 29% or about 29%, 30% or about 30%, 31% or about 31%, 32% or about 32%, 33% or about 33%, 34% or about 34%, 35% or about 35%, 36% or about 36%, 37% or about 37%, 38% or about 38%, 39% or about 39%, 40% or about 40%, 41% or about 41%, 42% or about 42%, 43% or about 43%, 44% or about 44% or 45% or about 45%, (w/w) of the concentrate. In one example, the concentration range of the non-polar active compounds is between 20% or about 20% and 50% or about 50%. In another example, the concentration range of the non-polar active compounds is between 20% or about 20% and 40% or about 40%, (w/w) of the concentrate. The non-polar compound(s) typically are added as part of an oil phase, according to the provided methods for making the concentrate.

The initial concentrate further contains at least one surfactant, which can be added to the water phase or the oil phase, typically added in batches to the water phase and/or to the oil phase, and typically has an HLB value of between 13 or about 13 and 20 or about 20, for example, 13, 14, 15, 16, 17, 18, 19, or 20, or about 13, or about 14, about 15, about 16, about 17, about 18, about 19, about 20, typically between at or about 13 and at or about 18, more typically between at or about 15 and at or about 18, including, but not limited to sugar ester surfactants (which typically are sucrose fatty acid surfactants containing monoesters), vitamin E derived surfactants containing a PEG moiety, such as TPGS, and analogs and derivatives thereof, and PEG-derived surfactants, such as PEG-sorbitan fatty acid esters, such as polysorbates, including polysorbate 80 and analogs (e.g. homologs) of polysorbate 80, such as, for example, polysorbate 20, polysorbate 40 and polysorbate 60, and other polysorbates. Typically, the surfactant is a natural surfactant, which is safe and/or approved for human consumption. Initial concentrates can further contain a mixture of one or more surfactants, selected from among any surfactant that typically has an HLB value of between 13 or about 13 and 20 or about 20, for example, 13, 14, 15, 16, 17, 18, 19, or 20, or about 13, or about 14, about 15, about 16, about 17, about 18, about 19, about 20, typically between at or about 13 and at or about 18, more typically between at or about 15 and at or about 18. Mixtures of one or more surfactants include, for example, a sucrose fatty acid ester or mixtures thereof, or an SFAE or mixtures thereof and a PEG-derivative of vitamin E or an analog thereof, or an SFAE or mixtures thereof and a PEG-derived surfactant, such as a PEG-sorbitan fatty acid ester, or a PEG-derivative of vitamin E or an analog thereof, and a PEG-derived surfactant, such as a PEG-sorbitan fatty acid ester, or an SFAE or mixtures thereof, a PEG-derivative of vitamin E or an analog thereof and a PEG-derived surfactant, such as a PEG-sorbitan fatty acid ester.

Typically, the starting concentration of a surfactant is chosen from within a concentration range of between 3% or about 3% and 16% or about 16% (w/w), typically between at or about 6% and at or about 14%, for example, 3% or about 3%, 4% or about 4%, 5% or about 5%, 6% or about 6%, 7% or about 7%, 8% or about 8%, 9% or about 9%, 10% or about 10%, 11% or about 11%, 12% or about 12%, 13% or about 13%, 14% or about 14%, 15% or about 15% or 16% or about 16%, by weight (w/w), of the concentrate, typically between 8% or about 8% and 11% or about 11%, such as, for example, 9.06%, 9.99% or 10.5%, (w/w) of the concentrate. Typically, when mixtures of one or more surfactants are included in the provided concentrates, the concentration range of the total amount of surfactants is between 16% or about 16% and 30% or about 30%, by weight (w/w), of the concentrate, such as, for example, between 16% or about 16% and 25% or about 25% (w/w) of the concentrate; between 17% or about 17% and 22% or about 22% (w/w) of the concentrate; such as, for example, 17% or about 17%, 18% or about 18%, 19% or about 19%, 20% or about 20%, 21% or about 21% or 22% or about 22%, (w/w) of the concentrate, such as, for example, 19.56%, (w/w) of the concentrate, provided that each surfactant is present in an amount between 3% or about 3% and 16% or about 16% (w/w), for example, 3% or about 3%, 4% or about 4%, 5% or about 5%, 6% or about 6%, 7% or about 7%, 8% or about 8%, 9% or about 9%, 10% or about 10%, 11% or about 11%, 12% or about 12%, 13% or about 13%, or 14% or about 14%, 15% or about 15% or 16% or about 16%, by weight (w/w), of the concentrate, typically between 8% or about 8% and 11% or about 11%, such as, for example, 9.06%, 9.99% and 10.5% (w/w) of the concentrate.

The concentrates further contain polar solvents (e.g., water, or other edible polar solvent, e.g., propylene glycol and glycerin) which are added to the water phase. Typically, the starting concentration of polar solvent is chosen from within a concentration range of between 30% or about 30% and 70% or about 70% (w/w) of the concentrate, for example, 30% or about 30%, 31% or about 31%, 32% or about 32%, 33% or about 33%, 34% or about 34%, 35% or about 35%, 36% or about 36%, 37% or about 37%, 38% or about 38%, 39% or about 39%, 40% or about 40%, 41% or about 41%, 42% or about 42%, 43% or about 43%, 44% or about 44%, 45% or about 45%, 46% or about 46%, 47% or about 47%, 48% or about 48%, 49% or about 49%, 50% or about 50%, 51% or about 51%, 52% or about 52%, 53% or about 53%, 54% or about 54%, 55% or about 55%, 56% or about 56%, 57 or about 57%, 58 or about 58%, 59 or about 59%, 60% or about 60%, 61% or about 61%, 62% or about 62%, 63% or about 63%, 64% or about 64%, 65% or about 65%, 66% or about 66%, 67% or about 67%, 68% or about 68%, 69% or about 69% or 70% or about 70%, (w/w) of the concentrate. In one example, the concentration range of the polar solvent is between 40% or about 40% and 60% or about 60% (w/w) of the concentrate. In another example, the concentration range of the polar solvent is between 45% or about 45% and 55% or about 55% (w/w) of the concentrate, such as, for example, 48.174%, 48.215%, 49.384%, 49.423% or 52.136% (w/w) of the concentrate. In yet another example, a mixture of one or more polar solvents, for example, a mixture of water and propylene glycol, or a mixture of water and glycerin, or a mixture of propylene glycol and glycerin, or a mixture of water, glycerin and propylene glycol is chosen from within a concentration range of between 30% or about 30% and 70% or about 70% (w/w) of the concentrate, for example, between 40% or about 40% and 60% or about 60% (w/w) of the concentrate, more typically between 45% or about 45% and 55% or about 55% (w/w) of the concentrate.

The concentrates further contain at least one emulsion stabilizer (e.g., a fatty acid-modified carbohydrate-based macromolecule, such as an n-octenyl succinic anhydride modified gum arabic) which is added to the water phase, the oil phase or typically to the water phase and the oil phase. When added to the water phase, the starting concentration of the emulsion stabilizer is chosen from within a concentration range of between 0.1% or about 0.1% and 2% or about 2%, typically between 1% or about 1% and 2% or about 2%, by weight (w/w) of the concentrate. When added to the oil phase, the starting concentration of the emulsion stabilizer is chosen from within a concentration range of between 0.01% or about 0.01% and 0.6% or about 0.6%, typically between 0.1% or about 0.1% and 0.6% or about 0.6%, by weight (w/w) of the concentrate. When added to the water phase and the oil phase, the starting concentration of the total amount emulsion stabilizer is chosen from within a concentration range of between 0.1% or about 0.1% and 10% or about 10%, typically between at or about 1% and at or about 3%, by weight (w/w), of the concentrate.

One or more, typically more than one, additional ingredients can be added to the initial concentrate. For example, the concentrates typically contain at least one preservative, typically a natural preservative, for example, benzyl alcohol. Exemplary of other additional ingredients that can be added to the concentrates, including the initial concentrates, are a soluble fiber, for example, an inulin; additional emulsion stabilizers, for example, an ester gum or a blend of gums; a non-polar solvent for the non-polar compound, for example, an oil other than the non-polar compound, for example, vitamin E oil, oleic acid or flaxseed oil; a pH adjuster, for example, citric acid or phosphoric acid; one or more flavoring agents, for example, D-limonene or lemon oil; a co-surfactant, for example, a phospholipid (e.g., phosphatidylcholine); or an antifoaming agent.

The appropriate concentration ranges for the additional ingredients are described in individual sections below. Typically, the concentration of the additional ingredients depends, in part, on the concentrations of the one or more non-polar active ingredient(s), the one or more surfactant(s), the one or more polar solvent(s) and the one or more emulsion stabilizer(s). Typically, the concentrations of these four ingredients (surfactant, polar solvent, non-polar compound, and emulsion stabilizer) are the focus of the formulating methods. For example, when it is determined that modifications to ingredient concentrations in the initial concentrate should be made, it typically is the concentrations of one or more of these three ingredients that are adjusted.

In one example, it can be desirable to add one or more of the additional ingredients after evaluation of the initial concentrate, for example, in order to improve the concentrate with respect to one or more desired properties.

ii. Evaluation of the Initial Concentrate

The formulation methods further include analysis of the initial concentrate based on one or more desired properties, for example, properties of a dilution composition containing the concentrate, for example, stability, presence of flocculation, creaming, "ringing" or forming of precipitates, clarity, turbidity value, particle size, color, smell, taste, safety and/or the presence of crystals. For example, the methods typically include analyzing the ability of the initial concentrate to form a stable composition upon dilution into a water-based finished food or beverage. Stability upon dilution into a beverage, such as an aqueous medium, is typically determined by analysis of the clarity/turbidity of the resulting aqueous liquid dilution composition containing the initial concentrate. Stability upon dilution into a food product, such as a non-clear liquid, a sauce, soup, dressing or cream, is typically determined by lack of phase separation of the resulting dilution composition containing the initial concentrate.

For evaluation of properties of the dilution composition, the initial concentrate is diluted into a water-based finished food or beverage, typically a beverage, such as water, a tinted nutritional beverage or a juice, or a food, such as a tomato-based food product, such as tomato sauce or vegetable juice, a dairy-based food product, such as fat free milk or sour cream, mayonnaise, salsa, queso cheese, a soup, a cream or a dressing, such as ranch dressing, for example, at a dilution factor of between 1:10 or about 1:10 and at most 1:1000 or about 1:1000, typically between 1:10 or about 1:10 and 1:500 or about 1:500, for example, at a dilution between 1:10 or about 1:10 and up to 1:250 or about 1:250, for example, diluted between 1:10 or about 1:10, 1:20 or about 1:20, 1:25 or about 1:25, 1:50 or about 1:50, 1:100 or about 1:100, 1:200 or about 1:200, 1:250 or about 1:250, or up to 1:500 or about 1:500, for example, 1:10, 1:20, 1:25, 1:30, 1:35, 1:40, 1:50, 1:55, 1:60, 1:65, 1:70, 1:75, 1:80, 1:85, 1:90, 1:95, 1:100, 1:110, 1:120, 1:130, 1:140, 1:150, 1:160, 1:170, 1:180, 1:190, 1:200, 1:210, 1:220, 1:230, 1:240, 1:250, 1:260, 1:270, 1:280, 1:290, 1:300, 1:350, 1:400, 1:500, or any other dilution, such as others provided herein. Typically, stability of the dilution composition containing the initial concentrate is evaluated using one or more approaches. Additionally, other properties can be evaluated, for example, smell and/or taste properties of the dilution composition, for example, when the non-polar compound is a polyunsaturated fatty acid (PUFA), particularly fish oil or algae oil, whether the dilution composition smells "fishy" can be evaluated empirically.

(1) Stability

In one example, dilution of the provided concentrates in a finished food or beverage yields a stable dilution composition. The stability of the dilution composition containing the initial concentrate can be evaluated by one or more of a plurality of approaches, such as by empirical observation, for example, sensory tasting tests or qualitative assessment and/or by measuring oxidative stability.

In one example, the concentrates can be diluted to form stable food or beverage products, by adding between 0.05 grams (g) or about 0.05 g and 10 g or about 10 g of the concentrate, typically between 0.05 g and 5 g, for example, 0.05 g, 0.06 g, 0.07 g, 0.08 g, 0.09 g, 0.1 g, 0.2 g, 0.3 g, 0.4 g, 0.5 g, 0.6 g, 0.7 g, 0.8 g, 0.9 g, 1 g, 2 g, 3 g, 4 g, 5 g, 6 g, 7 g, 8 g, 9 g, or 10 g of the concentrate to a serving, about a serving, or a least a serving, for example 1, 2, 3, 4, 5, 6, 7, 8, 9, 10, 11, 12, 13, 14, 15, 16 or more, servings of a food or beverage, for example, a food, such as a tomato-paste based product, dairy-based product, salsa, salsa queso, cream, soup or dressing or a beverage, such as juice, nutritional beverage or milk, forming a stable food or beverage dilution composition containing the non-polar compound. In another example, the concentrates can be diluted to form stable liquid dilution compositions by adding between 1 mL or about 1 mL and 10 mL or about 10 mL of the concentrate, for example, 1 mL, 2 mL, 3 mL, 4 mL, 5 mL, 6 mL, 7 mL, 8 mL, 9 mL or 10 mL of the concentrate to a serving, about a serving, or a least a serving, for example 1, 2, 3, 4, 5, 6, 7, 8, 9, 10, 11, 12, 13, 14, 15, 16 or more, servings of a finished food or beverage, forming a stable food or beverage that contains the non-polar compound.

In another example, the concentrates can be diluted in a food or beverage to form stable dilution compositions when at least 25 mg or about 25 mg, typically at least 35 mg, for example, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 325, 350, 375, 400, 425, 450, 475, 500, 550, 600, 700, 800, 900, 1000, 1500, 2000, 2500, 3000 mg, or more, of the non-polar active ingredient, is contained in at least a serving or about a serving of the food or beverage.

In another example, the concentrate can be diluted in a water-based finished food or beverage to form a stable liquid dilution composition at a dilution factor of between 1:10 or about 1:10 and at most 1:1000 or about 1:1000, typically between 1:10 or about 1:10 and 1:500 or about 1:500, for example, at a dilution between 1:10 or about 1:10 and up to 1:250 or about 1:250, for example, diluted between 1:10 or about 1:10, 1:20 or about 1:20, 1:25 or about 1:25, 1:50 or about 1:50, 1:100 or about 1:100, 1:200 or about 1:200, 1:250 or about 1:250, or up to 1:500 or about 1:500, for example, 1:10, 1:20, 1:25, 1:30, 1:35, 1:40, 1:50, 1:55, 1:60, 1:65, 1:70, 1:75, 1:80, 1:85, 1:90, 1:95, 1:100, 1:110, 1:120, 1:130, 1:140, 1:150, 1:160, 1:170, 1:180, 1:190, 1:200, 1:210, 1:220, 1:230, 1:240, 1:250, 1:260, 1:270, 1:280, 1:290, 1:300, 1:350, 1:400 or at most 1:500. In another example, the stable dilution composition is formed at dilutions less dilute than 1:10 of the concentrate.

The provided liquid emulsion concentrates can be formulated using any non-polar compound for dilution in a food or beverage. In one example, the concentrates can be diluted in food or beverage, for example, over a wide dilution range to form stable compositions, for example, at a dilution factor of between 1:10 or about 1:10 and at most 1:500 or about 1:500, typically between 1:10 or about 1:10 and at most 1:1000 or about 1:1000, typically between 1:10 or about 1:10 and 1:500 or about 1:500, for example, at a dilution between 1:10 or about 1:10 and up to 1:250 or about 1:250, for example, diluted between 1:10 or about 1:10, 1:20 or about 1:20, 1:25 or about 1:25, 1:50 or about 1:50, 1:100 or about 1:100, 1:200 or about 1:200, 1:250 or about 1:250, or up to 1:500 or about 1:500, for example, 1:10, 1:20, 1:25, 1:30, 1:35, 1:40, 1:50, 1:55, 1:60, 1:65, 1:70, 1:75, 1:80, 1:85, 1:90, 1:95, 1:100, 1:110, 1:120, 1:130, 1:140, 1:150, 1:160, 1:170, 1:180, 1:190, 1:200, 1:210, 1:220, 1:230, 1:240, 1:250, 1:260, 1:270, 1:280, 1:290, 1:300, 1:350, 1:400 or at most 1:500.

Stability of a food or beverage dilution composition can be evaluated using one or more of a plurality of approaches, for example, quantitatively, for example, by measuring oxidative stability or qualitatively, by empirical evaluation. In one example, a particular quantitative or qualitative stability value is desired. In another example, it is desired that the dilution composition is as stable as, about as stable or more stable than another food or beverage, for example, a food or beverage dilution composition made according to the provided methods or a food or beverage, for example, a food or beverage that does not contain the concentrate. For example, a food or beverage dilution composition, containing the liquid concentrate diluted in a food or beverage, can be as stable or about as stable as the same food or beverage, containing no concentrate. The evaluation can be done qualitatively, for example by empirical observation, or quantitatively, for example, by measuring oxidative stability.

(2) Clarity

In one example, dilution of the provided concentrates in aqueous media yield clear liquids. The clarity of the aqueous liquid dilution composition containing the initial concentrate can be evaluated by one or more of a plurality of approaches, such as by empirical observation, by measuring particle size and/or by measuring the turbidity value of the liquid.

In one example, the concentrates can be diluted to form clear liquids (or liquids that are equal in clarity to known liquids), by adding between 0.05 grams (g) or about 0.05 g and 10 g or about 10 g of the concentrate, typically between 0.05 g and 5 g, for example, 0.05 g, 0.06 g, 0.07 g, 0.08 g, 0.09 g, 0.1 g, 0.2 g, 0.3 g, 0.4 g, 0.5 g, 0.6 g, 0.7 g, 0.8 g, 0.9 g, 1 g, 2 g, 3 g, 4 g, 5 g, 6 g, 7 g, 8 g, 9 g, or 10 g of the concentrate, to 8 fluid ounces, about 8 fluid ounces, or at least 8 fluid ounces or at least about 8 fluid ounces, for example 8, 9, 10, 11, 12, 13, 14, 15, 16, 17, 18, 19, 20, 25, 30, 35, 40, 45, 50, 100, 200 or more fluid ounces, of aqueous medium, for example, water, forming a clear aqueous liquid dilution composition that contains the non-polar compound. In another example, the concentrates can be diluted to form clear aqueous liquid dilution compositions by adding between 1 mL or about 1 mL and 10 mL or about 10 mL of the concentrate, for example, 1 mL, 2 mL, 3 mL, 4 mL, 5 mL, 6 mL, 7 mL, 8 mL, 9 mL or 10 mL of the concentrate to 8 fluid ounces, about 8 fluid ounces, or at least 8 fluid ounces or at least about 8 fluid ounces, for example 8, 9, 10, 11, 12, 13, 14, 15, 16, 17, 18, 19, 20, 25, 30, 35, 40, 45, 50, 100, 200 or more fluid ounces, of aqueous medium, for example, water, forming a clear aqueous liquid dilution composition that contains the non-polar compound.

In another example, the concentrate can be diluted in aqueous medium to form a clear aqueous liquid dilution composition when at least 25 mg or about 25 mg, typically at least 35 mg, for example, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 325, 350, 375, 400, 425, 450, 475, 500, 550, 600, 700, 800, 900, 1000, 1500, 2000, 2500, 3000 mg, or more, of the non-polar active ingredient, is contained in at least 8 fluid ounces or at least about 8 fluid ounces of aqueous liquid dilution composition, for example, a beverage, for example, water.

In another example, the concentrate can be diluted in an aqueous medium to form a clear aqueous liquid dilution composition at a dilution factor of between 1:10 or about 1:10 and at most 1:1000 or about 1:1000, typically between 1:10 or about 1:10 and 1:500 or about 1:500, for example, at a dilution between 1:10 or about 1:10 and up to 1:250 or about 1:250, for example, diluted between 1:10 or about 1:10, 1:20 or about 1:20, 1:25 or about 1:25, 1:50 or about 1:50, 1:100 or about 1:100, 1:200 or about 1:200, 1:250 or about 1:250, or up to 1:500 or about 1:500, for example, 1:10, 1:20, 1:25, 1:30, 1:35, 1:40, 1:50, 1:55, 1:60, 1:65, 1:70, 1:75, 1:80, 1:85, 1:90, 1:95, 1:100, 1:110, 1:120, 1:130, 1:140, 1:150, 1:160, 1:170, 1:180, 1:190, 1:200, 1:210, 1:220, 1:230, 1:240, 1:250, 1:260, 1:270, 1:280, 1:290, 1:300, 1:350, 1:400 or at most 1:500. In another example, the clear liquid is formed at dilutions less dilute than 1:10 of the concentrate.

The provided liquid emulsion concentrates can be formulated using any non-polar compound for dilution in an aqueous medium. In one example, the concentrates can be diluted in aqueous medium, for example, over a wide dilution range to form clear liquids, for example, at a dilution factor of between 1:10 or about 1:10 and at most 1:500 or about 1:500, typically between 1:10 or about 1:10 and at most 1:1000 or about 1:1000, typically between 1:10 or about 1:10 and 1:500 or about 1:500, for example, at a dilution between 1:10 or about 1:10 and up to 1:250 or about 1:250, for example, diluted between 1:10 or about 1:10, 1:20 or about 1:20, 1:25 or about 1:25, 1:50 or about 1:50, 1:100 or about 1:100, 1:200 or about 1:200, 1:250 or about 1:250, or up to 1:500 or about 1:500, for example, 1:10, 1:20, 1:25, 1:30, 1:35, 1:40, 1:50, 1:55, 1:60, 1:65, 1:70, 1:75, 1:80, 1:85, 1:90, 1:95, 1:100, 1:110, 1:120, 1:130, 1:140, 1:150, 1:160, 1:170, 1:180, 1:190, 1:200, 1:210, 1:220, 1:230, 1:240, 1:250, 1:260, 1:270, 1:280, 1:290, 1:300, 1:350, 1:400 or at most 1:500.

Clarity of an aqueous liquid dilution composition can be evaluated using one or more of a plurality of approaches, for example, quantitatively, for example, by measuring particle size and/or by measuring the turbidity value of the liquid, or qualitatively, by empirical evaluation. In one example, a particular quantitative or qualitative clarity value is desired. In another example, it is desired that the aqueous liquid dilution composition is as clear as, less clear or more clear than another liquid, for example, an aqueous liquid dilution composition made according to the provided methods or a beverage, for example, a beverage or other aqueous medium that does not contain the concentrate. For example, an aqueous liquid dilution composition, containing the liquid concentrate diluted in a beverage, can be as clear or about as clear as the same beverage, containing no concentrate. The evaluation can be done qualitatively, for example by empirical observation, or quantitatively, for example, by calculating particle size and/or turbidity value (NTU) for the liquid(s).

(3) Empirical Evaluation

The stability, or shelf life, of a dilution composition containing the initial concentrate can be assessed qualitatively by observation. In one example, a food or beverage dilution composition is considered stable if it does not exhibit phase separation, flocculation, precipitation, creaming, coagulation and/or sedimentation when looking at the food or beverage with the naked eye. Stability can be assessed empirically by comparison with other foods or beverages. For example, it can be desirable that the food or beverage is as stable as another food or beverage not containing the initial concentrate. In a related example, it can be desired that there is no substantial difference, for example, no observable difference, between the food or beverage dilution composition containing the concentrate and the food or beverage without the concentrate.

Stability can also be determined by evaluating sensory attributes of the food or beverage compositions containing the initial concentrates. For example, the food or beverage dilution compositions can be evaluated for a variety of different sensory attributes by a tasting panel. Sensory attributes include, for example, appearance, taste, aroma and flavor, for example, "fishiness", feeling factors, such as burning or irritation by smelling, texture, such as viscosity or oily mouth feeling, aftertaste, and any other attribute that is warranted. Evaluation of sensory attributes can be assessed empirically for the food or beverage dilution compositions alone, or by comparison of the dilution compositions to a food or beverage not containing the non-polar compounds. In one example, the food or beverage dilution composition has desirable sensory attributes, such as a lack of "fishy" smell or taste. In another example, there is no difference between the evaluated sensory attributes of the food or beverage dilution composition as compared to a food or beverage not containing the initial concentrate.

The relative clarity/turbidity of an aqueous liquid dilution composition containing the concentrate can be assessed qualitatively by observation. In one example, a liquid is considered clear if it does not have a cloudy appearance and/or if no particles are visible when looking at the liquid with the naked eye. Clarity can be assessed empirically by comparison to other liquids, for example, water, fruit juice, soda and/or milk. For example, it can be desirable that the liquid is as clear or about as clear as water or another liquid, for example a beverage. For example, it can be desirable that the liquid (containing the liquid concentrate diluted in an aqueous medium, for example, a beverage) is as clear or about as clear as the aqueous medium not containing the initial concentrate. In a related example, it can be desired that there is no substantial difference, for example, no observable difference, between the aqueous liquid dilution composition containing the concentrate and the aqueous medium without the concentrate. A clear liquid is not necessarily colorless, for example, a yellow liquid that contains no visible particles or cloudiness can be considered clear.

(4) Oxidative Stability

Alternatively, the stability, or shelf life, of a food or beverage dilution composition containing the initial concentrate can be assessed quantitatively, for example, by measuring oxidative stability of polyunsaturated fatty acids. Oxidative deterioration can be assessed by chemical methods such as determining peroxide value (PV), which measures peroxides resulting from primary oxidation, or p-anisidine value (AV), which measures 2-alkenals resulting from secondary oxidation. Typically it is desired that the food or beverage dilution compositions remain free from oxidative deterioration over a period of time, for example, 1, 2, 3, 4, 5, 6, 7, 8, 9, 10, 11 or 12 months, 1, 2, 3, 4 or more years. In one example, the composition is stable if it is formulated such that it remains free from oxidation or substantial oxidation over time.

(5) Particle Size

Alternatively, the clarity of the aqueous liquid dilution composition containing the initial concentrate can be assessed by measuring the particle size of the liquid. Methods for measuring particle size are known and any method for measuring particle size that can measure particle sizes in the appropriate ranges as described below, can be used.

Particle size can be analyzed by commercial services, for example, from Delta Analytical Instruments, Inc, such as using a light-scattering analyzer, for example, a dynamic light scattering analyzer, for example, the Horiba® LB-550, which can measure particle sizes within a range of 0.001 microns to 6 microns and uses a Fourier-Transform/Iterative Deconvolution technique for reporting data and can measure sample concentrations from ppm to 40% solids; the Horiba® LA-920, which is a laser light-scattering instrument having an He—Ne laser and a tungsten lamp and can determine particle sizes from 0.02 microns to 2000 microns using Mie Theory; or other analyzers available from Delta Analytical Instruments, Inc.

Alternatively, the particle size can be measured microscopically, for example, by viewing the liquid under a microscope, for example, at 640× magnification. With this method, particle size can be quantified by comparing to a measuring device, for example, a ruler, which is visible when viewing the liquid under the microscope. If any particles are observable at this magnification, they are measured by comparison to the measuring device. At a magnification of 640×, for example, any particle that is about 25 nm, 25 nm, or greater than 25 nm are visible, while particle sizes smaller than 25 nm typically are not visible.

Typically, it is desired that the aqueous liquid dilution compositions have a particle size less than 200 nm or less than about 200 nm, for example, 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm. Typically, it is desired that the aqueous liquid dilution compositions have a particle size less than 100 nm or about 100 nm, less than 50 nm or about 50 nm, or less than 25 nm or about 25 nm. Typically, the particle size of the aqueous liquid dilution composition containing the concentrate is between 5 nm or about 5 nm and 200 nm or about 200 nm, typically between 5 nm or about 5 nm and 50 nm or about 50 nm.

(6) Turbidity Measurement

Alternatively, clarity of a liquid dilution composition can be analyzed by taking an optical turbidity measurements, which indicates the level of cloudiness or haziness of a liquid, which correlates to size/number of particles in suspension in the liquid. The more clear a particular liquid, the lower its turbidity value.

Turbidity can measured optically, for example, by using a nephelometer, an instrument with a light and a detector. The nephelometer measures turbidity by detecting scattered light resulting from exposure of the liquid to an incident light. The amount of scattered light correlates to the amount of particulate matter in the liquid. For example, a beam of light will pass through a sample with low turbidity with little disturbance. Other methods for measuring turbidity are well known and can be used with the provided methods and compositions.

The units of a turbidity value measured with a nephelometer are Nephelometric Turbidity Units (NTU). In one example, it is desired that the aqueous liquid dilution composition containing the diluted concentrate has low turbidity, for example, a turbidity value (NTU) of 30 or about 30; or an NTU value of less than 30 or about 30, for example, less than 29 or about 29, less than 28 or about 28, less than 27 or about 27, less than 26 or about 26, less than 25 or about 25, less than 24 or about 24, less than 23 or about 23, less than 22 or about 22, less than 21 or about 21, less than 20 or about 20, less than 19 or about 19, less than 18 or about 18, less than 17 or about 17, less than 16 or about 16, less than 15 or about 15, less than 14 or about 14, less than 13 or about 13, less than 12 or about 12, less than 11 or about 11, less than 10 or about 10, less than 9 or about 9, less than 8 or about 8, less than 7 or about 7, less than 6 or about 6, less than 5 or about 5, less than 4 or about 4, less than 3 or about 3, less than 2 or about 2, less than 1 or about 1; or 29 or about 29, 28 or about 28, 27 or about 27, 26 or about 26, 25 or about 25, 24 or about 24, 23 or about 23, 22 or about 22, 21 or about 21, 20 or about 20, 19 or about 19, 18 or about 18, 17 or about 17, 16 or about 16, 15 or about 15, 14 or about 14, 13 or about 13, 12 or about 12, 11 or about 11, 10 or about 10, 9 or about 9, 8 or about 8, 7 or about 7, 6 or about 6, 5 or about 5, 4 or about 4, 3 or about 3, 2 or about 2, 1 or about 1, or 0 or about 0. In another example, the turbidity value of the aqueous liquid dilution composition is less than 200 or less than about 200, for example, 200, 175, 150, 100, 50, 25 or less.

In another example, it is desirable that the aqueous liquid dilution composition contains a turbidity value that is comparable, for example, about the same as, the same as, or less than or greater than, the turbidity value of another liquid, for example, a beverage not containing the liquid concentrate or an aqueous liquid dilution composition made by the provided methods.

iii. Selecting a Formulation and Modifying Formulations

After evaluation of the initial concentrate(s), either a particular formula is chosen or one or more modifications are made to the initial concentrate formula based on the results of the evaluation. When an initial concentrate does not display one or more desired properties, e.g., to the desired extent, based on the evaluation, the concentration of one or more ingredients can be adjusted and another initial concentrate made, in order to repeat the process until a concentrate with the desired properties is made. For modification of the initial concentrate, the amount of the polar solvent, surfactant, emulsion stabilizer and/or non-polar active ingredient can be adjusted, e.g., to another concentration within the appropriate concentration range. Alternative ingredients also can be chosen. In one example, modification of the initial concentrate involves the addition of one or more additional ingredients. For example, if evaluation reveals that the oil and water phases of the concentrate or aqueous liquid dilution composition containing the diluted concentrate are separating, an additional emulsion stabilizer can be added to the formulation. In another example, a co-surfactant can be added to help emulsify the components of the concentrate. In another example, the phase (oil phase or water phase), to which a particular ingredient is added, is modified. For example, the formulation can be modified to change whether the surfactant is added to the oil phase or the water phase or to both.

In one example, when evaluation of the initial concentrate reveals that it has desired properties, no modifications are made. In this example, the formula of the initial concentrate is used for making the concentrate. When two or more initial concentrates are made, for example, with increasing concentrations of an ingredient, the formula of one of the initial concentrates can be chosen. Which formula is chosen can be based on which formula has the most desirable property. Alternatively, desirable properties can be balanced with relative amounts of ingredients. In one example, it is desirable to choose the formulation that uses the lowest or the highest concentration of a particular ingredient but still provides a concentrate that yields a clear liquid upon dilution in an aqueous medium. In one example, the desired formulation is the formulation that has the lowest concentration of the surfactant, while still providing a concentrate that yields a clear liquid upon dilution in an aqueous medium. In another example, the desired formulation is the formulation that has the highest concentration of the non-polar active ingredient, while still providing a concentrate that yields a stable composition upon dilution into a food or beverage. In another example, the formulation that yields the most stable composition is desired.

In another example, however, modifications are made to the formula even if the initial concentrate bears desired properties. For example, upon determining that a particular concentrate formulation results in desired properties, it can be desirable to modify the concentration of one or more ingredients to determine whether the same desired properties can be achieved if a higher or lower concentration of the ingredient(s) is used. For example, it can be desirable to determine the lowest concentration of surfactant that can be used, while still generating a concentrate with a desired property, for example, the ability to form a stable composition upon dilution in a food or beverage. In another example, it can be desirable to determine the highest concentration of the non-polar ingredient that can be incorporated into a concentrate, while still maintaining the desired property, for example, the ability of the concentrate to form a stable composition upon dilution in a food or beverage. In another example, one or more additional ingredients can be added after making an initial concentrate with desirable properties, for example, flavoring agents and/or pH adjusting agents.

The following sections describe ingredients used in the provided liquid emulsion concentrates.

b. Emulsion Stabilizers (Co-Emulsifier)

The provided liquid concentrates further contain one or more emulsion stabilizers (co-emulsifiers) in addition to the surfactant(s), such as SFAE or TPGS as described herein. They are included in an amount of at or about 1% or greater than 1%, whereby the concentrates can contain a non polar compound, particularly a non-polar active ingredient, in an amount up to at least 50% by weight of the concentrate. The amount of emulsion stabilizer included, by weight of the concentrate, is generally more than 1% up to 3, 4, 5, 6, 7, 8, 9, 10, 11, 12, 13, 14 or 15% or up to about 3, 4, 5, 6, 7, 8, 9, 10, 11, 12, 13, 14 or 15%, such as more than 1% to 3%, or more than 1.5% to 3%, 4% or 5%.

In one example, the emulsion stabilizer decreases the viscosity of the liquid concentrate. In one example, one or more emulsion stabilizers are added, during formulation, after evaluation of an initial concentrate, particularly if the oil and water phases of the initial concentrate (or the dilution composition resulting from dilution of the initial concentrate) appear to be separating. Addition of the emulsion stabilizer prevents separation of the oil and water phases and also adjusts the viscosity, typically reducing it.

The emulsion stabilizers can be natural or synthetic emulsifiers. For example, the emulsion stabilizer can be chemically modified, enzymatically modified, physically modified, or modified by combinations thereof. For example, natural emulsion stabilizers are modified by esterification with a fatty acid chain, such that the modified emulsion stabilizer has balanced lipophilic and hydrophilic properties. The emulsions stabilizers in the provided compositions typically are carbohydrate-based macromolecules, including modified carbohydrate-based macromolecules, for example polysaccharides, celluloses, and starches, such as natural gums or modified gums, including but not limited to gum acacia, or gum arabic, modified gum acacia, ester gum, guar gum, modified guar gum, xanthan gum, sodium alginate, and gum ghatti, including mixtures of gums or blends of similar gums, and other gums, for example, sugar beet pectin; cellulose derivatives, for example, cetyl hydroxyethylcelluloses, hydroxypropylmethylcelluloses, modified hydroxypropylmethylcelluloses, hydroxyethylcelluloses and modified hydroxyethylcelluloses; and starches and modified starches, for example, maize or corn starches and modified corn starches. Exemplary emulsion stabilizers are fatty acid-modified carbohydrates, for example, modified gums and starches, for example, gums and starches modified by reaction with any fatty acid chain containing from 6-30 carbons, such that the emulsion stabilizer has hydrophobic (fatty acid chain) and hydrophilic (carbohydrate) properties. Typically, the carbohydrates are modified by esterification with a fatty acid anhydride, such as an n-octenyl succinic anhydride.

Emulsion stabilizers that can be used in the compositions provided herein are known to those of skill in the art. For example, Caldwell et al., in U.S. Pat. No. 2,661,349, describes water-dispersible reaction products of starch or cellulose with, inter alia, alkyl- and alkenyl-substituted dicarboxylic acid anhydrides. Specifically, starch reacted with octenylsuccinic anhydride (OSAn) is an established commercial product. While starch itself has no emulsifying properties, the octenylsuccinylated starch is characterized by having hydrophilic and hydrophobic groups and does provide emulsifying properties. Various improvements of Caldwell's process have been described, such as by Richards in U.S. Pat. No. 4,035,235, Billman in U.S. Pat. No. 5,672,699, Maliczyszyn et al. in U.S. Pat. No. 6,037,466 and Ward in U.S. Pat. No. 6,455,512. Harris et al., in U.S. Pat. No. 5,977,348, describe the esterification of various polysaccharides in a densified liquid such as supercritical carbon dioxide. Harris et al. lists starches, gums, celluloses, dextrins, glycogen, hemicelluloses, dextrans, inulins, and gums (agar, arabic gum, karaya gum, tragacanth gum, pectin, carrageenan, alginates, tamarind seed gum, xanthan gum, konjac gum, guar gum, gum acacia (also known as gum arabic) and locust bean (or carob seed) gum) as "bases" that may be treated. Harris et al. states that "bases" such as guar gum cannot be efficiently modified, as, when solubilized in water or organic solvents, they are too viscous to process in solutions containing above about 1% solids by weight. Thus the use of supercritical carbon dioxide allows efficient esterification. Nakajima, in U.S. Pat. No. 5,580,553, describes the reaction of saccharides (mono-, di-, and oligo-saccharides) with at least 30 parts by weight of an alkenylsuccinic anhydride per 100 parts of the saccharide to make surfactants providing desired foaming properties in cosmetic applications. OSAn-starch is used as an emulsifier for oil-in-water emulsions in, for example, bakery items, beverages, and salad dressings. U.S. Pat. No. 6,455,512, whose process is discussed herein, describes improvements in these processes and describes the resulting product sold under the trademark TICAMULSION. In one example, the addition of an OSAn-modified gum acacia, for example, TICAMULSION®, decreases the viscosity of the liquid concentrate. For example, addition of an OSAn-modified gum acacia to the water phase and/or the oil phase reduces the viscosity decreasing the pressure of the resulting concentrate allowing easier mixing and thereby reducing the amount of air introduced into the concentrate.

Thus, for example, the emulsion stabilizer used in the concentrates provided herein is a modified gum acacia, for example, a gum acacia modified such that it has balanced lipophilic and hydrophilic properties, such as an n-octenyl succinic anhydride-modified gum arabic (OSAn-modified-gum arabic). Exemplary of an OSAn-modified gum arabic is the emulsion stabilizer sold under the brand name TICAMULSION®, available from TIC Gums, Inc. (Belcamp, Md., its preparation is described in U.S. Pat. No. 6,455,512). The gum acacia polysaccharide chain contains three fractions: (i) The main fraction is a highly branched polysaccharide (MW: 3.105 g/mol) containing a backbone of β-(1,3) linked galactose units with linked branches of arabinose and rhamnose units and terminating in a glucuronic acid unit in the form of a magnesium, potassium or a calcium salt; (ii) A smaller fraction (~10 wt % of the total) contains a higher molecular weight (~1.106 g/mol) arabinogalactan-protein complex (GAGP-GA glycoprotein) in which arabinogalactan chains are covalently linked to a protein chain through serine and hydroxyproline groups; the attached arabinogalactan in the complex contains ~13% (by mole) glucuronic acid; and (iii) The smallest fraction (~1% of the total) has the highest protein content (~50 wt %) and contains a glycoprotein which differs in its amino acids composition from that of the GAGP complex (Randall et al., (1988) *Food Hydrocolloids* 2(2):131-140; Islam et al., (1997) *Food Hydrocolloids* 11:493-505; Idris et al., (1998) *Food Hydrocolloids* 12:379-389; and Goodrum et al., (2000) *Phytochemistry* 54:99). The modified gum acacia is generated by reaction (esterification) of a gum acacia with a dicarboxylic acid anhydride, such as one that contains a substituent group containing 5 to 18 carbon atoms, such as an alkenyl succinate anhydride, including, but not limited to, 1-octenylsuccinic anhydride (OSAn, also referred to as n-octenyl butanedioate). For example, OSAn-modified gum acacia TICAMULSION® is derived from the exudates of the tree species *Acacia seyal* or *Acacia senegal* by esterification in aqueous solution with not more than 3% n-octenyl succinic anhydride in a process analogous with the production of starch sodium octenyl succinate (see U.S. Pat. No. 6,455,512). This emulsion stabilizer is typically generated using gum arabic that is grown throughout Africa in abundant quantities, for example, from *Acacia senegal*. The emulsion stabilizer is the esterification reaction product of a hydrocolloid, for example, gum acacia, having a viscosity of about from 2 to 500 cP in 10% aqueous solution at 20° C. with 2 to 15%, by weight, based on the hydrocolloid, of n-octenyl succinic anhydride. The emulsion stabilizers further contain up to about 95%, by weight of the total solids, of at least one carbohydrate bulking agent. The degree of esterification of this OSAn-modified gum acacia is reported to be not more than 0.6%.

The emulsion stabilizer is the product of a esterification reaction of a hydrocolloid, such as a water soluble gum, having a viscosity of about from 2 to 500 cP in 10% aqueous solution at 20° C. with 2 to 15%, by weight, based on the hydrocolloid, of a dicarboxylic acid anhydride. More preferably, the hydrocolloid has a viscosity of about or at 2-250 cP, 2-100 cP, 50-100 cP, 50-200 cP or 2-150 cP in 10% aqueous solution at 20° C. and contains at least about or at least 10%, by weight of the hydrocolloid, of each of gum acacia and guar gum. The dicarboxylic acid anhydride is an alkane- or alkene-substituted dicarboxylic acid anhydride of the formula:

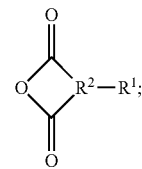

where $R^1$ is a straight or branched alkyl radical or ethylenically-unsaturated alkyl radical having 3-18 carbon atoms and $R^2$ is a divalent radical having 2-3 carbon atoms. More preferably R' is a straight or branched alkyl radical or ethylenically-unsaturated alkyl radical having 6-10 carbon atoms and $R^2$ is a divalent radical having 2 carbons. Typically, the dicarboxylic acid anhydride is an alkenyl succinate anhydride that is n-octenylsuccinic anhydride. The emulsion stabilizers also contain up to about 95%, by weight of the total solids, of at least one carbohydrate bulking agent, such as hydrolyzed polysaccharides, oligosaccharides or monosaccharides. In some instances the carbohydrate bulking agent contains at least one dextrin. In other instances the carbohydrate bulking agent contains essentially dextrose.

In another example, the emulsion stabilizer is a modified guar gum, for example, a hydroxypropyl guar modified by behenyl (or docosanol) chains, sold under the name Esaflor HM 22, by Lamberti (Conshohocken, Pa.). In another example, the emulsion stabilizer is a modified starch, for example, a modified corn starch obtained through the chemical conversion of a waxy corn starch, such as by modification with an n-octenyl succinic anhydride. Exemplary of an OSAn-modified corn starch is a calcium starch octenyl succinate, sold under the name Farmal™ MS 6135, from Corn Products International Inc., Westchester, Ill., available from Cosmetic Specialties, Inc., Haddon Heights, N.J. (see, for example, U.S. Pat. No. 2,661,349). Other fatty acid modified starches include N-Creamer 46, sold by National Starch Food Innovation, National Starch and Chemical Company, Bridgewater, N.J., and Farmal™ MS 5110, from Corn Products International Inc., Westchester, Ill., available from Cosmetic Specialties, Inc., Haddon Heights, N.J.

Exemplary natural emulsion stabilizers containing an ester gum are, for example, the emulsion stabilizer sold under the name Tic Pretested® Ester Gum 8BG, available from TIC Gums, Inc. (Belcamp, Md.) or Ester Gum 8BG, available from Hercules/Pinova (Brunswick, Ga.).

The one or more emulsion stabilizers can be added to the water phase, the oil phase, and typically to the water and the oil phase, during formation of the liquid concentrates. In one example, the emulsion stabilizer is added to the water phase at a concentration range of between 0.1% or about 0.1% and 5% or about 5%, w/w of the concentrate, for example, between 0.1% or about 0.1% and 3% or about 3%, between 0.1% or about 0.1% and 2% or about 2%, between 0.5% or about 0.5% and 3% or about 3%, between 0.5% or about 0.5% and 2% or about 2%, between 1% or about 1% and 3 and 3% or about 3%, or between 1% or about 1% and 2% or about 2%. For example, the emulsion stabilizer is added to the water phase at a concentration of at or about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9% or 2%, w/w, of the concentrate. In another example, the emulsion stabilizer is added to the oil phase at a concentration range of between 0.01% or about 0.01% and 1% or about 1%, w/w of the concentrate, for example, between 0.01% or about 0.01% and 0.5% or about 0.5%, between 0.05% or about 0.05% and 1% or about 1%, between 0.05% or about 0.05% and 0.5% or about 0.5%, between 0.1% or about 0.1% and 0.5% or about 0.5%, or between 0.1% or about 0.1% and 0.5% or about 0.5%. For example, the emulsion stabilizer is added to the oil phase at a concentration of at or about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9% or 1%, w/w of the concentrate. In yet another example, the emulsion stabilizer is added to the water phase or to the oil phase, or to the water phase and the oil phase, for a final concentration of between 1% or about 1% and 6% or about 6%, w/w of the concentrate, for example, between 1% or about 1% and 5% or about 5%, between 1% or about 1% and 3% or about 3%, between 2% or about 2% and 5% or about 5%, or between 2% or about 2% and 3% or about 3%. For example, the emulsion stabilizer is added to the water phase or the oil phase for a final concentration of at or about 1%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3%, 3.5%, 4%, 4.5%, 5%, 5.5% or 6%, w/w, of the concentrate.

In one example, the emulsion stabilizer is added to the water phase at a concentration, such that it represents at least more than 1% and less than 2, 3, 4 or 5% or about 2, 3, 4, 5% w/w of the liquid concentrate. For example, the emulsion stabilizer is added to the water phase or to the oil phase for a final concentration of between more than 1% or about more than 1% and 2, 3, 4 or 5% or about 2, 3, 4 or 5%, typically between more than 1% or about more than 1% and 2% or about 2%, for example, more than 1%, 1.1%, 1.2%, 1.3%, 1.4%, 1.5%, 1.6%, 1.7%, 1.8%, 1.9% or 2% w/w of the liquid concentrate, up to about 3, 4, 5, 6, 7, 8, 9, 10, 11, 12, 13, 14 or 15%. In a further example, the emulsion stabilizer(s) is added to the water phase and the oil phase, for example, at a concentration within the oil and water phase concentration ranges listed above. In one such example, the emulsion stabilizer represents more than 1% but less than 3, 4 or 5%, for example, between more than 1% and up to 2.5% or 3% or about 2.5% or 3% (w/w), for example, between at or about more than 1% and at or about 2.5%, typically between 1% or about 1% and 2.5% or about 2.5%, more typically between 1.5% or about 1.5% and 2.5% or about 2.5%, for example, 1.1%, 1.2%, 1.3%, 1.4%, 1.5%, 1.6%, 1.7%, 1.8%, 1.9%, 2.0%, 2.1%, 2.2%, 2.21%, 2.22%, 2.23%, 2.24%, 2.25%, 2.26%, 2.27%, 2.28%, 2.29%, 2.3%, 2.4%, 2.5% up o 3%, by weight (w/w), of the liquid concentrate. For example, the concentration of the total amount of emulsion stabilizer(s) is within the concentration range of between more than 1% or about more than 1% and 3% or about 3%, more typically between greater than 1.0% up to at or about 2.3, 2.5, 2.7, 2.9 and 3%. (w/w).

In one example, the emulsion stabilizer is a modified gum acacia that is added to the water phase at an amount of at or about 1.7% to at or about 2% (w/w) and is added to the oil phase at an amount of at or about 0.5% (w/w) to at or about 2%, of the concentrate, such that the resulting concentrate contains at or about 2.2% (w/w) to at or about 4% emulsion stabilizer. In another example, the concentrate contains at or about 2% to at or about 3%, such as at or about 2.2% of a modified gum acacia emulsion stabilizer and additionally contains an additional emulsion stabilizer, for example, an ester gum, added to the oil phase at an amount of at or about 0.05% to at or about 1%, such as at or about 0.06%, such that the resulting concentrate has a total amount of at or about 2% to at or about 3%, such as 2.26%, (w/w), emulsion stabilizer. In yet another example, the concentrate contains a modified gum acacia emulsion stabilizer that is added to the water phase at an amount of at or about 1.0% to at or about 1.5% (w/w) and is added to the oil phase at an amount of at or about 0.5% to at or about 1%, (w/w) of the concentrate, and an ester gum emulsion stabilizer that is added to the oil phase at an amount of at or about 0.05% to at or about 1%, such as 0.06%, (w/w) of the concentrate, such that the resulting concentrate contains at or about 1.5% to at or about 3.5%, such as 1.56%, (w/w), emulsion stabilizer.

c. Non-Polar Compounds

The concentrates contain one or more non-polar compounds. Non-polar compounds include any lipophilic or lipid soluble compounds, for example, active ingredients, that have greater solubility in organic solvents (e.g., ethanol, methanol, ethyl ether, acetone, and benzene) and in fats and oils, than in aqueous liquids, for example, water. Typically, the non-polar compounds are poorly water soluble, for example, water insoluble or compounds having low water solubility. The non-polar compounds include, but are not limited to, drugs, hormones, vitamins, nutrients and other lipophilic compounds. Exemplary non-polar compounds are listed herein below. The provided compositions and methods can be used to dilute (e.g., dissolve/disperse) any non-polar compound in a water-based finished food or beverage. In one example, the non-polar compound differs from the surfactant, for example, is not a Vitamin E. Exemplary of non-polar compounds that can be used in the provided concentrates are:

Non-polar compounds containing essential fatty acids, for example, polyunsaturated fatty acids (PUFAs), for example, gamma-linolenic acid (GLA), for example, borage oil and evening primrose (*Oenothera biennis*) oil, blackcurrant seed oil, hemp seed oil, and spirulina extract; compounds containing omega-3 fatty acids, for example, natural and synthetic omega-3 fatty acids, for example, compounds containing omega-3 polyunsaturated long-chain fatty acids, including Eicosapentaenoic acid (EPA) (20:5ω3); Docosahexaenoic acid (DHA) (22:6ω3); Eicosatetraenoic acid (24:4ω3); Docosapentaenoic acid (DPA, Clupanodonic acid) (22:5ω3); 16:3 ω3; 24:5 ω3 and/or nisinic acid (24:6ω3), for example, fish oil, algae oil, krill oil, canola oil, flaxseed oil, soybean oil and walnut oil; compounds containing short-chain omega-3 fatty acids, for example, Alpha-Linolenic acid (α-Linolenic acid; ALA) (18:3ω3) and Stearidonic acid (18:4ω3), esters of an omega-3 fatty acid and glycerol, for example, monoglycerides, diglycerides and triglycerides, esters of an omega-3 fatty acid and a primary alcohol, for example, fatty acid methyl esters and fatty acid esters, precursors of omega-3 fatty acid oils, for example, EPA precursor, DHA precursor, derivatives such as polyglycolized derivatives or polyoxyethylene derivatives, oils containing the omega-3 fatty acids, for example, fish oil (marine oil), for example, highly purified fish oil concentrates, *perilla* oil, krill oil, and algae oil, for example, microalgae oil; compounds containing omega-6 fatty acids, for example, compounds containing Linoleic acid (18:2ω6) (a short-chain fatty acid); Gamma-linolenic acid (GLA) (18:3ω6); Dihomo gamma linolenic acid (DGLA) (20:3ω6); Eicosadienoic acid (20:2ω6); Arachidonic acid (AA) (20:4ω6); Docosadienoic acid (22:2ω6); Adrenic acid (22:4ω6); and/or Docosapentaenoic acid (22:5ω6), for example, borage oil, corn oil, cottonseed oil, grapeseed oil, peanut oil, primrose oil, for example, evening primrose *Oenothera biennis*) oil, blackcurrant seed oil, hemp seed oil, spirulina extract, safflower oil, sesame oil and soybean oil;

Other fatty acids, for example, triglycerides, including medium chain triglycerides, polar lipids, for example, ether lipids, phosphoric acid, choline, fatty acids, glycerol, glycolipids, triglycerides, and phospholipids (e.g., phosphatidylcholine (lecithin), phosphatidylethanolamine, and phosphatidylinositol); saw palmetto extract; and ethyl linoleate; and herb oils, for example, garlic oils and scordinin; short-chain saturated fatty acids (4:0-10:0), Lauric acid (12:0), Myristic acid (14:0), Pentadecanoic acid (15:0), Palmitic acid (16:0), Palmitoleic acid (16:1 ω7), Heptadecanoic acid (17:0), Stearic acid (18:0), Oleic acid (18:1 ω9), Arachidic acid (20: 0);

Micronutrients, for example, vitamins, minerals, co-factors, for example, Coenzyme Q10 (CoQ10, also called ubiquinone), ubiquinol, tumeric extract (cucuminoids), saw palmetto lipid extract (saw palmetto oil), echinacea extract, hawthorn berry extract, ginseng extract, lipoic acid (thioctic acid), ascorbyl palmitate, kava extract, St. John's Wort (hypericum, Klamath weed, goat weed), extract of quercitin, dihydroepiandrosterone, and indol-3-carbinol;

Carotenoids, including hydrocarbons and oxygenated, alcoholic derivatives of hydrocarbons, for example, beta carotene, mixed carotenoids complex, lutein, lycopene, Zeaxanthin, Cryptoxanthin, for example, beta-crytoxanthin, beta carotene, mixed carotenoids complex, astaxanthin, bixin, canthaxanthin, capsanthin, capsorubin, apo-carotenal, beta-12'-apo-carotenal, "Carotene" (mixture of alpha and beta-carotene), gamma carotene, ciolerythrin, zeaxanthin, and esters of hydroxyl- or carboxyl-containing members thereof;

Fat-soluble vitamins, for example, Vitamins A, D, particularly $D_3$, E and K, and corresponding provitamins and vitamin derivatives such as esters with an action resembling that of vitamin A, D, E or K for example, retinol (vitamin A) and pharmaceutically acceptable derivatives thereof, for example, palmitate ester of retinol and other esters of retinol, for example, Vitamin A Palmitate, and calciferol (vitamin D) and its pharmaceutically acceptable derivatives thereof and precursors of vitamin D, d-alpha tocopherol (vitamin E) and derivatives thereof, including pharmaceutical derivatives thereof, for example, Tocotrienols, d-alpha tocopherol acetate and other esters of d-alpha tocopherol, and ascorbyl palmitate, a fat-soluble version of vitamin C;

Phytochemicals, including phytoestrogens, for example, genistein and daidzein, for example, isoflavones, for example; soy isoflavones, flavonoids, phytoalexins, for example, Resveratrol (trans-3,5,4'-trihydroxystilbene), red clover extract, and phytosterols;

Lipid-soluble drugs, including natural and synthetic forms of immunosuppressive drugs, such as Cyclosporin, protease inhibitors such as Ritonavir, macrolide antibiotics and oil soluble anesthetics such as Propofol, natural and synthetic forms of steroidal hormones, for example, estrogens, estradiols, progesterone, testosterone, cortisone, phytoestrogens, dehydroepiandrosterone (DHEA), growth hormones and other hormones; and Oil-soluble acids and alcohols, for example, tartaric acid, lactylic acid, butylated hydroxyanisole, butylated hydroxytoluene, lignin, sterols, polyphenolic compounds, oryzanol, cholesterol, phytosterols, flavonoids, such as quercetin and resveratrol, and diallyl disulfides.

The concentrates provided herein contain one or more non-polar compound(s), such that the total amount of the one or more non-polar compound(s) typically is up to at least or up to and including 50%, such as a concentration range of between 15% or about 15% and 50% or about 50% (w/w) of the concentrate, for example within a range of between 20% or about 20% and 50% or about 50%, for example, typically between at or about 20% and at or about 45%, or between at or about 25% and at or about 45%, or between at or about 20% and at or about 40%, such as a starting concentration of 15% or about 15%, 16% or about 16%, 17% or about 17%, 18% or about 18%, 19% or about 19%, 20% or about 20%, 21% or about 21%, 22% or about 22%, 23% or about 23%, 24% or about 24%, 25% or about 25%, 26% or about 26%, 27% or about 27%, 28% or about 28%, 29% or about 29%, 30% or about 30%, 31% or about 31%, 32% or about 32%, 33% or about 33%, 34% or about 34%, 35% or about 35%, 36% or about 36%, 37% or about 37%, 38% or about 38%, 39% or about 39%, 40% or about 40%, 41% or about 41%, 42% or about 42%, 43% or about 43%, 44% or about 44%, 45% or about 45%, 46% or about 46%, 47% or about 47%, 48% or about 48%, 49% or about 49%, or 50 or about 50% (w/w) of the concentrate. Typically, the concentration of the total amount of non-polar compounds is between at or about 20% and at or about 36%, (w/w) of the concentrate. Exemplary of the total amount of non-polar compound concentrations within the appropriate range are 21.04%, 32.001%, 35.751%, 35.79%, 35.801% and 35.84%, (w/w) of the concentrate.

Typically, the amount of each individual non-polar compound within the provided compositions is added at a concentration such that the total concentration of the one or more non-polar compounds (non-polar active ingredients) is within a concentration range of between 15% or about 15% and 50% or about 50% (w/w) of the concentrate, more typically within a range of between 20% or about 20% and 50% or about 50%, for example, between at or about 20% and at or about 45%, between at or about 25% and at or about 45%, or between at or about 20% and at or about 40%, (w/w) of the concentrate. For example, when the concentrate contains a polyunsaturated fatty acid-containing active ingredient, the PUFA-containing compound is typically present in an amount between 15% or about 15% and 40% or about 40%, (w/w) of the concentrate, more typically at an amount between at or about 20% and at or about 36%, such as, for example, 21%, 21.25%, 25% and 35.8%, (w/w) of the concentrate. In some examples, when the concentrate contains a vitamin non-polar active ingredient, the vitamin non-polar compound is typically present in an amount between 0.0001% or about 0.0001% and 1% or about 1%, more typically between at or about 0.001% and at or about 0.1%, such as, for example, 0.001% or 0.04%. In other examples, when the concentrate contains a phytochemical-, carotenoid-, or coenzyme Q-containing active ingredient, the phytochemical-, carotenoid-, or coenzyme Q-containing compounds are typically present in an amount between 5% or about 5% and 15% or about 15%, more typically between at or about 8% and at or about 13%, such as, for example, 10.75%. In other example, when the concentrate contains a lipoic acid containing active ingredient, the lipoic acid compound is typically present in an amount between 5% or about 5% and 15% or about 15%, more typically between at or about 8% and at or about 13%, such as, for example, 10.50% or 10.75%.

Typically, the concentrates provided herein contain one or more non-polar compounds, at an amount such that upon dilution of the concentrate in a water-based finished food or beverage, a serving of the food or beverage provides a specific amount of non-polar active ingredient. For example, the concentrates provided herein provide between at or about 1.5 to at or about 3.0 grams (g) of omega-6 fatty acids per serving, between at or about 16 to at or about 220 milligrams (mg), for example, between at or about 32 to at our about 220 mg docosahexaenoic acid (DHA) and eicosapentaenoic acid (EPA) per serving, between at or about 100 and at or about 500 mg phytosterols per serving, between at or about 10 and at or about 200 mg, for example, between at or about 50 and at or about 200 mg Coenzyme Q10 per serving, between at or about 40 and at or about 400 micrograms (mcg) Vitamin A per serving, or between at or about 200 and at or about 2000 international units (IU), for example between at or about 400 and at or about 800 IU Vitamin D3 per serving of food or beverage, for example, per 8 ounces of a beverage.

i. Polyunsaturated Fatty Acid (PUFA)-Containing Active Ingredients

Exemplary of the non-polar compounds contained in the concentrates are compounds containing fatty acids, for example, active ingredients containing polyunsaturated fatty acids (PUFAs). Fatty acids are straight-chain hydrocarbon molecules with a carboxyl (COOH) group at one end of the chain. PUFAs are fatty acids that contain more than one carbon-carbon double bond in the carbon chain of the fatty acid. PUFAs, particularly essential fatty acids, are useful as dietary supplements.

Different nomenclatures can be used to describe fatty acid molecules. Lipid nomenclature, for example, 18:3 ω-3, indicates the carbon chain length, number of double bonds and the position along the carbon chain of the first carbon-carbon double bond in a fatty acid. Using this nomenclature, each carbon along the chain is labeled according to its position relative to one end of the chain. For example, the first carbon away from the carboxylate end is named α, the second is named β, and so forth. The last carbon in the molecule (furthest from the carboxy group) always is labeled ω (or omega, or n). The number of carbons and the number of double bonds are listed first in the lipid name of a fatty acid, separated by a colon. For example, the name "18:3" indicates that the molecule has eighteen (18) carbons and three (3) double bonds. Following these numbers, the position at which the first double bond appears, relative to the last (ω) carbon, is listed. For example, the nomenclature, 18:3 ω-3 (or 18:3 omega-3; or 18:3 n-3), describes a fatty acid with eighteen (18) carbons and three (3) double bonds, the first of which occurs at the third carbon away from the omega carbon.

Alternatively, chemical nomenclature can be used. The chemical name of a fatty acid describes the position of each double bond. In the chemical naming, the carbons are numbered, beginning with 1, starting with the carbon that is part of the carboxy (COOH) group. Thus, with this numbering system, the α carbon is labeled "2." The chemical name of the fatty acid lists the first carbon (from the COOH end) to participate in each double bond.

Certain PUFAs are called essential fatty acids because mammals, including humans, cannot synthesize them using any known chemical pathway, and must obtain them from diet or by supplementation. (U.S. Pat. No. 6,870,077; Covington, *American Family Physician* (2004), 70(1): 133-140). The essential PUFAs are the omega-3 (ω3; n-3) fatty acids and the omega-6 (ω-6; n-6) fatty acids. Omega-3 and omega-6 fatty acids are methylene interrupted polyenes, which have two or more cis double bonds, separated by a single methylene group. Exemplary of omega-3 fatty acids are Alpha-Linolenic acid (α-Linolenic acid; ALA) (18:3 ω3) (a short-chain fatty acid); Stearidonic acid (18:40) (a short-chain fatty acid); Eicosapentaenoic acid (EPA) (20:5 ω3); Docosahexaenoic acid (DHA) (22:6 ω3); Eicosatetraenoic acid (24:4 ω3); Docosapentaenoic acid (DPA, Clupanodonic acid) (22:5 ω3); 16:3 ω3; 24:5 ω3; and nisinic acid (24:6 ω3). Longer chain Omega-3 fatty acids can be synthesized from ALA (the short-chain omega-3 fatty acid). Exemplary of omega-6 fatty acids are Linoleic acid (18:2 ω6) (a short-chain fatty acid); Gamma-linolenic acid (GLA) (18:3 ω6); Dihomo gamma linolenic acid (DGLA) (20:3 ω6); Eicosadienoic acid (20:2 ω6); Arachidonic acid (AA) (20:4 ω6); Docosadienoic acid (22:2 ω6); Adrenic acid (22:4 ω6); and Docosapentaenoic acid (22:5 ω6).

While the longer chain omega-3 and omega-6 essential fatty acids can be synthesized from ALA (the short-chain omega-3 fatty acid) and Linolenic acid (LA), respectively, evidence suggests that conversion of these short chain fatty acids in humans is slow. Thus, a major source of long chain essential PUFAs is dietary (see e.g., Ross et al. (2007) *Lipids in Health and Disease* 6:21; Lands (1992) *FASEB* 6(8): 2530). Dietary supplements containing PUFAs, particularly essential PUFAs, are desirable for protection against cardiovascular disease, inflammation and mental illnesses (see e.g., Ross et al. (2007) *Lipids in Health and Disease* 6:21; Lands (1992) *FASEB* 6(8): 2530; U.S. Pat. No. 6,870,077). Evidence suggests that essential fatty acids, particularly EPA and DHA, in the form of food and nutritional supplements, play a role in preventing a number of disease states, including cardiovascular diseases, inflammation, mental health and behavioral diseases and disorders (see e.g., Ross et al. (2007) *Lipids in Health and Disease* 6:21; Lands (1992) *FASEB* 6(8): 2530; U.S. Pat. No. 6,870,077; Covington (2004) *American Family Physician* 70(1): 133-140).

Omega-9 fatty acids are non-essential PUFAs. Exemplary of omega-9 fatty acids are Oleic acid (which is monounsaturated) (18:1 ω9); Eicosenoic acid (20:1 ω9); Mead acid (20:3 ω9); Erucic acid (22:1 ω9); and Nervonic acid (24:1 ω9). Exemplary of an omega-9 fatty acid is oleic acid, for example, Oleic Acid 70% Food Grade Kosher Vegetable-Based, 100% Natural, sold by KIC Chemicals, Inc., Armonk, N.Y., containing at least 70% oleic acid and not more than 18% other fatty acids.

Conjugated fatty acids are PUFAs with two or more conjugated double bonds. Conjugated fatty acids can be used as nutritional supplements. Exemplary of conjugated fatty acids are Conjugated Linoleic acid (CLA), for example, 18:2 ω7, 18:2 ω6; Conjugated Linolenic acid, for example, 18:3ω6, 18:3ω5; and other conjugated fatty acids, for example, 18:3 ω3, 18:4 ω3, and 20:5 ω6.

(1) Omega-3 Fatty Acid Compounds

Exemplary of the PUFA-containing active ingredients that can be used in the provided compositions are compounds that contain one or more omega-3 (ω3; n-3) fatty acids, for example, compounds containing DHA and/or EPA fatty acids, for example, marine oils, for example, fish oil, krill oil and algae oil; and compounds containing ALA fatty acids, for example, flax seed oil.

Typically, oils and aqueous compositions containing long-chained polyunsaturated fatty acids (PUFA) are susceptible to oxidation, making them unstable and giving them an unpleasant taste. The ingredients and relative concentrations thereof, as well as the methods for making the concentrates, contribute to desirable properties of DHA/EPA-containing concentrates. In one example, ingredients and methods minimize the "fishy" odor and/or taste of DHA/EPA compositions and increase their stability over time. In one aspect, the compounds in the concentrates have low oxidation, contributing to these desirable properties.

(a) DHA/EPA

Exemplary of non-polar active ingredients that contain one or more omega-3 fatty acids, which can be used in the provided compositions, are compounds containing DHA and/or EPA, for example, marine oil, for example, fish oil, krill oil and algae oil. Any oil containing DHA and/or EPA can be used. In one example, the non-polar active ingredient contains between 10% or about 10% and 40% or about 40% DHA. In another example, the non-polar active ingredient contains between 25% or about 25% and 35% or about 35% DHA. In another example, the non-polar active ingredient contains at least 70% or about 70%, by weight (w/w), DHA, for example, at least 75% or about 75%, at least 80% or about 80%, at least 85% or about 85%, or at least 90% or about 90%, by weight (w/w), DHA. In another example, the non-polar active ingredient contains between 5% or about 5% and 20% or about 20% EPA, for example, at or about 5, 6, 7, 8, 9, 10, 11, 12, 13, 14, 15, 16, 17, 18, 19 or 20%, by weight (w/w), EPA. In another example, the non-polar active ingredient contains not more than 10% or about 10% EPA or less than 10% or about 10% EPA. In another example, the non-polar active ingredient contains DHA and EPA, for example, DHA representing at least 20% or about 20%, by weight of the non-polar active ingredient and EPA representing not more than 13% or about 13% of the non-polar active ingredient, for example, not more than 10% or about 10%, by weight of the non-polar active ingredient. In another example, the non-polar active ingredient contains DHA, representing at least 35% or about 35% of the non-polar active ingredient and EPA representing not more than 13% or about 13% of the non-polar active ingredient, for example, not more than 10% or about 10% of the non-polar active ingredient. In another example, the non-polar active ingredient contains DHA and EPA, for example, DHA representing at least 70% or about 70% of the non-polar active ingredient and EPA representing not more than 13% or about 13% of the non-polar active ingredient, for example, not more than 10% or about 10% of the non-polar active ingredient. In another example, the non-polar active ingredient contains DHA and EPA, for example, DHA representing at least 9% or about 9% of the non-polar active ingredient, for example, at least 11% or about 11% or the non-polar active ingredient and EPA representing at least 15% or about 15% of the non-polar active ingredient, for example, at least 17% or about 17% of the non-polar active ingredient. Omega-3 containing non-polar active ingredients are typically added to the compositions in amounts such that when diluted in a food or beverage, one serving of the food or beverage provides an amount of the DHA and EPA between at or about 16 and at or about 220 mg, typically between at or about 32 and at or about 220 mg, between at or about 50 and at or about 150 mg, between at or about 100 and at or about 220 mg, for example, at or about 16, at or about 32, at or about 50, at or about 100, at or about 150, at or about 200 or at or about 220 mg, per serving of the food or beverage, such as for example, 8 ounces of a beverage.

(i) Fish Oils

Exemplary of the PUFA-containing non-polar active ingredients that can be used in the provided compositions are oils derived from fish, which contain DHA, EPA or DHA and EPA. Particularly, cold water marine fish are a known source of Omega-3 fatty acids (U.S. Pat. No. 4,670,285). Suitable fish oil containing DHA, EPA or DHA and EPA can be obtained from any of a number of commercial sources, for example, fish oils available from Hormel Foods Specialty Products, any of which can be used with the provided compositions.

Fish oils typically are extracted from fish tissue, for example, frozen fish tissue. In one example, the fish oil is a tasteless fish oil, for example, a cod liver oil, which has been isolated from fish, for example, from cod liver, and then refined and deodorized, or in some other way treated so its taste becomes neutral, for example, as described in International Publication Nos. WO 00/23545 and WO 2004/098311. In one example, these fish oils are isolated from frozen fish tissue by a process that minimizes oxidation. Exemplary of such a tasteless fish oil is Denomega™ 100, Borregaard Ingredients, Sarpsborg, Norway; distributed by Denomega Nutritional Oils AS, Boulder, Colo. Typically, the tasteless fish oil, for example, cod liver oil, contains between 25% or about 25% and 35% or about 35% Omega-3 fatty acids, for example, 34% Omega-3 fatty acids. In one example, the fish oil, for example, the Denomega™ 100 oil, contains 13% or about 13% DHA and 13% or about 13% EPA.

Also exemplary of the fish oils that can be included in the provided compositions are fish oils containing high amounts of Omega-3 fatty acids, for example, high amounts of DHA. One example of such a fish oil contains at least about 85 DHA, typically greater than 85% DHA and at least about 90%

Omega-3 fatty acids, typically greater than, 90% Omega-3 fatty acids. In another example, the fish oil can contain 98% PUFA, 89% Omega-3 fatty acids, about 70% DHA, about 10% EPA, 8.9% Omega-6 fatty acids and 0.7% Omega-9 fatty acids.

Exemplary of a fish oil containing high amounts of Omega-3 fatty acids that can used as the non-polar compound in the provided compositions is an Omega-3 Fish Oil EE (O3C Nutraceuticals, supplied by Jedwards International Inc., Quincy, Mass.), which contains 89% Omega-3 fatty acids, 8.9% Omega-6 fatty acids, 0.7% Omega-9 fatty acids, 0.1% saturated fatty acids, 1.0% monounsaturated fatty acids, 74.5% Docosahexanoic (DHA) fatty acids, 9.3% Eicosapentaenoic (EPA) fatty acids and 98% polyunsaturated fatty acids (PUFA). This fish oil also contains 0.1% (16:0) palmitic acid, 0.1% (16:1ω7) palmitoleic acid, 0.1% (18:0) stearic acid, 0.6% (18:1 ω9) oleic acid, 0.1% (18:1 w 7) oleic acid, 0.3% (18:2ω6) linoleic acid, 0.2% (18:3 ω3) linolenic acid, 0.2% (18:4 ω3) octadecatetraenoic acid, 0.1% (20:1 ω9) eicosanoic acid, 0.1% (20:2ω6) eicosadienoic acid, 0.2% (20:3 ω6) Eicosatrienoic Acid, 2.4% (20:4 ω6) arachidonic acid, 0.6% (20:4 ω3) arachidonic acid, 0.1% (22:1 ω11) erucic acid, 0.6% (21:5 ω3) uncosapentaenoic acid, 0.5% (22:4 ω6) docosatetraenoic acid, 5.4% (22:5 ω6), docosapentaenoic acid, 3.6% (22:5 ω3) docosapentaenoic acid and 0.9% other fatty acids.

Also exemplary of a fish oil containing high amounts of Omega-3 fatty acids that can be used in the provided compositions is Omega Concentrate 85 DHA TG Ultra (O3C Nutraceuticals AS, Oslo, Norway), which contains greater than 85% DHA (C22:6n-3) and greater than 90% total omega-3 fatty acids and is isolated from fatty fish species Eugraulidae, Clupeidae and Scombridae families. This fish oil is produced by purifying and concentrating the oils from these fish with gentle technologies to increase the concentration of omega-3 fatty acid DHA.

Any fish oil containing DHA and/or EPA can be used as the non-polar compound in the provided compositions. Exemplary of the fish oils that can be included in the provided compositions is Eterna™ Omegasource™ Oil (supplied by Hormel Foods Specialty Products Division, Austin, Minn.), which contains at least 30% Omega-3 fatty acids (DHA, EPA and ALA), is odorless, virtually free of cholesterol and bland in flavor. This fish oil contains about 28% DHA and EPA, typically 17% EPA and 11% DHA, and additionally contains 4.5% Omega-6 fatty acids. Also exemplary of the fish oils that can be included in the provided compositions are Omega 30 TG Food Grade (Non-GMO) MEG-3™ Fish Oil (supplied by Ocean Nutrition Canada, Dartmouth, Nova Scotia, Canada), a Kosher fish oil which contains about 30% DHA/EPA and Marinol C-38 (supplied by Lipid Nutrition B.V., Channahon, Ill.), which contains about 52% omega-3 fatty acids, including at least 38% DHA/EPA, more specifically includes about 22% EPA and 14% DHA. Also exemplary of the fish oils are other fish oils made by O3C Nutraceuticals, AS and other fish oils supplied by Jedwards, International, Inc. Also exemplary of a fish oil is Marinol D-40 (supplied by Lipid Nutrition B.V., Channahon, Ill.), which contains about 40% DHA and 7% EPA.

Also exemplary of the fish oils are hill oils, made according to International Publication No. WO 2007/080515.

(ii) Algae Oil

Also exemplary of non-polar compounds containing Omega-3 PUFAs, particularly DHA (and optionally EPA), that can be used as the non-polar compound in the provided compositions are oils derived from microorganisms, for example, oils derived from marine dinoflagellates, for example, microalgae, for example, *Crypthecodinium* sp, particularly, *Crypthecodinium cohnii*. Microalgae oils, like algal oil, are an excellent source of omega-3 fatty acids, particularly DHA (see e.g., U.S. Pat. Nos. 5,397,591, 5,407,957, 5,492,938 and 5,711,983). Exemplary of oils derived from microalgae are the oils disclosed in, and oils made according to the methods described in, U.S. Pat. Nos. 5,397,591, 5,407, 957, 5,492,938 and 5,711,983 and U.S. Publication number 2007/0166411, including DHASCO® and DHASCO-S® (Martek Biosciences Corporation).

For example, U.S. Pat. No. 5,397,591 describes, inter alia, single cell edible oils (algae oils) (and methods for making the oils), which contain at least 70% triglycerides, which contain about 20-35% DHA and lack EPA, isolated from *Crypthecodinium cohnii*, generally containing more than 70% triglycerides, having 15-20% myristic acid; 20-25% palmitic acid; 10-15% oleic acid; 30-40% DHA and 0-10% other triglycerides. U.S. Pat. No. 5,407,957 describes, inter alia, algae oils (and methods for making the oils) derived from *Crypthecodinium cohnii*, generally containing greater than about 90% triglycerides, at least 35% DHA by weight (w/w), in one example, having 15-20 myristic acid, 20-25% palmitic acid, 10-15% oleic acid, 40-45% DHA, and 0-5% other oils. U.S. Pat. No. 5,492,938 describes, inter alia, single cell edible oils (and methods for making the oils) containing at least 70% triglycerides, which contain about 20-35% DHA and lack EPA, isolated from *Crypthecodinium cohnii*, in one example, containing more than 70% triglycerides, having 15-20% myristic acid; 20-25% palmitic acid; 10-15% oleic acid; 30-40% DHA; 0-10% other triglycerides. U.S. Pat. No. 5,711,983 describes, inter alia, single cell edible oils (and methods for making the oils) containing at least 70% triglycerides, which contain about 20-35% DHA and lack EPA, isolated from *Crypthecodinium cohnii*, in one example, containing more than 70% triglycerides, having 15-20% myristic acid; 20-25% palmitic acid; 10-15% oleic acid; 30-40% DHA and 0-10% other triglycerides.

Also exemplary of suitable microalgae oils are those disclosed, for example, in U.S. Pat. No. 6,977,166 and U.S. Publication Number US 2004/0072330. Exemplary of an algal oil that can be included in the provided compositions is Martek DHA™-S (supplied by Martek Biosciences Corporation, Columbia, Md.), derived from the marine alga *Schizochytrium* sp., containing not less than 35% DHA. This algal oil additionally contains 16.1% (22:5 ω6) docosapentaenoic acid, 1.3% (20:5 ω3) eicosapentaenoic acid, 0.6% (20:4 ω6) arachidonic acid, 1.6% (18:2 ω6) linoleic acid, 16.9% (18:1 ω9) oleic acid and 19.8% other fatty acids. Also exemplary of an algal oil that can be included in the provided compositions is Docosahexaenoic acid (supplied by VB Medicare Private Limited, Bangalore, Ind.), derived from the marine alga *Schizochytrium* sp., containing not less than 35% DHA. Any oil derived from dinoflagellate, for example, microalgae, which contains DHA, and optionally EPA, is suitable as an algae oil for use with the provided compositions, for example, V-Pure algae oil (Water4Life, Switzerland), which contains EPA and DHA.

(b) Flax Seed Oil—Omega 3 (ALA)

Also exemplary of the Omega-3 containing non-polar compounds used in the provided compositions is flaxseed oil (flaxseed oil, linseed oil). Flaxseed oils, which are good sources of omega-3 fatty acids, particularly alpha-linolenic acid, have been used as nutritional supplements. Flaxseed oils are produced by pressing the flax seed and refining the oil from the flax seeds. Exemplary of a flaxseed oil that can be used as the non-polar compound in the provided compositions is flaxseed oil derived from *Linum usitatissimum* L., for example, flaxseed oil supplied by Sanmark LLC, Greensboro, N.C. (Sanmark Limited, Dalian, Liaoning Province, China), which contains not less than (NLT) 50% C18:3 alpha-linolenic acid, and further contains other fatty acids, for example, 3-8% C16:0 Palmitic acid, 2-8% C18:0 Stearic acid, 11-24% C18:1 Oleic acid, 11-24% C18:2 linoleic acid and 0-3% other fatty acids. Also exemplary of suitable flaxseed oil is a flaxseed oil containing 6% Palmitic acid, 2.5% stearic acid, 0.5% arachidic acid, 19% oleic acid, 24.1% linoleic acid, 47.4% linolenic acid, and 0.5% other fatty acids. Also exemplary of flaxseed oil that can be used as the non-polar compound in the provided compositions is Barlean's Organic Flaxseed Oil (supplied by Barlean's Organic Oils, Ferndale, Wash.), containing not less than 55% alpha-linolenic acid, and further contains other fatty acids, for example, 5.5% C16:0 Palmitic acid, 5% C18:0 Stearic acid, 17% C18:1 Oleic acid, 17% C18:2 linoleic acid and 0-1% other fatty acids. The fatty acid composition of flaxseed oil can vary. Any flaxseed oil can be used as the non-polar compound in the provided compositions. In one example, the flaxseed oil contains at least 45% alpha-linolenic acid or at least about 45% alpha-linolenic acid. In another example, the flaxseed oil contains at least 65% or about 65% or 70% or about 70% alpha-linolenic acid. Exemplary of a flaxseed containing greater than 65% linolenic acid content (of total fatty acid content), for example, 70-80% or 70-75%, is the flaxseed described in U.S. Pat. No. 6,870,077.

(2) Omega-6 Compounds

Also exemplary of the non-polar compounds used in the provided compositions are compounds containing omega-6 PUFAs, for example, gamma-linolenic acid (GLA), for example, borage oil and evening primrose (*Oenothera biennis*) oil, blackcurrant seed oil, hemp seed oil, fungal oil and spirulina extract. Any oil containing omega-6 fatty acids can be used in the provided compositions.

(a) Borage Oil (Gamma-Linolenic Acid (GLA))

Exemplary of the omega-6 containing non-polar compounds are compounds containing GLA, for example, borage oil. GLA is an omega-6 PUFA, which primarily is derived from vegetable oils, for example, evening primrose (*Oenothera biennis*) oil, blackcurrant seed oil, hemp seed oil, and spirulina extract. GLA has been used as a nutritional supplement. It has been proposed that GLA has a role in treating various chronic diseases and in particular that it has anti-inflammatory effects (Fan and Chapkin, *The Journal of Nutrition* (1998), 1411-1414). In one example, the non-polar active ingredient contains at least about 22% or about 22%, by weight (w/w), GLA, for example, at or about 22, 23, 24, 25, 26, 27, 28, 29, 30, 31, 32, 33, 34, 35, 36, 37, 38, 39, 40, 50, 60%, or more, by weight (w/w), GLA. Omega-6 containing non-polar active ingredients are typically added to the compositions in amounts such that when diluted in a food or beverage, one serving of the food or beverage provides an amount of the GLA between at or about 1.5 and at or about 3 g, typically between at or about 1.5 and at or about 2 g, between at or about 1.5 and at or about 2.5 g, between at or about 2 and at or about 2.5 g, between at or about 2 and at or about 3 g, between at or about 2.5 and at or about 3, for example, at or about 1.5, at or about 2, at or about 2.5 or at or about 3 g, per serving of the food or beverage, such as for example, 8 ounces of a beverage.

Borage (*Borago officinalis*), also known as "starflower," is an herb with seeds containing high amounts of GLA. Exemplary of a borage oil that is used as a non-polar active ingredient in the provided compositions is the borage oil supplied by Sanmark LLC, Greensboro, N.C. (Sanmark Limited, Dalian, Liaoning Province, China), derived by pressing and isolating oil from the seeds of *Borago officinalis* L. This oil contains not less than (NLT) 22% C18:3 gamma-linolenic acid (GLA), between 9 and 12% C16:0 Palmitic acid, between 3% and 5% C18:0 Stearic acid, between 15% and 20% C18:1 Oleic acid, between 35% and 42% C18:2 linoleic acid, between 3% and 5% C20:1 Ocosenoic acid, between 1% and 4% C22:1 Docosenoic acid and between 0% and 4% other fatty acids. Other borage oils can be used. Other GLA-containing oils also can be used as the non-polar compound.

(3) Saw Palmetto Extract

Also exemplary of the non-polar compounds used in the provided compositions is saw palmetto extract, a lipophilic extract of the ripe berries of the American dwarf palm (also called *Serenoa repens* or *Sabal serrulata*), which has been used to treat genitourinary and other diseases and to enhance sperm production, breast size and libido, as a mild diuretic, a nerve sedative, an expectorant and a digestive tract tonic, and particularly to treat benign prostate hyperplasia (BPI-1) (Ernst, *Academia and Clinic* (2002), 136:42-53; Gordon and Shaughnessy, *Complementary and Alternative Medicine* (2003) 76(6):1281-1283). Saw palmetto extract is commercially available from a number of sources. Any saw palmetto lipid extract can be used in the provided compositions. Exemplary of the saw palmetto extract that can be used in the provided compositions is Saw Palmetto Lipophilic Extract, commercially available from Natural Medicinals, Inc., Felda, Fla. This Saw Palmetto Lipophilic Extract is carbon dioxide extracted and, in one example, contains, 85.9% total fatty acids, including 0.8% Caproic acid, 2% Caprylic acid, 2.4% Capric acid, 27.1 Lauric acid, 10.3 Myristic acid, 8.1% Palmitic acid, 0.2% Palmitoleic acid, 2% Stearic acid, 26.7 Oleic acid, 4.9% Linoleic acid, 0.7% linolenic acid, 0.42%; 0.42% phytosterols, including 0.42% beta Sitosterol, 0.09% Campesterol, 0.03% Stigmasterol; and 0.2% moisture. Other sources of saw palmetto extract can be used.

(4) Conjugated Linoleic Acid (CLA)

Also exemplary of the PUFA non-polar compounds that can be used in the provided compositions are non-polar compounds containing conjugated fatty acids. Conjugated fatty acids are PUFAs with two or more conjugated double bonds. Conjugated fatty acids can be used as nutritional supplements. Exemplary of the active ingredients containing conjugated fatty acids are compounds containing Conjugated Linoleic acid (CLA), for example, 18:2 ω7, 18:2 ω6; Conjugated Linolenic acid, for example, 18:3ω6, 18:3ω5; and other conjugated fatty acids, for example, 18:3 ω3, 18:4 ω3, and 20:5 ω6. CLA refers to a family of linoleic acid isomers found primarily in meat and dairy products of ruminants. Typically, the CLA compounds contain a mixture of different CLA isomers, for example, C18:2 CLA c9,t11, CLA t10, c12 and other CLA isomers. Exemplary of the CLA that can be used as an active ingredient in the provided compositions is CLA (80%) commercially available from Sanmark, LTD (Dalian, Liaoning Province, China; product code 01057-A80). This CLA is clear white to pale yellow oil and has the following fatty acid composition: NMT (not more than) 9.0% C16:0 Palmitic acid, NMT 4.0% Stearic acid, NMT 15.0% C18:1 Oleic acid, NMT 3.0% C18:2 Linoleic acid, NLT (not less than) 80% C18:2 CLA (including the following isomers: NLT 37.5% C18:2 CLA c9,t11, 37.5% C18:2 CLA t10, c12, and NMT 5.0% other CLA isomers); and NMT 5.0% other fatty acids. Also exemplary of the CLA that can be used as an active ingredient in the provided compositions is Clarinol G-80 (supplied by Lipid Nutrition B.V., Channahon, Ill.), containing about 80% CLA, including about 40% C18:2 CLA c9,t11 and 40% C18:2 CLA t10,c12. Also exemplary of the CLA that can be used as an active ingredient in the provided compositions is Tonalin TG 80 (supplied by Cognis Corporation, La Grange, Ill.), containing about 80% CLA, including about 40% C18:2 CLA c9,t11 and 40% C18:2 CLA t10,c12, additionally containing about 13% oleic acid, 2% palmitic acid, 3% stearic acid and less than 1% linoleic acid. Any CLA containing compounds can be used in the provided compositions.

ii. Coenzyme Q Active Ingredients

Exemplary of the non-polar active ingredients are compounds containing Coenzyme Q, for example, Coenzyme Q10 (also called CoQ10, ubiquinone, ubidecarenone, ubiquinol and vitamin Q10). Coenzyme Q compounds are benzoquinone compounds containing isoprenyl units. The number of isoprenyl units in each of the different CoQ species is indicated with a number following CoQ. For example, CoQ10 contains 10 isoprenyl units. Coenzyme Q10 is a predominant Coenzyme Q species.

Coenzyme Q can exist in two different forms: an oxidized form and a reduced form. When the oxidized form of a Coenzyme Q species is reduced by one equivalent, it becomes a ubisemiquinone, denoted QH, which contains a free radical on one of the oxygens in the benzene ring of the benzoquinone. Oxidized and reduced coenzyme Q containing compounds can be used as active ingredients in the provided compositions.

Typically, a coenzyme-containing compound used as an active ingredient in the provided compositions is included in the compositions within a concentration range of between 0% or about 0% and 15% or about 15%, typically between 5% or about 5% and 15% or about 15%, such as between at or about 8% and at or about 13%, for example, at or about 5%, 6%, 7%, 8%, 9%, 10%, 10.75%, 10.89%, 11%, 12%, 13%, 14% or 15%, w/w, of the concentrate. Coenzyme Q-containing non-polar compounds are typically added to the compositions in amounts such that when diluted in a food or beverage, one serving of the food or beverage provides between at or about 10 and at or about 200 mg, typically, between at or about 10 and at or about 100 mg, between at or about 10 and at or about 150 mg, between at or about 50 and at or about 150 mg, between at or about 50 and at or about 200 mg, between at or about 100 and at or about 200 mg, for example, at or about 10, at or about 20, at or about 50, at or about 100, at or about 150 or at or about 200 mg coenzyme Q, for example Coenzyme Q10, per serving of the food or beverage, such as for example, 8 ounces of a beverage.

(1) Coenzyme Q10

Exemplary of the Coenzyme Q containing non-polar compounds that can be used in the provided compositions are non-polar compounds containing Coenzyme Q10. Coenzyme Q10 (also called CoQ10, ubiquinone, ubidecarenone, ubiquinol, and vitamin Q10) is a benzoquinone compound that contains 10 isoprenoid units. The "Q" in the name refers to Quinone and the 10 refers to the number of isoprenoid units. CoQ10 typically refers to the oxidized form of CoQ10, which also is referred to as ubidecarenone, as opposed to the reduced form of CoQ10. In both the reduced and oxidized CoQ10 are exemplary of the coenzyme Q species that can be used as active ingredients in the provided compositions.

CoQ10 has electron-transfer ability and is present in cellular membranes, such as those of the endoplasmic reticulum, peroxisomes, lysosomes, vesicles and the mitochondria. A decrease in natural CoQ10 synthesis has been observed in sick and elderly people. Because of this observation and its potent antioxidant properties, CoQ10 is used as a dietary supplement and a treatment for diseases such as cancer and heart disease. CoQ10, however, exhibits relatively poor bioavailability.

CoQ10 containing compounds are available commercially. Any CoQ10 compound or reduced CoQ10 compound can be used with the provided composition. Exemplary of the CoQ10 compounds that can be used as active ingredients are coenzyme Q10 compounds containing greater than 98% or greater than about 98% ubidecarenone, for example, the compound sold under the name Kaneka Q10™ (USP Ubidecarenone) by Kaneka Nutrients, L.P., Pasadena, Tex. The compound sold under the name Kaneka Q10™ is fermented entirely from yeast and is identical to the body's own CoQ10 and free from the cis isomer found in some synthetically produced CoQ10 compounds. Any CoQ10 compound can be used in the provided compositions.

iii. Phytochemical-Containing Active Ingredients

Exemplary of the non-polar compounds used as active ingredients in the provided compositions are phytochemical-containing compounds, for example, phytosterols (plant sterols), phytoestrogens, for example, genistein and daidzein, flavonoids, for example, isoflavones, for example, soy isoflavones, phytoalexins, for example, Resveratrol (trans-3,5,4'-trihydroxystilbene) and red clover extract.

Typically, phytochemical-containing compounds are used in the provided compositions within a concentration range of between 0% or about 0% and 15% or about 15%, typically between 5% or about 5% and 15% or about 15%, such as between at or about 8% and at or about 13%, for example, at or about 5%, 6%, 7%, 8%, 9%, 10%, 10.75%, 10.89%, 11%, 12%, 13%, 14% or 15%, w/w, of the concentrate.

(1) Phytosterols

Exemplary of the phytochemical-containing compounds used as active ingredients in the provided compositions are phytosterols (plant sterols). Plant sterols are structurally similar to cholesterol and have been found to reduce the absorption of dietary cholesterol, which can affect the levels of serum cholesterol. According to the U.S. Food and Drug Administration (FDA), two servings per day, each containing 0.4 grams of plant sterols, for a total daily intake of at least 0.8 grams, as part of a diet low in saturated fat and cholesterol, may reduce the risk of heart disease. Thus, plant sterols are used in nutritional supplements.

Phytosterol non-polar compounds are typically added to the compositions in amounts such that when diluted in a food or beverage, one serving of the food or beverage provides between at or about 100 and at or about 1000 mg, typically between at or about 100 and at or about 500 mg, between at or about 100 and at or about 800 mg, between at or about 300 and at or about 500 mg, between at or about 300 and at or about 800 mg, between at or about 500 and at or about 1000 mg, for example, at or about 100, at or about 200, at or about 300, at or about 400, at or about 500, at or about 600, at or about 700, at or about 800, at or about 900 or at or about 1000 mg phytosterols, per serving of the food or beverage, such as for example, 8 ounces of a beverage.

Any phytosterol-containing compound can be used as an active ingredient in the provided compositions. Exemplary of the phytosterol-containing compounds that can be used as active ingredients in the provided compositions are compounds containing plant sterols, for example, the compound sold under the name CardioAid™, distributed by B&D Nutrition and manufactured by ADM Natural Health and Nutrition, Decatur, Ill. This compound contains Kosher, Pareve, and Halal plant sterols that are produced under current food GMPs. The sterols are PCR negative and the material is derived from genetically modified organisms (GMOs). This phytosterol compound contains a minimum of 95% plant sterols, which can include up to 5 plant sterols. The compound can contain, for example, 40-58% Beta sitosterol, 20-30% Campesterol, 14-22% Stigmasterol, 0-6% Brassicasterol and 0-5% Sitostanol. The compound further can contain tocopherols, for example, 0-15 mg/g tocopherols. The compound is tested and is negative for microorganisms, such as *Salmonella*, *E. coli* and *Staphylococcus aureus*.

(2) Resveratrol

Exemplary of the phytochemical-containing compounds used as active ingredients in the provided compositions is resveratrol. Resveratrol, or trans-resveratrol (trans-3,5,4'-trihydroxystilbene), is a phytoalexin naturally produced by several plants, such as the Japanese knotweed, and also is found in the skin and seeds of grapes, numerous berries, including mulberry, blueberries, bilberries and cranberries, and in peanuts. This polyphenolic compound can act as an antioxidant and additionally aid in cancer prevention and reduction of cardiovascular disease.

Any resveratrol-containing compound can be used as an active ingredient in the provided compositions. Exemplary of the resveratrol-containing compounds that can be used as active ingredients in the provided compositions are compounds containing trans-resveratrol, for example the compounds sold under the name ReserveNature™, sold by Jiaherb, Shaanxi, China. This compound contains trans-resveratrol from the botanical source *Polygonum cuspidatum* (Japanese knotweed). This resveratrol compound contains a minimum of 98.5% trans resveratrol and does not contain emodin. The compound is tested and is negative for microorganisms, such as *Salmonella*, *E. coli*, yeast and mold.

iv. Carotenoid-Containing Active Ingredients

Exemplary of the non-polar compounds used as active ingredients in the provided compositions are carotenoid-containing compounds, for example, carotenoids, including hydrocarbons (carotenes) and oxygenated, alcoholic derivatives of hydrocarbons (xanthophylls), for example, beta carotene, mixed carotenoids complex, lutein, Zeaxanthin, cryptoxanthin, for example, beta-crytoxanthin, lycopene, beta carotene, mixed carotenoids complex, astaxanthin, bixin, canthaxanthin, capsanthin, capsorubin, apo-carotenal, beta-12'-apo-carotenal, "Carotene" (mixture of alpha and beta-carotene), gamma carotene, ciolerythrin, zeaxanthin, and esters of hydroxyl- or carboxyl-containing members thereof.

Carotenoids are efficient free-radical scavengers, or anti-oxidants, and are capable of enhancing the vertebrate immune system.

Typically, carotenoid-containing compounds are used in the provided compositions within a concentration range of between 0% or about 0% and 15% or about 15%, typically between 5% or about 5% and 15% or about 15%, such as between at or about 8% and at or about 13%, for example, at or about 5%, 6%, 7%, 8%, 9%, 10%, 10.75%, 10.89%, 11%, 12%, 13%, 14% or 15%, w/w, of the concentrate.

(1) Carotenes

Exemplary of the carotenoid-containing compounds used as active ingredients in the provided compositions are carotenes, for example, alpha-carotene, beta-carotene and lycopene. Any carotene-containing compound can be used as an active ingredient in the provided compositions. Exemplary of the carotene-containing compounds that can be used as active ingredients in the provided compositions is lycopene, sold by Zhejiang Medicine CO., LTD, Xinchang Pharmaceutical Factory, Xinchang, China, a purple or red crystalline powder containing not less than 70% all E-lycopene, not more than 23% 5-Z-lycopene and not more than 9% related substances.

(2) Xanthophylls

Exemplary of the carotenoid-containing compounds used as active ingredients in the provided compositions are xanthophylls, for example, neoxanthin, violaxanthin, α- and β-cryptoxanthins, lutein and zeaxanthin. Xanthophylls, or phylloxanthins, are oxygen containing carotenoids that are typically yellow pigments. Any carotene-containing compound can be used as an active ingredient in the provided compositions. Exemplary of the carotene-containing compounds that can be used as active ingredients in the provided compositions are lutein and zeaxanthin, sold under the name Xanmax®-80 (Lutein crystals), by Katra Phytochem (India) Private Limited, Bangalore, India, containing 80% lutein and 4.5% zeaxanthin.

v. Micronutrient-Containing Active Ingredients

Exemplary of the non-polar compounds used as active ingredients in the provided compositions are micronutrient-containing compounds, for example, vitamins, including Vitamins A, D, E and K, and corresponding provitamins and vitamin derivatives with an action resembling that of vitamin A, D, E, or K, and alpha lipoic acid (thioctic acid).

(1) Vitamins

Exemplary of the vitamins used as active ingredients in the provided compositions are fat-soluble vitamins, for example, Vitamins A, D, E and K, and corresponding provitamins and vitamin derivatives such as esters with an action resembling that of vitamin A, D, E or K for example, retinol (vitamin A) and pharmaceutically acceptable derivatives thereof, for example, palmitate ester of retinol and other esters of retinol, for example, Vitamin A Palmitate, and calciferol (vitamin D) and its pharmaceutically acceptable derivatives thereof, for example, cholecalciferol (Vitamin D3), and precursors of vitamin D, d-alpha tocopherol (vitamin E) and derivatives thereof, including pharmaceutical derivatives thereof, for example, Tocotrienols, d-alpha tocopherol acetate and other esters of d-alpha tocopherol, and ascorbyl palmitate, a fat-soluble version of vitamin C.

Any vitamin can be used as an active ingredient in the provided compositions. Exemplary of the vitamins that can be used as active ingredients in the provided compositions are vitamin A palmitate, for example, vitamin A palmitate containing 1.7 mIU/g, produced by DSM Nutritional Products, Inc., Belvidere, N.J., and distributed through Stauber Performance Ingredients, Inc., Fullerton, Calif., and vitamin D3, for example, vitamin D3 in corn oil, containing about 1 mIU/g, produced by DSM Nutritional Products, Inc., Belvidere, N.J., and distributed through Stauber Performance Ingredients, Inc., Fullerton, Calif.

Typically, vitamin non-polar active ingredients are included in the provided compositions within a concentration range of between 0.0001% or about 0.0001% and 1% or about 1%, more typically between at or about 0.001% and at or about 0.1%, for example, at or about 0.0001%, 0.0005%, 0.0008%, 0.0009%, 0.001%, 0.002%, 0.003%, 0.004%, 0.005%, 0.01%, 0.02%, 0.03%, 0.04%, 0.05%, 0.1%, 0.5% or 1%, w/w, of the concentrate. Vitamin non-polar active ingredients are typically added to the compositions in amounts such that when diluted in a food or beverage, one serving of the food or beverage provides an amount of the vitamin that corresponds to the dietary reference intakes. For example, vitamin A is added such that, when diluted in a food or beverage, a serving of the food or beverage provides between at or about 10 to at or about 2000 micrograms (mcg), for example, between at or about 20 to at or about 900 mcg, more typically between at or about 40 to at or about 400 mcg of vitamin A per serving, for example, between at or about 40 and at or about 200 mcg, or between at or about 100 and at or about 400 mcg, or between at or about 100 and at or about 300 mcg per serving. For example, the food or beverage can contain 40 or about 40, 50 or about 50, 60 or about 60, 70 or about 70, 80 or about 80, 90 or about 90, 100 or about 100, 110 or about 110, 120 or about 120, 130 or about 130, 140 or about 140, 150 or about 150, 200 or about 200, 250 or about 250, 300 or about 300, 350 or about 350, or 400 or about 400 mcg Vitamin A per serving. In another example, vitamin D3 is added such that, when diluted in a food or beverage, a serving of the food or beverage provides between at or about 100 to at or about 2000 International Units (IU), for example, between at or about 100 to at or about 1000 IU, more typically, between at or about 400 and at or about 800 IU, per serving, for example between at or about 400 and at or about 600 or between at or about 500 and at or about 800, or between at or about 600 and at or about 800 IU per serving. For example, the food or beverage can contain 400 or about 400, 450 or about 450, 500 or about 500, 550 or about 550, 600 or about 600, 650 or about 650, 700 or about 700, 750 or about 750 or 800 or about 800 IU Vitamin D3 per serving.

(2) Alpha Lipoic Acid

The alpha lipoic acid active ingredients include Alpha Lipoic Acid, sold by NutriChem Resources Company, Walnut, Calif., and Alpha Lipoic Acid, sold by Zhejiang Medicines & Health Products Import & Export Co., Ltd, Hangzhou, China and other alpha lipoic acids. Typically, alpha lipoic acid is used in the provided compositions within a concentration range of between 0% or about 0% and 15% or about 15%, typically between 5% or about 5% and 15% or about 15%, such as between at or about 8% and at or about 13%, for example, at or about 5%, 6%, 7%, 8%, 9%, 10%, 10.50%, 10.75%, 10.89%, 11%, 12%, 13%, 14% or 15%, w/w, of the concentrate.

d. Surfactants

The provided compositions contain surfactants. For example, in addition to the non-polar compound(s), the liquid concentrates contain one or more surfactants. In the provided methods for producing the concentrates, the surfactant is added to the water phase, the oil phase, or to the water and the oil phase. The compositions can further contain one or more co-surfactants or emulsifiers. Typically, the surfactants are natural surfactants, for example, a surfactant that is G.R.A.S. (generally recognized as safe) by the FDA and/or Kosher certified.

The surfactants aggregate in aqueous liquids, such as in the provided compositions (e.g., concentrates and aqueous liquid dilution compositions) to form micelles, which contain the non-polar compound(s). The hydrophilic portion(s) of the surfactant molecules are oriented toward the outside of the micelle, in contact with the aqueous medium, while the hydrophobic portion(s) of the surfactant molecules are oriented toward the center of the micelle, in contact with the non-polar compound(s), which is contained in the center of the micelle. The micelles can contain more than one surfactant and/or co-surfactant. Properties of the provided compositions, for example, the particle size of the compositions and desirable properties related to the particle size, are influenced by the choice of surfactant(s) and the relative amount (concentration) of surfactant. For example, the HLB of the surfactant(s) can affect particle size, clarity, taste, smell, crystal formation, stability and other properties of the provided compositions. Similarly, the concentration of the surfactant compared with the concentration(s) of other ingredients, particularly compared with the concentration of the polar solvent(s) and the concentration of the non-polar compound(s), can affect various desirable properties, for example, the ability to disperse or dissolve in a water-based food or beverage, e.g., to form a stable dilution compositions or dilution compositions with a pleasant taste and/or smell.

Surfactants (and co-surfactants) are molecules that contain hydrophobic and hydrophilic portions. In one example, the hydrophobic portion is a hydrophobic tail and the hydrophilic portion is a hydrophilic head of the surfactant molecule.

The HLB value of a surfactant is derived from a semi-empirical formula; HLB values are used to index surfactants according to their relative hydrophobicity and hydrophilicity. An HLB value is a numerical representation of the relative representation of hydrophilic groups and hydrophobic groups in a surfactant or mixture of surfactants. The weight percent of these respective groups indicates properties of the molecular structure. See, for example, Griffin, W. C., *J. Soc. Cos. Chem.* 1:311 (1949).

Surfactant HLB values range from 1-45, while the range for non-ionic surfactants typically is from 1-20. The more lipophilic a surfactant is, the lower its HLB value. Conversely, the more hydrophilic a surfactant is, the higher its HLB value. Lipophilic surfactants have greater solubility in oil and lipophilic substances, while hydrophilic surfactants dissolve more easily in aqueous liquids. In general, surfactants with HLB values greater than 10 or greater than about 10 are called "hydrophilic surfactants," while surfactants having HLB values less than 10 or less than about 10 are referred to as "hydrophobic surfactants." HLB values are known for a number of surfactants Tables 1A and 1B list HLB values of exemplary surfactants and co-surfactants.

Exemplary of surfactants that can be used in the provided methods and compositions are surfactants having an HLB value of between 13 or about 13 and 20 or about 20, for example, 13 or about 13, 14 or about 14, 15 or about 15, 16 or about 16, 17 or about 17, 18 or about 18, 19 or about 19, or 20 or about 20. The surfactants typically are non-ionic surfactants, and typically have an HLB value between at or about 13 and at or about 18, more typically between at or about 15 and at or about 18. Particular examples of suitable surfactants for use in the provided compositions include non-ionic surfactants, such as sugar derived surfactants, including fatty acid esters of sugars and sugar derivatives, Vitamin E-derived surfactants and PEG-derived surfactants, such as PEG-sorbitan fatty acid esters.

Exemplary sugar derived surfactants include, but are not limited to, sugar fatty acid esters including fatty acid esters of sucrose, glucose, maltose and other sugars, esterified to fatty acids of varying lengths (e.g., containing a varying numbers of carbons). The fatty acids typically have carbon chains between 8 and 28 carbons in length, and typically between 8 and 20, or between 8 and 18 or between 12 and 18, such as, but not limited to, stearic acid (18 carbons), oleic acid (18 carbons), palmitic acid (16 carbons), myristic acid (14 carbons) and lauric acid (12 carbons). Typically, the sugar ester surfactants are sucrose ester surfactants, typically sucrose fatty acid ester surfactants.

Exemplary Vitamin E-derived surfactants include, but are not limited to, surfactants such as tocopherol and/or tocotrienol-derived surfactants, in which the Vitamin E moiety represents the hydrophobic region of the surfactant, and is attached, via a linker, to another moiety, such as a polyethylene glycol (PEG) moiety, that provides the hydrophilic portion of the surfactant. Vitamin-E derived surfactants include, but are not limited to, tocopherol derived surfactants, including polyalkylene glycol derivatives of tocopherol, typically polyethylene glycol (PEG) derivatives of tocopherol, such as tocopherol polyethylene glycol succinate (TPGS), TPGS analogs, TPGS homologs and TPGS derivatives. Alternatively, the surfactants can be other PEG derivatives having similar properties, for example, PEG derivatives of sterols, e.g. a cholesterol or a sitosterol (including, for example, any of the PEG derivatives disclosed in U.S. Pat. No. 6,632,443) or PEG-derivatives of other fat-soluble vitamins, for example, some forms of Vitamin A (e.g. Retinol) or Vitamin D (e.g. Vitamin D1-D5).

Exemplary PEG-derived surfactants include but are not limited to PEG-sorbitan fatty acid esters, such as polysorbates, including polyoxyethylene (20) sorbitan monooleate (also called polysorbate 80) and analogs (e.g. homologs) of polysorbate 80, such as, for example, polysorbate 20 (polyoxyethylene (20) sorbitan monolaurate), polysorbate 40 (polyoxyethylene (20) sorbitan monopalmitate) and polysorbate 60 (polyoxyethylene (20) sorbitan monostearate).

Exemplary concentrates provided herein also include those containing a mixture of one or more surfactants, selected from among any surfactant that typically has an HLB value of between 13 or about 13 and 20 or about 20, for example, 14, 15, 16, 17, 18, 19, or 20, or about 13, about 14, about 15, about 16, about 17, about 18, about 19, about 20, typically between at or about 13 and at or about 18, more typically between at or about 15 and at or about 18. Exemplary mixtures of one or more surfactants include, for example, a SFAE or mixtures thereof, or a SFAE or mixtures thereof and a PEG-derivative of vitamin E or an analog thereof, or a SFAE or mixtures thereof and a PEG-derived surfactant, such as a PEG-sorbitan fatty acid ester, or a PEG-derivative of vitamin E or an analog thereof, and a PEG-derived surfactant, such as a PEG-sorbitan fatty acid ester, or a SFAE or mixtures thereof, a PEG-derivative of vitamin E or an analog thereof and a PEG-derived surfactant, such as a PEG-sorbitan fatty acid ester.

i. Sucrose Fatty Acid Ester Surfactants

Sucrose fatty acid ester surfactants contain one or more sucrose fatty acid esters, which are non-ionic surfactants that contain sucrose in the hydrophilic portions and fatty acids in the hydrophobic portions. The sucrose fatty acid esters can be made by well-known methods (see, for example, U.S. Pat. Nos. 3,480,616, 3,644,333, 3,714,144, 4,710,567, 4,898,935, 4,996,309, 4,995,911, 5,011,922 and 5,017,697 and International Patent Application Publication No. WO 2007/082149), typically in an esterification reaction as described below.

Because sucrose contains eight hydroxy (OH) groups, the esterification reaction can join the sucrose molecule to one fatty acid molecule, or can join it to a plurality of fatty acid molecules, producing different degrees of esterification, e.g., mono-, di-, tri- and poly-(up to octa-) fatty acid esters, but primarily mono-, di-, and/or tri-esters. The degree of esterification can depend on conditions of esterification. The esterification reaction can be carried out with a single type of fatty acid, or a plurality of fatty acids, such as fatty acids with varying carbon chain lengths, branched and linear fatty acids, and/or saturated or unsaturated fatty acids. The esterification reaction with a single fatty acid can produce a single ester, and typically forms more than one ester, such as mono- di-, tri- and/or poly-esters, formed from one reaction. The relative amounts of mono- di- tri- and/or poly-esters can depend on reaction conditions.

The fatty acid in the sucrose fatty acid ester can be any fatty acid, and can contain between 4 and 28 carbon atoms, typically between 8 and 28 carbon atoms, and typically between 8 and 25 carbon atoms, such as between 8 and 18 carbon atoms, such as 8, 9, 10, 11, 12, 13, 14, 15, 16, 17 and 18 carbon atoms. The fatty acid can be synthetic or naturally occurring, and include linear and branched fatty acids. The fatty acids include, but are not limited to, myristic acid, palmitic acid, stearic acid, oleic acid, caproic acid, capric (or decanoic) acid, lauric acid, caprylic acid and pelargonic (or nonanoic) acid.

Thus, the sucrose fatty acid ester surfactants include sucrose monoesters, diesters, triesters and polyesters, and mixtures thereof, and typically contain sucrose monoesters. The sucrose fatty acid ester surfactants include single fatty acid esters and also include homogeneous mixtures of sucrose esters, containing members with different lengths of fatty acid carbon chain and/or members with different degrees of esterification. For example, the sucrose fatty acid ester surfactants include mixtures of monoesters, diesters, triesters, and/or polyesters. The sugar ester surfactants further include sucrose fatty acid ester analogs and homologs and mixtures thereof.

Sucrose fatty acid esters are compounds having the following formula shown in Scheme I below.

Scheme I

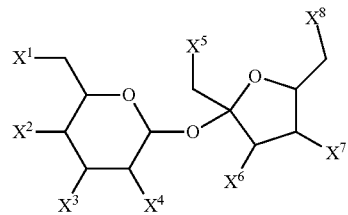

where each of $X^1$, $X^2$, $X^3$, $X^4$, $X^5$, $X^6$, $X^7$ and $X^8$ independently is:

a hydroxyl (—OH) group, or

where:
each R is an alkyl group having 3-27 carbon atoms; and when more than one of $X^1, X^2, X^3, X^4, X^5, X^6, X^7$ and $X^8$ is

each R can be a different alkyl group (e.g., having different number of carbon atoms and/or different saturation), or can be the same alkyl group.

Typically, in the provided sucrose fatty acid ester surfactants, each R has between 7 and 27 carbon atoms, and typically between 7 and 19 atoms, such as 7, 8, 9, 10, 11, 12, 13, 14, 15, 16, 17, 18, or 19 carbon atoms or between 7 and 17 carbon atoms.

An alkyl group can be a straight chain or branched alkyl group, can be substituted or unsubstituted, and can be a saturated "saturated alkyl group," meaning that it does not contain any alkene or alkyne groups; or an "unsaturated alkyl group," meaning that it contains at least one alkene or alkyne group. An alkyl group that includes at least one carbon-carbon double bond (C═C) also is referred to by the term "alkenyl," and alkenyl groups optionally can be substituted. An alkyl group that includes at least one carbon-carbon triple bond (C≡C) also is referred to by the term "alkynyl," and alkynyl groups optionally can be substituted.

Typically, the sucrose fatty acid ester surfactants contain sucrose fatty acid monoesters, having the structure set forth in Scheme I, where one of $X^1, X^2, X^3, X^4, X^5, X^6, X^7$ and $X^8$ (typically $X^1$) is

and the other seven of $X^1, X^2, X^3, X^4, X^5, X^6, X^7$ and $X^8$ are each, independently, —OH. An exemplary monoester has the following structure:

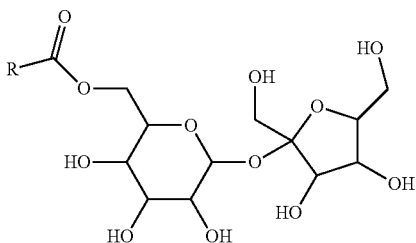

where R is an alkyl group having 3-27 carbons, and typically 7-27 carbons.

The sucrose fatty acid esters include blends of sucrose fatty acid esters, which typically include monoesters, and can also include diesters, triesters and polyesters, which have structures according to Scheme I, above, where two (diesters), three (triesters) or more (polyesters) of $X^1, X^2, X^3, X^4, X^5, X^6, X^7$ and $X^8$, (and typically $X^1$ and $X^8$) independently, are

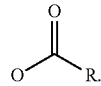

In general, sucrose fatty acid esters, including mixtures of sucrose fatty acid esters, can have varying HLB values, such as HLB values ranging from at or about 1 to at or about 20. The HLB value of the sucrose fatty acid ester generally depends on the degree of esterification (e.g., the average degree of esterification in a mixture of different esters). Typically, the lower the degree of esterification (e.g., average degree), the higher the HLB value of the sucrose fatty acid ester or mixture thereof. Exemplary sucrose esters include sucrose distearate (HLB=3), sucrose distearate/monostearate (HLB 12), sucrose dipalmitate (HLB=7.4), sucrose monostearate (HLB=15), sucrose monopalmitate (HLB>10), sucrose monolaurate (HLB 15). Typically, the sucrose fatty acid ester surfactants in the provided compositions have an HLB value of between at or about 13 and at or about 20, such as at or about 13, 14, 15, 16, 17, 18, 19, or 20, and typically between at or about 13 and at or about 18, such as, but not limited to, HLB values of at or about 15, 16 and 17, such as, for example, sucrose ester surfactants including sucrose monopalmitate, sucrose monolaurate and sucrose monostearate.

The sugar ester surfactants include sucrose ester blends, for example, sucrose ester mixtures containing a specified amount (e.g., percent, by weight) of sucrose monoesters. Exemplary surfactants include sucrose ester mixtures having at least at or about 50%, by weight (w/w), monoester, such as at or about or at least at or about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%, by weight (w/w), sucrose monoesters, and typically at least at or about 60%, by weight or at least at or about 70%, by weight (w/w), monoesters. The surfactants include mixtures of sucrose esters containing at least at or about 50% sucrose monoesters, mixtures of sucrose esters containing at least at or about 60% sucrose monoesters, mixtures of sucrose esters containing at least at or about 70% sucrose monoesters, mixtures of sucrose esters containing at least at or about 80% sucrose monoesters, and mixtures of sucrose esters containing at least at or about 90% sucrose monoesters, for example, mixtures containing at or about 72% sucrose monoesters, at or about 61% sucrose monoesters, or at or about 90% sucrose monoesters.

The sucrose fatty acid ester surfactants include sucrose fatty acid monoesters, such as sucrose monocaprylate, sucrose monodecanoate, sucrose monolaurate, sucrose monomyristate, sucrose monopalmitate, sucrose monostearate, sucrose monopelargonate, sucrose monoundecanoate, sucrose monotridecanoate, sucrose monopentadecanoate and sucrose monoheptadecanoate. The sucrose fatty acid esters further include mixtures containing varying percentages of monoesters, diesters, triesters and polyesters, such as, but not limited to, a mixture having at or about 72% monoesters, 23% diesters, 5% triesters and 0% polyesters; a mixture having at or about 61% monoesters, 30% diesters, 7% triesters, and 2% polyesters; and a mixtures having at or about 52% monoesters, 36% diesters, 10% triesters and 2% polyesters.

The sucrose fatty acid ester surfactants include sucrose fatty acid esters sold under the trade name DK Ester®, produced by Dai-Ichi Kogyo Seiyaku Co., Ltd of Japan (which, in some examples, can be produced according to the methods described in U.S. Pat. Nos. 4,898,935, 4,996,309, 4,995,911, 5,011,922 and 5,017,697, and distributed through Montello Inc., Tulsa, Okla., such as the F-160 and F-140 grade esters sold under the trade name DK Ester®, and sucrose esters sold under the trade name SURFHOPE® SE PHARMA, by Mitsubishi-Kagaku Foods Corporation, distributed by Mitsubishi Chemical Performance Polymers, Inc. These sucrose fatty acid esters are mixtures of esters with different degrees of esterification. The sucrose fatty acid esters further include Ryoto sugar esters, which are food-grade esters sold by Mitsubishi-Kagaku Foods Corporation, distributed by Mitsubishi Chemical Performance Polymers, Inc. Exemplary sucrose fatty acid esters sold under the trade name DK Ester®, and those sold under the trade name SURFHOPE® SE PHARMA and Ryoto sugar esters, are listed in Table 1B, below. The table lists the average degree of esterification or the fatty acid composition within the mixture, and the HLB of the sucrose fatty acid ester surfactant. Any of the surfactants in Table 1B can be used. Typically, the surfactant (e.g., a surfactant listed in Table 1B), has an HLB value between at or about 13 and at or about 20, typically between at or about 13 and at or about 18, more typically between at or about 15 and at or about 18, e.g., but not limited to, those surfactants in the table having an HLB of 15 or 16, such as the sucrose fatty acid ester surfactant sold under the name DK ESTER® F-160, produced by Dai-Ichi Kogyo Seiyaku Co., Ltd of Japan, and distributed through Montello Inc., Tulsa, Okla. and the sucrose fatty acid ester surfactant sold under the name Ryoto Sugar Ester S-1670, by Mitsubishi-Kagaku Foods Corporation, distributed by Mitsubishi Chemical Performance Polymers, Inc. Other exemplary sucrose fatty acid ester surfactants are described in Youan et al., *AAPS PharmaSci* 2003; 5(2) Article 22; 1-9 and in Okamoto et al., *Biol. Pharm. Bull.* 28(9):1689-1694 (2005).

TABLE 1B

Exemplary Sucrose Fatty Acid Ester (SFAE) Surfactants

| Sucrose Fatty Acid Ester | Average Degree of Esterification | Fatty acid composition | H.L.B. | Distribution (by weight) of Ester Mono: Di: Tri: Poly |
|---|---|---|---|---|
| DK Ester ® F-160 | 1.23 | | 16 | 72% monoester; 23% diester; 5% triester |
| DK Ester ® F-140 | 1.35 | | 13 | 61% monoester; 30% diester; 7% triester; 2% polyester |
| DK Ester ® F-110 | 1.48 | | 11 | 52% monoester; 36% diester; 10% triester; 2% polyester |
| DK Ester ® F-90 | 1.53 | | 9.5 | 45% monoester; 39% diester; 12% triester; 4% polyester |
| DK Ester ® F-70 | 1.60 | | 8 | 39% monoester; 45% diester; 12% triester; 4% polyester |
| DK Ester ® F-50 | 1.69 | | 6 | 34% monoester; 46% diester; 17% triester; 3% polyester |
| DK Ester ® F-20W | 3.11 | | 2 | 11% monoester; 21% diester; 14% triester; 54% polyester |
| DK Ester ® F-10 | 4.85 | | 1 | 0% monoester; 5% diester; 11% triester; 84% polyester |
| SURFHOPE ® SE PHARMA J-1205 | | C12 (100%) | 5 | 32% monoester; 68% di-/tri-/poly-esters |
| SURFHOPE ® SE PHARMA J-1216 | | C12 (100%) | 16 | 81% monoester; 19% di-/tri-/poly-esters |
| SURFHOPE ® SE PHARMA J-1616 | | C16 (80%); C18 (20%) | 16 | 79% monoester; 21% di-/tri-/poly-esters |
| SURFHOPE ® SE PHARMA J-1805 | | C16 (70%); C18 (30%) | 5 | 30% monoester; 70% di-/tri-/poly-esters |
| SURFHOPE ® SE PHARMA J-1807 | | C16 (70%); C18 (30%) | 7 | 41% monoester; 59% di-/tri-/poly-esters |
| SURFHOPE ® SE PHARMA J-1816 | | C16 (70%); C18 (30%) | 16 | 75% monoester; 25% di-/tri-/poly-esters |
| SURFHOPE ® SE PHARMA D-1803 | | Sucrose stearate (approximately 70% stearate) | 3 | Approximately 20% monoester; approximately 80% di-/tri-/poly-esters |
| SURFHOPE ® SE PHARMA D-1803F | | Sucrose stearate (70% stearate) | 3 | 20% monoester; 80% di-/tri-/poly-esters |

TABLE 1B-continued

Exemplary Sucrose Fatty Acid Ester (SFAE) Surfactants

| Sucrose Fatty Acid Ester | Average Degree of Esterification | Fatty acid composition | H.L.B. | Distribution (by weight) of Ester Mono: Di: Tri: Poly |
|---|---|---|---|---|
| SURFHOPE ® SE PHARMA D-1805 | | Sucrose stearate (70% stearate) | 5 | 30% monoester; 70% di-/tri-/poly-esters |
| SURFHOPE ® SE PHARMA D-1807 | | Sucrose stearate (70% stearate) | 7 | 40% monoester; 60% di-/tri-/poly-esters |
| SURFHOPE ® SE PHARMA D-1809 | | Sucrose stearate (70% stearate) | 9 | 50% monoester; 50% di-/tri-/poly-esters |
| SURFHOPE ® SE PHARMA D-1811 | | Sucrose stearate (70% stearate) | 11 | 55% monoester; 45% di-/tri-/poly-esters |
| SURFHOPE ® SE PHARMA D-1811F | | Sucrose stearate (70% stearate) | 11 | 55% monoester; 45% di-/tri-/poly-esters |
| SURFHOPE ® SE PHARMA D-1815 | | Sucrose stearate (70% stearate) | 15 | 70% monoester; 30% di-/tri-/poly-esters |
| SURFHOPE ® SE PHARMA D-1816 | | Sucrose stearate (70% stearate) | 16 | 75% monoester; 25% di-/tri-/poly-esters |
| SURFHOPE ® SE PHARMA D-1615 | | Sucrose palmitate (80% palmitate) | 15 | 70% monoester; 30% di-/tri-/poly-esters |
| SURFHOPE ® SE PHARMA D-1616 | | Sucrose palmitate (80% palmitate) | 16 | 80% monoester; 20% di-/tri-/poly-esters |
| SURFHOPE ® SE PHARMA D-1216 | | Sucrose laurate (95% laurate) | 16 | 80% monoester; 20% di-/tri-/poly-esters |
| Ryoto S-970 | | Sucrose stearate | 9 | 50% monoester |
| Ryoto S-1170 | | Sucrose stearate | 11 | 55% monoester |
| Ryoto S-1570 | | Sucrose stearate | 15 | 70% monoester |
| Ryoto S-1670 | | Sucrose stearate | 16 | 75% monoester |
| Ryoto P-1570 | | Sucrose palmitate | 15 | 70% monoester |
| Ryoto P-1670 | | Sucrose palmitate | 16 | 80% monoester |
| Ryoto LWA-1570 | | Sucrose laurate | 15 | 70% monoester |
| Ryoto L-1695 | | Sucrose laurate | 16 | 80% monoester |
| Ryoto OWA-1570 | | Sucrose oleate | 15 | 70% monoester |

(1) Production of Sucrose Esters

As noted above, methods for producing sucrose esters are well known (see, for example, U.S. Pat. Nos. 3,480,616, 3,644,333, 3,714,144, 4,710,567, 4,898,935, 4,996,309, 4,995,911, 5,011,922 and 5,017,697 and International Patent Application, Publication No. WO 2007/082149). The sucrose fatty acid surfactants can be produced by any well known method, and typically in an esterification reaction, for example, by reacting sucrose with a methyl ester of the desired fatty acid, such as a solvent process, where sucrose is reacted with a methyl ester of a fatty acid in the presence of a catalyst (e.g., potassium carbonate) and an organic solvent (e.g., dimethyl formamide (DMF) or dimethyl sulfoxide (DMSO)), followed by purification, or in an aqueous medium process, where sucrose is mixed in a molten mixture with fatty acid salt using water without an organic solvent and then reacted with a higher fatty acid methyl ester in the presence of a catalyst, followed by purification, and such as by any of the methods described in International Patent Application Publication No. WO 2007/082149, whereby a sucrose molecule (which is a disaccharide containing one six-carbon aldo-sugar glucose linked to a five-carbon keto-sugar fructose, having the formula: $C_{12}H_{22}O_{11}$) is joined to one or more fatty acids.

For example, the sucrose fatty acid ester can be produced by esterification using dimethyl formamide (DMF) as a solvent, by producing a methyl ester of the fatty acid and then reacting the methyl ester with sucrose in DMF in the presence of a catalyst (e.g., potassium carbonate), for example, for 4-6 hours at 83-95° C., for example, using 30 to 127 parts sucrose to 30 parts methyl ester of the fatty acid (e.g., methyl stearate), 2 parts potassium carbonate and 300 parts solvent; by a similar method, but using dimethyl sulfoxide (DMSO) as the solvent, for example, as described in U.S. Pat. No. 3,480,616; or, as described in U.S. Pat. No. 3,644,333, by mixing sucrose with methyl fatty acid and sodium fatty acid and previously prepared sucrose ester, using potassium carbonate as a catalyst and water as a solvent; or, as described in U.S. Pat. No. 3,714,144, where sodium, potassium or lithium soap of the fatty acid is reacted in a molten sugar solution for two to twenty minutes under vacuum at 170-190° C., and purified, for example, as described in U.S. Pat. No. 4,710,567, by adding aqueous salt solution followed by three-phase separation. In one example, the sucrose fatty acid esters are prepared and purified as described in U.S. Pat. Nos. 4,898,935, 4,996,309, 4,995,911, 5,011,922 and 5,017,697, by producing the esters by chemical catalysis, such as with the solvent process, e.g., using a DMSO solvent and potassium carbonate catalyst, or aqueous solution method, followed by extraction and purification of the sucrose fatty acid esters, e.g., by adjusting pH, precipitation, separation and neutralization and filtration.

In another example, the sucrose fatty acid esters can be produced, as described in International Patent Application Publication No. WO 2007/082149, by mixing and reacting sucrose and vinyl esters of the fatty acids which can produce sucrose fatty acid ester mixtures with a monoester content of at or about 90%, and/or an acid value of less than 1. Briefly, this process can be carried out by dissolving sucrose in a solvent (e.g., DMSO), at a reaction temperature of between at or about 30° C. and at or about 60° C., such as between about 40° C. and 60° C. (e.g., at 60° C.), to which a catalyst is added and the mixture stirred, such as for 30 minutes, followed by removal of undissolved catalyst by decanting or filtration, followed by addition of vinyl fatty acid, and reaction, such as for at or about 15 minutes, with monitoring to measure the amount of vinyl fatty acid ester, for example, until the amount of vinyl fatty acid ester reaches no more than at or about 10%, by weight (w/w), of the starting amount. The amount of sucrose and vinyl ester can vary. In one example, the ratio of sucrose to vinyl ester is between at or about 2:1 and at or about 8:1. In one example, the sucrose is added at a concentration of at or about 400 nM and the vinyl ester added at a concentration of at or about 100 nM. The catalyst can be catalyzed by a base, such as metal oxides, metal hydroxides and metal carbonates, such as potassium hydroxide, sodium hydroxide, potassium carbonate, sodium carbonate and lithium carbonate, which can be added at a concentration of between at or about 1.5 g/L and at or about 6 g/L of reaction volume. In one example, the vinyl ester is vinyl stearate and the catalyst is potassium carbonate. The resulting mixture can then purified, such as by vacuum distillation and addition of sodium chloride to effect emulsification and purification methods described in International Patent Application Publication No. WO 2007/082149.

ii. Vitamin E Derived Surfactants

Vitamin E-derived surfactants, such as tocopherol and/or tocotrienol-derived surfactants, contain a Vitamin E moiety which represents the hydrophobic region of the surfactant, attached, via a linker, to another moiety, such as a polyethylene glycol (PEG) moiety that provides the hydrophilic portion of the surfactant. The vitamin-E derived surfactants include, but are not limited to, tocopherol derived surfactants, including polyalkylene glycol derivatives of tocopherol, typically polyethylene glycol (PEG) derivatives of tocopherol, such as tocopherol polyethylene glycol succinate (TPGS), TPGS analogs, TPGS homologs and TPGS derivatives. Alternatively, the surfactants can be other PEG derivatives having similar properties as TPGS and TPGS analogs, for example, PEG derivatives of sterols, e.g., a cholesterol or a sitosterol (including, for example, any of the PEG derivatives disclosed in U.S. Pat. No. 6,632,443) or PEG-derivatives of other fat-soluble vitamins, for example, some forms of Vitamin A (e.g., Retinol) or Vitamin D (e.g., Vitamin D1-D5).

(1) PEG-Derivatives of Vitamin E

The Vitamin E-derived surfactants (e.g., tocopherol-derived or a tocotrienol-derived surfactants) include polyalkylene glycol derivatives of Vitamin E, typically polyethylene glycol (PEG) derivatives of Vitamin E, for example, PEG derivatives of tocopherol or tocotrienol. Suitable PEG derivatives of Vitamin E typically contain one or more tocopherols or tocotrienols, joined (for example, by an ester, ether, amide or thioester bond) with one or more PEG moieties, via a linker, for example, a dicarboxylic acid linker. An exemplary surfactant is shown schematically below:

where the line between the PEG and Linker; and the line between the Linker and Vitamin E each independently represent a covalent bond selected from among an ester, ether, amide or thioester.

Typically, the Vitamin E PEG derivatives are made by joining the PEG moiety, via esterification, to a vitamin E-linker conjugate (e.g., a tocopherol-linker conjugate). In one example, the tocopherol-linker conjugate first is formed by covalently joining (by esterification) the hydroxyl moiety of tocopherol with a dicarboxylic acid to produce an ester bond. In this example, the tocopherol-linker conjugate is a tocopherol ester (such as tocopherol succinate). The esterification reaction can be performed by any of a number of known methods (see, for example, U.S. Pat. Nos. 2,680,749, 4,665,204, 3,538,119 and 6,632,443). To make the tocopherol-PEG surfactant, the resulting tocopherol ester then is joined (via the linker) to the PEG molecule, in another esterification reaction. In this example, the resulting surfactant is a tocopherol polyethylene glycol diester (TPGD).

Alternatively, PEG derivatives of a tocopherol-linker or tocotrienol-linker conjugate can be made by other methods. Various methods known in the art for producing PEG derivatives can be used to join a PEG molecule to tocopherol-linker or tocotrienol-linker compounds. For example, a tocopherol-linker conjugate can be covalently bonded to the PEG molecule via an amide, ether or thioether bond. For example, a tocopherol-linker conjugate that contains an amine group can be reacted with a PEG-NHS derivative to form an amide bond between the tocopherol-linker and the PEG molecule. A tocopherol-linker conjugate that contains an amine group can be reacted with a PEG-aldehyde derivative to form an amide bond between the tocopherol-linker and the PEG molecule. In another example, a tocopherol-linker that contains an carboxylic acid can be activated to the corresponding acid halide and reacted with a PEG-SH derivative to form a thioester bond between the tocopherol-linker and the PEG molecule.

(a) Tocopherols and Tocotrienols

The tocopherol(s) used to make the surfactant can be any natural or synthetic Vitamin E tocopherol, including but not limited to alpha-tocopherols, beta-tocopherols, gamma-tocopherols and delta-tocopherols, either in pure forms or in heterogenous mixtures of more than one form. Exemplary tocopherols are d-α-tocopherols and d,l-tocopherols. To make the surfactant, the tocopherol typically is esterified with a linker, for example, a dicarboxylic acid, to form a tocopherol ester, which then is joined to a PEG moiety.

The tocotrienol(s) used to make the surfactants can be any natural or synthetic Vitamin E tocotrienol, including but not limited to alpha-tocotrienols, beta-tocotrienols, gamma-tocotrienols and delta-tocotrienols, either in pure forms or in heterogenous mixtures of more than one form. Mixtures of tocopherols and tocotrienols, are contemplated for use in the provided methods and compositions. A tocotrienol can be esterified with a linker, such as a dicarboxylic acid, before joining with a PEG moiety.

(b) PEG Moieties

The PEG used in the tocopherol-PEG derivative can be any of a plurality of known PEG moieties. Exemplary of suitable PEG moieties are PEG moieties having varying chain lengths, and varying molecular weights, for example, PEG 1000, PEG 200, PEG 500, and PEG 20,000. The numbers following individual PEG moieties indicate the molecular weight (in kilodaltons (kDa)) of the PEG moieties. The PEG moiety of the tocopherol-derived surfactant typically has a molecular weight of between 200 kDa or about 200 kDa and 20,000 kDa or about 20,000 kDa, typically between 200 kDa or about 200 kDa and 6000 kDa or about 6000 kDa, for example, between 600 kDa or about 600 kDa and 6000 kDa or about 6000 kDa, typically between 200 kDa or about 200 kDa and 2000 or about 2000 kDa, between 600 or about 600 kDa and 1500 kDa or about 1500 kDa, such as but not limited to 200, 300, 400, 500, 600, 800, and 1000 kDa. Exemplary of a PEG-derivative of tocopherol ester having a PEG moiety with 1000 kDa is TPGS-1000. Also exemplary of suitable PEG moieties are PEG moieties that are modified, for example, methylated PEG (m-PEG), which is a PEG chain capped with a methyl group. Other known PEG analogs also can be used. The PEG moieties can be selected from among any reactive PEG, including, but not limited to, PEG-OH, PEG-NHS, PEG-aldehyde, PEG-SH, PEG-NH$_2$, PEG-CO$_2$H, and branched PEGs.

(c) Linkers

Typically, the PEG derivatives of Vitamin E are diesters or other esters, e.g., triesters. When the PEG derivative is a diester, the linker joining the Vitamin E to the PEG typically is a carboxylic acid, typically a dicarboxylic acid, as in, for example, tocopherol polyethylene glycol succinate (TPGS), where the linker is a succinic acid, and the surfactant is made by an esterification reaction joining a PEG moiety and a tocopherol ester of the dicarboxylic acid. In another example, the linker is another molecule, for example, an amino acid, such as glycine, alanine, 5-aminopentanoic acid or 8-aminooctanoic acid; or an amino alcohol, such as ethanolamine.

(d) Tocopherol Polyethylene Glycol and Tocotrienol Polyethylene Glycol Diesters (Dicarboxylic Acid Esters of Vitamin E Linked to PEG)

Typically, the Vitamin E PEG derivatives are vitamin E polyethylene glycol diesters, which are Vitamin E esters of PEG, made by joining a Vitamin E ester to one or more PEG moieties by esterification. Exemplary of the Vitamin E diesters are tocopherol polyethylene glycol diesters (TPGD) and tocotrienol polyethylene glycol diesters.

When the tocopherol or tocotrienol ester linked with the PEG moiety is a tocopherol ester of a dicarboxylic acid (e.g., tocopherol succinate), the linker is a dicarboxylic acid (a carboxylic acid having two carboxy groups, e.g., succinic acid). In this example, the tocopherol or tocotrienol PEG diester is formed by esterification reaction, in which PEG is attached to a tocopherol ester of a dicarboxylic acid.

Exemplary of dicarboxylic acids that can be used as linkers in these tocopherol and tocotrienol PEG diester surfactants are succinic acid, sebacic acid, dodecanedioic acid, suberic acid, or azelaic acid, citraconic acid, methylcitraconic acid, itaconic acid, maleic acid, glutaric acid, glutaconic acid, fumaric acid and phthalic acids. Accordingly, exemplary of the tocopherol esters that can be esterified to form the PEG-derivatives are tocopherol succinate, tocopherol sebacate, tocopherol dodecanodioate, tocopherol suberate, tocopherol azelaate, tocopherol citraconate, tocopherol methylcitraconate, tocopherol itaconate, tocopherol maleate, tocopherol glutarate, tocopherol glutaconate, and tocopherol phthalate, among others.

Exemplary of the vitamin E polyethylene glycol diesters made with dicarboxylic acids are compounds having the following formula shown in scheme II below (and homologs, analogs and derivatives thereof):

Scheme II

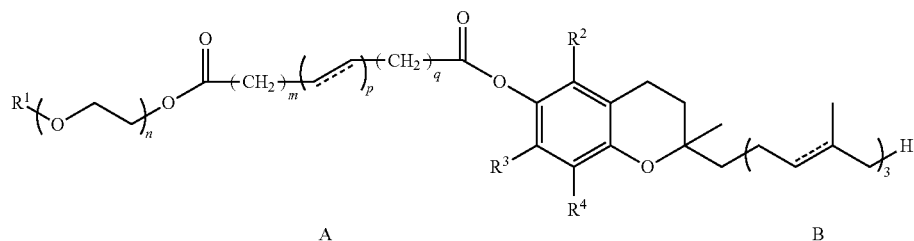

where $R^1$, $R^2$, $R^3$ and $R^4$ each independently is H or Me; each dashed line is independently a single or double bond; n is an integer from 1-5000; m and q each independently are 0 or 1; and p is an integer from 1-20. In one example, the surfactant is a compound where, when both m and q are 0, p is an integer between 2-20.

In one example, the surfactant has the following formula shown in Scheme III below (including homologs, analogs and derivatives thereof):

Scheme III

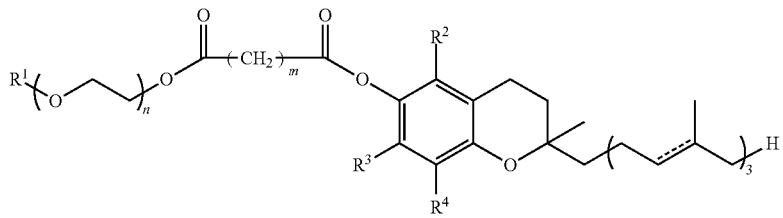

where $R^1$, $R^2$, $R^3$ and $R^4$ each independently is hydrogen (H) or methyl ($CH_3$); the bond represented by the dashed line is either a single or double bond, m is an integer from 1 to 20, and n is an integer from 1 to 5000.

In another example, the surfactant is a TPGS analog, such as, but not limited to, a compound other than TPGS having the formula shown in SCHEME IV:

Scheme IV

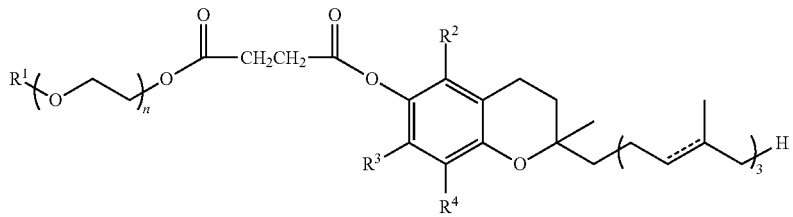

where $R^1$, $R^2$, $R^3$ and $R^4$ each independently is hydrogen (H) or methyl ($CH_3$); the bond represented by the dashed line is either a single or double bond, and n is an integer from 1 to 5000.

Exemplary of tocopherol and tocotrienol PEG diesters that can be used as surfactants in the provided compositions and methods include, but are not limited to: tocopherol polyethylene glycol succinates (TPGS; including D-α TPGS and d,l-TPGS; see for example, U.S. Pat. No. 3,102,078), tocopherol polyethylene glycol sebacate (PTS; see for example, U.S. Pat. No. 6,632,443), tocopherol polyethylene glycol dodecanodioate (PTD; see for example, U.S. Pat. No. 6,632,443), tocopherol polyethylene glycol suberate (PTSr; see for example, U.S. Pat. No. 6,632,443) and tocopherol polyethylene glycol azelaate (PTAz; see for example, U.S. Pat. No. 6,632,443), polyoxyethanyl tocotrienyl sebacate (PTrienS, for example, PTrienS-600; see for example, U.S. Pat. No. 6,632,443), as well as analogs, homologs and derivatives or any of the tocopherol diesters.

(e) Other Vitamin E PEG Esters

In another example, the tocopherol ester joined to the PEG to form the tocopherol PEG diester is a tocopherol ester of a tricarboxylic acid, for example, Citric acid, Isocitric acid, Aconitic acid and Propane-1,2,3-tricarboxylic acid (tricarballylic acid, carballylic acid) or a carboxylic acid having three or more carboxy groups.

In another example, the PEG derivatives of tocopherol are tocopherol polyethylene glycol triesters (TPGT), for example, esters containing a tocopherol, a linker, a PEG moiety, and an additional moiety, for example, an additional tocopherol, a second PEG moiety, or a water-soluble group, such as a quaternary amine. In one example, when the triester contains two PEG moieties, each PEG moiety has a smaller chain length (and lower molecular weight) than the PEG moiety in a PEG derivative of tocopherol, having similar properties, that contains only one PEG chain.

(f) TPGS Surfactants

Exemplary of the tocopherol polyethylene glycol diester surfactants are TPGS, and analogs, homologs and derivatives thereof. TPGS is a natural surfactant that is GRAS and Kosher certified and thus, desirable for use in products designated for human consumption, for example, beverages, food and nutritional supplements. TPGS typically has an HLB value of between 13 or about 13 and 18 or about 18. Exemplary of the TPGS surfactants is TPGS-1000, which has a PEG moiety of 1000 kDa. Exemplary of the TPGS surfactants that can be used in the provided compositions are the food grade TPGS surfactant sold under the name Eastman Vitamin E TPGS®, food grade, by Eastman Chemical Company, Kingsport, Tenn., D-α-tocopherol polyethylene glycol 1000 succinate supplied by Sigma-Aldrich, Buchs, Switzerland and Vitamin E Polyethylene Glycol Succinate, sold by Zhejiang Medicine CO., LTD, Zhinchang Pharma, Zhejiang, China. This surfactant is a water-soluble form of natural-source vitamin E, which is prepared by esterifying the carboxyl group of crystalline d-alpha-tocopheryl acid succinate with polyethylene glycol 1000 (PEG 1000), contains between 260 and 300 mg/g total tocopherol and has an HLB value between at or about 16 and at or about 18. A similar compound can be made by esterifying the carboxyl group of the d,l form of synthetic Vitamin E with PEG 1000. It forms a clear liquid when dissolved 20% in water. This tocopheryl polyethylene glycol is a water-soluble preparation of a fat-soluble vitamin (vitamin E), for example, as disclosed in U.S. Pat. Nos. 3,102,078 and 2,680,749 and U.S. Published Application Nos. 2007/0184117 and 2007/0141203. The PEG moiety of alternative TPGS surfactants can have a molecular weight range of between about 200 kDa or 200 kDa to 20,000 kDa or about 20,000 kDa, for example, between 600 kDa or about 600 kDa and 6000 kDa or about 6000 kDa, typically between 600 kDa or about 600 kDa and 1500 kDa or about 1500 kDa. Also exemplary of the TPGS surfactant that can be used in the provided compositions is the Water Soluble Natural Vitamin E (TPGS), sold by ZMC-USA, The Woodlands, Tex. Any known source of TPGS, or any analog, homolog or derivative thereof, can be used.

Exemplary of TPGS analogs are compounds, other than TPGS, that are similar to a parent TPGS compound, but differ slightly in composition, for example, by the variation, addition or removal of an atom, one or more units (e.g., methylene unit(s)-$(CH_2)_n$) or one or more functional groups.

At room temperature, TPGS typically is a waxy low-melting solid. In one example, the TPGS is heated prior to use, for example, to at least the melting temperature, for example, between 37° C. or about 37° C. and 41° C. or about 41° C. and the desired amount is poured out. In another example, the TPGS can be added as a waxy solid to a vessel and heated with the heating apparatus.

Also exemplary of the surfactants are TPGS analogs, which include Vitamin E derived surfactants, including PEG derivatives of Vitamin E, including vitamin E PEG diesters, such as, but not limited to, tocopherol polyethylene glycol sebacate (PTS), tocopherol polyethylene glycol dodecanodioate (PTD), tocopherol polyethylene glycol suberate (PTSr), tocopherol polyethylene glycol azelaate (PTAz) and polyoxyethanyl tocotrienyl sebacate (PTrienS) as well as other PEG derivatives of Vitamin E.

iii. PEG-Derived Surfactants

Exemplary of surfactants that can be used in the provided methods are PEG-derived surfactants, such as PEG-sorbitan fatty acid esters, such as polysorbates, including polysorbate 80 and analogs (e.g. homologs) of polysorbate 80, such as, for example, polysorbate 20, polysorbate 40 and polysorbate 60, and other polysorbates.

Polysorbates are compounds belonging to the family of oily liquids containing esters derived from PEGylated sorbitan (derivative of sorbitol) esterified with one or more fatty acids. Exemplary polysorbate surfactants are Polysorbate 20 (polyoxyethylene (20) sorbitan monolaurate; sold under the trade name Tween 20®); polysorbate 40 (Tween 40® or polyoxyethylene (20) sorbitan monopalmitate); polysorbate 60 (Tween 60® or polyoxyethylene (20) sorbitan monostearate); and polysorbate 80 (Tween 80® or polyoxyethylene (20) sorbitan monooleate). With the parenthetically indicated naming convention for the polysorbates above, the number 20 following "polyoxyethylene" refers to the number of oxyethylene —$(CH_2CH_2O)$— groups in the molecule. With the naming convention beginning with "polysorbate" (e.g. "polysorbate 80), the number refers to the type of fatty acid used to esterify the polyoxyethylene sorbitan to generate the polysorbate. For example, the number 20 indicates monolaurate; the number 40 indicates monopalmitate; the number 60 indicates monostearate; and the number 80 indicates monooleate. In one example, the surfactant(s) used in the provided compositions are polysorbate surfactants, including polysorbate 80, for example, the polysorbate 80 sold under the trademark, Tween 80®.

The PEG used in the PEG-derived surfactants can be any of a plurality of known PEG moieties. Exemplary of suitable PEG moieties are PEG moieties having varying chain lengths, and varying molecular weights, for example, PEG 1000, PEG 200, PEG 500, and PEG 20,000. The numbers following individual PEG moieties indicate the molecular weight (in kilodaltons (kDa)) of the PEG moieties. The PEG moiety of the surfactant typically has a molecular weight of between 200 kDa or about 200 kDa and 20,000 kDa or about 20,000 kDa, typically between 200 kDa and 6000 kDa, for example, between 600 kDa or about 600 kDa and 6000 kDa or about 6000 kDa, typically between 200 kDa or about 200 kDa and 2000 kDa or about 2000 kDa, between 600 kDa or about 600 kDa and 1500 kDa or about 1500 kDa, or 200, 300, 400, 500, 600, 800, or 1000 kDa.

Also exemplary of suitable PEG moieties are PEG moieties that are modified, for example, methylated PEG (m-PEG), which is a PEG chain capped with a methyl group. Other known PEG analogs also can be used. The PEG moieties can be selected from among any reactive PEG, including, but not limited to, PEG-OH, PEG-NHS, PEG-aldehyde, PEG-SH, PEG-$NH_2$, PEG-$CO_2H$, and branched PEGs.

iv. Concentration of the Surfactant

Typically, the concentration of the surfactant(s) in a particular concentrate composition is selected, as described herein, by formulating an initial concentrate with a surfactant(s) concentration within a starting concentration range, followed by evaluation of the initial concentrate and, optionally, adjusting the surfactant(s) concentration. Alternatively, the surfactant concentration can be chosen based on the concentration of surfactant in one or more existing liquid concentrate formulas. Typically, the concentration of the surfactant is between 3% or about 3% and 16% or about 16% (w/w), for example, 3% or about 3%, 4% or about 4%, 5% or about 5%, 6% or about 6%, 7% or about 7%, 8% or about 8%, 9% or about 9%, 10% or about 10%, 11% or about 11%, 12% or about 12%, 13% or about 13% or 14% or about 14%, by weight (w/w), of the concentrate, more typically between at or about 3% and at or about 14%, or between at or about 8% and at or about 11%, by weight (w/w) of the concentrate. Exemplary of surfactant concentrations within the appropriate range are 9.06%, 9.99% and 10.5% (w/w) of the concentrate. Typically, the concentration of the surfactant is less than or equal to 14% or about 14% (w/w) of the concentrate.

When mixtures of one or more surfactants are included in the provided concentrates, the concentration range of the total amount of surfactants is between 16% or about 16% and 30% or about 30%, by weight (w/w), of the concentrate, such as, for example, between 16% or about 16% and 25% or about 25% (w/w) of the concentrate; between 17% or about 17% and 22% or about 22% (w/w) of the concentrate; such as, for example, 17% or about 17%, 18% or about 18%, 19% or about 19%, 20% or about 20%, 21% or about 21% or 22% or about 22%, (w/w) of the concentrate, such as, for example, 19.56%, (w/w) of the concentrate, provided that each surfactant is present in an amount between 3% or about 3% and 16% or about 16% (w/w), for example, 3% or about 3%, 4% or about 4%, 5% or about 5%, 6% or about 6%, 7% or about 7%, 8% or about 8%, 9% or about 9%, 10% or about 10%, 11% or about 11%, 12% or about 12%, 13% or about 13% or 14% or about 14%, by weight (w/w), of the concentrate, typically between at or about 3% and at or about 14%, more typically between at or about 8% and at or about 11%, such as, for example, 9.06%, 9.99% and 10.5% (w/w) of the concentrate.

v. HLB

Exemplary of the properties of the surfactant(s) that contribute to the desirable properties of the compositions is the HLB (hydrophilic-lipophilic balance) of the surfactant(s). Generally, HLB is a value, derived from a semi-empirical formula, which is used to index surfactants according to their relative hydrophobicity/hydrophilicity. An HLB value is a numerical representation of the relative representation of hydrophilic groups and hydrophobic groups in a surfactant or mixture of surfactants. The weight percent of these respective groups indicates properties of the molecular structure. See, for example, Griffin, W. C. J. Soc. Cos. Chem. 1:311 (1949).

Surfactant HLB values range from 1-45, while the range for non-ionic surfactants typically is from 1-20. The more lipophilic a surfactant is, the lower its HLB value. Conversely, the more hydrophilic a surfactant is, the higher its HLB value. Lipophilic surfactants have greater solubility in oil and lipophilic substances, while hydrophilic surfactants dissolve more easily in aqueous media. In general, surfactants with HLB values greater than 10 or greater than about 10 are called "hydrophilic surfactants," while surfactants having HLB values less than 10 or less than about 10 are referred to as "hydrophobic surfactants."

HLB values have been determined and are available for a plurality of surfactants (e.g., see U.S. Pat. No. 6,267,985). It should be appreciated that HLB values for a given surfactant or co-surfactant can vary, depending upon the empirical method used to determine the value. HLB values also are influenced by factors such as temperature and pH, such that accepted values vary as much as ±10% (see, e.g., Nonionic Surfactants Physical Chemistry, Surfactant Science Series, Volume 23, Martin J. Schick, ed., 1987). Thus, HLB values of surfactants and co-surfactants provide a rough guide for formulating compositions based on relative hydrophobicity/hydrophilicity. For example, a surfactant typically is selected from among surfactants having HLB values within a particular range of the surfactant or co-surfactant that can be used to guide formulations. Table 1A lists HLB values of exemplary surfactants and co-surfactants.

The surfactants and HLB values set forth in Table 1A are exemplary. Any known surfactant or co-surfactant can be used with the provided compositions (e.g., see U.S. Pat. No. 6,267,985), provided that it has appropriate HLB value, such as an HLB value between at or about 13 and at or about 20. The surfactant(s) used in the provided concentrate typically has an HLB value between 13 or about 13 and 20 or about 20, more typically between 15 or about 15 and 18 or about 18, for example, 13, 14, 15, 16, 17, 18, 19, 20, about 13, about 14, about 15, about 16, about 17, about 18, about 19 or about 20. Exemplary of the surfactants include, but are not limited to, non-ionic surfactants, such as sugar esters and polyethylene glycol (PEG)-derived surfactants, such as sucrose fatty acid esters and mixtures thereof, PEG-derivatives of Vitamin E, such as sucrose fatty acid ester mixtures including monoesters, including any of the sucrose fatty acid esters, tocotrienol or tocopherol PEG diesters, such as TPGS (e.g., TPGS 1000) and TPGS and analogs, homologs and derivatives thereof, and PEG-derived surfactants, such as PEG-sorbitan fatty acid esters, such as polysorbates, including polysorbate 80 and analogs (e.g. homologs) of polysorbate 80, such as, for example, polysorbate 20, polysorbate 40 and polysorbate 60, and other polysorbates. Other known surfactants having HLB values between 13 or about 13 and 20 or about 20, typically between at our about 13 and at or about 18, more typically between about 15 and 18, also can be suitable. For example, surfactants having similar properties to TPGS, a sucrose fatty acid ester or a polysorbate 80 also can be used. Typically, the surfactant is a natural surfactant, for example, a surfactant that is G.R.A.S. (generally recognized as safe) by the FDA and/or Kosher certified.

e. Polar Solvents

The compositions, including the liquid emulsion concentrates and the dilution compositions, further include one or more polar solvents. Polar solvents are well known in the art. The polarity of a solvent generally indicates which compounds are soluble in the solvent, and with which other solvents/liquids the solvent is miscible. Generally speaking, polar compounds are more readily solubilized in water and other polar solvents than are non-polar compounds. Polar solvents are more likely to be miscible with water and other polar solvents and liquids.

The polarity of a solvent can be assessed by measuring a number of different parameters according to well known methods (see, e.g., Prizbytek, "High Purity Solvent Guide," Burdick and Jackson Laboratories, Inc., 1980), such as by determining a property of the solvent such as the dielectric constant, the dipole moment, or the polarity index. For example, polar solvents generally have high dielectric constants, typically dielectric constants greater than at or about 15 (see, e.g., Lowery et al., Mechanism and Theory in Organic Chemistry, Harper Collins Publishers, $3^{rd}$ ed., 1987, p. 177), such as at or about 15, 16, 17, 18, 19, 20, 21, 22, 23, 24, 25, 26, 27, 28, 29, 30, 31, 32, 33, 34, 35, 40, 45, 50, 55, 60, 65, 70, 75, 80 85, 90, or greater than 90. For example, the dielectric constant of water is at or about 80.10. Polar solvents generally have high polarity indices, typically greater than at or about 3 (see, e.g., Snyder, "Classification of the solvent properties of common liquids," J. Chromatography A, 92:223-230, 1974), such as at or about 3, 4, 5, 6, 7, 8 or 9 or greater than 9. Polar solvents generally have large dipole moments, typically greater than at or about 1.4 Debye, such as at or about, 1.4, 1.5, 1.6, 1.7, 1.8, 1.9, 2.0, 2.1, 2.2, 2.3, 2.4, 2.5, 2.6, 3.0, 3.5, 4 or greater than 4 Debye (see, e.g., "CRC Handbook of Chemistry and Physics," Lide, ed., $82^{nd}$ edition, CRC Press, 2001, p. 15(14)-15(18)). Other methods of assessing solvent polarity are known in the art, including, but not limited to, the Kosower Z scale (Kosower, "An introduction to physical organic chemistry," Wiley, 1969, p. 293), the donor number and donor acceptor scale (Gutmann, "Solvent effects on the reactivities of organometallic compounds," Coord. Chem. Rev., 18:225-255, 1976), and the Hildebrand solubility parameters (see, e.g., Giddings et al., "High pressure gas chromatography of nonvolatile species. Compressed gas is used to cause migration of intractable solutes," Science, 162:67-73, 1968).

Polar solvents include polar protic solvents and polar aprotic solvents. A polar protic solvent (e.g., water, methanol, ethanol) contains a hydrogen atom attached to an electronegative atom, such that the hydrogen has a proton-like character and/or the bond between the hydrogen and electronegative atom is polarized. Polar aprotic solvents, on the other hand, (e.g., acetone, acetonitrile), generally do not contain positively polarized hydrogen atoms.

The polar solvents in the provided compositions typically are polar protic solvents, including, but not limited to, water; alcohols, including, but not limited to, dihydric alcohols (e.g., glycols, e.g., propylene glycol, ethylene glycol, tetraethylene glycol, triethylene glycol, trimethylene glycol), which contain two hydroxyl groups, trihydric alcohols (e.g., glycerin, butane-1,2,3-triol, pentane-1,3,5-triol, 2-amino-2-hydroxymethyl-propane-1,3-diol), which contain three hydroxyl groups, monohydric alcohols (e.g., methanol, ethanol, propanol, isopropanol, n-butanol and t-butanol) and other alcohols; and acids, including but not limited to acetic acid and formic acid. Other polar solvents include, but are not limited to, acetone, acetonitrile, butyl acetate, dimethylformamide, dimethyl sulfoxide, dioxane, ethyl acetate, tetrahydrofuran and hexamethylphosphoric triamide. Typically, the polar solvent is water, or is an alcohol that typically contains two or more hydroxyl groups, such as a trihydric or dihydric alcohol, such as, but not limited to, glycerol and propylene glycol. The polar solvents further include low molecular weight polyethylene glycols (PEGs), such as PEGs having a molecular weight not more than at or about 600 kDa, such as between at or about 200 kDa and at or about 600 kDa, typically not more than at or about 400 kDa, for example, not more than 200 kDa.

Exemplary concentrates provided herein also include those containing a mixture of one or more polar solvents, selected from among, but not limited to, water, propylene glycol, ethylene glycol, tetraethylene glycol, triethylene glycol, trimethylene glycol, methanol, ethanol, propanol, isopropanol, n-butanol and t-butanol, other alcohols, acids, including but not limited to acetic acid and formic acid, acetone, acetonitrile, butyl acetate, dimethylformamide, dimethyl sulfoxide, dioxane, ethyl acetate, tetrahydrofuran and hexamethylphosphoric triamide. In the compositions provided herein, mixtures of one or more solvents typically include water and glycerin, or water and propylene glycol, or glycerin and propylene glycol.

In one example, the polar solvent has a dielectric constant greater than at or about 15, and typically between at or about 20 and at or about 80, such as at or about 80.1, 46.53, or 28.67. In another example, the polar solvent has a polarity index between at or about 3 and at or about 9. In another example, the dipole moment of the polar solvent is between 1.5 and 3, and typically between at or about 1.8 and 2.8, such as 1.9, 2.6, and 2.2 (for dielectric constants of solvents, see, for example, Landolt-Bornstein, New Series IV/17, Static Dielectric Constants of Pure Liquids and Binary Liquid Mixtures, Springer, 2008; and CRC Handbook of Chemistry and Physics," Lide, ed., $82^{nd}$ edition, CRC Press, 2001; for dipole moment of solvents, see, for example, CRC Handbook of Chemistry and Physics," Lide, ed., $82^{nd}$ edition, CRC Press, 2001) and for polarity indices of solvents, see, for example, Snyder, "Classification of the solvent properties of common liquids," *J. Chromatography A*, 92:223-230, 1974).

The total amount of the polar solvent typically is, for example, within a concentration range of between 30% or about 30% and 70% or about 70% (w/w) of the concentrate, for example, 30% or about 30%, 31% or about 31%, 32% or about 32%, 33% or about 33%, 34% or about 34%, 35% or about 35%, 36% or about 36%, 37% or about 37%, 38% or about 38%, 39% or about 39%, 40% or about 40%, 41% or about 41%, 42% or about 42%, 43% or about 43%, 44% or about 44%, 45% or about 45%, 46% or about 46%, 47% or about 47%, 48% or about 48%, 49% or about 49%, 50% or about 50%, 51% or about 51%, 52% or about 52%, 53% or about 53%, 54% or about 54%, 55% or about 55%, 56% or about 56%, 57 or about 57%, 58 or about 58%, 59 or about 59%, 60% or about 60%, 61% or about 61%, 62% or about 62%, 63% or about 63%, 64% or about 64%, 65% or about 65%, 66% or about 66%, 67% or about 67%, 68% or about 68%, 69% or about 69% or 70% or about 70%, (w/w) of the concentrate. Exemplary of polar solvent concentrations in the provided liquid concentrates are 48.174%, 48.215%, 49.384%, 49.423%, 49.673% and 52.136% (w/w) of the concentrate. In one example, the concentration range of the polar solvent is between 40% or about 40% and 60% or about 60% (w/w) of the concentrate. In another example, the concentration range of the polar solvent is between 45% or about 45% and 55% or about 55% (w/w) of the concentrate.

In the provided methods for making the concentrates, the polar solvent (e.g., water, propylene glycol or glycerin) is added to the water phase. In one example, the polar solvent is water, e.g., purified water, such as water that is purified prior to adding it to the concentrate formula, for example, by charcoal filter, ion exchange, reverse osmosis, UV sterilization and/or filtering using a filter, for example, a 50-100 micron filter. Typically, when a filter is used, it is an end point of use filter, which filters the water before it reaches the tank in the provided process. Alternatively, previously filtered water can be added to the concentrates.

f. Soluble Fiber

In one example, the liquid concentrate further contains one or more soluble fibers. For example, the soluble fiber can be included to increase the stability of the liquid concentrate and additionally as a fiber additive. Exemplary soluble fiber that can be used in the provided concentrates include but are not limited to fructo-oligosaccharides, for example, inulins, for example, inulins found in chicory, Jerusalem artichoke, dahlia, garlic, leeks and onions, fructans and water-soluble soybean fiber. Exemplary of a soluble fiber that can be used in the provided concentrates is an inulin, for example, Oliggo-Fiber Instant Inulin (Fibruline® Instant) (supplied by Cosucra-Groupe Warcoing SA, Belgium, sold by Gillco Products, San Marcos, Calif.), containing chicory inulin.

Typically, the concentration of the soluble fiber is within a concentration range of between 0.5% or about 0.5% and 5% or about 5%, for example, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.03%, 2.1%, 2.2%, 2.3%, 2.4%, 2.5%, 2.6%, 2.7%, 2.8%, 2.9%, 3.0%, 3.5%, 4.0%, 4.5% or 5%, w/w, of the concentrate. For example, the concentration is within the concentration range of between 1% or about 1% and 3% or about 3%, w/w, of the liquid concentrate.

g. Co-Surfactants (Emulsifiers)

In one example, the liquid concentrate further contains one or more co-surfactants (emulsifiers). For example, a co-surfactant can be included to improve emulsification of the active ingredient and/or the stability of the composition, for example, by preventing or slowing oxidation of the non-polar compound. Exemplary of a co-surfactant used in the provided concentrates is a phospholipid, for example, phosphatidylcholine.

i. Phospholipids

Exemplary of the co-surfactants that can be used in the provided compositions are phospholipids. Phospholipids are amphipathic lipid-like molecules, typically containing a hydrophobic portion at one end of the molecule and a hydrophilic portion at the other end of the molecule. A number of phospholipids can be used as ingredients in the provided compositions, for example, lecithin, including phosphatidylcholine (PC), phosphatidylethanolamine (PE), distearoylphosphatidylcholine (DSPC), phosphatidylserine (PS), phosphatidylglycerol (PG), phosphatidic acid (PA), phosphatidylinositol (PI), sphingomyelin (SPM) or a combination thereof. Typically, the phospholipid is phosphatidylcholine (PC), which sometimes is referred to by the general name "lecithin." Exemplary of the phospholipids that can be used as co-surfactants in the provided compositions are the phospholipids sold by Lipoid, LLC, Newark, N.J., for example, Purified Egg Lecithins, Purified Soybean Lecithins, Hydrogenated Egg and Soybean Lecithins, Egg Phospholipids, Soybean Phospholipids, Hydrogenated Egg and Soybean Phospholipids. Synthetic Phospholipids, PEG-ylated Phospholipids and phospholipid blends sold by Lipoid, LLC. Exemplary of the phosphatidylcholine that can be used as a co-surfactant in the provided compositions is the phosphatidylcholine composition sold by Lipoid, LLC, under the name Lipoid S100, which is derived from soy extract and contains greater than 95% or greater than about 95% phosphatidylcholine.

In one example, the phospholipid, for example, PC, represents less than or equal to 1% or about 1%, by weight (w/w) of the concentrate. In one example, the phosphatidylcholine represents between 0.1% or about 0.1% and 1% or about 1%, for example, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95 or 1%, per weight (w/w), of the concentrate. In one example, the phospholipid represents between 0.15% or about 0.15% and 0.7% or about 0.7%, by weight (w/w) of the concentrate.

h. Preservatives and Sterilizers

In one example, the provided liquid concentrate further contains one or more preservatives (or preservativers) and/or sterilizers. The preservative(s) can be included to improve the stability of the concentrate, and the compositions made by diluting the concentrate, over time. Preservatives, particularly food and beverage preservatives, are well known. Any known preservative can be used in the provided compositions. Exemplary of the preservatives that can be used in the provided compositions are oil soluble preservatives, for example, benzyl alcohol, Benzyl Benzoate, Methyl Paraben, Propyl Paraben, antioxidants, for example, Vitamin E, Vitamin A Palmitate and Beta Carotene. Typically, a preservative is selected that is safe for human consumption, for example, in foods and beverages, for example, a GRAS certified and/or Kosher-certified preservative, for example, benzyl alcohol.

The preservative typically represents less than 1%, less than about 1%, 1% or about 1%, by weight (w/w), of the liquid emulsion concentrate or between 0.1% or about 0.1% and 1% or about 1%, by weight (w/w), of the concentrate, for example, 0.1%, 0.2%, 0.3%, 0.4%, 0.5%, 0.6%, 0.7%, 0.725%, 0.75%, 0.8%, 0.9%, 1%, about 0.1%, about 0.2%, about 0.3%, about 0.4%, about 0.5%, about 0.6%, about 0.7%, about 0.8%, about 0.9%, about 1%, by weight (w/w), of the liquid concentrate.

i. Non-Polar Solvents

In one example, the liquid concentrates further contain one or more non-polar solvents, for example, an oil. Typically, the non-polar solvent is included in the composition in addition to the non-polar active ingredient, and is used to dissolve the non-polar active ingredient. In one example, the solvent is an oil that is not contained in the non-polar active ingredient. When a non-polar solvent is included in the concentrate, it typically is used to dissolve the non-polar compound before mixing with the other ingredients, for example, before mixing with the other oil phase ingredients. In one example, use of a non-polar solvent reduces the crystal size and/or increase the clarity of the aqueous liquid dilution composition containing the diluted concentrate. Exemplary of non-polar solvents that can be used in the provided concentrates are oils (in addition to the non-polar active ingredient), for example, Vitamin E oil, oleic acid, flaxseed oil, CLA, Borage Oil, D-limonene, Canola oil, corn oil, MCT oil and oat oil. Other oils also can be used. Exemplary of the Vitamin E oil, used as a non-polar solvent in the provided compositions, is the oil sold by ADM Natural Health and Nutrition, Decatur, Ill., under the name Novatol™ 5-67 Vitamin E (D-alpha-Tocopherol; ADM product code 410217). This Vitamin E oil contains at least 67.2% Tocopherol and approximately 32.8% soybean oil.

Typically, the concentration of the non-polar solvent is within a concentration range of between 1% or about 1% and 10% or about 10%, for example, 1%, 2%, 3%, 3.25%, 3.5%, 3.75%, 4%, 5%, 5.25%, 5.5% or 5.75%, w/w, of the concentrate. For example, the concentration is within the concentration range of between 3% or about 3% and 6% or about 6%, w/w, of the liquid concentrate.

j. Flavors

In one example, the concentrate further contains one or more flavors or flavoring agents, for example, any compound to add flavor to the concentrate and/or to the aqueous liquid dilution composition containing the diluted concentrate, for example, the food or beverage containing the concentrate. Several flavors are well known. Any flavor can be added to the concentrates, for example, any flavor sold by Mission Flavors, Foothill Ranch, Calif. Exemplary of flavors that can be used are fruit flavors, such as guava, kiwi, peach, mango, papaya, pineapple, banana, strawberry, raspberry, blueberry, orange, grapefruit, tangerine, lemon, lime and lemon-lime; cola flavors, tea flavors, coffee flavors, chocolate flavors, dairy flavors, root beer and birch beer flavors, methyl salicylate (wintergreen oil, sweet birch oil), citrus oils and other flavors. Typically, the flavors are safe and/or desirable for human consumption, for example, GRAS or Kosher-certified flavors. Exemplary of flavoring agents that can be used in the compositions are lemon oil, for example lemon oil sold by Mission Flavors, Foothill Ranch, Calif.; and D-limonene, for example, 99% GRAS certified D-Limonene, sold by Florida Chemical, Winter Haven, Fla. Typically, the flavor is added, using the provided methods, to the emulsion concentrates after combining the oil and water phases. Alternatively, flavor(s) can be added to the water and/or oil phase directly.

Typically, the concentration of flavoring agent added to the provided concentrates is less than 5% or about 5%, typically less than 1% or about 1%, for example, 0.1%, 0.2%, 0.3%, 0.4%, 0.5%, 0.6%, 0.7%, 0.8% or 0.9%.

k. pH Adjusters

In one example, one or more pH adjusters is added to the provided concentrates, typically to the emulsion that is formed after combining the water and oil phases according to the provided methods. In particular, the pH adjuster is used in compositions containing water. Alternatively, the pH adjuster can be added, at an appropriate concentration to achieve a desired pH, to the oil phase and/or the water phase. Typically, the pH adjuster is added to adjust the pH of the concentrate to within a range of 2.0 or about 2.0 to 4.0 or about 4.0. One or more of a plurality of pH adjusting agents can be used. Typically, the pH adjusting agent is safe for human consumption, for example, GRAS certified. Exemplary of a pH adjuster is citric acid, for example, the citric acid sold by Mitsubishi Chemical, Dublin, Ohio.

Typically, the concentration of pH adjuster added to the provided concentrates is less than 5% or about 5%, typically less than 3.5% or about 3.5%, for example, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.11%, 2.12%, 2.13%, 2.14%, 2.1415%, 2.15%, 2.16%, 2.17%, 2.18%, 2.19%, 2.2%, 2.3%, 2.4%, 2.5%, 2.6%, 2.8%, 2.9%, 3.0%, 3.1%, 3.18%, 3.2%, 3.3%, 3.4% or 3.5%.

l. Antifoaming Agent

In one example, an antifoaming agent is added to the provided concentrates, typically to the water phase, or to the oil phase, or to the water phase or the oil phase according to the provided methods. In particular, an antifoaming agent is added to the water phase. Typically the antifoaming agent is added dropwise to the provided concentrate until a reduction in air bubbles is observed. More typically, about 1 drop of antifoaming agent is added per liter of concentrate. Any antifoaming agent can be used in the provided concentrates. Exemplary of an antifoaming agent that can be added is Tramfloc 1147, sold by Tramfloc Inc, Forney, Tex., containing an emulsion of polydimethylsiloxane fluid and amorphous silica.

2. Powder Forms of the Compositions

The compositions also can be provided in powder form, i.e., powder that is made by converting the provided emulsion concentrates into a powder, using one of several well-known methods (e.g., spray-drying and/or milling). The powder compositions include, but are not limited to, coated or uncoated swallowable or chewable tablets, dry powders in hard or soft gelatin capsules, and dry powders in individual or multiple use packages for reconstituted suspensions or sprinkles. Exemplary solid dosage forms include coated or uncoated swallowable or chewable tablets. Suitable methods for manufacturing the powder compositions are known in the art.

Additionally, the powder composition can further contain at least one excipient. Excipients include, but are not limited to, diluents (sometimes referred to as fillers) including, for example, microcrystalline cellulose, mannitol, lactose, calcium phosphate, dextrates, maltodextrin, starch, sucrose, and pregelatinized starch; disintegrants including, for example, crospovidone, sodium starch glycolate, croscarmellose sodium, starch, pregelatinized starch, and carboxymethylcellulose sodium; binders including, for example, starch, hydroxypropyl cellulose, hydroxypropylmethyl cellulose, pregelatinized starch, guar gum, alginic acid, acacia, carboxymethylcellulose sodium, and polyvinyl pyrrolidone; glidants including, for example, colloidal silicon dioxide and talc; and lubricants/antiadherents including, for example, magnesium stearate, calcium stearate, stearic acid, sodium stearyl fumarate, glyceryl monostearate, hydrogenated vegetable oil, and talc. In one particular example, the excipients are selected from any one or more of maltodextrin and gum acacia.

The powder forms can be used for any convenient dosage amount of the non-polar compound. Generally, the level of non-polar compound can be increased or decreased according to the judgment of the physician, pharmacist, pharmaceutical scientist, or other person of skill in the art. The amount of the remaining non-active ingredients can be adjusted as needed.

Typically, the concentration of the excipients is within a concentration range of between 50% or about 50% and 85% or about 85%, for example, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85 or more, %, by weight, of the free flowing powder.

In one example, the powder form is a free-flowing powder. Free-flowing powders can be obtained using techniques well known in the art, such as, but not limited to, spray drying, freeze drying or absorption plating. In one example, in order to achieve a free flowing powder, the protein derivative is formulated with an excipient such as lactose or starch. For example, the formulation can be a spray dried lactose formulation (see e.g., U.S. Pat. No. 4,916,163).

The methods for forming the powders include spray drying. Spray drying processes and spray drying equipment are described generally in Perry's Chemical Engineers' Handbook, pages 20-54 to 20-57 (Sixth Edition 1984). More details on spray drying processes and equipment are reviewed by Marshall, "Atomization and Spray-Drying," 50 Chem. Eng. Prog. Monogr. Series 2 (1954), and Masters, Spray Drying Handbook (Fourth Edition 1985). Methods for spray drying are well known (see, e.g. U.S. Pat. Nos. 5,430,021 and 6,534,085 and U.S. Application Publication No. US 2007/0184117). In general, spray drying is used to dry a heated liquid by passing it through hot gas. One or more spray nozzles is used to atomize the liquid in a cooling tower or chamber. As the material is atomized (sprayed), the surface tension causes a uniform spherical particle to form, which is passed through the cooling chamber and hardens into a solid intact sphere. The spray dried particles can be between at or about 0.5 microns and at or about 100 microns, and typically are less than at or about 10 microns, typically less than at or about 5 microns, and typically less than at or about, or at or about, 1 micron.

Provided are methods for spray drying the liquid emulsion compositions to form powder compositions. In the spray drying methods, the liquid emulsion compositions can be heated, e.g. to a temperature between at or about 100 and at or about 150° F., typically between 110° F. and 140° F., e.g. at or about 110, 115, 120, 125, 130, 135 or 140° F. The compositions can be mixed while heating, such as with any of the mixers described herein, for example, homogenizers (e.g. reversible homogenizers and piston-driven homogenization).

For spray drying, one or more excipients are mixed with a polar solvent, typically water, and heated, e.g. to a temperature between at or about 100° F. and at or about 150° F., typically between 110° F. and 140° F., e.g. at or about 110, 115, 120, 125, 130, 135 or 140° F. In one example, the excipient is mixed with water in an amount of one part excipient (by weight) to two parts water (by weight). The excipient-solvent (e.g. water) mixture can be mixed while heating, e.g. using any of the mixers described herein, for example, homogenizers (e.g. reversible homogenizers and piston-driven homogenizers) with heating during the mixing. The heated liquid emulsion composition and the heated water-excipient mixture then are mixed together, such as by transferring one mixture to the other, e.g. by any of the transfer means provided herein. Typically, the two mixtures are homogenized, e.g. with a reversible homogenizer or piston-driven homogenizer or any other homogenizer. The homogenized mixture then is subject to spray drying using a spray dryer.

Exemplary of the spray dryers are cyclone spray dryers. During spray drying with cyclone spray dryers, the homogenized mixture is pumped into an atomizing device where it is broken into small droplets. Upon contact with a stream of hot air, the moisture is removed very rapidly from the droplets while still suspended in the drying air. The dry powder is separated from the moist air in cyclones by centrifugal action. The centrifugal action is caused by the great increase in air speed when the mixture of particles and air enters the cyclone system. The dense powder particles are forced toward the cyclone walls while the lighter, moist air is directed away through the exhaust pipes. The powder settles to the bottom of the cyclone where it is removed through a discharging device. Sometimes the air-conveying ducts for the dry powder are connected with cooling systems which admit cold air for transport of the product through conveying pipes. Cyclone dryers have been designed for large production schedules capable of drying ton-lots of powder per hour.

As will be appreciated by one of skill in the art, the inlet temperature and the outlet temperature of the spray drier are not critical but will be of such a level to provide the desired particle size, of less than at or about 1 micron, and to result in a powder that has a desired property. Typically, the ability of the free flowing powder to yield a clear (or relatively clear) liquid dilution composition upon dilution in an aqueous medium is the desired property that is evaluated. In this regard, the inlet and outlet temperatures are adjusted depending on the melting characteristics of the liquid emulsion components and the composition of the homogenized liquid emulsion concentrate/excipient mixture. The inlet temperature is between at or about 60° C. and at or about 170° C. with outlet temperatures between at or about 40° C. to at or about 120° C. Typically inlet temperatures are from at or about 90° C. to at or about 120° C. and outlet temperatures are from at or about 60° C. to at or about 90° C. The flow rate which is used in the spray drying equipment will generally be at or about 3 mL per minute to at or about 15 mL per minute. The atomizer air flow rate will vary between values of at or about 25 L per minute to at or about 50 L per minute. Commercially available spray dryers are well known to those of skill in the art, and suitable settings for any particular dispersion can be readily determined by one of skill in the art without undue experimentation. Operating conditions such as inlet temperature and outlet temperature, feed rate, atomization pressure, flow rate of the drying air, and nozzle configuration can be adjusted in accordance with the manufacturer's guidelines.

In some examples, the dry powder is stored into a capsule form or is pressed into a tablet. For use as tablets, the compositions typically contain multiple other excipients. These excipients include tablet disintegrants, such as corn starch, glidants, such as silicon dioxide, and lubricants such as magnesium stearate. Ordinarily these compositions contain minor amounts by weight of glidants and lubricants, e.g., each two percent (2%) or less by weight. Tablet disintegrants are optionally present, and, if present, are included in sufficient amounts to assure that the tablet disintegrates upon ingestion. For example, disintegrants, such as corn starch, can be employed at concentrations of from about zero to about 30 percent by weight of the composition.

Free flowing powders also can be used to administer the active agent by inhalation using a dry powder inhaler. Such dry powder inhalers typically administer the active agent as a free-flowing powder that is dispersed in a patient's air-stream during inspiration. In order to achieve a free flowing powder, the active agent is typically formulated with a suitable excipient such as lactose or starch. For example, such a dry powder formulation can be made, for example, by combining the lactose with the active agent and then dry blending the components. Alternatively, if desired, the active agent can be formulated without an excipient. The pharmaceutical composition is then typically loaded into a dry powder dispenser, or into inhalation cartridges or capsules for use with a dry powder delivery device. Examples of dry powder inhaler delivery devices include Diskhaler (GlaxoSmithKline, Research Triangle Park, N.C.) (see, e.g., U.S. Pat. No. 5,035,237); Diskus (GlaxoSmithKline) (see, e.g., U.S. Pat. No. 6,378,519; Turbuhaler (AstraZeneca, Wilmington, Del.) (see, e.g., U.S. Pat. No. 4,524,769); Rotahaler (GlaxoSmithKline) (see, e.g., U.S. Pat. No. 4,353,365) and Handihaler (Boehringer Ingelheim). Further examples of suitable DPI devices are described in U.S. Pat. Nos. 5,415,162, 5,239,993, and 5,715,810 and references cited therein.

3. Compositions Containing the Liquid Emulsion Concentrates

Among the compositions provided herein are food and beverage compositions, typically water-based finished food or beverages, containing the non-polar compounds. The dilution compositions are made by diluting the liquid emulsion concentrates into a variety of foods and beverages. For example, the liquid emulsion concentrates are diluted into a variety of foods including, but not limited to, dairy compositions, e.g., butter, milk, yogurt, and cheese, savory food compositions, sweet food compositions, frozen food, egg products, margarines, spreads, peanut butter, almond butter, sauces and dressings, e.g., mayonnaise, thousand island, ranch and tartar sauce, soups, dips, fillings for cakes and cookies, confections, whipped desserts, e.g., mousse, custard, chiffon, meringue, and whipped topping, frozen desserts, e.g., frozen yogurt and ice cream, candies, baby foods, e.g., infant formula, pet food or any food product, and beverages, for example, water, flavored water, soda, milk, juices, including fruit juices, sauces, syrups, soups, sports drinks, nutritional beverages, energy drinks, vitamin-fortified beverages, or any beverage. More typically, the liquid emulsion concentrates are diluted into a variety of water-based foods and beverages including, but not limited to, tomato-paste based products, dairy-based products, creams, sauces, soups, pastes, dressings, water, flavored water, soda, milk, juices, including fruit juices, sauces, syrups, sports drinks, fitness drinks, nutritional beverages, nutritional supplement, energy drinks and vitamin-fortified beverages.

In one example, the liquid emulsion concentrates are diluted into tomato-paste based products, such as tomato sauce and vegetable juice. In another example, the liquid emulsion concentrates are diluted into dairy products, such as fat free milk and fat free sour cream. In yet another example, the liquid emulsion concentrates are diluted into beverages, for example, juices, for example, nectar juices and orange juice, or tinted nutritional beverages. In further examples, the liquid emulsion concentrates are diluted into mayonnaise, salsa, queso cheese, and salad dressing, for example, ranch dressing.

The dilution compositions are typically made by diluting the liquid emulsion concentrates into a variety of foods and beverages, such that the food and beverage dilution compositions contain a specific amount of non-polar active ingredient per serving of the food or beverage, such as, for example, the dietary reference intake for a particular non-polar active ingredient. For example, the food and beverage dilution compositions provided herein contain between at or about 1.5 to at or about 3.0 grams (g) of omega-6 fatty acids, between at or about 16 to at or about 220 milligrams (mg), for example, between at or about 32 to at our about 220 mg docosahexaenoic acid (DHA) and eicosapentaenoic acid (EPA), between at or about 100 and at or about 500 mg phytosterols, between at or about 10 and at or about 200 mg, for example, between at or about 50 and at or about 200 mg Coenzyme Q10, between at or about 40 and at or about 400 micrograms (mcg) Vitamin A, or between at or about 200 and at or about 2000 international units (IU), for example between at or about 400 and at or about 800 IU Vitamin D3, per serving of the food or beverage, for example, 1 teaspoon (0.166667 ounce, 4.7249 g), 1 tablespoon (0.5 fluid ounce, 14.1747 g), 2 tablespoons (1 fluid ounce, 28.3495 g), 0.25 cup (2 fluid ounces, 56.6990 g), 0.5 cup (4 fluid ounces, 113.398 g), 0.75 cup (6 fluid ounces, 170.097 g) or 1 cup (8 fluid ounces, 226.796 g), for example, per 8 ounces of a beverage.

Properties of the provided liquid emulsion concentrates that are diluted into the food or beverage contribute to various properties of the provided resulting dilution compositions, for example, stability, for example, lack of phase separation, flocculation, creaming, of oxidation, "ringing" and/or precipitation over time; desirability for human consumption, for example, pleasant taste, and/or smell, for example, lack of "fishy" taste/smell, lack of "ringing" and lack of crystal formation; clarity; and safety for human consumption. As described above, the liquid emulsion concentrates are formulated according to the desired properties of the food and beverage dilution compositions containing the concentrates.

a. Stability

Typically, the provided dilution compositions containing the concentrates are stable, for example, free from one or more changes over a period of time, for example, 1, 2, 3, 4, 5, 6, 7, 8, 9, 10, 11 or 12 months, 1, 2, 3, 4 or more years.

In one example, the compositions are stable because they are free from oxidation or substantial oxidation over time. In another example, they are stable because they remain clear over time. In another example, the stable compositions remain safe and/or desirable for human consumption over time. In one example, stability refers to the lack of precipitates forming in the compositions over the period of time. In a related example, the compositions are stable because they do not exhibit "ringing," formation of a whitish or opaque ring around the perimeter of the container holding the liquid, typically at the surface of the liquid. Ringing typically is undesirable, particularly in the case of a liquid for human consumption, for example, a beverage. In yet another example, the compositions are stable because they do not exhibit flocculation over time.

In another example, the composition is stable if it does not exhibit any visible phase separation or creaming over a period of time, for example, after 24 hours, after one week or after one month. In one example, the compositions are stable if they exhibit one or more of these described characteristics, over time, when kept at a particular temperature. In one example, the compositions remain stable at room temperature, for example, 25° C. or about 25° C. In another example, the compositions remain stable at between 19° C. and 25° C. In another example, the compositions remain stable at refrigerated temperatures, for example, 4° C. or about 4° C., or at frozen temperature, for example, at −20° C. or about −20° C.

Stability refers to a desirable property of the provided compositions, for example, the ability of the provided compositions to remain free from one or more changes over a period of time, for example, 1, 2, 3, 4, 5, 6, 7, 8, 9, 10, 11 or 12 months, 1, 2, 3, 4 or more years. In one example, the composition is stable if it is formulated such that it remains free from oxidation or substantial oxidation over time. In another example, the stable compositions remain clear over time. In another example, the stable compositions remain safe and/or desirable for human consumption over time. In one example, stability refers to the lack of precipitates forming in the compositions over the period of time. In a related example, stability refers to the lack of "ringing" over the period of time. In another example, the composition is stable if it does not exhibit any visible phase separation over a period of time, for example, after 24 hours, after one week or after one month. In one example, the compositions are stable if they exhibit one or more of these described characteristics, over time, when kept at a particular temperature.

In one example, the compositions are stable at room temperature, for example, 25° C. or about 25° C. In another example, the compositions remain stable at between 19° C. and 25° C. In another example, the compositions remain stable at refrigerated temperatures, for example, 4° C. or about 4° C., or at frozen temperature, for example, at −20° C. or about −20° C.

i. Stability Determined by Empirical Evaluation

In one example, the stability, or shelf life, of a dilution composition containing the initial concentrate can be assessed qualitatively by observation. For example, a food or beverage dilution composition is considered stable if it does not exhibit phase separation, flocculation, precipitation, creaming, coagulation and/or sedimentation when looking at the food or beverage with the naked eye. Stability can be assessed empirically by comparison with other foods or beverages. For example, it can be desirable that the food or beverage is as stable as another food or beverage not containing the initial concentrate. In a related example, it can be desired that there is no substantial difference, for example, no observable difference, between the food or beverage dilution composition containing the concentrate and the food or beverage without the concentrate.

In another example, stability is determined by evaluating sensory attributes of the food or beverage compositions containing the initial concentrates. For example, the food or beverage dilution compositions can be evaluated for a variety of different sensory attributes by a tasting panel. Sensory attributes include, for example, appearance, taste, aroma and flavor, for example, "fishiness", feeling factors, such as burning or irritation by smelling, texture, such as viscosity or oily mouth feeling, aftertaste, and any other attribute that is warranted. Evaluation of sensory attributes can be assessed empirically for the food or beverage dilution compositions alone, or alternatively by comparison of the dilution compositions to a food or beverage not containing the non-polar compounds. In one example, the food or beverage dilution composition has desirable sensory attributes, such as a lack of "fishy" smell or taste. In another example, there is no difference between the evaluated sensory attributes of the food or beverage dilution composition as compared to a food or beverage not containing the initial concentrate. Typically, the food or beverage dilution compositions are considered stable if they retain desired sensory attributes over a period of time, for example, 1, 2, 3, 4, 5, 6, 7, 8, 9, 10, 11 or 12 months, 1, 2, 3, 4 or more years.

ii. Oxidative Stability

In one example, the shelf life of a food or beverage dilution composition containing the initial concentrate is assessed quantitatively, for example, by measuring oxidative stability of polyunsaturated fatty acids. Oxidative deterioration can be assessed by chemical methods such as determining peroxide value (PV), which measures peroxides resulting from primary oxidation, or p-anisidine value (AV), which measures 2-alkenals (aldehydes) resulting from secondary oxidation. Peroxide value typically is measured by reaction of the peroxide with an ion followed by determination of the amount of oxidation, either directly or indirectly. For example, PV can be determined by measuring the amount of iodine formed by the reaction of peroxides with iodide ion in the presence of an indicator ion, for example, sodium thiosulfate. In another example, PV is determined by reaction with $Fe^{+++}$ followed by direct measurement of colorimetric intensity at a wavelength of 505 nm. A p-anisidine value test measures the amount of aldehydes formed from secondary oxidation of fatty substances upon reaction with p-anisidine by measuring absorption at 366 nm. Any method known to one of skill in the art can be used to determine oxidative deterioration. Typically, the food or beverage dilution compositions are considered stable if they remain free from oxidative deterioration over a period of time, for example, 1, 2, 3, 4, 5, 6, 7, 8, 9, 10, 11 or 12 months, 1, 2, 3, 4 or more years.

b. Clarity

In one example, the dilution compositions are clear aqueous liquid dilution compositions or non-turbid aqueous liquid dilution compositions, for example, as determined, as described below, empirically or by measuring turbidity and/or particle size. In another example, the aqueous liquid dilution compositions are not clear, or not completely clear. The liquids can be more or less clear, or have the same clarity as another liquid, for example, an aqueous liquid dilution composition made according to the provided methods or a beverage, for example, a beverage that does not contain the diluted concentrate. Properties of the liquid concentrates can affect the clarity of the liquid. A number of parameters can vary the clarity of the liquids, for example, the relative concentration of surfactant, non-polar compound and/or water; the type of non-polar ingredient; the concentration of excipient(s) in the particular non-polar compound; and the purity of the non-polar compound, for example, whether it has been standardized to a high purity, or whether it is an extract or a filtered extract. For example, an aqueous liquid dilution composition made by diluting a concentrate containing a non-polar active ingredient that contains lecithin, for example a high amount of lecithin, can be less clear than one made with a concentrate containing a non-polar compound that does not contain lecithin. In another example, a liquid concentrate containing a non-polar compound that is a filtered extract can produce a clearer aqueous liquid dilution composition when diluted than a concentrate containing a crude extract.

i. Clarity Determined by Empirical Evaluation

In one example, the clarity/turbidity of the aqueous liquid dilution composition containing the diluted concentrate is evaluated qualitatively by observation. In one example, a liquid can be considered clear if it does not have a cloudy appearance and/or if no or few particles are visible when viewing the liquid with the naked eye or if it is the same or substantially similar in clarity to another liquid, for example, a beverage, for example, water, fruit juice, soda or milk. In some cases, the aqueous liquid dilution composition is as clear or about as clear as water or another liquid, for example a beverage. For example, the liquid (containing the liquid concentrate diluted in an aqueous medium, for example, a beverage) can be as clear or about as clear as the aqueous medium not containing the liquid concentrate. In a related example, there is no substantial difference, for example, no observable difference, between the aqueous liquid dilution composition containing the concentrate and the aqueous medium without the concentrate. A clear liquid is not necessarily colorless, for example, a yellow liquid that contains no visible particles or cloudiness can be considered clear. In another example, the liquid is clear or partially clear or substantially clear if no crystals are visible and/or if no "ringing" is observed on the container containing the liquid.

ii. Clarity Determined by Particle Size or Number of Particles

In another example, clarity of the aqueous liquid dilution composition is evaluated by measuring the particle size and/or number of particles of the liquid.

In one example, the aqueous liquid dilution compositions have a particle size less than 200 nm or less than about 200 nm, for example, 5, 10, 15, 20, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm. In another example, the aqueous liquid dilution composition has a particle size less than 100 nm or about 100 nm, less than 50 nm or about 50 nm or less than 25 nm or about 25 nm. Typically, the particle size of the aqueous liquid dilution composition is between 5 nm or about 5 nm and 200 nm or about 200 nm, or between 5 nm or about 5 nm and 50 nm or about 50 nm.

Typically, the particle size of the provided aqueous liquid dilution composition containing the liquid concentrate, which contains the non-polar compound, is smaller than the particle size of a liquid containing the non-polar compound (not formulated in a liquid concentrate).

iii. Turbidity

In another example, the clarity of the liquid is evaluated and/or expressed using a turbidity measurement, for example, Nephelometric Turbidity Units (NTU), as measured using the provided methods, described below. In this example, turbidity is measured optically, to get value indicating the cloudiness or haziness of the liquid, which correlates with particles in suspension in the liquid. The more clear a liquid is, the lower its turbidity value.

In one example, the clear aqueous liquid dilution composition has a turbidity value (NTU) of 30 or about 30; or an NTU value of less than 30 or about 30, for example, less than 29 or about 29, less than 28 or about 28, less than 27 or about 27, less than 26 or about 26, less than 25 or about 25, less than 24 or about 24, less than 23 or about 23, less than 22 or about 22, less than 21 or about 21, less than 20 or about 20, less than 19 or about 19, less than 18 or about 18, less than 17 or about 17, less than 16 or about 16, less than 15 or about 15, less than 14 or about 14, less than 13 or about 13, less than 12 or about 12, less than 11 or about 11, less than 10 or about 10, less than 9 or about 9, less than 8 or about 8, less than 7 or about 7, less than 6 or about 6, less than 5 or about 5, less than 4 or about 4, less than 3 or about 3, less than 2 or about 2, less than 1 or about 1; or 29 or about 29, 28 or about 28, 27 or about 27, 26 or about 26, 25 or about 25, 24 or about 24, 23 or about 23, 22 or about 22, 21 or about 21, 20 or about 20, 19 or about 19, 18 or about 18, 17 or about 17, 16 or about 16, 15 or about 15, 14 or about 14, 13 or about 13, 12 or about 12, 11 or about 11, 10 or about 10, 9 or about 9, 8 or about 8, 7 or about 7, 6 or about 6, 5 or about 5, 4 or about 4, 3 or about 3, 2 or about 2, 1 or about 1, or 0 or about 0.

In another example, the turbidity value of the aqueous liquid dilution composition is less than 200 or less than about 200, for example, 200, 175, 150, 100, 50, 25 or less.

In another example, it is desirable that the aqueous liquid dilution composition contains a turbidity value that is comparable, for example, about the same as, the same as, or less than or greater than, the turbidity value of another liquid, for example, a beverage not containing the liquid concentrate or an aqueous liquid dilution composition made by the provided methods.

c. Desirable Characteristics for Human Consumption

In one example, the dilution composition is desirable for human consumption, for example, for use in a food or beverage. Different properties of the dilution composition can contribute to its desirability as a consumable product. For example, taste, smell, clarity, color, crystal formation, precipitation and "ringing," all can relate to desirability.

In one example, the dilution composition has a pleasant taste and/or smell, for example, due to one or more flavors added to the concentrate and/or to the aqueous medium. In another example, the dilution composition containing the concentrate is free from an unpleasant taste or smell, for example, a "fishy" taste or smell. In one example, the concentrate smells or tastes less unpleasant, for example, fishy, compared to another dilution composition.

In one example, the aqueous liquid dilution composition is desirable because it does not have crystals or has fewer crystals compared with another aqueous liquid dilution composition. In another example, the dilution composition is desirable because it does not exhibit ringing. In a further example, the dilution composition is desirable because it does not exhibit phase separation, or flocculation.

d. Safety

Typically, the dilution compositions containing the concentrates are safe for human consumption, for example, containing only ingredients approved by the FDA for human consumption, for example GRAS-certified ingredients. In one example, one or more of the ingredients, for example, all the ingredients, are Kosher-certified. Safety of the compositions also relates to stability over time. Lack of or minimum oxidation of the compositions over time can contribute to the safety of the compositions.

e. Oral Bioavailability

In one example, the non-polar compounds, for example, the non-polar active ingredients, contained in the dilution compositions exhibit a high or relatively high bioavailability, for example, a bioavailability that is higher than a composition containing the non-polar active ingredient alone (i.e., not formulated in the liquid concentrate). Bioavailability relates to the ability of the body to absorb the non-polar active ingredient into a particular space, tissue cell and/or cellular compartment. Typically, non-polar active ingredients in liquids having small particle sizes are better absorbed than those with larger particle sizes.

C. METHODS FOR MAKING LIQUID EMULSION CONCENTRATES CONTAINING NON-POLAR COMPOUNDS

Also provided are methods for making the liquid emulsion concentrates. General equipment and steps of the methods are detailed below. In one example, the general methods for making the concentrates are performed using a bench-top manufacturing process, which is used for making relatively smaller-sized batches of the concentrates. In another example, the general methods for making the concentrates are performed using a scaled-up manufacturing processes, which is used for making relatively larger batches of the concentrates. The bench-top process can be scaled up to the scaled-up process. Any concentrate made using the bench-top method can be made using the scaled-up process, by scaling up the method.

1. Equipment for Making the Concentrates

Various equipment, for example, vessels for mixing the oil phase, water phase and emulsion, for example, tanks; scales; mixers, including standard mixers and homogenizers; heating and cooling apparatuses, including water-jacketed tanks, hot plates, water baths and chillers (coolers), including recirculating coolers; transfer apparatuses, for example, transfer means, for example, pumps, hoses, sanitary fittings; ball valves; purifiers, for example, filters, for example, carbon filters, ion exchange equipment, reverse osmosis equipment, end-point filters and end product filters; evaluation means, for example, pH and temperature meters; and other equipment, is used in various steps of the provided methods for making the concentrates. The choice of equipment depends on a plurality of factors, including batch size and manufacturing process.

a. Scales

One or more scales are typically used to measure the ingredients before adding them to the appropriate vessel. Alternatively, the ingredients can be weighed in the vessel, for example, in a tank on top of a scale.

Any of a plurality of well-known, commercially sold scales can be used to weigh the ingredients. Choice of scale(s) can depend on a number of factors, including the mass of the final concentrate being made and the ingredient being weighed. In one example, multiple scales are used to weigh the various ingredients of the concentrate. In general, relatively larger capacity (weight) scale(s) are used in making larger batches of concentrate while relatively smaller capacity scale(s) are used in making smaller batches.

Exemplary of the scales used with the provided methods to weigh the ingredients are a Toledo Scale (Model GD13x/USA), a Sartorius Basic Analytical Scale (Model BA110S) which is a basic series analytical scale with a 110 g capacity and a resolution of 0.1 mg; and an OHAUS Scale (Model CS2000), which is a compact portable digital scale having a 2000 g capacity and a resolution of 1 g.

b. Purifiers, Including Filters

Purifiers, typically more than one purifier, for example, filters, are used in the provided methods to remove impurities in the ingredients prior to their addition to the concentrate and/or from the final concentrate and/or an intermediate phase of the concentrate. For example, when the polar solvent is water, the water typically is purified water. In one example, one or more purifiers, for example, carbon filters, ion exchange purifiers, reverse osmosis purifiers, and/or end point filters are used to filter water, for example, city water, prior to its addition to the water phase, for example, to remove impurities, for example, sediment, from the water.

Exemplary of the purifiers that can be used with the provided methods are filters, for example, 100 micron filters and carbon filters, which are filters that use activated carbon to remove impurities by chemical adsorption. Carbon filtering typically is used for water purification and is particularly effective at filtering out chlorine, sediment, volatile organic compounds and other impurities. Typically, the particles removed by carbon filters are between about 0.5 microns and about 50 microns. Other filters are well known and can be used with the provided methods.

Also exemplary of the purifiers that can be used in the provided methods are reverse osmosis purifiers, which use mechanical pressure to purify liquids, for example, water. In one example, the pressure forces the water through a semipermeable membrane to remove impurities.

Also exemplary of the purifiers that can be used in the provided methods are ion exchange purifiers, for example, an ion exchange purifier using a resin bed, for example, a zeolite resin bed, to replace salts, e.g., cations, for example, magnesium and calcium, with other cations, for example, sodium and potassium cations. Such purifiers can be purchased, for example, from Aquapure Filters, Clarkston, Mich.

In another example, an end product filter (e.g., a 100 micron FSI filter, Product Number BPEM 100-5GP) is used to filter any impurities out of the final product (e.g., the final liquid emulsion composition). Other filters are known and can be used with the provided methods.

c. Vessels for Mixing the Ingredients

One or more, typically two or more, vessels, for example, tanks, for example, water-jacketed tanks; pots; and/or beakers, for example, Pyrex® beakers, are used in the provided methods to contain the ingredient(s) of the liquid concentrates, for example, during mixing and/or heating or cooling. Typically, separate vessels (an oil phase tank and a water phase tank) are used for mixing and heating the ingredients of the oil phase and the water phase, prior to combining the two phases to form an emulsion. In another example, an additional vessel, for example, a holding and/or packaging tank, is used for holding and/or packaging the emulsion and/or for addition/mixing of additional ingredients to the emulsion.

A number of vessels are available for mixing ingredients. Typically, the vessels are cleaned, for example, rinsed, soaped and/or sanitized according to known procedures, prior to use and between uses.

In one example, typically used with the bench-top process, the vessel is a container, for example, a bench-top container, for example, flasks, beakers, for example, Pyrex® beakers, vials, measuring containers, bottles and/or other bench-top containers.

In another example, typically used with the scaled-up manufacturing process, the vessels are tanks, for example, water phase tanks, oil phase tanks and holding/packaging tanks. Typically, the tanks are equipped with one or more mixers, for example, a standard mixer and/or homogenizer, which are used to mix the ingredients added to the tank. In one example, the tank further is equipped with a heating and/or cooling device. For example, the tank can be a water-jacketed tank. The temperature of the water jacketed tank is controlled through the water-jacket, for example, to heat the contents, for example, while mixing.

Exemplary of the tanks that can be used with the provided methods are water-, jacketed tanks, for example, the Overly 550 Gallon water jacketed tank (Model 10576501G), which has a 550 gallon capacity and typically is used as a water-phase tank, the Schweitzers 450 gallon tank (Model #5214-C), which has a 450 gallon capacity and typically is used as an oil phase tank and the Royal 190 gallon water jacketed tank (Model 9977-5), which has a 190 gallon capacity and can be used as a water or oil phase tank when mixing smaller volumes. Other tanks are well known and can be used with the provided methods for mixing the concentrates, for example, the phases of the concentrates.

d. Mixers

Mixers are used in the provided methods to blend, mix and/or emulsify the liquid concentrates and/or various ingredients and/or phases of the liquid concentrates. In one example, the mixers are used to keep the ingredients and/or mixture circulating to maintain temperature, viscosity and/or other parameters of the mixture. Exemplary of the mixers that can be used in the provided methods are standard mixers, which can be used, for example, to mix the ingredients in the water and/or oil phases, to maintain a homogeneous mixture while heating. Exemplary of the standard mixers is a LIGHTNIN® mixer (LIGHTNIN, Rochester, N.Y.), for example, Model Numbers XJC117 and ND-2. In one example, the LIGHTNIN® mixers are fixed-mount, gear drive high-flow mixers, for use with closed tanks. Another example of a standard mixer is a mixer sold by IKA®, for example, overhead IKA® mixers, for example, model Nos. RW-14 Basic and RE-16S, which are laboratory stirrers and can be used to mix ingredients, for example, to generate the oil and water phases. In one example, the mixers are attached to the vessels, for example, the tanks, for example, mounted or clamped onto the tanks, for example, the top of the tanks. In another example, the mixers are placed in the vessels for mixing.

Also exemplary of the mixers used with the provided methods are homogenizers (also called shears), which typically are used to form the emulsion by emulsifying the oil and water phases after they are combined. The homogenizers typically provide high shear dispersion of solids and emulsification of immiscible liquids at high shear rates. Exemplary of the homogenizers that can be used in the provided methods are high-shear homogenizers, for example, reversible homogenizers sold by Arde Barinco, Inc., Norwood, N.J., for example, Model CJ-50, which is a 3600 rpm mixer having a 6 inch rotor diameter, a tip speed of 5575 ft/minute and an emersion depth of 33 inches and has six separate openings at the bottom and top, which concentrates the liquid into six chambers, reducing the surface volume and creating a shear effect; and Model CJ-4E, which is a 10,000 rpm mixer with fan-cooled motor, optimized for 1 to 5 gallon batch sizes, having a 1.875 inch rotor diameter, a tip speed of 4920 rpm and an immersion depth of 16 inches. Other homogenizers, for example, other reversible homogenizers sold by Arde Barinco Inc., can be used with the provided methods.

In one example, the homogenizer is attached to the top of the vessel, for example, the tank, for example, by clamps or by channel locks and an electrical hoist. In another example, the homogenizer is placed in the vessel. The Arde Barinco reversible homogenizers contain axial flow impellers, which create two distinct mixing actions, depending on direction. Downward "vortex flow" pulls solids from top and bottom of the mixture, while upward "umbrella flow" controls mixing at the highest shear and recirculation rates without splashing or incorporation of air. The reversible homogenizers typically are equipped with an adjustable baffle plate, which can be adjusted to control the type of mixing, for example at different times during emulsification.

A number of additional mixers are well known and can be used with the provided methods. Exemplary of the mixers that can be used with the provided methods are shears, inline mixers/mixing, Ribbon, Plow/Paddle Blenders Forberg Mixers, Conveyors, Bag Dumps & Compactors, V-Blenders, Blade Mixers, Double Cone Mixers, Continuous Mixers, Speedflow Mixers, Batch Mixers, Double Ribbon Blenders, Paddle and Ribbon Mixers with Choppers, Plow Blenders/Turbulent Mixers, Fluidizing Forberg-Type Mixers, Air Mixers, Active Mixers, Passive Mixers, Top Entry Mixers, Side Entry Mixers, Static Mixers, Fixed Entry Mixers, Portable Mixers—direct and gear drive, Sanitary Mixers, Drum Mixers, Bulk Container (IBC) Mixers, Lab Stirrers, Variable Speed Mixers, dough mixer, vertical mixer, spiral mixer, twin arm mixer, fork mixer, double spiral mixer, all agitators, agitator mixers, Banbury Mixers, Rubber Mixers, Blondheim Mixers, Churn Mixers, Conical Mixers, Continuous Mixers, Disperser Mixers, Pan Mixers, Emulsifier Mixers, Hobart Mixers, Liquifier Mixers, Littleford Mixers, Meat Mixers, Plow Mixers, Mixmuller Mixers, Nauta Mixers, Oakes Mixers, Planetary Mixers, Pony Mixers, PUG Mixers, Ribbon Mixers, Ross Mixers, Rotary Mixers, Sigma Mixers, Single Arm Mixers, Tote Bin Mixers, Tumble Mixers, Vacuum Mixers, Turbolizer Mixers, Twin Shell Mixers, V-Type Mixers, Zig-Zag Mixers side arm mixers, hand-held mixers, stir rods, stir bars, magnetic mixers and overhead mixers, for example, mechanical and/or electric overhead mixers.

e. Heating Apparatuses

One or more, typically more than one, heating apparatuses are used in the provided methods to control the temperature of the ingredients, phases and/or concentrate, typically while mixing.

In one example, the heating apparatuses are water-jackets. In this example, the vessels used to mix the ingredients and/or emulsify the phases are water jacketed tanks. The water jacket can be controlled, for example, using a control panel, to adjust the temperature of the contents of the vessel.

Alternatively, other heating apparatuses can be used to heat the ingredients, phases, and/or concentrates. Exemplary of heating apparatuses that can be used with the provided methods are immersible and/or submersible heaters, for example, 12 KW or 13 KW sanitary heaters, which are food-grade heaters that are immersed into the tanks while mixing, typically for applications requiring high heat, for example, temperatures greater than 60° C. or about 60° C., or greater than 80° C. or about 80° C. Also exemplary of heating apparatuses are stoves, for example, propane stoves. Also exemplary of the heating apparatuses are hot plates, for example, the Thermolyne hot plate, model number 846925 and model number SP46615. Typically, the heater is capable of heating the mixture to between 45° C. or about 45° C. and 85° C. or about 85° C., for example, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84 or 85° C. Typically, the heater is capable of heating the mixture to 60° C. or about 60° C., for example, providing low heat.

f. Cooling Apparatuses

One or more cooling apparatuses can be used with the provided methods, for example, to cool the ingredients during mixing, for example, to chill the mixture while emulsifying the oil and water phases. Exemplary of the cooling apparatuses are chillers, for example, recirculating coolers, which can be attached to the vessel, for example, remotely or by a tank mounted in the cooler, to recirculate fluid from the tank, through the chiller and back to the tank, in order to rapidly cool and maintain the temperature of the mixture during mixing. Exemplary of an open-loop chiller that can be attached to the tank and used with the provided methods are chillers sold by Turmoil, West Swanzey, N.H., for example, open or closed-loop coolers, for example, model No. OC-1000 RO. Other cooling apparatuses are well known and can be used with the provided methods.

Also exemplary of the cooling apparatuses are water baths and ice baths, for example, water baths and/or ice baths in which the vessel(s) are placed, for example, during homogenizing.

Typically, the cooling apparatus can be used to cool the liquid to between 25° C. or about 25° C. and 45° C. or about 45° C., for example, 25, 26, 27, 28, 29, 30, 31, 32, 33, 34, 35, 36, 37, 38, 39, 40, 41, 42, 43, 44 or 45° C., typically between 25° C. and 43° C., typically between 35° C. and 43° C., for example, 26.5° C. Typically, the cooling is rapid cooling, for example, cooling to between 25° C. or about 25° C. and 45° C. or about 45° C., for example, between 35° C. and 43° C., for example, 26.5° C., in between 15 minutes or about 15 minutes and 2 hours or about 2 hours, typically, between 30 minutes or about 30 minutes and 60 minutes or about 60 minutes, for example, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 minutes.

g. Transfer Means

Transfer means are used with the provided methods to transfer liquid from one vessel to another vessel, for example, to transfer the contents of one or more vessels to one or more other vessels, for example, to transfer the water phase to the oil phase vessel (e.g., the oil phase tank) or to transfer the oil phase to the water phase vessel (e.g., the water phase tank), in order to form the emulsion. Exemplary of the equipment used for the transfer means are transfer pumps and associated accessories, for example, ball valves, sanitary fittings (for example, sanitary fittings sold by Granger, Inc., Lake Forrest, Ill.) and transfer hoses (for example, hoses sold by Sani-Tech West, Oxnard, Calif.), for example, food grade hoses attached to the transfer pumps. Exemplary of the transfer pumps that can be used with the provided methods is the Teel Pump (Model 2P377B), Grainger, Inc. Lake Forest, Ill., a self-priming pump having a power rating of 2 HP, 60 Hz voltage 208-230/460 AC, speed of 3450 rpm. Other pumps, for example, other self-priming pumps from Grainger, Inc., can be used as part of the transfer means in the provided methods. Alternatively, transfer means can include means for manually transferring the liquid to another vessel, for example, by pouring, pipetting and/or other well-known methods of manually transferring liquids.

h. Evaluation Equipment

Evaluation equipment is used to evaluate one or more properties of the compositions, for example, the phases of the compositions and/or the final concentrates. For example, evaluation equipment can be used to measure one or more parameters of the concentrates and/or the phases, for example, the temperature and the pH of the liquids. Exemplary of the evaluation equipment are pH meters and temperature meters. Exemplary of the pH/temperature meters is the pH and temperature meter sold by Hanna Instruments, (model number HI 8314), which can be used to measure the temperature and the pH of the mixture(s). Also exemplary of temperature meters are temperature probes, for example, digital and/or water-proof temperature probes, for example, temperature probes sold by Cooper-Atkins, Middlefield, Conn., for example, the digital waterproof temperature probe (Model #DPP400W) from Cooper-Atkins. Other evaluation equipment for evaluating liquids and/or emulsions is well known and can be used with the provided methods.

2. General Methods for Making the Liquid Emulsion Concentrates

In general, the provided methods for making the concentrates include steps for generating phases (e.g., oil phase(s) and water phase(s)) and steps for combining and emulsifying the phases, to form the liquid emulsion concentrates. In some examples, the methods include additional steps, such as evaluation, addition of further ingredients, packaging and filtering. The provided methods can be performed using a bench-top manufacturing process (typically for small batch sizes). Alternatively, the methods can be performed using a scaled-up manufacturing process (typically for larger batch sizes). Each of the provided concentrates can be made using either a scaled-up process or a bench-top process. In one example, after the concentrate first is made using the bench-top process, the method is scaled up to make larger quantities of the concentrate using the scaled-up process. When formulating the concentrates according to the provided methods, the initial concentrate typically is made by a bench-top method. In one example of the formulation methods, a selected formulation then is made using a scaled-up process. Any of the concentrates provided herein can be made with the provided methods, using either manufacturing process. Any method described herein, where the bench-top method is used, can be scaled-up for production of the concentrates using the scaled-up process.

Generally, the provided methods for making the liquid emulsion concentrates include first generation steps, whereby one or more oil phases and one or more water phases are produced. Generation of the water phase and generation of the oil phase typically are performed in at least two separate vessels, for example, an oil phase vessel and a water phase vessel. Each of the generation steps typically includes a mixing step and a heating step, which can be performed simultaneously, sequentially in any order, or partially simultaneously.

To generate the water phase, water phase ingredient(s) (e.g., the polar solvent (e.g., water, propylene glycol, glycerin or other polar solvent) and, in some examples, additional water phase ingredients) are added to a water phase vessel. The ingredient(s) are mixed, typically using a standard mixer, and heated, for example, using a heating apparatus. Typically, the water phase ingredients are heated to a low heat temperature, for example, to 60° C. or about 60° C. To make the oil phase, the oil phase ingredients (e.g., non-polar compound(s), surfactant(s) and, in some examples, other oil phase ingredient(s)) are added to an oil phase vessel. The oil phase ingredient(s) are mixed, typically using a standard mixer, and heated, for example, using a heating apparatus. Typically, the ingredients are heated to a low heat temperature, for example, to 60° C. or about 60° C. The mixing/heating of the water and oil phase can be performed simultaneously or sequentially, in any order. In one example, generation of the oil phase is performed subsequently to generation of the water phase, for example, to preserve the non-polar active ingredient, for example, to prevent its oxidation. Typically, both phases are heated to the desired temperature, for example, low heat temperature, and/or until the ingredients dissolve, prior to combining the oil and the water phases in a subsequent emulsification step. An antifoaming agent can be added to either the water phase or the oil phase or both phases to reduce air bubbles and lower the viscosity of the provided concentrate.

In general, the methods further include an emulsifying step. For the emulsifying step, the oil and water phases are combined, for example, using one or more transfer means. The oil and water phases are emulsified, typically with mixing, typically homogenizing, for example, using high shear, in order to generate an emulsion (e.g., the liquid emulsion concentrate). The emulsifying step can be performed in the water phase vessel, the oil phase vessel, or a separate vessel.

In some examples, during the emulsifying step, the forming emulsion is cooled, for example, rapidly cooled, for example, using one or more cooling apparatuses. Typically, the cooling step is performed simultaneously with the emulsifying step. In one example, the cooling is performed until the emulsion reaches a temperature of between 25° C. or about 25° C. and 43° C. or about 43° C.

The provided methods can include additional steps, for example, evaluation steps, steps for adding additional ingredients, purification (e.g., filtration) steps, and/or packaging/holding steps, as detailed below.

a. Generating the Water Phase

Typically the water phase ingredients are weighed and/or measured, for example, using one or more scales (e.g., one or more of the scales described herein), before addition to the water phase vessel (e.g., any vessel described herein). In one example, the amount of each ingredient to be added to the water phase vessel is determined according to the provided methods for formulating the concentrates. Typically, the desired concentration, by weight (w/w), of the final emulsion concentrate is used to calculate the amount of each water phase ingredient that is added to the water phase vessel. Alternatively, the desired volume per weight, volume per volume or weight per volume can be used to calculate the correct amount of an ingredient to be measured and added to the vessel.

In one example, when water is the polar solvent, impurities in the water, for example, city water, are removed using one or more purifiers (e.g., one or more purifiers as described herein) above, before adding the water to the water phase tank. In one example, the water is purified by passage through using the following purifiers, sequentially: a carbon filter, an ion exchange purifier, a reverse osmosis purifier and an end-point filter, for example, a 100 micron end-point filter, before being added to the water phase vessel.

Typically, the water phase ingredient(s) are mixed in the water phase vessel using a standard mixer (e.g., any of the standard mixers described herein) and heated, typically simultaneously or, in part, simultaneously, using a heating apparatus (e.g., any of the heating apparatuses described herein). Typically, the water phase is heated such that the water phase ingredients reach a low heat temperature, for example, between about between 45° C. or about 45° C. and 85° C. or about 85° C., for example, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84 or 85° C., typically, 60° C. or about 60° C., for example, to prevent oxidation of the non-polar ingredients and/or maintain the stability of the ingredients. Typically, the surfactant is added to the water phase in one or more batches thereby reducing viscosity and allowing easier homogenization. Typically, an antifoaming agent is added to the water phase to reduce air bubbles and lower viscosity. Typically, mixing and/or heating of water phase ingredients in the water phase vessel is continued, for example, prior to combining the water phase and the oil phase. In one example, the water phase is mixed and/or heated until the water phase ingredients have dissolved. Typically, the temperature of the water phase is maintained with mixing prior to combining the oil and water phases.

i. Water Phase Ingredients

The water phase includes one or more polar solvent, such as water, diols, such as propylene glycol and sugar alcohols, such as glycerin, and, in some examples includes other water phase ingredients. Typically, water phase ingredients are hydrophilic and/or amphipathic ingredients of the liquid emulsion concentrate. For example, oils and other lipophilic ingredients typically are not added to the water phase. Certain ingredients, for example, ingredients having hydrophobic and hydrophilic moieties, for example, surfactants and co-surfactants, can be added to either the oil or the water phase, or to the oil and the water phase. Exemplary water phase ingredients include, but are not limited to, polar solvents, e.g., water, typically filtered water, propylene glycol, glycerin and other diols; soluble fiber; emulsion stabilizers; pH adjusters, for example, phosphoric acid and/or citric acid; flavors; surfactants; co-surfactants, for example, phosphatidylcholine and/or quillaja saponin; and preservatives. Typically, the water phase contains at least a polar solvent, a surfactant and an emulsion stabilizer.

Water phase ingredients can be added to the water phase simultaneously and/or sequentially, in a specific order. In one example, one or more water phase ingredients is added first and heated, prior to addition of further ingredient(s). In one example, when the water phase ingredients include a polar solvent and an emulsion stabilizer, these ingredients are added sequentially, in the following order: 1) polar solvent; 2) emulsion stabilizer. In one example, when the water phase ingredients include water and a surfactant, these ingredients are added sequentially, in the following order: 1) water; 2) surfactant. In other examples, when the water phase ingredients include water and a surfactant, the surfactant is added in two fractions, such that the ingredients are added sequentially, in the following order: 1) water; 2) $1^{st}$ fraction surfactant; 3) $2^{nd}$ fraction surfactant. In another example, when the water phase ingredients include a surfactant, a polar solvent (e.g., water) and an emulsion stabilizer, these ingredients are added to the water phase vessel sequentially, in the following order: 1) polar solvent (e.g., water); 2) emulsion stabilizer; 3) surfactant. In another example, when the water phase ingredients include a polar solvent (e.g., water), a surfactant, an emulsion stabilizer and an antifoaming agent, these ingredients are added to the water phase vessel sequentially, in the following order: 1) polar solvent; 2) emulsion stabilizer; 3) antifoam; 4) surfactant. Alternatively, when the water phase ingredients include a polar solvent (e.g., water), a surfactant, an emulsion stabilizer and an antifoaming agent, the surfactant is added in two fractions, such that these ingredients are added to the water phase vessel sequentially, in the following order: 1) polar solvent; 2) emulsion stabilizer; 3) antifoam; 4) $1^{St}$ fraction surfactant; 5) $2^{nd}$ fraction surfactant. In another example, when the water phase ingredients include a polar solvent (e.g., water), a surfactant, an emulsion stabilizer, an antifoaming agent and a soluble fiber, these ingredients are added to the water phase vessel sequentially, in the following order: 1) polar solvent; 2) emulsion stabilizer; 3) antifoam; 4) surfactant; 5) soluble fiber. In another example, when the water phase ingredients include a polar solvent (e.g., water), a surfactant, an emulsion stabilizer, an antifoaming agent and a soluble fiber, the surfactant is added in two fractions, such that these ingredients are added to the water phase vessel sequentially, in the following order: 1) polar solvent; 2) emulsion stabilizer; 3) antifoam; 4) $1^{St}$ fraction surfactant; 5) $2^{nd}$ fraction surfactant; 6) soluble fiber. Alternatively, the water phase ingredients can be added in any other order.

Typically, when the water phase includes a surfactant, particularly when the surfactant is a sucrose fatty acid ester surfactant, for example, the surfactant is added in two separate fractions to the water phase vessel.

b. Generating the Oil Phase

Typically the oil phase ingredient(s) are weighed and/or measured, for example, using one or more scales (e.g., one or more of the scales described herein), before addition to the oil phase vessel (e.g., any of the vessels described herein). In one example, the amount of each oil phase ingredient to be added is determined according to the provided methods for formulating the concentrates. Typically, the desired concentration, by weight (w/w), of the final emulsion concentrate is used to calculate the amount of each oil phase ingredient that should be added to the oil phase vessel. Alternatively, the volume per weight, volume per volume or weight per volume can be used to calculate the correct amount of an ingredient to be measured and added to the vessel.

Typically, the oil phase ingredients are mixed in the oil phase vessel using a standard mixer (e.g., any of the standard mixers described herein) and heated, typically simultaneously, using a heating apparatus (e.g., any of the heating apparatuses described herein). Typically, the oil phase is heated such that it reaches a low heat temperature, for example, between 45° C. or about 45° C. and 85° C. or about 85° C., for example, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84 or 85° C., typically 60° C. or about 60° C., for example, to prevent oxidation of the non-polar ingredients and/or maintain the stability of the ingredients. In one example, one or more of the oil phase ingredients are mixed and heated according to the provided methods, prior to addition of the rest of the oil phase ingredients. For example, the non-polar compound can be mixed and heated with one or more solvents, for example, an oil, for example, flaxseed oil, oleic acid and/or Vitamin E oil, until the non-polar compound is dissolved in the oil, prior to addition of the other oil ingredients. Typically, the oil phase ingredients are mixed in the oil phase vessel until dissolved. Typically, the temperature of the oil phase is maintained with mixing prior to combining the oil and water phases.

In some examples the oil and/or the water phase can be made in more than one vessel, for example, by mixing one or more of the oil phase ingredients in one vessel and mixing the one or more other oil ingredients in another vessel. In this example, the mixed oil phase ingredients in the separate vessels either can be mixed together prior to emulsifying with the water phase, or alternatively, can be added separately, during emulsification, to the water phase.

i. Oil Phase Ingredients

The oil phase includes the non-polar compound, for example, the non-polar active ingredient and, in some examples, other oil phase ingredients. Typically, oil phase ingredients include one or more lipophilic and/or amphipathic ingredients of the liquid emulsion concentrate. Oil phase ingredients typically do not include aqueous ingredients or hydrophilic ingredients. Certain ingredients, for example, ingredients having hydrophobic and hydrophilic moieties, for example, surfactants and co-surfactants, can be added to either the oil or the water phase, or to the oil and the water phase. Exemplary of ingredients used in the oil phase of the provided concentrates are non-polar compounds, for example, non-polar active ingredients, including any of the non-polar active ingredients provided herein; emulsion stabilizers, pH adjusters, for example, phosphoric acid and/or citric acid; surfactants; co-surfactants, for example, phosphatidylcholine and/or quillaja saponin; preservatives, and oils, for example, solvents and other oil phase ingredients. Typically, the oil phase contains at least one or more non-polar compounds, one or more emulsion stabilizers and one or more surfactants.

Oil phase ingredients can be added to the oil phase simultaneously and/or sequentially, for example, in any order or in a specific order. In one example, one or more oil phase ingredients is added first and heated, prior to addition of further ingredient(s). In one example, when the oil phase ingredients include a surfactant, a preservative, one or more emulsion stabilizers, and a non-polar compound, these ingredients are added sequentially, in the following order: 1) ester gum emulsion stabilizer; 2) preservative; 3) non-polar compound; 4) gum arabic emulsion stabilizer; 5) surfactant. In another example, when the oil phase ingredients include a surfactant, a preservative, one or more stabilizers, and one or more non-polar compounds, these ingredients are added sequentially, in the following order: 1) ester gum emulsion stabilizer; 2) non-polar compound; 3) preservative; 4) non-polar compound; 5) gum acacia emulsion stabilizer; 6) surfactant. In another example, when the oil phase ingredients include a surfactant, a preservative, one or more stabilizers, one or more non-polar compounds and a non-polar solvent, these ingredients are added sequentially, in the following order: 1) preservative; 2) ester gum emulsion stabilizer; 3) one or more non-polar compounds; 4) non-polar solvent; 5) non-polar compound; 6) surfactant. In another example, when the oil phase ingredients include one or more surfactants, a preservative, one or more stabilizers, and one or more non-polar compounds, these ingredients are added sequentially, in the following order: 1) surfactant; 2) preservative; 3) ester gum emulsion stabilizer; 4) non-polar compound; 5) non-polar compound; 6) gum acacia emulsion stabilizer; 7) surfactant. Alternatively, the oil phase ingredients can be added in a different order, for example, any order. Two or more oil phase ingredients can be added simultaneously.

Typically, when the oil phase includes a surfactant, particularly when the surfactant is a surfactant that is solid at room temperature, the surfactant is the first oil phase ingredient added to the oil phase vessel. Typically, the surfactant is the last ingredient added to the oil phase vessel.

c. Combining and Emulsifying the Oil Phase and the Water Phase

Generally, in the provided methods, following the generation of the oil phase and the water phase, the oil and water phases are combined, for example, using one or more transfer means (e.g., any of the transfer means described herein). The combined phases are emulsified, for example, by mixing, for example, homogenizing, to form an emulsion (e.g., the liquid emulsion concentrate). Typically, the phases are mixed during the combining and the emulsifying steps, for example, using a homogenizer (e.g., any of the homogenizers described herein). In one example, the oil and water phases (e.g., the forming emulsion) further are cooled, for example, rapidly cooled, during the emulsifying and/or combining steps.

i. Combining the Oil and Water Phases

In order to emulsify them, the oil and water phases first are combined, typically by transfer, using one or more transfer means (e.g., any of the transfer means described herein). In one example, the oil phase is transferred to the water phase vessel. In another example, the water phase is transferred to the oil phase vessel. In another example, a plurality of oil phases or water phases are transferred to a water phase or an oil phase vessel. In another example, the water phase(s) and the oil phase(s) are transferred to another vessel, for example, an emulsification vessel.

Any transfer means can be used to combine the phases. For example, any means for transferring the contents of one vessel to another vessel as described above, for example, transfer pumps and associated equipment, for example, sanitary fittings, hoses and/or ball valves; and manual transfer means, for example, pouring and/or pipetting means or other known transfer means. In some examples, the phases are kept clean, for example, sterile during transfer, for example, by using transfer means with sanitary fittings and/or combining the phases in a sterile environment.

ii. Emulsifying the Oil and Water Phases

Simultaneous to and/or subsequent to the combination of the phases, the phases are mixed (e.g., homogenized), for example, using a homogenizer (e.g., any of the described homogenizers), to form an emulsion. Typically, the emulsifying is performed in the vessel containing the combined liquids, for example, the oil phase or the water phase vessel. For this emulsifying step, the oil and water phases are mixed, for example, after the combining step, typically during and after the combining step, using a mixer that is capable of emulsifying liquids, for example, a homogenizer, for example, a reversible homogenizer. Typically, the liquids are homogenized using the mixer (e.g., homogenizer) at low speed, for example, low rpm, for example, between 850 rpm or about 850 rpm and 1200 rpm or about 1200 rpm, for example, 850, 900, 950, 1000, 1050, 1100, 1150 or 1200 rpm. Lower speeds can reduce the incorporation of air into the emulsion. In some examples, the homogenization can be performed at speeds less than 850 rpm, such as, for example, between 25 or about 25 rpm and 50 rpm or about 50 rpm, for example at or about 30 rpm, to further reduce incorporation of air into the emulsion.

The liquids typically are mixed, continuously or intermittently, until the liquids are emulsified, for example, in a emulsion. In one example, the mixing speed is maintained in order to emulsify the oil and water phases. In one example, the baffle plate of the mixer is adjusted, for example, by moving the baffle plate further down into the mixture or further up out of the mixture, to control the type of mixing, for example, to switch from downward flow to upward flow and vice versa, during mixing of the emulsion. In another example, the homogenizer can be adjusted to increase or decrease shear or to maintain the shear at a particular speed. Methods for homogenizing oil and water phases are well known and other methods can be used to homogenize the oil and water phases in the provided methods.

iii. Cooling

In some examples, the emulsion is cooled during mixing, for example, by rapid cooling. In one example, the emulsion is cooled to promote stability of the emulsion and emulsification of the phases, for example, by preventing or minimizing oxidization, for example, oxidization of the non-polar compound. The cooling, for example, rapid cooling, typically is performed using one or more cooling apparatuses, for example, any of the cooling apparatuses described herein or any known cooling apparatus. In one example, the cooling apparatus is a recirculating cooler. In another example, the cooling apparatus is a water bath or an ice bath. In one example, when the apparatus is a recirculating cooler, fluid from the vessel being used for the emulsifying step is recirculated through the cooler, and then back to the vessel, to rapidly cool and maintain the temperature of the mixture during mixing. Typically, the forming emulsion is mixed and cooled until the phases are emulsified and the temperature reaches between 25° C. or about 25° C. and 43° C. or about 43° C., for example, 25, 26, 27, 28, 29, 30, 31, 32, 33, 34, 35, 36, 37, 38, 39, 40, 41, 42 or 43° C. Typically, when the cooling is rapid cooling, the temperature is reached in less than 2 hours or about 2 hours, typically less than 1 hour or about 1 hour, for example, in at least between 30 minutes or about 30 minutes and 60 minutes or about 60 minutes, for example, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 minutes.

Once the oil and water phases have been emulsified, thereby forming an emulsion, for example, a liquid emulsion concentrate, the emulsion can be used, for example, in the provided dilution methods to make a liquid dilution composition, for example, a beverage, containing the concentrate. Alternatively, one or more additional steps can be performed before using the concentrate.

d. Additional Steps

Typically, one or more additional steps is carried out, following emulsifying the phases, prior to use of the concentrate. For example, the emulsion can be evaluated (e.g., by measuring pH and/or temperature of the concentrate). In another example, one or more additional ingredients can be added to the emulsion. In another example, the emulsion concentrate is transferred to a holding vessel or a packaging vessel, for example, a holding/packaging vessel, for example, a holding/packaging tank. In another example, the emulsion is purified, for example, filtered, prior to use. In one example, addition of additional ingredients, evaluation and/or purification, can be performed in the holding/packaging vessel. Other additional steps can be performed prior to use.

i. Additional Ingredients

In one example, additional ingredients, for example pH adjusters and/or flavors, can be added to the emulsion after it is formed. In one example, citric acid and/or phosphoric acid is added to adjust the pH, for example, until the pH reaches a pH between 2.5 and 3.5, typically, between 2.0 or about 2.0 and 3.0 or about 3.0, for example, 2.0, 2.1, 2.2, 2.3, 2.4, 2.5, 2.6, 2.7, 2.8, 2.9 or 3.0. In another example, one or more flavors is added to the concentrate, for example, to improve the taste and/or smell of the concentrate and/or beverages containing the concentrate. In another example, additional polar solvent, e.g., water, can be added to the emulsion, for example, in the case of evaporation, to bring the concentrate to the appropriate volume. Other additional ingredients also can be added to the emulsion. Typically, the additional ingredients are added to the vessel containing the emulsion, for example, the water phase vessel, the oil phase vessel, the emulsion vessel, or another vessel, for example, a holding/packaging vessel. Typically, the emulsion is mixed (e.g., using any of the described mixers, typically standard mixers), while the additional ingredients are added.

ii. Evaluation of the Concentrate

Typically, the concentrate is evaluated prior to use. Typically, the pH and/or temperature are measured, for example, using a pH and temperature meter. In one example, the pH and/or temperature are evaluated after additional ingredients have been added. In one example, further ingredients can be added to adjust the parameters after evaluation.

iii. Filtering the Concentrate

In one example, the concentrate is purified (e.g., with any of the described purifiers), for example, using an end product filter, prior to use of the concentrate, for example, prior to diluting the concentrate into a food or beverage.

3. Bench-Top Process

In one example of the provided methods for making the liquid emulsion concentrates, the steps of the methods are performed using a bench-top manufacturing process, which is performed on a bench, counter, table or other surface. Typically, the bench-top process is used to make emulsions having relatively smaller volumes than those made with the scaled-up process, for example, volumes less than 1 L or about 1 L or less than 1 gallon or about 1 gallon, for example, less than about 500 mL, for example, 1000, 900, 800, 700, 600, 500, 450, 400, 350, 300, 250, 200, 150, 100, 50, or less.

For the bench-top process, the equipment typically is sufficiently compact to be used on a bench top or other similar surface, typically sufficiently compact to be moved, for example, lifted, by the artisan using the methods. For example, the vessels, for example, water phase vessels, oil phase vessels, holding vessels, and packaging vessels typically are bench-top vessels, for example, flasks, beakers, vials, measuring containers, bottles and/or other bench-top containers. In one example, the vessel in the bench-top process is a Pyrex® beaker. Typically, the mixers are mixers that can be used in the bench-top vessels, for example, standard mixers, including hand-held mixers, stir rods, stir bars, magnetic mixers and overhead mixers, for example, mechanical and/or electric overhead mixers and/or other mixers that can be used in the vessels. Exemplary of appropriate bench-top mixers are standard mixers, for example, standard mixers sold by IKA®, for example, overhead IKA® mixers, for example, model Nos. RW-14 Basic and RE-16S, which are laboratory stirrers and can be used to mix ingredients, for example, to generate the oil and water phases. Also exemplary of appropriate bench-top mixers are homogenizers, for example, reversible homogenizers, including The Arde Barinco reversible homogenizer, Model No. CJ-4E, which can be used to emulsify the phases. Typically, the heating apparatuses are those that can be used with the bench-top vessels, for example, hot plates. The cooling apparatuses typically are apparatuses suited for use with the smaller bench-top vessels, for example, ice baths and/or water baths into which the vessels can be placed, for example, for rapid cooling. The evaluation means used in the bench-top process, for example, the temperature and/or pH meters, typically are capable of being placed in the bench-top vessels.

Generally, for the bench-top process, the oil phase and water phase are generated by mixing and heating in separate bench-top vessels, for example, flasks, beakers, vials, measuring containers, bottles and/or other bench-top containers. The mixing typically is performed using an appropriate bench-top mixer, for example, a standard mixer, such as a hand-held mixer, stir rod, stir bar, magnetic mixer and/or overhead mixer. Typically, heating the oil and water phases is performed using a heating apparatus appropriate to the bench-top method, for example, a heating apparatus that one or more of the vessels can be placed upon, for example, a hot plate. For combining the oil phase and the water phase, one or more phases, typically one phase, typically is transferred manually to another vessel, for example, by pouring, pipetting and/or another manual transfer means. For emulsifying the oil and water phases, a reverse homogenizer typically is used. For cooling the forming emulsion, for example, for rapidly cooling the emulsion, a cooling apparatus appropriate to the bench-top method typically is used, for example, a cooling apparatus that the vessel can be placed upon or inside, for example, a water bath or an ice bath.

4. Scaled-Up Manufacturing Processes

The provided methods for making the liquid emulsion concentrates can be performed using a scaled-up manufacturing process. A scaled-up manufacturing process typically is used when the liquid emulsion concentrate being made has a relatively larger volume than a concentrate being made with the bench-top process, for example, volumes greater than 1 L or about 1 L or greater than 1 gallon or about 1 gallon, for example, greater than about 500 mL, for example, at least 0.5 L, 1 L, 2 L, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 150, 200, 250, 300, 350, 400, 450, 500, 550, 600, 650, 700, 800, 900, 1000, or more gallons.

In general, the scaled-up manufacturing processes are performed with equipment that is compatible with these larger volume batches (batch sizes). For example, the vessels used in the scaled up process typically are tanks, e.g., water jacketed tanks, which are equipped with water jackets that can be used as heating apparatuses to heat the oil and water phase ingredients during generation of the oil and water phases. The water jackets typically are controlled via control panels. Similarly, the transfer means used in the scaled-up process typically include transfer pumps and associated fittings, for example, ball valves and hoses. Exemplary of mixers that are used in the scaled-up process are standard mixers, for example, mounted mixers, for example LIGHTNIN® mixers, for example, Model XJC117, a fixed-mount, gear drive high-flow mixer, and Model ND2. An exemplary scaled-up process is described in this section, below. The provided methods for making the concentrates can be performed using this exemplary scaled-up process, or any variation of the scaled-up process, for example, eliminating one or more steps of the exemplary process, adding one or more steps according to the provided method, and/or substituting steps and/or equipment according to the methods provided herein.

This exemplary scaled-up process includes the following steps:

a. Water Purification

As noted herein, the polar solvent can include water (including purified water) and other polar solvents, e.g., glycerin and propylene glycol. For example, the polar solvent is water (e.g., city water), which is purified before addition to the water phase vessel by passing the water through the following purifiers, sequentially, in the following order: a carbon filter, ion exchange equipment, reverse osmosis equipment, a 100 micron end-point filter, and a 50 micron point-of-use filter.

b. Generation of the Water Phase and Oil Phase:

As described above, for generation of the water phase, the polar solvent and any other water phase ingredients typically are weighed and/or measured, and added to the water phase vessel and mixed, using a standard mixer or other mixer, such as a homogenizer or other mixer described herein, and typically heated during mixing, whereby the water phase is generated with mixing and heating, typically to low heat (e.g., 60° C., 70° C., 71° C.), according to the provided methods. For example, in the scaled-up manufacturing process, the water phase vessel is a water phase tank, which is a water-jacketed tank. For example, the water phase ingredient(s) are mixed using a standard mixer, for example, a LIGHTNIN® mixer (for example, model no. XJC117, a fixed-mount gear drive high-flow mixer), attached to the tank, for example, mounted on the top of the tank. For example, the heating apparatus used to heat the water phase ingredients is the water jacket of the water jacketed tank; temperature on the water jacket is controlled via a control panel.

As described above, for generation of the oil phase, the oil phase ingredients typically are weighed and/or measured, and added to the oil phase vessel and mixed, using a standard mixer or other mixer, such as a homogenizer or other mixer described herein, and typically are heated during mixing, whereby the oil phase is generated with mixing and heating, typically to low heat (e.g., 60° C.), according to the provided methods. In one example of the scaled-up manufacturing process, the oil phase vessel is a water jacketed oil phase tank. For example, the oil phase ingredients are mixed using a standard mixer, for example, a LIGHTNIN® mixer (e.g., model ND2), attached to the oil phase tank, for example, mounted on the tank. The heating apparatus used to heat oil phase ingredients is the water jacket of the water jacketed oil phase tank; temperature on the water jacket is controlled via a control pane.

c. Combining and Emulsifying the Phases

As described herein, once the oil and water phases reach the desired temperature (e.g., 60° C., 70° C., 71° C. or other temperature), after oil phase and/or water phase ingredients have dissolved, and optionally after cooling one of the phases, e.g., cooling the water phase to 60° C. according to the provided methods, the oil and water phases are combined, via transfer, and emulsified, typically via homogenization. In one example, the transfer is carried out slowly to prevent clumping in the forming emulsion, such as by stopping the transfer periodically while continuing to mix the emulsion, or by combining the phases slowly with mixing. In one example of the scaled-up manufacturing processes, the combining of phases is effected by transferring the oil phase to the water phase vessel, via transfer means, which include a transfer pump (e.g., a Teel pump, model 2P377B, sold by Granger, Inc.), sanitary fittings, transfer hose(s) (e.g., food grade hoses sold by Sani-Tech West) and ball valve(s). Alternatively, the water phase can be transferred to the oil phase. For example, to begin the combining/emulsifying steps, a homogenizer (e.g., an Arde Barinco, Inc. reversible homogenizer), mounted on the water phase tank, is turned on, for example, at 850-1200 rpm. The ball valves then are opened and the transfer pump turned on, thereby effecting transfer of the oil phase liquid to the water phase tank via the transfer hose(s). As the phases are combined, the mixture is homogenized by continued mixing with the homogenizer.

In some examples of the scaled-up manufacturing process, to prevent clumping, the pump is periodically stopped (e.g., by turning off the pump), while continuing to mix with the mixer, during emulsification. In one aspect of this example, this method to prevent clumping is used when the polar solvent is a solvent other than water, such as propylene glycol or glycerin. During mixing, the homogenizer can be adjusted, for example, by adjusting the baffle plate on the homogenizer to achieve and maintain an emulsion, for example, by moving the baffle plate further into the forming emulsion and/or further out of the forming emulsion. In one example, the shear speed is adjusted to a speed where the oil phase can be seen coming out the top of the mixer. In one example, this adjustment is used when the polar solvent is a solvent other than water, such as propylene glycol or glycerin.

d. Cooling

As described herein, in some examples, the forming emulsion is cooled, typically rapidly cooled, during the emulsion step. In the scaled-up process, the rapid cooling typically is effected by repeatedly passing the forming emulsion through a recirculating cooler (e.g., Model No. OC-1000 RO, sold by Turmoil, West Swanzey, N.H.), which is attached to the water phase tank. Homogenization continues during the cooling step, for example, at between 850 and 1200 rpm. The cooling continues, for example, until the temperature of the emulsion reaches between at or about 25° C. and at or about 43° C., such as between at or about 25° C. and at or about 35° C., between at or about 35° C. and at or about 43° C., or at or about 40° C. Typically, the rapid cooling is carried out for between at or about 30 and at or about 60 minutes.

e. Additional Steps

As described herein, additional steps can be performed after the emulsion is formed. For example, in the scaled-up manufacturing process, the additional steps include transferring the emulsion, via transfer means, which include a transfer pump (e.g., a Teel pump, model 2P377B, sold by Grainger, Inc.), sanitary fittings, transfer hose(s) (e.g., food grade hoses sold by Sani-Tech West) and ball valve(s), to a holding/packaging tank. Transfer is performed by turning on the transfer pump and opening the ball valves. Additional ingredients can be added, for example, pH adjusters, for example, while monitoring pH, sufficient to bring the emulsion to an appropriate pH, for example, between about 2.0 and 3.0. Flavors can also be added. The additional ingredients are mixed into the concentrate using a standard mixer. The addition and mixing of additional ingredients, and/or evaluation can be performed in the holding/packaging tank; alternatively it can be performed prior to transfer to the holding/packaging tank, for example, in the water phase tank.

Variations of this exemplary scaled-up process also can be performed using the provided methods, including any of the variations described herein, to make the concentrates. For example, by elimination and/or modification of one or more steps and/or equipment, according to the general methods provided herein.

D. METHODS FOR MAKING THE FOOD AND BEVERAGE DILUTION COMPOSITIONS CONTAINING THE CONCENTRATES

Also provided herein are methods for diluting the liquid emulsion concentrates to make dilution compositions, typically, food or beverage dilution compositions, containing the non-polar compounds. Generally, the emulsion concentrate is diluted into a variety of foods including, for example, solid or liquid foods or beverages, for example, dairy compositions, e.g., butter, milk, yogurt, and cheese, savory food compositions, sweet food compositions, frozen food, egg products, margarines, spreads, peanut butter, almond butter, sauces and dressings, e.g., mayonnaise, thousand island, ranch and tartar sauce, soups, dips, fillings for cakes and cookies, confections, whipped desserts, e.g., mousse, custard, chiffon, meringue, and whipped topping, frozen desserts, e.g., frozen yogurt and ice cream, candies, baby foods, e.g., infant formula, pet food or any other food product, or an aqueous medium, for example, a beverage, for example, water, flavored water, soda, milk, juices, including fruit juices, sauces, syrups, soups, sports drinks, fitness drinks, nutritional beverages, nutritional supplement, energy drinks, vitamin-fortified beverages, or any other beverage. More typically, the liquid emulsion concentrates are diluted into a variety of water-based foods and beverages including, but not limited to, tomato-paste based products, dairy-based products, creams, sauces, soups, pastes, dressings, water, flavored water, soda, milk, juices, including fruit juices, sauces, syrups, sports drinks, fitness drinks, nutritional beverages, nutritional supplement, energy drinks and vitamin-fortified beverages. The concentrate and the food or beverage can be mixed, for example, by stirring and/or blending or by any known mixing means. The concentrate disperses into the food or beverage to form a dilution composition, for example, a homogenous food composition or a clear or partially clear aqueous liquid dilution composition. The dilution composition can be evaluated, for example, to assess the stability, clarity, taste and/or smell of the composition.

In one example, the liquid emulsion concentrate is incorporated directly and without further modification into the food or beverage by techniques such as mixing, infusion, injection, blending, immersion, spraying and kneading. In another example, the liquid emulsion concentrate can be applied directly into a food or beverage by the consumer prior to ingestion. In one example, the liquid emulsion concentrate is diluted in the aqueous medium, for example, water by heating the aqueous medium, for example, by heating the aqueous medium, for example, to at least 40° C. or at least about 40° C., for example, 40, 41, 42, 43, 44, 45, 46, 47, 48, 49, 50 or more ° C., for example, 48.9° C. In this example, the liquid emulsion concentrate is added, at an appropriate dilution, as described herein, to the heated aqueous medium, and stirred until dispersed or dissolved in the solution. The resulting liquid dilution composition can then be cooled, for example, to room temperature, for example, 25° C. or about 25° C. Following dilution, a food or beverage dilution composition can be packaged, for example, by transferring to containers, for example, vials or containers. In one example, a portion of the dilution composition is transferred to a vial for analysis, for example, evaluation of properties, such as stability, clarity, turbidity, taste, smell, ringing, crystal formation and/or other properties.

Exemplary of equipment used for diluting the liquid emulsion concentrates to form the dilution compositions containing the diluted concentrates are beakers, for example, Pyrex® glass beakers, hot plates, for example, the Thermolyne hot plate, model number 846925 or model number SP46615, stir rods, temperature meters, for example, temperature probes, for example, Cooper Temperature Probes (model no. DPP400W) and scales, for example, the OHUAS 2.0 Kg scale (Model #CS2000) and/or the Sartorius Analytical Scale (model BA110S).

1. Dilutions

Typically, the provided concentrates can be diluted into a food or beverage to form dilution compositions over a wide range of dilutions. In one example, the concentrate can be diluted so that the food or beverage dilution composition contains between 0.05 g or about 0.05 g and 10 g or about 10 g, typically between 0.05 g and 5 g, of the liquid concentrate per serving of the food or beverage. For example, the concentrate can be diluted so that the aqueous liquid dilution composition contains 0.05 g, 0.06 g, 0.07 g, 0.08 g, 0.09 g, 0.1 g, 0.2 g, 0.3 g, 0.4 g, 0.5 g, 0.6 g, 0.7 g, 0.8 g, 0.9 g, 1 g, 2 g, 3 g, 4 g, 5 g, 6 g, 7 g, 8 g, 9 g, or 10 g of the concentrate per serving, about a serving, or a least a serving, for example 1, 2, 3, 4, 5, 6, 7, 8, 9, 10, 11, 12, 13, 14, 15, 16 or more, servings of a food or beverage, for example, 1 teaspoon (0.166667 ounce, 4.7249 g), 1 tablespoon (0.5 fluid ounce, 14.1747 g), 2 tablespoons (1 fluid ounce, 28.3495 g), 0.25 cup (2 fluid ounces, 56.6990 g), 0.5 cup (4 fluid ounces, 113.398 g), 0.75 cup (6 fluid ounces, 170.097 g) or 1 cup (8 fluid ounces, 226.796 g) of the food or beverage.

In another example, the concentrate is diluted so that the food or beverage dilution composition contains between 1 mL or about 1 mL and 10 mL or about 10 mL of the liquid concentrate, for example, 1 mL, 2 mL, 3 mL, 4 mL, 5 mL, 6 mL, 7 mL, 8 mL, 9 mL or 10 mL of the concentrate, per serving, about a serving, or a least a serving, for example 1, 2, 3, 4, 5, 6, 7, 8, 9, 10, 11, 12, 13, 14, 15, 16 or more, servings of a food or beverage, for example, 1 teaspoon (0.166667 ounce, 4.7249 g), 1 tablespoon (0.5 fluid ounce, 14.1747 g), 2 tablespoons (1 fluid ounce, 28.3495 g), 0.25 cup (2 fluid ounces, 56.6990 g), 0.5 cup (4 fluid ounces, 113.398 g), 0.75 cup (6 fluid ounces, 170.097 g) or 1 cup (8 fluid ounces, 226.796 g) of the food or beverage.

In another example, the liquid concentrate is diluted so that the food or beverage dilution composition contains at least 10 mg or about 10 mg, typically at least 25 mg or about 25 mg, typically at least 35 mg, of the non-polar compound, for example, the non-polar active ingredient, per a serving, about a serving, or a least a serving; for example, 10, 11, 12, 13, 14, 15, 16, 17, 18, 19, 20, 21, 22, 23, 25, 25, 26, 27, 28, 29, 30, 31, 32, 33, 34, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 325, 350, 375, 400, 425, 450, 475, 500, 550, 600, 700, 800, 900, 1000, 1500, 2000, 2500, 3000 mg, or more, of the non-polar compound per at least a serving, for example, 1 teaspoon (0.166667 ounce, 4.7249 g), 1 tablespoon (0.5 fluid ounce, 14.1747 g), 2 tablespoons (1 fluid ounce, 28.3495 g), 0.25 cup (2 fluid ounces, 56.6990 g), 0.5 cup (4 fluid ounces, 113.398 g), 0.75 cup (6 fluid ounces, 170.097 g) or 1 cup (8 fluid ounces, 226.796 g), of the food or beverage.

For example, the liquid concentrate is diluted so that the food or beverage dilution composition contains between at or about 1.5 to at or about 3.0 grams (g) of omega-6 fatty acids per serving, between at or about 16 to at or about 220 milligrams (mg), for example, between at or about 32 to at our about 220 mg docosahexaenoic acid (DHA) and eicosapentaenoic acid (EPA) per serving, between at or about 100 and at or about 500 mg phytosterols per serving, between at or about 10 and at or about 200 mg, for example, between at or about 50 and at or about 200 mg Coenzyme Q10 per serving, between at or about 1 and at or about 20 mg beta carotene per serving, between at or about 1 and at or about 200 mg lutein, lycopene or zeaxanthin per serving, between at or about 40 and at or about 400 micrograms (mcg) Vitamin A per serving, or between at or about 400 and at or about 800 international units (IU) per a serving of a food or beverage, for example, 1 teaspoon (0.166667 ounce, 4.7249 g), 1 tablespoon (0.5 fluid ounce, 14.1747 g), 2 tablespoons (1 fluid ounce, 28.3495 g), 0.25 cup (2 fluid ounces, 56.6990 g), 0.5 cup (4 fluid ounces, 113.398 g), 0.75 cup (6 fluid ounces, 170.097 g) or 1 cup (8 fluid ounces, 226.796 g), such as 8 ounces of a beverage.

2. Analyzing the Dilution Compositions Containing the Liquid Concentrates

Properties of the dilution compositions containing the liquid concentrates can be evaluated using a number of different evaluation means. For example, the stability, for example, lack of oxidation, "ringing," precipitation, flocculation, creaming and/or visible phase separation, over time; clarity; desirability for human consumption, for example, pleasant taste, and/or smell, for example, lack of "fishy" taste/smell, lack of "ringing" and lack of crystal formation; and safety for human consumption, can be evaluated. Several of these properties can be evaluated empirically, for example, by observing the liquids immediately or over time, or by smelling and/or tasting the liquids. In one example, after evaluation of an aqueous liquid dilution composition, the concentrates are re-formulated to adjust one or more parameters. In another example, the dilution factor can be adjusted.

a. Stability

Typically, the provided dilution compositions containing the concentrates are stable, for example, free from one or more changes over a period of time, for example, 1, 2, 3, 4, 5, 6, 7, 8, 9, 10, 11 or 12 months, 1, 2, 3, 4 or more years.

In one example, the compositions are stable because they are free from oxidation or substantial oxidation over time. In another example, they are stable because they remain clear over time. In another example, the stable compositions remain safe and/or desirable for human consumption over time. In one example, stability refers to the lack of precipitates forming in the compositions over the period of time. In a related example, the compositions are stable because they do not exhibit "ringing," formation of a whitish or opaque ring around the perimeter of the container holding the liquid, typically at the surface of the liquid. Ringing typically is undesirable, particularly in the case of a liquid for human consumption, for example, a beverage. In yet another example, the compositions are stable because they do not exhibit flocculation.

In another example, the composition is stable if it does not exhibit any visible phase separation or creaming over a period of time, for example, after 24 hours, after one week or after one month. In one example, the compositions are stable if they exhibit one or more of these described characteristics, over time, when kept at a particular temperature. In one example, the compositions remain stable at room temperature, for example, 25° C. or about 25° C. In another example, the compositions remain stable at between 19° C. and 25° C. In another example, the compositions remain stable at refrigerated temperatures, for example, 4° C. or about 4° C., or at frozen temperature, for example, at −20° C. or about −20° C.

Stability refers to a desirable property of the provided compositions, for example, the ability of the provided compositions to remain free from one or more changes over a period of time, for example, 1, 2, 3, 4, 5, 6, 7, 8, 9, 10, 11 or 12 months, 1, 2, 3, 4 or more years. In one example, the composition is stable if it is formulated such that it remains free from oxidation or substantial oxidation over time. In another example, the stable compositions remain clear over time. In another example, the stable compositions remain safe and/or desirable for human consumption over time. In one example, stability refers to the lack of precipitates forming in the compositions over the period of time. In a related example, stability refers to the lack of "ringing" over the period of time. In another example, the composition is stable if it does not exhibit any visible phase separation over a period of time, for example, after 24 hours, after one week or after one month. In one example, the compositions are stable if they exhibit one or more of these described characteristics, over time, when kept at a particular temperature.

In one example, the compositions are stable at room temperature, for example, 25° C. or about 25° C. In another example, the compositions remain stable at between 19° C. and 25° C. In another example, the compositions remain stable at refrigerated temperatures, for example, 4° C. or about 4° C., or at frozen temperature, for example, at −20° C. or about −20° C.

i. Stability Determined by Empirical Evaluation

In one example, the stability, or shelf life, of the dilution composition is evaluated qualitatively, for example, by observation. In one example, a food or beverage dilution composition is considered stable if it does not exhibit phase separation, flocculation, precipitation, creaming, coagulation and/or sedimentation when looking at the food or beverage with the naked eye. In another example, a food or beverage can be considered stable based on comparison with other food or beverage compositions made according to the provided method. For example, the food or beverage can be as stable as another food or beverage not containing the initial concentrate. In a related example, the food or beverage can be stable when there is no substantial difference, for example, no observable difference, between the food or beverage dilution composition containing the concentrate and the food or beverage without the concentrate.

In another example, stability is determined by evaluating sensory attributes of the food or beverage compositions containing the initial concentrates. For example, the food or beverage dilution compositions can be evaluated for a variety of different sensory attributes by a tasting panel. Sensory attributes include, for example, appearance, taste, aroma and flavor, for example, "fishiness", feeling factors, such as burning or irritation by smelling, texture, such as viscosity or oily mouth feeling, aftertaste, and any other attribute that is warranted. Evaluation of sensory attributes can be assessed empirically for the food or beverage dilution compositions alone, or alternatively by comparison of the dilution compositions to a food or beverage not containing the non-polar compounds. In one example, the food or beverage dilution composition is considered stable based on desirable sensory attributes over time, such as a lack of "fishy" smell or taste, over a period of time, for example, 1, 2, 3, 4, 5, 6, 7, 8, 9, 10, 11 or 12 months, 1, 2, 3, 4 or more years. In another example, there is no difference between the evaluated sensory attributes of the food or beverage dilution composition as compared to a food or beverage not containing the initial concentrate.

ii. Oxidative Stability

In one example, the shelf life of a food or beverage dilution composition containing the initial concentrate is assessed quantitatively, for example, by measuring oxidative stability of polyunsaturated fatty acids. Oxidative deterioration can be assessed by chemical methods such as determining peroxide value (PV), which measures peroxides resulting from primary oxidation, or p-anisidine value (AV), which measures 2-alkenals (aldehydes) resulting from secondary oxidation. Peroxide value typically is measured by reaction of the peroxide with an ion followed by determination of the amount of oxidation, either directly or indirectly. For example, PV can be determined by measuring the amount of iodine formed by the reaction of peroxides with iodide ion in the presence of an indicator ion, for example, sodium thiosulfate. In another example, PV is determined by reaction with $Fe^{+++}$ followed by direct measurement of colorimetric intensity at 505 nm. A p-anisidine value test measures the amount of aldehydes formed from secondary oxidation of fatty substances upon reaction with p-anisidine by measuring absorption at 366 nm. Any method known to one of skill in the art can be used to determine oxidative deterioration. Typically, the food or beverage dilution compositions remain free from oxidative deterioration over a period of time, for example, 1, 2, 3, 4, 5, 6, 7, 8, 9, 10, 11 or 12 months, 1, 2, 3, 4 or more years.

b. Clarity/Turbidity

Clarity of the aqueous liquid dilution compositions can be evaluated using one or more of several approaches, for example, empirical observation, measurement of particle size and/or measurement of a turbidity value. The measurement can be qualitative or quantitative. In one example, a particular quantitative or qualitative clarity value is specified. In another example, the clarity of a liquid can be expressed in relation to the clarity of another liquid, for example, an aqueous liquid dilution composition made according to the provided methods, or a beverage, for example, a beverage that does not contain the liquid concentrate. In this example, the liquid can be as clear as, less clear, or more clear than the other liquid. For example, an aqueous liquid dilution composition containing the liquid concentrate diluted in a beverage can be as clear or about as clear as the same beverage that does not contain the concentrate. Either type of evaluation can be done qualitatively, for example, by empirical evaluation, or quantitatively, for example, by taking a measurement of particle size or turbidity.

i. Empirical Evaluation

In one example, the clarity/turbidity of the aqueous liquid dilution composition is evaluated qualitatively, for example, by observation. In one example, a liquid is considered clear if it does not have a cloudy appearance and/or if it contains no particles or few particles that are observable with the naked eye. In another example, the liquid can be considered relatively clear or relatively turbid based on comparison to other liquids, for example, water, fruit juice, soda, and/or milk and/or other aqueous liquid dilution composition(s) made according to the provided methods. For example, the aqueous liquid dilution composition can be as clear or about as clear as water or another liquid, for example, a beverage. For example, the liquid containing the liquid concentrate diluted in a beverage can be as clear or about as clear as the beverage that does not contain the liquid concentrate. In a related example, the liquid can be clear or partially clear when there is no substantial difference, for example, no observable difference, between the aqueous liquid dilution composition containing the concentrate and the aqueous medium that does not contain the concentrate. A clear liquid is not necessarily colorless. For example, a yellow liquid that contains no (or few) visible particles or cloudiness can be clear. In another example, the lack of crystal formation or of "ringing" can be indicative of a clear liquid.

ii. Particle Size

In another example, clarity/turbidity are assessed by quantitatively measuring particle size and/or number of particles, in the aqueous liquid dilution composition. In this example, the clarity can be expressed as a numerical representation of the particle size, or as a comparison to the particle size of another liquid.

Methods for measuring particle size of liquids are well known. Any method for measuring particle size can be used, provided that it is sensitive to the particle size in the expected and/or appropriate ranges of the provided aqueous liquid dilution compositions. For example, particle size analysis is available commercially, for example, from Delta Analytical Instruments, Inc., North Huntingdon, Pa. In one example, the particle size of the aqueous liquid dilution composition is measured, for example, by Delta Analytical Instruments, Inc., using a light-scattering analyzer, for example, a dynamic light scattering analyzer, for example, the Horiba® LB-550, which can measure particle sizes within a range of 0.001 micron to 6 micron and uses a Fourier-Transform/Iterative Deconvolution technique for reporting data and can measure sample concentrations from ppm to 40% solids; the Horiba® LA-920, which is a laser light-scattering instrument having an He—Ne laser and a tungsten lamp that can determine particle sizes from 0.02 micron to 2000 micron using Mie Theory; and other analyzers available from Delta Analytical Instruments, Inc.

Alternatively, particle size can be measured by viewing the liquid under a microscope under magnification, for example, a 640× magnification. Particle size then can be measured by comparison to a measuring standard, for example, a ruler, which also is viewed under the magnification. In one example, particles about 25 nm or greater than about 25 nm are visible, while particles less than 25 nm are not visible, for example under a 640× magnification.

iii. Turbidity Measurement

In another example, the clarity/turbidity of the liquid is evaluated and/or expressed using a turbidity measurement, for example, Nephelometric Turbidity Units (NTU). In this example, turbidity is measured optically, to obtain a value indicating the cloudiness or haziness of the liquid, which correlates with the number and size of particles suspended in the liquid. The more clear a liquid is, the lower its turbidity value. Turbidity can be measured optically, for example, using a nephelometer, an instrument with a light and a detector. The nephelometer measures turbidity by detecting scattered light resulting from exposure of the aqueous liquid dilution composition to an incident light. The amount of scattered light correlates with the amount and size of particulate matter in liquid, and thus, the clarity. For example, a beam of light will pass through a sample having low turbidity with little disturbance, creating very little scattered light, resulting in a low turbidity (NTU) value reading. Other methods for measuring turbidity can be used, including commercial services for measuring turbidity, for example, the services available through ACZ Laboratories, Inc., Steamboat Springs, Colo.

The following examples are included for illustrative purposes only and are not intended to limit the scope of the invention.

Example 1

General Procedure for Preparation of Liquid Emulsion Concentrates

Tables 2A(i)-8B below, set forth ingredients that were used to make exemplary liquid emulsion concentrates, described in further detail in Examples 2-8, according to the provided methods. Each of these concentrates contained, one or more non-polar active ingredients, selected from among polyunsaturated fatty acids, vitamins, phytochemicals, carotenoids and fatty acids; a polar solvent, such as, but not limited to, water; a surfactant; and optionally, a soluble fiber, such as, but not limited to, inulin. Each concentrate further contained one or more emulsion stabilizers, such as, but not limited to, ester gum and/or gum arabic, and a natural, GRAS-certified, preservative (benzyl alcohol), and was produced, according to this general method, in a 1000 gram (g), 800 g or 320 g batch (batch sizes indicated in Tables).

Each of Tables 2A(i)-8B sets forth the milligrams (mg) per 2 mL serving of each ingredient in the exemplary concentrate, the percentage, by weight (of the total concentrate), for each ingredient and the amount in grams (g) of each ingredient per batch. Also indicated in each table, in the "phase" column, is whether each ingredient was added to the water phase ("water"), the oil phase ("oil") or was added later, to the emulsion formed after combining the oil and water phases in the emulsification step ("emulsion").

Each of the liquid emulsion concentrates set forth in Examples 2-6 was made using a bench-top process of the provided methods. To make larger batch sizes, the bench-top process can be scaled up to make any of these exemplary concentrates in Examples 2-8, using a scaled-up manufacturing process of the provided methods as described herein.

The bench-top process for making the concentrates in Examples 2-8 was performed using the following general steps (further details are provided in the individual examples):

To make the concentrates, the indicated amount of each ingredient was weighed using a Sartorius Basic Analytical Scale (Model BA110S) or a CTS 6000 Scale (Model CTS-6000). Selection of scale(s) depended on the weight of the particular ingredient(s).

To generate the water phase, the water phase ingredients (indicated by "water" in each table in the "phase" column), were added, in the indicated amount (g/batch), to a water phase vessel (a Pyrex® beaker), and mixed using a reversible homogenizer (Arde Barinco, Inc., Model CJ-4E). During mixing, the water phase ingredients were heated until the ingredients reached the desired temperature of 60° C., using a hot plate as the heating apparatus (a Thermolyne hot Plate Model #SP46615, Barnstead International, Dubuque, Iowa). In the initial step, water was added to the water phase vessel and heated to 60° C. while slowly mixing at 30 RPM on forward. Subsequently, the homogenizer was raised, switched to reverse mode and lowered back into the water to generate a vortex at a speed of 20-30 RPM prior to adding additional water phase ingredients. After addition of all of the water phase ingredients, the homogenizer was raised, switched to forward mode, and lowered back into the water phase vessel to allow mixing at a speed of 30 RPM. The temperature of the water phase and speed of mixing was maintained before combining and emulsifying the water and oil phases. A temperature meter (temperature probe (Model #DPP400W, Cooper-Atkins)) was used to evaluate (measure) the temperature of the water phase. The water phase ingredients included a polar solvent (water) and additional water phase ingredients, where indicated.

The oil phase ingredients (indicated by "oil" in each table in the "phase" column) were added to an oil phase vessel (a Pyrex® beaker), and mixed using a standard mixer (IKA® model No. RE-161S, which is an overhead mixer (laboratory stirrer) compatible with the bench-top process). The oil phase ingredients included a non-polar active ingredient and other oil ingredients as indicated in the Example.

As the oil phase ingredients were mixed, they were heated using a hot plate as a heating apparatus (a Thermolyne hot Plate Model #SP46615, Barnstead International, Dubuque, Iowa), to a desired temperature of 60° C. and generally mixed at this temperature until ingredients had dissolved, and maintained at the temperature before mixing with the water phase. A temperature meter (temperature probe (Model #DPP400W, Cooper-Atkins)) was used to evaluate (measure) the temperature of the oil phase.

After both phases had reached the appropriate temperatures (60° C.) and the oil phase components had dissolved, the phases were combined and emulsified. Emulsification was effected with a reversible homogenizer (Arde Barinco, Inc., Model CJ-4E). The reversible homogenizer, which was used to mix the water phase ingredients, was maintained at 30 RPM for mixing during the emulsification step. While mixing with the homogenizer at this speed, the oil phase was transferred to the water phase vessel by pouring it from the oil phase vessel into the water phase vessel. Mixing with the homogenizer was continued at 30 RPM.

In some examples, after emulsifying, additional ingredients were added, where indicated, in the individual Examples/Tables. In some examples, a pH adjuster (e.g., citric acid) was added after combining and emulsifying the oil and water phases (indicated by "emulsion" in the phase column) while mixing with the reversible homogenizer (Arde Barinco, Inc., Model CJ-4E). The pH of the emulsion was measured using a pH and temperature meter (Hanna Instruments, model HI 8314). When needed, the pH was adjusted with the appropriate amount of a pH adjuster (amount indicated in tables), for example, citric acid, until the emulsion reached a pH of between 2.0 and 3.0.

As a final step, the concentrates were filtered using a 200-1000 micron end-product filter, before hot-filling into a package container.

Example 2

Liquid Emulsion Concentrates with PUFA-Containing Non-Polar Compounds

Examples 2A-2C set forth the details of exemplary liquid emulsion concentrates containing non-polar compounds (non-polar active ingredients) containing polyunsaturated fatty acids (PUFAs) and vitamins. The PUFA-containing non-polar active ingredients in the exemplified compositions were omega-3 fatty acids, omega-6 fatty acids and conjugated fatty acids, including:

Fish oil, containing about 28% DHA/EPA (sold under the name Eterna™ Omegasource™ Oil by Hormel Foods Specialty Products Division, Austin, Minn.). The fish oil non-polar active ingredient was added at an amount of 35.8%, by weight of the final concentrate, whereby the concentrate contained 10% DHA+EPA;

Algal oil, containing about 35% DHA (sold under the name Martek DHA™-S by Martek Biosciences Corporation, Columbia, Md.), which was derived from the marine alga, *Schizochytrium* sp. The algal oil non-polar active ingredient was added at an amount of 35.8%, by weight of the final concentrate, whereby the concentrate contained 10.5% DHA;

Flaxseed oil, containing about not less than (NLT) 50% C18:3 alpha-linolenic acid (obtained from Sanmark LLC, Greensboro, N.C. (Sanmark Limited, Dalian, Liaoning Province, China). The flaxseed oil non-polar active ingredient was added at an amount of 35.8%, by weight of the final concentrate, whereby the concentrate contained 15% ALA;

Borage oil, obtained from Sanmark LLC, Greensboro, N.C. (Sanmark Limited, Dalian, Liaoning Province, China), which was derived by pressing and isolating oil from the seeds of *Borago officinalis* L. This oil contained not less than (NLT) 22% C18:3 gamma-linolenic acid (GLA). The borage oil non-polar active ingredient was added at an amount of 35.8%, by weight of the final concentrate, whereby the concentrate contained 7.9% GLA; and Conjugated linoleic acid (CLA) oil, containing about 80% CLA (obtained from Sanmark, LTD (Dalian, Liaoning Province, China; product code 01057-A80). The CLA oil non-polar active ingredient was added at an amount of 35.8%, by weight of the final concentrate, whereby the concentrate contained 22% CLA.

The vitamin non-polar active ingredients exemplified in the compositions were vitamin A and vitamin D, including:

Vitamin A Palmitate containing 1.7 mIU/g, produced by DSM Nutritional Products, Inc., Belvidere, N.J., and distributed through Stauber Performance Ingredients, Inc., Fullerton, Calif. The vitamin A palmitate was added in an amount such that the emulsion concentrate contained 400 micrograms (mcg) vitamin A per gram concentrate; and Vitamin D3, which was Vitamin D3 in corn oil, containing about 1 mIU/g, produced by DSM Nutritional Products, Inc., Belvidere, N.J., and distributed through Stauber Performance Ingredients, Inc., Fullerton, Calif. The vitamin D3 was added in an amount such that the emulsion concentrate contained 400 IU vitamin D per gram concentrate.

The liquid emulsion concentrates further contained one or more of the following additional ingredients:

A soluble fiber that was Oliggo-Fiber Instant Inulin (Fibruline® Instant), a chicory inulin, produced by Cosucra Groupe Warcoing, Belgium, and distributed through Gillco Products Inc., San Marcos, Calif.;

Emulsion stabilizers, including a modified gum acacia and an ester gum. The modified gum acacia emulsion stabilizer was Tic Pretested® Ticamulsion A-2010 Powder, by Tic Gums, Inc., Belcamp, Md. The ester gum emulsion stabilizer was Ester Gum 8BG by Pinova/Hercules, Brunswick, Ga.;

A preservative that was a natural (GRAS-certified) preservative, benzyl alcohol;

An antifoaming agent that was Tramfloc 1147, sold by Tramfloc Inc, Forney, Tex., that was added to the aqueous phase (approximately 1 drop per liter);

A surfactant that was a sucrose fatty acid ester (SFAE) surfactant (sold under the name Ryoto Sugar Ester S-1760, by Mitsubishi-Kagaku Foods Corporation, Tokyo, Japan); and Water, that was city water, which was purified prior to addition to the water phase vessel, by passage through using the following purifiers, sequentially in the following order: a carbon filter, an ion exchange purifier, a reverse osmosis purifier, a UV sterilizer and an end-point filter (a 100 micron end-point filter).

Tables 2A(i)-2C(ii) set forth ingredients and other details of liquid emulsion concentrates, each containing at least one or more of the PUFA-containing non-polar compounds described above, a polar solvent, and a sucrose fatty acid ester surfactant. The specific non-polar active ingredients are indicated in each table.

Each of the concentrates containing these non-polar active ingredients was made using the general procedure outlined in Example 1 above with the following details: The water phase was made by adding the purified water and heating to 60° C., followed by addition of the following water phase ingredients to the water phase vessel, sequentially, in the following order: 1) Ticamulsion® stabilizer; 2) antifoam; 3) $1^{st}$ fraction surfactant; 4) $2^{nd}$ fraction surfactant; and 5) soluble fiber, and mixing while heating to a temperature of 60° C., which was maintained until combining with the oil phase. The oil phase was generated by adding the following oil phase ingredients to the oil phase vessel, sequentially, in the following order: 1) Ester Gum stabilizer; 2) vitamin non-polar active ingredient; 3) preservative, and heating to a temperature of 60° C., followed by the addition of 4) non-polar active ingredient; 5) Ticamulsion® stabilizer; and 6) surfactant, and mixing and heating to a temperature of 60° C., which was maintained until combining.

The pH of the emulsion was measured using a pH and temperature meter (Hanna Instruments, model HI 8314) and adjusted with the amount of citric acid indicated in the table until the emulsion reached a pH of between 2.0 and 3.0.

A. Liquid Emulsion Concentrates with Omega-3 Containing Non-Polar Compounds

Examples 2A(i)-2A(vii) below set forth the details of liquid emulsion concentrates containing non-polar compounds that include omega-3 fatty acids (e.g., DHA, EPA, ALA) and vitamin A or vitamin D3.

Example 2A(i)

Liquid Emulsion Concentrate with 35.8% of a DHA-Containing Non-Polar Compound (Fish Oil) and 9% SFAE Surfactant Table 2A(i), below, sets forth the ingredients to make a 1000 g batch (2 mL serving size) of a liquid emulsion concentrate containing fish oil (e.g., DHA, EPA) and vitamin A palmitate, which was made according to the procedure set forth in Example 1. The resulting liquid emulsion concentrate was opaque to white in color and contained 100 mg DHA+EPA and 400 mcg vitamin A per gram of the concentrate.

TABLE 2A(i)

Liquid Emulsion Concentrate with 35.8% of a DHA-containing Non-Polar Compound (Fish Oil) and 9% SFAE Surfactant

| Ingredient | mg/2 mL serving | Phase | Percent (by weight) of concentrate | g/batch |
| --- | --- | --- | --- | --- |
| Hormel Eterna ™ Omegasource ™ Oil* (Fish Oil 28% DHA/EPA) (non-polar active ingredient) | 716 | Oil | 35.80 | 358.0 |
| Vitamin A Palmitate* (non-polar active ingredient) | 0.84 | Oil | 0.04 | 0.4200 |
| Fibruline Instant ® (soluble fiber) | 40.5 | Water | 2.03 | 20.25 |
| Tic Pretested ® TICAMULSION A-2010 (stabilizer) | 34.000 | Water | 1.70 | 17.0 |
| Sucrose Fatty Acid Ester (Ryoto Sugar Ester S-1670) ($1^{st}$ Fraction surfactant) | 93.2 | Water | 4.66 | 46.60 |
| Sucrose Fatty Acid Ester (Ryoto Sugar Ester S-1670) ($2^{nd}$ Fraction surfactant) | 62.9 | Water | 3.15 | 31.45 |
| Water | 963.48 | Water | 48.174 | 481.74 |

TABLE 2A(i)-continued

Liquid Emulsion Concentrate with 35.8% of a DHA-containing Non-Polar Compound (Fish Oil) and 9% SFAE Surfactant

| Ingredient | mg/2 mL serving | Phase | Percent (by weight) of concentrate | g/batch |
|---|---|---|---|---|
| Benzyl Alcohol (Preservative) | 10.000 | Oil | 0.50 | 5.0 |
| Sucrose Fatty Acid Ester (Ryoto Sugar Ester S-1670) (surfactant) | 25.0 | Oil | 1.25 | 12.5 |
| Ester Gum 8BG Pinova/Hercules (stabilizer) | 1.25 | Oil | 0.06 | 0.625 |
| Tic Pretested ® TICAMULSION A-2010 (stabilizer) | 10 | Oil | 0.5000 | 5.000 |
| Citric Acid (pH adjuster) | 42.83 | Emulsion | 2.1415 | 21.4150 |
| Totals | 2000.000 | | 100.0000 | 1000 |

*This ingredient was added at 5% overage to insure the final composition contained the stated amount of this ingredient.

Example 2A(ii)

Liquid Emulsion Concentrate with 35.8% of a DHA-Containing Non-Polar Compound (Fish Oil) and 9% SFAE Surfactant Table 2A(ii), below, sets forth the ingredients to make a 800 g batch (2 mL serving size) of a liquid emulsion concentrate containing fish oil (e.g., DHA, EPA) and vitamin A palmitate, which was made according to the procedure set forth in Example 1. The resulting liquid emulsion concentrate was opaque to white in color and contained 100 mg DHA+EPA and 400 mcg vitamin A per gram of the concentrate.

TABLE 2A(ii)

Liquid Emulsion Concentrate with 35.8% of a DHA-containing Non-Polar Compound (Fish Oil) and 9% SFAE Surfactant

| Ingredient | mg/2 mL serving | Phase | Percent (by weight) of concentrate | g/batch |
|---|---|---|---|---|
| Hormel Eterna ™ Omegasource ™ Oil* (28% DHA/EPA) (non-polar active ingredient) | 716 | Oil | 35.80 | 286.4 |
| Vitamin A Palmitate* (non-polar active ingredient) | 0.84 | Oil | 0.04 | 0.3360 |
| Fibruline Instant ® (soluble fiber) | 40.5 | Water | 2.03 | 16.20 |
| Tic Pretested ® TICAMULSION A-2010 (stabilizer) | 34.000 | Water | 1.70 | 13.6 |
| Sucrose Fatty Acid Ester (Ryoto Sugar Ester S-1670) (1st Fraction surfactant) | 93.2 | Water | 4.66 | 37.28 |
| Sucrose Fatty Acid Ester (Ryoto Sugar Ester S-1670) (2nd Fraction surfactant) | 62.9 | Water | 3.15 | 25.16 |
| Water | 963.48 | Water | 48.174 | 385.392 |
| Benzyl Alcohol (Preservative) | 10.000 | Oil | 0.50 | 4.0 |
| Sucrose Fatty Acid Ester (Ryoto Sugar Ester S-1670) (surfactant) | 25.0 | Oil | 1.25 | 10.00 |
| Ester Gum 8BG Pinova/Hercules (stabilizer) | 1.25 | Oil | 0.06 | 0.5 |
| Tic Pretested ® TICAMULSION A-2010 (stabilizer) | 10 | Oil | 0.5000 | 4.000 |
| Citric Acid (pH adjuster) | 42.83 | Emulsion | 2.1415 | 17.1320 |
| Totals | 2000.000 | | 100.0000 | 800 |

*This ingredient was added at 5% overage to insure the final composition contained the stated amount of this ingredient.

Example 2A(iii)

Liquid Emulsion Concentrate with 35.8% of a DHA-Containing Non-Polar Compound (Fish Oil) and 9% SFAE Surfactant Table 2A(iii), below, sets forth the ingredients to make a 800 g batch (2 mL serving size) of a liquid emulsion concentrate containing fish oil (e.g., DHA, EPA) and vitamin D3, which was made according to the procedure set forth in Example 1. The resulting liquid emulsion concentrate was opaque to white in color and contained 100 mg DHA+EPA and 400 IU vitamin D3 per gram of the concentrate.

TABLE 2A(iii)

Liquid Emulsion Concentrate with 35.8% of a DHA-containing Non-Polar Compound (Fish Oil) and 9% SFAE Surfactant

| Ingredient | mg/2 mL serving | Phase | Percent (by weight) of concentrate | g/batch |
| --- | --- | --- | --- | --- |
| Hormel Eterna ™ Omegasource ™ Oil* (28% DHA/EPA) (non-polar active ingredient) | 716 | Oil | 35.80 | 286.4 |
| Vitamin D3* (non-polar active ingredient) | 0.02 | Oil | 0.001 | 0.0084 |
| Fibruline Instant ® (soluble fiber) | 40.5 | Water | 2.03 | 16.20 |
| Tic Pretested ® TICAMULSION A-2010 (stabilizer) | 34.000 | Water | 1.70 | 13.6 |
| Sucrose Fatty Acid Ester (Ryoto Sugar Ester S-1670) (1$^{st}$ Fraction surfactant) | 93.2 | Water | 4.66 | 37.28 |
| Sucrose Fatty Acid Ester (Ryoto Sugar Ester S-1670) (2$^{nd}$ Fraction surfactant) | 62.9 | Water | 3.15 | 25.16 |
| Water | 964.30 | Water | 48.215 | 385.72 |
| Benzyl Alcohol (Preservative) | 10.000 | Oil | 0.50 | 4.0 |
| Sucrose Fatty Acid Ester (Ryoto Sugar Ester S-1670) (surfactant) | 25.0 | Oil | 1.25 | 10.00 |
| Ester Gum 8BG Pinova/Hercules (stabilizer) | 1.25 | Oil | 0.06 | 0.5 |
| Tic Pretested ® TICAMULSION A-2010 (stabilizer) | 10 | Oil | 0.5000 | 4.000 |
| Citric Acid (pH adjuster) | 42.83 | Emulsion | 2.1415 | 17.1320 |
| Totals | 2000.000 | | 100.0000 | 800 |

*This ingredient was added at 5% overage to insure the final composition contained the stated amount of this ingredient.

Example 2A(iv)

Liquid Emulsion Concentrate with 35.8% of a DHA-Containing Non-Polar Compound (Algal Oil) and 9% SFAE Surfactant Table 2A(iv), below, sets forth the ingredients to make a 800 g batch (2 mL serving size) of a liquid emulsion concentrate containing algal oil (e.g., DHA) and vitamin A palmitate, which was made according to the procedure set forth in Example 1. The resulting liquid emulsion concentrate was opaque to white in color and contained 105 mg DHA and 400 mcg vitamin A per gram of the concentrate.

TABLE 2A(iv)

Liquid Emulsion Concentrate with 35.8% of a DHA-containing Non-Polar Compound (Algal Oil) and 9% SFAE Surfactant

| Ingredient | mg/2 mL serving | Phase | Percent (by weight) of concentrate | g/batch |
| --- | --- | --- | --- | --- |
| Martek DHA ™-S Algal Oil* (35% DHA) (non-polar active ingredient) | 716 | Oil | 35.80 | 286.4 |

TABLE 2A(iv)-continued

Liquid Emulsion Concentrate with 35.8% of a DHA-containing Non-Polar Compound (Algal Oil) and 9% SFAE Surfactant

| Ingredient | mg/2 mL serving | Phase | Percent (by weight) of concentrate | g/batch |
|---|---|---|---|---|
| Vitamin A Palmitate* (non-polar active ingredient) | 0.84 | Oil | 0.04 | 0.3360 |
| Fibruline Instant ® (soluble fiber) | 40.5 | Water | 2.03 | 16.20 |
| Tic Pretested ® TICAMULSION A-2010 (stabilizer) | 34.000 | Water | 1.70 | 13.6 |
| Sucrose Fatty Acid Ester (Ryoto Sugar Ester S-1670) (1st Fraction surfactant) | 93.2 | Water | 4.66 | 37.28 |
| Sucrose Fatty Acid Ester (Ryoto Sugar Ester S-1670) (2nd Fraction surfactant) | 62.9 | Water | 3.15 | 25.16 |
| Water | 963.48 | Water | 48.174 | 385.392 |
| Benzyl Alcohol (Preservative) | 10.000 | Oil | 0.50 | 4.0 |
| Sucrose Fatty Acid Ester (Ryoto Sugar Ester S-1670) (surfactant) | 25.0 | Oil | 1.25 | 10.00 |
| Ester Gum 8BG Pinova/Hercules (stabilizer) | 1.25 | Oil | 0.06 | 0.5 |
| Tic Pretested ® TICAMULSION A-2010 (stabilizer) | 10 | Oil | 0.5000 | 4.000 |
| Citric Acid (pH adjuster) | 42.83 | Emulsion | 2.1415 | 17.1320 |
| Totals | 2000.000 | | 100.0000 | 800 |

*This ingredient was added at 5% overage to insure the final composition contained the stated amount of this ingredient.

Example 2A(v)

Liquid Emulsion Concentrate with 35.8% of a DHA-Containing Non-Polar Compound (Algal Oil) and 9% SFAE Surfactant Table 2A(v), below, sets forth the ingredients to make a 800 g batch (2 mL serving size) of a liquid emulsion concentrate containing algal oil (e.g., DHA) and vitamin D3, which was made according to the procedure set forth in Example 1. The resulting liquid emulsion concentrate was opaque to white in color and contained 105 mg DHA and 400 IU vitamin D3 per gram of the concentrate.

TABLE 2A(v)

Liquid Emulsion Concentrate with 35.8% of a DHA-containing Non-Polar Compound (Algal Oil) and 9% SFAE Surfactant

| Ingredient | mg/2 mL serving | Phase | Percent (by weight) of concentrate | g/batch |
|---|---|---|---|---|
| Martek DHA ™-S Algal Oil* (35% DHA) (non-polar active ingredient) | 716 | Oil | 35.80 | 286.4 |
| Vitamin D3* (non-polar active ingredient) | 0.02 | Oil | 0.001 | 0.0084 |
| Fibruline Instant ® (soluble fiber) | 40.5 | Water | 2.03 | 16.20 |
| Tic Pretested ® TICAMULSION A-2010 (stabilizer) | 34.000 | Water | 1.70 | 13.6 |
| Sucrose Fatty Acid Ester (Ryoto Sugar Ester S-1670) (1st Fraction surfactant) | 93.2 | Water | 4.66 | 37.28 |
| Sucrose Fatty Acid Ester (Ryoto Sugar Ester S-1670) (2nd Fraction surfactant) | 62.9 | Water | 3.15 | 25.16 |
| Water | 964.30 | Water | 48.215 | 385.72 |
| Benzyl Alcohol (Preservative) | 10.000 | Oil | 0.50 | 4.0 |
| Sucrose Fatty Acid Ester (Ryoto Sugar Ester S-1670) (surfactant) | 25.0 | Oil | 1.25 | 10.00 |
| Ester Gum 8BG Pinova/Hercules (stabilizer) | 1.25 | Oil | 0.06 | 0.5 |

TABLE 2A(v)-continued

Liquid Emulsion Concentrate with 35.8% of a DHA-containing Non-Polar Compound (Algal Oil) and 9% SFAE Surfactant

| Ingredient | mg/2 mL serving | Phase | Percent (by weight) of concentrate | g/batch |
|---|---|---|---|---|
| Tic Pretested ® TICAMULSION A-2010 (stabilizer) | 10 | Oil | 0.5000 | 4.000 |
| Citric Acid (pH adjuster) | 42.83 | Emulsion | 2.1415 | 17.1320 |
| Totals | 2000.000 | | 100.0000 | 800 |

*This ingredient was added at 5% overage to insure the final composition contained the stated amount of this ingredient.

Example 2A(vi)

Liquid Emulsion Concentrate with 35.8% of an ALA-Containing Non-Polar Compound (Flaxseed Oil) and 9% SFAE Surfactant Table 2A(vi), below, sets forth the ingredients to make a 800 g batch (2 mL serving size) of a liquid emulsion concentrate containing flaxseed oil (e.g., ALA) and vitamin A palmitate, which was made according to the procedure set forth in Example 1. The resulting liquid emulsion concentrate was opaque to white in color and contained 150 mg ALA and 400 mcg vitamin A per gram of the concentrate.

TABLE 2A(vi)

Liquid Emulsion Concentrate with 35.8% of an ALA-containing Non-Polar Compound (Flaxseed Oil) and 9% SFAE Surfactant

| Ingredient | mg/2 mL serving | Phase | Percent (by weight) of concentrate | g/batch |
|---|---|---|---|---|
| SanMark Flaxseed Oil* (50% ALA) (non-polar active ingredient) | 716 | Oil | 35.80 | 286.4 |
| Vitamin A Palmitate* (non-polar active ingredient) | 0.84 | Oil | 0.04 | 0.3360 |
| Fibruline Instant ® (soluble fiber) | 40.5 | Water | 2.03 | 16.20 |
| Tic Pretested ® TICAMULSION A-2010 (stabilizer) | 34.000 | Water | 1.70 | 13.6 |
| Sucrose Fatty Acid Ester (Ryoto Sugar Ester S-1670) ($1^{st}$ Fraction surfactant) | 93.2 | Water | 4.66 | 37.28 |
| Sucrose Fatty Acid Ester (Ryoto Sugar Ester S-1670) ($2^{nd}$ Fraction surfactant) | 62.9 | Water | 3.15 | 25.16 |
| Water | 963.48 | Water | 48.174 | 385.392 |
| Benzyl Alcohol (Preservative) | 10.000 | Oil | 0.50 | 4.0 |
| Sucrose Fatty Acid Ester (Ryoto Sugar Ester S-1670) (surfactant) | 25.0 | Oil | 1.25 | 10.00 |
| Ester Gum 8BG Pinova/Hercules (stabilizer) | 1.25 | Oil | 0.06 | 0.5 |
| Tic Pretested ® TICAMULSION A-2010 (stabilizer) | 10 | Oil | 0.5000 | 4.000 |
| Citric Acid (pH adjuster) | 42.83 | Emulsion | 2.1415 | 17.1320 |
| Totals | 2000.000 | | 100.0000 | 800 |

*This ingredient was added at 5% overage to insure the final composition contained the stated amount of this ingredient.

Example 2A(vii)

Liquid Emulsion Concentrate with 35.8% of an ALA-Containing Non-Polar Compound (Flaxseed Oil) and 9% SFAE Surfactant Table 2A(vii), below, sets forth the ingredients to make a 800 g batch (2 mL serving size) of a liquid emulsion concentrate containing flaxseed oil (e.g., ALA) and vitamin D3, which was made according to the procedure set forth in Example 1. The resulting liquid emulsion concentrate was opaque to white in color and contained 150 mg ALA and 400 IU vitamin D3 per gram of the concentrate.

TABLE 2A(vii)

Liquid Emulsion Concentrate with 35.8% of an ALA-containing Non-Polar Compound (Flaxseed Oil) and 9% SFAE Surfactant

| Ingredient | mg/2 mL serving | Phase | Percent (by weight) of concentrate | g/batch |
|---|---|---|---|---|
| SanMark Flaxseed Oil* (50% ALA) (non-polar active ingredient) | 716 | Oil | 35.80 | 286.4 |
| Vitamin D3* (non-polar active ingredient) | 0.02 | Oil | 0.001 | 0.0084 |
| Fibruline Instant ® (soluble fiber) | 40.5 | Water | 2.03 | 16.20 |
| Tic Pretested ® TICAMULSION A-2010 (stabilizer) | 34.000 | Water | 1.70 | 13.6 |
| Sucrose Fatty Acid Ester (Ryoto Sugar Ester S-1670) (1st Fraction surfactant) | 93.2 | Water | 4.66 | 37.28 |
| Sucrose Fatty Acid Ester (Ryoto Sugar Ester S-1670) (2nd Fraction surfactant) | 62.9 | Water | 3.15 | 25.16 |
| Water | 964.30 | Water | 48.215 | 385.72 |
| Benzyl Alcohol (Preservative) | 10.000 | Oil | 0.50 | 4.0 |
| Sucrose Fatty Acid Ester (Ryoto Sugar Ester S-1670) (surfactant) | 25.0 | Oil | 1.25 | 10.00 |
| Ester Gum 8BG Pinova/Hercules (stabilizer) | 1.25 | Oil | 0.06 | 0.5 |
| Tic Pretested ® TICAMULSION A-2010 (stabilizer) | 10 | Oil | 0.5000 | 4.000 |
| Citric Acid (pH adjuster) | 42.83 | Emulsion | 2.1415 | 17.1320 |
| Totals | 2000.000 | | 100.0000 | 800 |

*This ingredient was added at 5% overage to insure the final composition contained the stated amount of this ingredient.

B. Liquid Emulsion Concentrates with Omega-6 Containing Non-Polar Compounds

Examples 2B(i)-2B(ii) below set forth the details of liquid emulsion concentrates containing non-polar compounds that include omega-6 fatty acids (e.g., GLA) and vitamin A or vitamin D3.

Example 2B(i)

Liquid Emulsion Concentrate with 35.8% of a GLA-Containing Non-Polar Compound (Borage Oil) and 9% SFAE Surfactant Table 2B(i), below, sets forth the ingredients to make a 800 g batch (2 mL serving size) of a liquid emulsion concentrate containing borage oil (e.g., GLA) and vitamin A palmitate, which was made according to the procedure set forth in Example 1. The resulting liquid emulsion concentrate was opaque to white in color and contained 79 mg GLA and 400 mcg vitamin A per gram of the concentrate.

TABLE 2B(i)

Liquid Emulsion Concentrate with 35.8% of a GLA-containing Non-Polar Compound (Borage Oil) and 9% SFAE Surfactant

| Ingredient | mg/2 mL serving | Phase | Percent (by weight) of concentrate | g/batch |
|---|---|---|---|---|
| Borage Oil* (22% GLA) (non-polar active ingredient) | 716 | Oil | 35.80 | 286.4 |
| Vitamin A Palmitate* (non-polar active ingredient) | 0.84 | Oil | 0.04 | 0.3360 |
| Fibruline Instant ® (soluble fiber) | 40.5 | Water | 2.03 | 16.20 |
| Tic Pretested ® TICAMULSION A-2010 (stabilizer) | 34.000 | Water | 1.70 | 13.6 |
| Sucrose Fatty Acid Ester (Ryoto Sugar Ester S-1670) (1st Fraction surfactant) | 93.2 | Water | 4.66 | 37.28 |

TABLE 2B(i)-continued

Liquid Emulsion Concentrate with 35.8% of a GLA-containing Non-Polar Compound (Borage Oil) and 9% SFAE Surfactant

| Ingredient | mg/2 mL serving | Phase | Percent (by weight) of concentrate | g/batch |
|---|---|---|---|---|
| Sucrose Fatty Acid Ester (Ryoto Sugar Ester S-1670) (2$^{nd}$ Fraction surfactant) | 62.9 | Water | 3.15 | 25.16 |
| Water | 963.48 | Water | 48.174 | 385.392 |
| Benzyl Alcohol (Preservative) | 10.000 | Oil | 0.50 | 4.0 |
| Sucrose Fatty Acid Ester (Ryoto Sugar Ester S-1670) (surfactant) | 25.0 | Oil | 1.25 | 10.00 |
| Ester Gum 8BG Pinova/Hercules (stabilizer) | 1.25 | Oil | 0.06 | 0.5 |
| Tic Pretested ® TICAMULSION A-2010 (stabilizer) | 10 | Oil | 0.5000 | 4.000 |
| Citric Acid (pH adjuster) | 42.83 | Emulsion | 2.1415 | 17.1320 |
| Totals | 2000.000 | | 100.0000 | 800 |

*This ingredient was added at 5% overage to insure the final composition contained the stated amount of this ingredient.

Example 2B(ii)

Liquid Emulsion Concentrate with 35.8% of a GLA-Containing Non-Polar Compound (Borage Oil) and 9% SFAE Surfactant Table 2B(ii), below, sets forth the ingredients to make a 800 g batch (2 mL serving size) of a liquid emulsion concentrate containing borage oil (e.g., GLA) and vitamin D3, which was made according to the procedure set forth in Example 1. The resulting liquid emulsion concentrate was opaque to white in color and contained 79 mg GLA and 400 IU vitamin D3 per gram of the concentrate.

TABLE 2B(ii)

Liquid Emulsion Concentrate with 35.8% of a GLA-containing Non-Polar Compound (Borage Oil) and 9% SFAE Surfactant

| Ingredient | mg/2 mL serving | Phase | Percent (by weight) of concentrate | g/batch |
|---|---|---|---|---|
| Borage Oil* (22% GLA) (non-polar active ingredient) | 716 | Oil | 35.80 | 286.4 |
| Vitamin D3* (non-polar active ingredient) | 0.02 | Oil | 0.001 | 0.0084 |
| Fibruline Instant ® (soluble fiber) | 40.5 | Water | 2.03 | 16.20 |
| Tic Pretested ® TICAMULSION A-2010 (stabilizer) | 34.000 | Water | 1.70 | 13.6 |
| Sucrose Fatty Acid Ester (Ryoto Sugar Ester S-1670) (1$^{st}$ Fraction surfactant) | 93.2 | Water | 4.66 | 37.28 |
| Sucrose Fatty Acid Ester (Ryoto Sugar Ester S-1670) (2$^{nd}$ Fraction surfactant) | 62.9 | Water | 3.15 | 25.16 |
| Water | 964.30 | Water | 48.215 | 385.72 |
| Benzyl Alcohol (Preservative) | 10.000 | Oil | 0.50 | 4.0 |
| Sucrose Fatty Acid Ester (Ryoto Sugar Ester S-1670) (surfactant) | 25.0 | Oil | 1.25 | 10.00 |
| Ester Gum 8BG Pinova/Hercules (stabilizer) | 1.25 | Oil | 0.06 | 0.5 |
| Tic Pretested ® TICAMULSION A-2010 (stabilizer) | 10 | Oil | 0.5000 | 4.000 |
| Citric Acid (pH adjuster) | 42.83 | Emulsion | 2.1415 | 17.1320 |
| Totals | 2000.000 | | 100.0000 | 800 |

*This ingredient was added at 5% overage to insure the final composition contained the stated amount of this ingredient.

C. Liquid Emulsion Concentrates with Conjugated Fatty Acid Containing Non-Polar Compounds Examples 2C(i)-2C(ii) below set forth the details of liquid emulsion concentrates containing non-polar compounds that include conjugated fatty acids (e.g., CLA) and vitamin A or vitamin D3.

Example 2C(i)

Liquid Emulsion Concentrate with 35.8% of a CLA-Containing Non-Polar Compound and 9% SFAE Surfactant Table 2C(i), below, sets forth the ingredients to make a 800 g batch (2 mL serving size) of a liquid emulsion concentrate containing conjugated linoleic acid oil (e.g., CLA) and vitamin A palmitate, which was made according to the procedure set forth in Example 1. The resulting liquid emulsion concentrate was opaque to white in color and contained 220 mg CLA and 400 mcg vitamin A per gram of the concentrate.

TABLE 2C(i)

Liquid Emulsion Concentrate with 35.8% of a CLA-containing Non-Polar Compound and 9% SFAE Surfactant

| Ingredient | mg/2 mL serving | Phase | Percent (by weight) of concentrate | g/batch |
|---|---|---|---|---|
| Clarinol ™ G-80 CLA Oil* (80% CLA) (non-polar active ingredient) | 716 | Oil | 35.80 | 286.4 |
| Vitamin A Palmitate* (non-polar active ingredient) | 0.84 | Oil | 0.04 | 0.3360 |
| Fibruline Instant ® (soluble fiber) | 40.5 | Water | 2.03 | 16.20 |
| Tic Pretested ® TICAMULSION A-2010 (stabilizer) | 34.000 | Water | 1.70 | 13.6 |
| Sucrose Fatty Acid Ester (Ryoto Sugar Ester S-1670) (1st Fraction surfactant) | 93.2 | Water | 4.66 | 37.28 |
| Sucrose Fatty Acid Ester (Ryoto Sugar Ester S-1670) (2nd Fraction surfactant) | 62.9 | Water | 3.15 | 25.16 |
| Water | 963.48 | Water | 48.174 | 385.392 |
| Benzyl Alcohol (Preservative) | 10.000 | Oil | 0.50 | 4.0 |
| Sucrose Fatty Acid Ester (Ryoto Sugar Ester S-1670) (surfactant) | 25.0 | Oil | 1.25 | 10.00 |
| Ester Gum 8BG Pinova/Hercules (stabilizer) | 1.25 | Oil | 0.06 | 0.5 |
| Tic Pretested ® TICAMULSION A-2010 (stabilizer) | 10 | Oil | 0.5000 | 4.000 |
| Citric Acid (pH adjuster) | 42.83 | Emulsion | 2.1415 | 17.1320 |
| Totals | 2000.000 | | 100.0000 | 800 |

*This ingredient was added at 5% overage to insure the final composition contained the stated amount of this ingredient.

Example 2C(ii)

Liquid Emulsion Concentrate with 35.8% of a CLA-Containing Non-Polar Compound and 9% SFAE Surfactant Table 2C(ii), below, sets forth the ingredients to make a 800 g batch (2 mL serving size) of a liquid emulsion concentrate containing conjugated linoleic acid oil (e.g., CLA) and vitamin D3, which was made according to the procedure set forth in Example 1. The resulting liquid emulsion concentrate was opaque to white in color and contained 220 mg CLA and 400 IU vitamin D3 per gram of the concentrate.

TABLE 2C(ii)

Liquid Emulsion Concentrate with 35.8% of a CLA-containing Non-Polar Compound and 9% SFAE Surfactant

| Ingredient | mg/2 mL serving | Phase | Percent (by weight) of concentrate | g/batch |
|---|---|---|---|---|
| Clarinol ™ G-80 CLA Oil* (80% CLA) (non-polar active ingredient) | 716 | Oil | 35.80 | 286.4 |
| Vitamin D3* (non-polar active ingredient) | 0.02 | Oil | 0.001 | 0.0084 |
| Fibruline Instant ® (soluble fiber) | 40.5 | Water | 2.03 | 16.20 |
| Tic Pretested ® TICAMULSION A-2010 (stabilizer) | 34.000 | Water | 1.70 | 13.6 |
| Sucrose Fatty Acid Ester (Ryoto Sugar Ester S-1670) ($1^{st}$ Fraction surfactant) | 93.2 | Water | 4.66 | 37.28 |
| Sucrose Fatty Acid Ester (Ryoto Sugar Ester S-1670) ($2^{nd}$ Fraction surfactant) | 62.9 | Water | 3.15 | 25.16 |
| Water | 964.30 | Water | 48.215 | 385.72 |
| Benzyl Alcohol (Preservative) | 10.000 | Oil | 0.50 | 4.0 |
| Sucrose Fatty Acid Ester (Ryoto Sugar Ester S-1670) (surfactant) | 25.0 | Oil | 1.25 | 10.00 |
| Ester Gum 8BG Pinova/Hercules (stabilizer) | 1.25 | Oil | 0.06 | 0.5 |
| Tic Pretested ® TICAMULSION A-2010 (stabilizer) | 10 | Oil | 0.5000 | 4.000 |
| Citric Acid (pH adjuster) | 42.83 | Emulsion | 2.1415 | 17.1320 |
| Totals | 2000.000 | | 100.0000 | 800 |

*This ingredient was added at 5% overage to insure the final composition contained the stated amount of this ingredient.

Example 3

Liquid Emulsion Concentrates with Phytochemical-Containing Non-Polar Compounds

Examples 3A-3E, below, set forth the details of exemplary liquid emulsion concentrates containing non-polar compounds (non-polar active ingredients) containing phytochemicals. The concentrates additionally contain one or more of polyunsaturated fatty acids (PUFAs), fatty acids and vitamins. The phytochemical-containing non-polar active ingredients in the exemplified compositions were phytosterols and resveratrol, including:

Phytosterols, sold under the name CardioAid™, distributed by B&D Nutrition and manufactured by ADM Natural Health and Nutrition, Decatur, Ill. This compound contained Kosher, Pareve, and Halal plant sterols that are produced under current food GMPs and contained a minimum of 95% plant sterols. The phytosterol non-polar active ingredient was added at an amount of 10.75%, by weight of the final concentrate, whereby the concentrate contained 10% phytosterols; and Resveratrol, containing trans-resveratrol, sold under the name ReserveNature™, sold by Jiaherb, Shaanxi, China, containing trans-resveratrol from the botanical source *Polygonum cuspidatum*. The resveratrol non-polar active ingredient was added at an amount of 10.75%, by weight of the final concentrate, whereby the concentrate contained 10% resveratrol.

The PUFA-containing non-polar active ingredients in the exemplified compositions were omega-3 fatty acids, omega-6 fatty acids and conjugated fatty acids, including:

Fish oil, containing about 28% DHA/EPA (sold under the name Eterna™ Omegasource™ Oil by Hormel Foods Specialty Products Division, Austin, Minn.). The fish oil non-polar active ingredient was added at an amount of 25%, by weight of the final concentrate, whereby the concentrate contained 6% DHA+EPA; Algal oil, containing about 35% DHA (sold under the name Martek DHA™-S by Martek Biosciences Corporation, Columbia, Md.), which was derived from the marine alga, *Schizochytrium* sp. The algal oil non-polar active ingredient was added at an amount of 25%, by weight of the final concentrate, whereby the concentrate contained 8% DHA;

Flaxseed oil, containing about not less than (NLT) 50% C18:3 alpha-linolenic acid (obtained from Sanmark LLC, Greensboro, N.C. (Sanmark Limited, Dalian, Liaoning Province, China). The flaxseed oil non-polar active ingredient was added at an amount of 25%, by weight of the final concentrate, whereby the concentrate contained 12% ALA;

Borage oil, obtained from Sanmark LLC, Greensboro, N.C. (Sanmark Limited, Dalian, Liaoning Province, China), which was derived by pressing and isolating oil from the seeds of *Borago officinalis* L. This oil contained not less than (NLT) 22% C18:3 gamma-linolenic acid (GLA). The borage oil non-polar active ingredient was added at an amount of 25%, by weight of the final concentrate, whereby the concentrate contained 6.6% GLA; and Conjugated linoleic acid (CLA) oil, containing about 80% CLA (obtained from Sanmark, LTD (Dalian, Liaoning Province, China; product code 01057-A80). The CLA oil non-polar active ingredient was added at an amount of 25%, by weight of the final concentrate, whereby the concentrate contained 18% CLA.

The fatty acid-containing non-polar active ingredient in the exemplified compositions was oleic acid, an omega-9 fatty acid, which was Oleic Acid 70% Food Grade Kosher Vegetable-Based, 100% Natural, sold by KIC Chemicals, Inc., Armonk, N.Y.

The vitamin non-polar active ingredients exemplified in the compositions were vitamin A and vitamin D3, including:

Vitamin A Palmitate containing 1.7 mIU/g, produced by DSM Nutritional Products, Inc., Belvidere, N.J., and distributed through Stauber Performance Ingredients, Inc., Fullerton, Calif. The vitamin A palmitate was added in an amount such that the emulsion concentrate contained 400 micrograms (mcg) vitamin A per gram concentrate; and Vitamin D3, which was Vitamin D3 in corn oil, containing about 1 mIU/g, produced by DSM Nutritional Products, Inc., Belvidere, N.J., and distributed through Stauber Performance Ingredients, Inc., Fullerton, Calif. The vitamin D3 was added in an amount such that the emulsion concentrate contained 400 IU vitamin D3 per gram concentrate.

The liquid emulsion concentrates further contained one or more of the following additional ingredients:

An emulsion stabilizer, that was a modified gum acacia emulsion stabilizer, sold under the name Tic Pretested® Ticamulsion A-2010 Powder, by Tic Gums, Inc., Belcamp, Md.;

A preservative that was a natural (GRAS-certified) preservative, benzyl alcohol;

An antifoaming agent that was Tramfloc 1147, sold by Tramfloc Inc, Forney, Tex., that was added to the aqueous phase (approximately 1 drop per liter);

A surfactant that was a sucrose fatty acid ester (SFAE) surfactant (sold under the name Ryoto Sugar Ester S-1760, by Mitsubishi-Kagaku Foods Corporation, Tokyo, Japan); and Water, that was city water, which was purified prior to addition to the water phase vessel, by passage through using the following purifiers, sequentially in the following order: a carbon filter, an ion exchange purifier, a reverse osmosis purifier, a UV sterilizer and an end-point filter (a 100 micron end-point filter).

Tables 3A(i)-3E(ii) set forth ingredients and other details of liquid emulsion concentrates, each containing at least one or more of the non-polar compounds described above, a polar solvent, and a sucrose fatty acid ester surfactant. The specific non-polar active ingredients are indicated in each table.

Each of the concentrates containing these non-polar active ingredients was made using the general procedure outlined in Example 1 above with the following details: The water phase was made by adding the purified water and heating to 60° C., followed by addition of the following water phase ingredients to the water phase vessel, sequentially, in the following order: 1) emulsion stabilizer; 2) antifoam; 3) $1^{st}$ fraction surfactant; and 4) $2^{nd}$ fraction surfactant, and mixing while heating to a temperature of 60° C., which was maintained until combining with the oil phase. The oil phase was generated by adding the following oil phase ingredients to the oil phase vessel, sequentially, in the following order: 1) preservative; 2) emulsion stabilizer; 3) vitamin non-polar active ingredient; heating to a temperature of 60° C., followed by the addition of 4) non-polar active ingredient and/or solvent; 5) phytochemical; and 6) surfactant, and mixing and maintaining temperature of 60° C., until combining.

The pH of the emulsion was measured using a pH and temperature meter (Hanna Instruments, model HI 8314) and adjusted with the amount of citric acid indicated in the table until the emulsion reached a pH of between 2.0 and 3.0.

A. Liquid Emulsion Concentrates with Phytosterols and Omega-3 Containing Non-Polar Compounds Examples 3A(i)-3A(iv) below set forth the details of liquid emulsion concentrates containing non-polar compounds that include phytosterols, omega-3 fatty acids (e.g., DHA, EPA, ALA) and vitamin A or vitamin D3.

Example 3A(i)

Liquid Emulsion Concentrate with 25% of a DHA-Containing Non-Polar Compound (Fish Oil), 10.75% Phytosterols and 10% SFAE Surfactant Table 3A(i), below, sets forth the ingredients to make a 320 g batch (2 mL serving size) of a liquid emulsion concentrate containing phytosterols, fish oil (e.g., DHA, EPA) and vitamin A palmitate, which was made according to the procedure set forth in Example 1. The resulting liquid emulsion concentrate was opaque to white in color and contained 100 mg phytosterols, 60 mg DHA+EPA and 400 mcg vitamin A per gram of the concentrate.

TABLE 3A(i)

Liquid Emulsion Concentrate with 25% of a DHA-containing Non-Polar Compound (Fish Oil), 10.75% Phytosterols and 10% SFAE Surfactant

| Ingredient | mg/2 mL serving | Phase | Percent (by weight) of concentrate | g/batch |
|---|---|---|---|---|
| Hormel Eterna ™ Omegasource ™ Oil* (28% DHA/EPA) (non-polar active ingredient) | 500 | Oil | 25.00 | 80.0 |
| Phytosterols* (non-polar active ingredient) | 215.00 | Oil | 10.75 | 34.4000 |
| Vitamin A Palmitate* (non-polar active ingredient) | 0.81 | Oil | 0.04 | 0.1296 |
| Tic Pretested ® TICAMULSION A-2010 (stabilizer) | 34.000 | Water | 1.70 | 5.4 |
| Sucrose Fatty Acid Ester (Ryoto Sugar Ester S-1670) ($1^{st}$ Fraction surfactant) | 110.8 | Water | 5.54 | 17.73 |
| Sucrose Fatty Acid Ester (Ryoto Sugar Ester S-1670) ($2^{nd}$ Fraction surfactant) | 63.9 | Water | 3.20 | 10.22 |
| Water | 987.67 | Water | 49.384 | 158.0272 |
| Benzyl Alcohol (Preservative) | 10.000 | Oil | 0.50 | 1.6 |
| Sucrose Fatty Acid Ester (Ryoto Sugar Ester S-1670) (surfactant) | 25.0 | Oil | 1.25 | 4.00 |
| Tic Pretested ® TICAMULSION A-2010 (stabilizer) | 10 | Oil | 0.5000 | 1.600 |
| Citric Acid (pH adjuster) | 42.83 | Emulsion | 2.1415 | 6.8528 |
| Totals | 2000.00 | | 100.000 | 320 |

*This ingredient was added at 5% overage to insure the final composition contained the stated amount of this ingredient.

Example 3A(ii)

Liquid Emulsion Concentrate with 25% of a DHA-Containing Non-Polar Compound (Fish Oil), 10.75% Phytosterols and 10% SFAE Surfactant Table 3A(ii), below, sets forth the ingredients to make a 320 g batch (2 mL serving size) of a liquid emulsion concentrate containing phytosterols, fish oil (e.g., DHA, EPA) and vitamin D3, which was made according to the procedure set forth in Example 1. The resulting liquid emulsion concentrate was opaque to white in color and contained 100 mg phytosterols, 60 mg DHA+EPA and 400 IU vitamin D3 per gram of the concentrate.

TABLE 3A(ii)

Liquid Emulsion Concentrate with 25% of a DHA-containing Non-Polar Compound (Fish Oil), 10.75% Phytosterols and 10% SFAE Surfactant

| Ingredient | mg/2 mL serving | Phase | Percent (by weight) of concentrate | g/batch |
|---|---|---|---|---|
| Hormel Eterna ™ Omegasource ™ Oil* (28% DHA/EPA) (non-polar active ingredient) | 500 | Oil | 25.00 | 80.0 |
| Phytosterols* (non-polar active ingredient) | 215.00 | Oil | 10.75 | 34.4000 |
| Vitamin D3* (non-polar active ingredient) | 0.02 | Oil | 0.001 | 0.0034 |
| Tic Pretested ® TICAMULSION A-2010 (stabilizer) | 34.000 | Water | 1.70 | 5.4 |
| Sucrose Fatty Acid Ester (Ryoto Sugar Ester S-1670) (1$^{st}$ Fraction surfactant) | 110.8 | Water | 5.54 | 17.73 |
| Sucrose Fatty Acid Ester (Ryoto Sugar Ester S-1670) (2$^{nd}$ Fraction surfactant) | 63.9 | Water | 3.20 | 10.22 |
| Water | 988.46 | Water | 49.423 | 158.1536 |
| Benzyl Alcohol (Preservative) | 10.000 | Oil | 0.50 | 1.6 |
| Sucrose Fatty Acid Ester (Ryoto Sugar Ester S-1670) (surfactant) | 25.0 | Oil | 1.25 | 4.00 |
| Tic Pretested ® TICAMULSION A-2010 (stabilizer) | 10 | Oil | 0.5000 | 1.600 |
| Citric Acid (pH adjuster) | 42.83 | Emulsion | 2.1415 | 6.8528 |
| Totals | 2000.00 | | 100.000 | 320 |

*This ingredient was added at 5% overage to insure the final composition contained the stated amount of this ingredient.

Example 3A(iii)

Liquid Emulsion Concentrate with 25% of a DHA-Containing Non-Polar Compound (Algal Oil), 10.75% Phytosterols and 10% SFAE Surfactant Table 3A(iii), below, sets forth the ingredients to make a 320 g batch (2 mL serving size) of a liquid emulsion concentrate containing phytosterols, algal oil (e.g., DHA) and vitamin A palmitate, which was made according to the procedure set forth in Example 1. The resulting liquid emulsion concentrate was opaque to white in color and contained 100 mg phytosterols, 80 mg DHA and 400 mcg vitamin A per gram of the concentrate.

TABLE 3A(iii)

Liquid Emulsion Concentrate with 25% of a DHA-containing Non-Polar Compound (Algal Oil), 10.75% Phytosterols and 10% SFAE Surfactant

| Ingredient | mg/2 mL serving | Phase | Percent (by weight) of concentrate | g/batch |
|---|---|---|---|---|
| Martek DHA ™-S Algal Oil DHA* (35% DHA) (non-polar active ingredient) | 500 | Oil | 25.00 | 80.0 |

TABLE 3A(iii)-continued

Liquid Emulsion Concentrate with 25% of a DHA-containing Non-Polar Compound (Algal Oil), 10.75% Phytosterols and 10% SFAE Surfactant

| Ingredient | mg/2 mL serving | Phase | Percent (by weight) of concentrate | g/batch |
|---|---|---|---|---|
| Phytosterols* (non-polar active ingredient) | 215.00 | Oil | 10.75 | 34.4000 |
| Vitamin A Palmitate* (non-polar active ingredient) | 0.81 | Oil | 0.04 | 0.1296 |
| Tic Pretested ® TICAMULSION A-2010 (stabilizer) | 34.000 | Water | 1.70 | 5.4 |
| Sucrose Fatty Acid Ester (Ryoto Sugar Ester S-1670) ($1^{st}$ Fraction surfactant) | 110.8 | Water | 5.54 | 17.73 |
| Sucrose Fatty Acid Ester (Ryoto Sugar Ester S-1670) ($2^{nd}$ Fraction surfactant) | 63.9 | Water | 3.20 | 10.22 |
| Water | 987.67 | Water | 49.384 | 158.0272 |
| Benzyl Alcohol (Preservative) | 10.000 | Oil | 0.50 | 1.6 |
| Sucrose Fatty Acid Ester (Ryoto Sugar Ester S-1670) (surfactant) | 25.0 | Oil | 1.25 | 4.00 |
| Tic Pretested ® TICAMULSION A-2010 (stabilizer) | 10 | Oil | 0.5000 | 1.600 |
| Citric Acid (pH adjuster) | 42.83 | Emulsion | 2.1415 | 6.8528 |
| Totals | 2000.00 | | 100.000 | 320 |

*This ingredient was added at 5% overage to insure the final composition contained the stated amount of this ingredient.

Example 3A(iv)

Liquid Emulsion Concentrate with 25% of an ALA-Containing Non-Polar Compound (Flaxseed Oil), 10.75% Phytosterols and 10% SFAE Surfactant Table 3A(iv), below, sets forth the ingredients to make a 320 g batch (2 mL serving size) of a liquid emulsion concentrate containing phytosterols, flaxseed oil (e.g., ALA) and vitamin A palmitate, which was made according to the procedure set forth in Example 1. The resulting liquid emulsion concentrate was opaque to white in color and contained 100 mg phytosterols, 120 mg ALA and 400 mcg vitamin A per gram of the concentrate.

TABLE 3A(iv)

Liquid Emulsion Concentrate with 25% of an ALA-containing Non-Polar Compound (Flaxseed Oil), 10.75% Phytosterols and 10% SFAE Surfactant

| Ingredient | mg/2 mL serving | Phase | Percent (by weight) of concentrate | g/batch |
|---|---|---|---|---|
| SanMark Flaxseed Oil* (50% ALA) (non-polar active ingredient) | 500 | Oil | 25.00 | 80.0 |
| Phytosterols* (non-polar active ingredient) | 215.00 | Oil | 10.75 | 34.4000 |
| Vitamin A Palmitate* (non-polar active ingredient) | 0.81 | Oil | 0.04 | 0.1296 |
| Tic Pretested ® TICAMULSION A-2010 (stabilizer) | 34.000 | Water | 1.70 | 5.4 |
| Sucrose Fatty Acid Ester (Ryoto Sugar Ester S-1670) ($1^{st}$ Fraction surfactant) | 110.8 | Water | 5.54 | 17.73 |
| Sucrose Fatty Acid Ester (Ryoto Sugar Ester S-1670) ($2^{nd}$ Fraction surfactant) | 63.9 | Water | 3.20 | 10.22 |
| Water | 987.67 | Water | 49.384 | 158.0272 |
| Benzyl Alcohol (Preservative) | 10.000 | Oil | 0.50 | 1.6 |
| Sucrose Fatty Acid Ester (Ryoto Sugar Ester S-1670) (surfactant) | 25.0 | Oil | 1.25 | 4.00 |
| Tic Pretested ® TICAMULSION A-2010 (stabilizer) | 10 | Oil | 0.5000 | 1.600 |
| Citric Acid (pH adjuster) | 42.83 | Emulsion | 2.1415 | 6.8528 |
| Totals | 2000.00 | | 100.000 | 320 |

*This ingredient was added at 5% overage to insure the final composition contained the stated amount of this ingredient.

B. Liquid Emulsion Concentrates with Phytosterols and Omega-6 Containing Non-Polar Compounds Example 3B below sets forth the details of liquid emulsion concentrates containing non-polar compounds that include phytosterols, omega-6 fatty acids (e.g., GLA) and vitamin A.

Example 3B

Liquid Emulsion Concentrate with 25% of a GLA-Containing Non-Polar Compound (Borage Oil), 10% Phytosterols and 10% SFAE Surfactant Table 3B, below, sets forth the ingredients to make a 320 g batch (2 mL serving size) of a liquid emulsion concentrate containing phytosterols, borage oil (e.g., GLA) and vitamin A palmitate, which was made according to the procedure set forth in Example 1. The resulting liquid emulsion concentrate was opaque to white in color and contained 100 mg phytosterols, 66 mg GLA and 400 mcg vitamin A per gram of the concentrate.

TABLE 3B

Liquid Emulsion Concentrate with 25% of a GLA-containing Non-Polar Compound (Borage Oil), 10% Phytosterols and 10% SFAE Surfactant

| Ingredient | mg/2 mL serving | Phase | Percent (by weight) of concentrate | g/batch |
| --- | --- | --- | --- | --- |
| Borage Oil* (22% GLA) (non-polar active ingredient) | 500 | Oil | 25.00 | 80.0 |
| Phytosterols* (non-polar active ingredient) | 215.00 | Oil | 10.75 | 34.4000 |
| Vitamin A Palmitate* (non-polar active ingredient) | 0.81 | Oil | 0.04 | 0.1296 |
| Tic Pretested ® TICAMULSION A-2010 (stabilizer) | 34.000 | Water | 1.70 | 5.4 |
| Sucrose Fatty Acid Ester (Ryoto Sugar Ester S-1670) ($1^{st}$ Fraction surfactant) | 110.8 | Water | 5.54 | 17.73 |
| Sucrose Fatty Acid Ester (Ryoto Sugar Ester S-1670) ($2^{nd}$ Fraction surfactant) | 63.9 | Water | 3.20 | 10.22 |
| Water | 987.67 | Water | 49.384 | 158.0272 |
| Benzyl Alcohol (Preservative) | 10.000 | Oil | 0.50 | 1.6 |
| Sucrose Fatty Acid Ester (Ryoto Sugar Ester S-1670) (surfactant) | 25.0 | Oil | 1.25 | 4.00 |
| Tic Pretested ® TICAMULSION A-2010 (stabilizer) | 10 | Oil | 0.5000 | 1.600 |
| Citric Acid (pH adjuster) | 42.83 | Emulsion | 2.1415 | 6.8528 |
| Totals | 2000.00 | | 100.000 | 320 |

*This ingredient was added at 5% overage to insure the final composition contained the stated amount of this ingredient.

C. Liquid Emulsion Concentrates with Phytosterols and Conjugated Fatty Acid Containing Non-Polar Compounds Example 3C below sets forth the details of liquid emulsion concentrates containing non-polar compounds that include phytosterols, conjugated fatty acids (e.g., CLA) and vitamin A.

Example 3C

Liquid Emulsion Concentrate with 25% of a CLA-Containing Non-Polar Compound, 10% Phytosterols and 10% SFAE Surfactant Table 3C, below, sets forth the ingredients to make a 320 g batch (2 mL serving size) of a liquid emulsion concentrate containing phytosterols, conjugated linoleic acid oil (e.g., CLA) and vitamin A palmitate, which was made according to the procedure set forth in Example 1. The resulting liquid emulsion concentrate was opaque to white in color and contained 100 mg phytosterols, 180 mg CLA and 400 mcg vitamin A per gram of the concentrate.

TABLE 3C

Liquid Emulsion Concentrate with 25% of a CLA-containing Non-Polar Compound, 10% Phytosterols and 10% SFAE Surfactant

| Ingredient | mg/2 mL serving | Phase | Percent (by weight) of concentrate | g/batch |
|---|---|---|---|---|
| Clarinol ™ G-80 CLA Oil* (80% CLA) (non-polar active ingredient) | 500 | Oil | 25.00 | 80.0 |
| Phytosterols* (non-polar active ingredient) | 215.00 | Oil | 10.75 | 34.4000 |
| Vitamin A Palmitate* (non-polar active ingredient) | 0.81 | Oil | 0.04 | 0.1296 |
| Tic Pretested ® TICAMULSION A-2010 (stabilizer) | 34.000 | Water | 1.70 | 5.4 |
| Sucrose Fatty Acid Ester (Ryoto Sugar Ester S-1670) (1st Fraction surfactant) | 110.8 | Water | 5.54 | 17.73 |
| Sucrose Fatty Acid Ester (Ryoto Sugar Ester S-1670) (2nd Fraction surfactant) | 63.9 | Water | 3.20 | 10.22 |
| Water | 987.67 | Water | 49.384 | 158.0272 |
| Benzyl Alcohol (Preservative) | 10.000 | Oil | 0.50 | 1.6 |
| Sucrose Fatty Acid Ester (Ryoto Sugar Ester S-1670) (surfactant) | 25.0 | Oil | 1.25 | 4.00 |
| Tic Pretested ® TICAMULSION A-2010 (stabilizer) | 10 | Oil | 0.5000 | 1.600 |
| Citric Acid (pH adjuster) | 42.83 | Emulsion | 2.1415 | 6.8528 |
| Totals | 2000.00 | | 100.000 | 320 |

*This ingredient was added at 5% overage to insure the final composition contained the stated amount of this ingredient.

D. Liquid Emulsion Concentrates with Phytosterols and Fatty Acid Containing Non-Polar Compounds Examples 3D(i)-3D(ii) below set forth the details of liquid emulsion concentrates containing non-polar compounds that include phytosterols, fatty acids and vitamin A or vitamin D3.

Example 3D(i)

Liquid Emulsion Concentrate with 10% Phytosterols and 10% SFAE Surfactant

Table 3D(i), below, sets forth the ingredients to make a 320 g batch (2 mL serving size) of a liquid emulsion concentrate containing phytosterols, oleic acid and vitamin A palmitate, which was made according to the procedure set forth in Example 1. The resulting liquid emulsion concentrate was opaque to white in color and contained 100 mg phytosterols, 250 mg oleic acid and 400 mcg vitamin A per gram of the concentrate.

TABLE 3D(i)

Liquid Emulsion Concentrate with 10% Phytosterols and 10% SFAE Surfactant

| Ingredient | mg/2 mL serving | Phase | Percent (by weight) of concentrate | g/batch |
|---|---|---|---|---|
| Oleic Acid (solvent) | 500 | Oil | 25.00 | 80.0 |
| Phytosterols* (non-polar active ingredient) | 215.00 | Oil | 10.75 | 34.4000 |
| Vitamin A Palmitate* (non-polar active ingredient) | 0.81 | Oil | 0.04 | 0.1296 |
| Tic Pretested ® TICAMULSION A-2010 (stabilizer) | 34.000 | Water | 1.70 | 5.4 |
| Sucrose Fatty Acid Ester (Ryoto Sugar Ester S-1670) (1st Fraction surfactant) | 110.8 | Water | 5.54 | 17.73 |
| Sucrose Fatty Acid Ester (Ryoto Sugar Ester S-1670) (2nd Fraction surfactant) | 63.9 | Water | 3.20 | 10.22 |
| Water | 987.67 | Water | 49.384 | 158.0272 |
| Benzyl Alcohol (Preservative) | 10.000 | Oil | 0.50 | 1.6 |

TABLE 3D(i)-continued

| | | Liquid Emulsion Concentrate with 10% Phytosterols and 10% SFAE Surfactant | | |
|---|---|---|---|---|
| Ingredient | mg/2 mL serving | Phase | Percent (by weight) of concentrate | g/batch |
| Sucrose Fatty Acid Ester (Ryoto Sugar Ester S-1670) (surfactant) | 25.0 | Oil | 1.25 | 4.00 |
| Tic Pretested ® TICAMULSION A-2010 (stabilizer) | 10 | Oil | 0.5000 | 1.600 |
| Citric Acid (pH adjuster) | 42.83 | Emulsion | 2.1415 | 6.8528 |
| Totals | 2000.00 | | 100.000 | 320 |

*This ingredient was added at 5% overage to insure the final composition contained the stated amount of this ingredient.

Example 3D(ii)

Liquid Emulsion Concentrate with 10% Phytosterols and 10% SFAE Surfactant

Table 3D(ii), below, sets forth the ingredients to make a 320 g batch (2 mL serving size) of a liquid emulsion concentrate containing phytosterols, oleic acid and vitamin D3, which was made according to the procedure set forth in Example 1. The resulting liquid emulsion concentrate was opaque to white in color and contained 100 mg phytosterols, 250 mg oleic acid and 400 IU vitamin D3 per gram of the concentrate.

TABLE 3D(ii)

| | | Liquid Emulsion Concentrate with 10% Phytosterols and 10% SFAE Surfactant | | |
|---|---|---|---|---|
| Ingredient | mg/2 mL serving | Phase | Percent (by weight) of concentrate | g/batch |
| Oleic Acid (solvent) | 500 | Oil | 25.00 | 80.0 |
| Phytosterols* (non-polar active ingredient) | 215.00 | Oil | 10.75 | 34.4000 |
| Vitamin D3* (non-polar active ingredient) | 0.02 | Oil | 0.001 | 0.0034 |
| Tic Pretested ® TICAMULSION A-2010 (stabilizer) | 34.000 | Water | 1.70 | 5.4 |
| Sucrose Fatty Acid Ester (Ryoto Sugar Ester S-1670) ($1^{st}$ Fraction surfactant) | 110.8 | Water | 5.54 | 17.73 |
| Sucrose Fatty Acid Ester (Ryoto Sugar Ester S-1670) ($2^{nd}$ Fraction surfactant) | 63.9 | Water | 3.20 | 10.22 |
| Water | 988.46 | Water | 49.423 | 158.1536 |
| Benzyl Alcohol (Preservative) | 10.000 | Oil | 0.50 | 1.6 |
| Sucrose Fatty Acid Ester (Ryoto Sugar Ester S-1670) (surfactant) | 25.0 | Oil | 1.25 | 4.00 |
| Tic Pretested ® TICAMULSION A-2010 (stabilizer) | 10 | Oil | 0.5000 | 1.600 |
| Citric Acid (pH adjuster) | 42.83 | Emulsion | 2.1415 | 6.8528 |
| Totals | 2000.00 | | 100.000 | 320 |

*This ingredient was added at 5% overage to insure the final composition contained the stated amount of this ingredient.

E. Liquid Emulsion Concentrates with Resveratrol Containing Non-Polar Compounds

Examples 3E(i)-3D(ii) below sets forth the details of liquid emulsion concentrates containing non-polar compounds that include resveratrol, vitamin D3 and additional non-polar active ingredients (set forth in Tables 3E(i)-3E(ii)).

xample 3E(i)

Liquid Emulsion Concentrate with 10% Resveratrol, 25% of a DHA-containing Non-Polar Compound (Fish Oil) and 10% SFAE Surfactant Table 3E(i) below, sets forth the ingredients to make a 320 g batch (2 mL serving size) of a liquid emulsion concentrate containing resveratrol, fish oil (e.g., DHA, EPA) and vitamin D3, which was made according to the procedure set forth in Example 1. The resulting liquid emulsion concentrate was whitish in color and contained 100 mg resveratrol, 60 mg DHA+EPA and 400 IU vitamin D3 per gram of the concentrate.

TABLE 3E(i)

Liquid Emulsion Concentrate with 10% Resveratrol, 25% of a DHA-containing Non-Polar Compound (Fish Oil) and 10% SFAE Surfactant

| Ingredient | mg/2 mL serving | Phase | Percent (by weight) of concentrate | g/batch |
|---|---|---|---|---|
| Hormel Eterna ™ Omegasource ™ Oil* (28% DHA/EPA) (non-polar active ingredient) | 500 | Oil | 25.00 | 80.0 |
| Resveratrol* (98%) (non-polar active ingredient) | 215.00 | Oil | 10.75 | 34.4000 |
| Vitamin D3* (non-polar active ingredient) | 0.02 | Oil | 0.001 | 0.0034 |
| Tic Pretested ® TICAMULSION A-2010 (stabilizer) | 34.000 | Water | 1.70 | 5.4 |
| Sucrose Fatty Acid Ester (Ryoto Sugar Ester S-1670) (1$^{st}$ Fraction surfactant) | 110.8 | Water | 5.54 | 17.73 |
| Sucrose Fatty Acid Ester (Ryoto Sugar Ester S-1670) (2$^{nd}$ Fraction surfactant) | 63.9 | Water | 3.20 | 10.22 |
| Water | 988.46 | Water | 49.423 | 158.1536 |
| Benzyl Alcohol (Preservative) | 10.000 | Oil | 0.50 | 1.6 |
| Sucrose Fatty Acid Ester (Ryoto Sugar Ester S-1670) (surfactant) | 25.0 | Oil | 1.25 | 4.00 |
| Tic Pretested ® TICAMULSION A-2010 (stabilizer) | 10 | Oil | 0.5000 | 1.600 |
| Citric Acid (pH adjuster) | 42.83 | Emulsion | 2.1415 | 6.8528 |
| Totals | 2000.00 | | 100.000 | 320 |

*This ingredient was added at 5% overage to insure the final composition contained the stated amount of this ingredient.

Example 3E(ii)

Liquid Emulsion Concentrate with 10% Resveratrol and 10% SFAE Surfactant

Table 3E(ii) below, sets forth the ingredients to make a 320 g batch (2 mL serving size) of a liquid emulsion concentrate containing resveratrol, oleic acid and vitamin D3, which was made according to the procedure set forth in Example 1. The resulting liquid emulsion concentrate was whitish in color and contained 100 mg resveratrol, 250 mg oleic acid and 400 IU vitamin D3 per gram of the concentrate.

TABLE 3E(ii)

Liquid Emulsion Concentrate with 10% Resveratrol and 10% SFAE Surfactant

| Ingredient | mg/2 mL serving | Phase | Percent (by weight) of concentrate | g/batch |
|---|---|---|---|---|
| Oleic Acid (solvent) | 500 | Oil | 25.00 | 80.0 |

TABLE 3E(ii)-continued

Liquid Emulsion Concentrate with 10% Resveratrol and 10% SFAE Surfactant

| Ingredient | mg/2 mL serving | Phase | Percent (by weight) of concentrate | g/batch |
|---|---|---|---|---|
| Resveratrol* (98%) (non-polar active ingredient) | 215.00 | Oil | 10.75 | 34.4000 |
| Vitamin D3* (non-polar active ingredient) | 0.02 | Oil | 0.001 | 0.0034 |
| Tic Pretested ® TICAMULSION A-2010 (stabilizer) | 34.000 | Water | 1.70 | 5.4 |
| Sucrose Fatty Acid Ester (Ryoto Sugar Ester S-1670) ($1^{st}$ Fraction surfactant) | 110.8 | Water | 5.54 | 17.73 |
| Sucrose Fatty Acid Ester (Ryoto Sugar Ester S-1670) ($2^{nd}$ Fraction surfactant) | 63.9 | Water | 3.20 | 10.22 |
| Water | 988.46 | Water | 49.423 | 158.1536 |
| Benzyl Alcohol (Preservative) | 10.000 | Oil | 0.50 | 1.6 |
| Sucrose Fatty Acid Ester (Ryoto Sugar Ester S-1670) (surfactant) | 25.0 | Oil | 1.25 | 4.00 |
| Tic Pretested ® TICAMULSION A-2010 (stabilizer) | 10 | Oil | 0.5000 | 1.600 |
| Citric Acid (pH adjuster) | 42.83 | Emulsion | 2.1415 | 6.8528 |
| Totals | 2000.00 | | 100.000 | 320 |

*This ingredient was added at 5% overage to insure the final composition contained the stated amount of this ingredient.

Example 4

Liquid Emulsion Concentrates with Carotenoid-Containing Non-Polar Compounds Examples 4A-4B, below, set forth the details of exemplary liquid emulsion concentrates containing non-polar compounds (non-polar active ingredients) containing carotenoids. The concentrates additionally contain one or more of polyunsaturated fatty acids (PUFAs), fatty acids and vitamins. The carotenoid-containing non-polar active ingredients in the exemplified compositions contained carotenes and xanthophylls, including lycopene, lutein and zeaxanthin, including:

Lycopene, a carotene-containing non-polar active ingredient, sold by Zhejiang Medicine CO., LTD, Xinchang Pharmaceutical Factory, Xinchang, China, containing 70% all E-lycopene. The lycopene non-polar active ingredient was added in an amount of 10.75%, by weight of the final concentrate, whereby the concentrate contained 7% lycopene; and Lutein/zeaxanthin, xanthophyll containing non-polar active ingredients, sold under the name Xanmax®-80 (Lutein crystals), by Katra Phytochem (India) Private Limited, Bangalore, India, containing 80% lutein and 4.5 zeaxanthin. The lutein/zeaxanthin non-polar active ingredient was added at an amount of 10.75%, by weight of the final concentrate, whereby the concentrate contained 8% lutein and 0.4% zeaxanthin.

The PUFA-containing non-polar active ingredient in the exemplified compositions was Fish oil, an omega-3 fatty acid, containing about 28% DHA/EPA (sold under the name Eterna™ Omegasource™ Oil by Hormel Foods Specialty Products Division, Austin, Minn.). The fish oil non-polar active ingredient was added at an amount of 25%, by weight of the final concentrate, whereby the concentrate contained 6% DHA+EPA.

The fatty acid-containing non-polar active ingredient in the exemplified compositions was oleic acid, an omega-9 fatty acid, which was Oleic Acid 70% Food Grade Kosher Vegetable-Based, 100% Natural, sold by KIC Chemicals, Inc., Armonk, N.Y.

The vitamin non-polar active ingredient exemplified in the compositions was vitamin D3, which was Vitamin D3 in corn oil, containing about 1 mIU/g, produced by DSM Nutritional Products, Inc., Belvidere, N.J., and distributed through Stauber Performance Ingredients, Inc., Fullerton, Calif. The vitamin D3 was added in an amount such that the emulsion concentrate contained 400 IU vitamin D3 per gram concentrate.

The liquid emulsion concentrates further contained one or more of the following additional ingredients:

An emulsion stabilizer, that was a modified gum acacia emulsion stabilizer, sold under the name Tic Pretested® Ticamulsion A-2010 Powder, by Tic Gums, Inc., Belcamp, Md.;

A preservative that was a natural (GRAS-certified) preservative, benzyl alcohol;

An antifoaming agent that was Tramfloc 1147, sold by Tramfloc Inc, Forney, Tex., that was added to the aqueous phase (approximately 1 drop per liter);

A surfactant that was a sucrose fatty acid ester (SFAE) surfactant (sold under the name Ryoto Sugar Ester S-1760, by Mitsubishi-Kagaku Foods Corporation, Tokyo, Japan); and Water, that was city water, which was purified prior to addition to the water phase vessel, by passage through using the following purifiers, sequentially in the following order: a carbon filter, an ion exchange purifier, a reverse osmosis purifier, a UV sterilizer and an end-point filter (a 100 micron end-point filter).

Tables 4A(i)-4B(ii) set forth ingredients and other details of liquid emulsion concentrates, each containing at least one or more of the non-polar compounds described above, a polar solvent, and a sucrose fatty acid ester surfactant. The specific non-polar active ingredients are indicated in each table.

Each of the concentrates containing these non-polar active ingredients was made using the general procedure outlined in Example 1 above with the following details: The water phase was made by adding the purified water and heating to 60° C., followed by addition of the following water phase ingredients to the water phase vessel, sequentially, in the following order: 1) emulsion stabilizer; 2) antifoam; 3) $1^{st}$ fraction surfactant; and 4) $2^{nd}$ fraction surfactant, and mixing while heating to a temperature of 60° C., which was maintained until combining with the oil phase. The oil phase was generated by adding the following oil phase ingredients to the oil phase vessel, sequentially, in the following order: 1) preservative; 2) emulsion stabilizer; 3) vitamin non-polar active ingredient; heating to a temperature of 60° C., followed by the addition of 4) fish oil or oleic acid; 5) carotenoid; and 6) surfactant, and mixing and maintaining temperature of 60° C., until combining.

The pH of the emulsion was measured using a pH and temperature meter (Hanna Instruments, model HI 8314) and adjusted with the amount of citric acid indicated in the table until the emulsion reached a pH of between 2.0 and 3.0.

A. Liquid Emulsion Concentrates with Lycopene Containing Non-Polar Compounds

Examples 4A(i)-4A(ii) below set forth the details of liquid emulsion concentrates containing non-polar compounds that include lycopene and vitamin D3 and additional non-polar active ingredients (set forth in Tables 4A(i)-4A(ii)).

Example 4A(i)

Liquid Emulsion Concentrate with 10% Lycopene, 25% of a DHA-Containing Non-Polar Compound (Fish Oil) and 10% SFAE Surfactant Table 4A(i) below, sets forth the ingredients to make a 320 g batch (2 mL serving size) of a liquid emulsion concentrate containing lycopene, fish oil (e.g., DHA, EPA) and vitamin D3, which was made according to the procedure set forth in Example 1. The resulting liquid emulsion concentrate was purplish in color and contained 70 mg lycopene, 60 mg DHA+EPA and 400 IU vitamin D3 per gram of the concentrate.

TABLE 4A(i)

Liquid Emulsion Concentrate with 10% Lycopene, 25% of a DHA-containing Non-Polar Compound (Fish Oil) and 10% SFAE Surfactant

| Ingredient | mg/2 mL serving | Phase | Percent (by weight) of concentrate | g/batch |
|---|---|---|---|---|
| Hormel Eterna ™ Omegasource ™ Oil* (28% DHA/EPA) (non-polar active ingredient) | 500 | Oil | 25.00 | 80.0 |
| Lycopene* (70%) (non-polar active ingredient) | 215.00 | Oil | 10.75 | 34.4000 |
| Vitamin D3* (non-polar active ingredient) | 0.02 | Oil | 0.001 | 0.0034 |
| Tic Pretested ® TICAMULSION A-2010 (stabilizer) | 34.000 | Water | 1.70 | 5.4 |
| Sucrose Fatty Acid Ester (Ryoto Sugar Ester S-1670) (1$^{st}$ Fraction surfactant) | 110.8 | Water | 5.54 | 17.73 |
| Sucrose Fatty Acid Ester (Ryoto Sugar Ester S-1670) (2$^{nd}$ Fraction surfactant) | 63.9 | Water | 3.20 | 10.22 |
| Water | 988.46 | Water | 49.423 | 158.1536 |
| Benzyl Alcohol (Preservative) | 10.000 | Oil | 0.50 | 1.6 |
| Sucrose Fatty Acid Ester (Ryoto Sugar Ester S-1670) (surfactant) | 25.0 | Oil | 1.25 | 4.00 |
| Tic Pretested ® TICAMULSION A-2010 (stabilizer) | 10 | Oil | 0.5000 | 1.600 |
| Citric Acid (pH adjuster) | 42.83 | Emulsion | 2.1415 | 6.8528 |
| Totals | 2000.00 | | 100.000 | 320 |

*This ingredient was added at 5% overage to insure the final composition contained the stated amount of this ingredient.

Example 4A(ii)

Liquid Emulsion Concentrate with 10% Lycopene and 10% SFAE Surfactant

Table 4A(ii) below, sets forth the ingredients to make a 320 g batch (2 mL serving size) of a liquid emulsion concentrate containing lycopene, oleic acid and vitamin D3, which was made according to the procedure set forth in Example 1. The resulting liquid emulsion concentrate was purplish in color and contained 70 mg lycopene, 250 mg oleic acid and 400 IU vitamin D3 per gram of the concentrate.

TABLE 4A(ii)

Liquid Emulsion Concentrate with 10% Lycopene and 10% SFAE Surfactant

| Ingredient | mg/2 mL serving | Phase | Percent (by weight) of concentrate | g/batch |
|---|---|---|---|---|
| Oleic Acid (solvent) | 500 | Oil | 25.00 | 80.0 |

TABLE 4A(ii)-continued

Liquid Emulsion Concentrate with 10% Lycopene and 10% SFAE Surfactant

| Ingredient | mg/2 mL serving | Phase | Percent (by weight) of concentrate | g/batch |
|---|---|---|---|---|
| Lycopene* (70%) (non-polar active ingredient) | 215.00 | Oil | 10.75 | 34.4000 |
| Vitamin D3* (non-polar active ingredient) | 0.02 | Oil | 0.001 | 0.0034 |
| Tic Pretested ® TICAMULSION A-2010 (stabilizer) | 34.000 | Water | 1.70 | 5.4 |
| Sucrose Fatty Acid Ester (Ryoto Sugar Ester S-1670) (1$^{st}$ Fraction surfactant) | 110.8 | Water | 5.54 | 17.73 |
| Sucrose Fatty Acid Ester (Ryoto Sugar Ester S-1670) (2$^{nd}$ Fraction surfactant) | 63.9 | Water | 3.20 | 10.22 |
| Water | 988.46 | Water | 49.423 | 158.1536 |
| Benzyl Alcohol (Preservative) | 10.000 | Oil | 0.50 | 1.6 |
| Sucrose Fatty Acid Ester (Ryoto Sugar Ester S-1670) (surfactant) | 25.0 | Oil | 1.25 | 4.00 |
| Tic Pretested ® TICAMULSION A-2010 (stabilizer) | 10 | Oil | 0.5000 | 1.600 |
| Citric Acid (pH adjuster) | 42.83 | Emulsion | 2.1415 | 6.8528 |
| Totals | 2000.00 | | 100.000 | 320 |

*This ingredient was added at 5% overage to insure the final composition contained the stated amount of this ingredient.

B. Liquid Emulsion Concentrates with Lutein and Zeaxanthin Containing Non-Polar Compounds Examples 4B(i)-4B(ii) below set forth the details of liquid emulsion concentrates containing non-polar compounds that include lutein and zeaxanthin and vitamin D3 and additional non-polar active ingredients (set forth in Tables 4B(i)-4B(ii)).

Example 4B(i)

Liquid Emulsion Concentrate with 10% Lutein and Zeaxanthin, 25% of a DHA-Containing Non-Polar Compound (Fish Oil) and 10% SFAE Surfactant Table 4B(i) below, sets forth the ingredients to make a 320 g batch (2 mL serving size) of a liquid emulsion concentrate containing lutein and zeaxanthin, fish oil (e.g., DHA, EPA) and vitamin D3, which was made according to the procedure set forth in Example 1. The resulting liquid emulsion concentrate was slightly orange to red in color and contained 80 mg lutein, 4 mg zeaxanthin, 60 mg DHA+EPA and 400 IU vitamin D3 per gram of the concentrate.

TABLE 4B(i)

Liquid Emulsion Concentrate with 10% Lutein and Zeaxanthin, 25% of a DHA-containing Non-Polar Compound (Fish Oil) and 10% SFAE Surfactant

| Ingredient | mg/2 mL serving | Phase | Percent (by weight) of concentrate | g/batch |
|---|---|---|---|---|
| Hormel Eterna ™ Omegasource ™ Oil* (28% DHA/EPA) (non-polar active ingredient) | 500 | Oil | 25.00 | 80.0 |
| Lutein (80%)/Zeaxanthin (4.5%)* (non-polar active ingredient) | 215.00 | Oil | 10.75 | 34.4000 |
| Vitamin D3* (non-polar active ingredient) | 0.02 | Oil | 0.001 | 0.0034 |
| Tic Pretested ® TICAMULSION A-2010 (stabilizer) | 34.000 | Water | 1.70 | 5.4 |
| Sucrose Fatty Acid Ester (Ryoto Sugar Ester S-1670) (1$^{st}$ Fraction surfactant) | 110.8 | Water | 5.54 | 17.73 |
| Sucrose Fatty Acid Ester (Ryoto Sugar Ester S-1670) (2$^{nd}$ Fraction surfactant) | 63.9 | Water | 3.20 | 10.22 |
| Water | 988.46 | Water | 49.423 | 158.1536 |
| Benzyl Alcohol (Preservative) | 10.000 | Oil | 0.50 | 1.6 |

TABLE 4B(i)-continued

Liquid Emulsion Concentrate with 10% Lutein and Zeaxanthin, 25% of a DHA-containing Non-Polar Compound (Fish Oil) and 10% SFAE Surfactant

| Ingredient | mg/2 mL serving | Phase | Percent (by weight) of concentrate | g/batch |
|---|---|---|---|---|
| Sucrose Fatty Acid Ester (Ryoto Sugar Ester S-1670) (surfactant) | 25.0 | Oil | 1.25 | 4.00 |
| Tic Pretested ® TICAMULSION A-2010 (stabilizer) | 10 | Oil | 0.5000 | 1.600 |
| Citric Acid (pH adjuster) | 42.83 | Emulsion | 2.1415 | 6.8528 |
| Totals | 2000.00 | | 100.000 | 320 |

*This ingredient was added at 5% overage to insure the final composition contained the stated amount of this ingredient.

Example 4B(ii)

Liquid Emulsion Concentrate with 10% Lutein and Zeaxanthin and 10% SFAE Surfactant Table 4B(ii) below, sets forth the ingredients to make a 320 g batch (2 mL serving size) of a liquid emulsion concentrate containing lutein and zeaxanthin, oleic acid and vitamin D3, which was made according to the procedure set forth in Example 1. The resulting liquid emulsion concentrate was slightly orange to red in color and contained 80 mg lutein, 4 mg zeaxanthin, 250 mg oleic acid and 400 IU vitamin D3 per gram of the concentrate.

TABLE 4B(ii)

Liquid Emulsion Concentrate with 10% Lutein and Zeaxanthin and 10% SFAE Surfactant

| Ingredient | mg/2 mL serving | Phase | Percent (by weight) of concentrate | g/batch |
|---|---|---|---|---|
| Oleic Acid (solvent) | 500 | Oil | 25.00 | 80.0 |
| Lutein (80%)/Zeaxanthin (4.5%)* (non-polar active ingredient) | 215.00 | Oil | 10.75 | 34.4000 |
| Vitamin D3* (non-polar active ingredient) | 0.02 | Oil | 0.001 | 0.0034 |
| Tic Pretested ® TICAMULSION A-2010 (stabilizer) | 34.000 | Water | 1.70 | 5.4 |
| Sucrose Fatty Acid Ester (Ryoto Sugar Ester S-1670) ($1^{st}$ Fraction surfactant) | 110.8 | Water | 5.54 | 17.73 |
| Sucrose Fatty Acid Ester (Ryoto Sugar Ester S-1670) ($2^{nd}$ Fraction surfactant) | 63.9 | Water | 3.20 | 10.22 |
| Water | 988.46 | Water | 49.423 | 158.1536 |
| Benzyl Alcohol (Preservative) | 10.000 | Oil | 0.50 | 1.6 |
| Sucrose Fatty Acid Ester (Ryoto Sugar Ester S-1670) (surfactant) | 25.0 | Oil | 1.25 | 4.00 |
| Tic Pretested ® TICAMULSION A-2010 (stabilizer) | 10 | Oil | 0.5000 | 1.600 |
| Citric Acid (pH adjuster) | 42.83 | Emulsion | 2.1415 | 6.8528 |
| Totals | 2000.00 | | 100.000 | 320 |

*This ingredient was added at 5% overage to insure the final composition contained the stated amount of this ingredient.

Example 5

Liquid Emulsion Concentrates with Coenzyme Q-Containing Non-Polar Compounds

Examples 5A-5B, below, set forth the details of exemplary liquid emulsion concentrates containing non-polar compounds (non-polar active ingredients) containing coenzyme Q. The concentrates additionally contain one or more of polyunsaturated fatty acids (PUFAs), fatty acids and vitamins.

The coenzyme Q-containing non-polar active ingredients in the exemplified compositions was Coenzyme Q10 (CoQ10), Kaneka Q10™ (USP Ubidecarenone) by Kaneka Nutrients, L.P., Pasadena, Tex., containing greater than 98% ubidecarenone (ubiquinone). The Coenzyme Q10-containing non-polar active ingredient was added at an amount of 10.75%, by weight of the final concentrate, whereby the concentrate contained 10% CoQ10.

The PUFA-containing non-polar active ingredient in the exemplified compositions was Fish oil, an omega-3 fatty acid, containing about 28% DHA/EPA (sold under the name Eterna™ Omegasource™ Oil by Hormel Foods Specialty Products Division, Austin, Minn.). The fish oil non-polar active ingredient was added at an amount of 25%, by weight of the final concentrate, whereby the concentrate contained 5.5 DHA+EPA.

The fatty acid-containing non-polar active ingredient in the exemplified compositions was oleic acid, an omega-9 fatty acid, which was Oleic Acid 70% Food Grade Kosher Vegetable-Based, 100% Natural, sold by KIC Chemicals, Inc., Armonk, N.Y.

The vitamin non-polar active ingredient exemplified in the compositions was vitamin D3, which was Vitamin D3 in corn oil, containing about 1 mIU/g, produced by DSM Nutritional Products, Inc., Belvidere, N.J., and distributed through Stauber Performance Ingredients, Inc., Fullerton, Calif. The vitamin D3 was added in an amount such that the emulsion concentrate contained 400 IU vitamin D3 per gram concentrate.

The liquid emulsion concentrates further contained one or more of the following additional ingredients:

A non-polar solvent, that was a Vitamin E oil, sold under the name Novatol™ 5-67 Vitamin E (D-alpha-Tocopherol; ADM product code 410217), by ADM Natural Health and Nutrition, Decatur, Ill., containing least 67.2% Tocopherol and approximately 32.8% soybean oil;

An emulsion stabilizer, that was a modified gum acacia emulsion stabilizer, sold under the name Tic Pretested® Ticamulsion A-2010 Powder, by Tic Gums, Inc., Belcamp, Md.;

A preservative that was a natural (GRAS-certified) preservative, benzyl alcohol;

An antifoaming agent that was Tramfloc 1147, sold by Tramfloc Inc, Forney, Tex., that was added to the aqueous phase (approximately 1 drop per liter);

A surfactant that was a sucrose fatty acid ester (SFAE) surfactant (sold under the name Ryoto Sugar Ester S-1760, by Mitsubishi-Kagaku Foods Corporation, Tokyo, Japan); and Water, that was city water, which was purified prior to addition to the water phase vessel, by passage through using the following purifiers, sequentially in the following order: a carbon filter, an ion exchange purifier, a reverse osmosis purifier, a UV sterilizer and an end-point filter (a 100 micron end-point filter).

Tables 5A-5B set forth ingredients and other details of liquid emulsion concentrates, each containing at least one or more of the non-polar compounds described above, a polar solvent, and a sucrose fatty acid ester surfactant. The specific non-polar active ingredients are indicated in each table.

Each of the concentrates containing these non-polar active ingredients was made using the general procedure outlined in Example 1 above with the following details: The water phase was made by adding the purified water and heating to 60° C., followed by addition of the following water phase ingredients to the water phase vessel, sequentially, in the following order: 1) emulsion stabilizer; 2) antifoam; 3) 1st fraction surfactant; and 4) $2^{nd}$ fraction surfactant, and mixing while heating to a temperature of 60° C., which was maintained until combining with the oil phase. The oil phase was generated by adding the following oil phase ingredients to the oil phase vessel, sequentially, in the following order: 1) preservative; 2) emulsion stabilizer; 3) vitamin non-polar active ingredient; 4) non-polar solvent; heating to a temperature of 60° C., followed by the addition of 5) fish oil or oleic acid; 6) coenzyme Q10; and 7) surfactant, and mixing and maintaining temperature of 60° C., until combining.

The pH of the emulsion was measured using a pH and temperature meter (Hanna Instruments, model HI 8314) and adjusted with the amount of citric acid indicated in the table until the emulsion reached a pH of between 2.0 and 3.0.

Example 5A

Liquid Emulsion Concentrate with 10% CoQ10, 21.25% of a DHA-Containing Non-Polar Compound (Fish Oil) and 10% SFAE Surfactant Table 5A below, sets forth the ingredients to make a 320 g batch (2 mL serving size) of a liquid emulsion concentrate containing coenzyme Q10, vitamin E oil, fish oil (e.g., DHA, EPA) and vitamin D3, which was made according to the procedure set forth in Example 1. The resulting liquid emulsion concentrate was orange to white in color and contained 100 mg coenzyme Q10, 37.5 mg vitamin E, 55 mg DHA+EPA and 400 IU vitamin D3 per gram of the concentrate.

TABLE 5A

Liquid Emulsion Concentrate with 10% CoQ10, 21.25% of a DHA-containing Non-Polar Compound (Fish Oil) and 10% SFAE Surfactant

| Ingredient | mg/2 mL serving | Phase | Percent (by weight) of concentrate | g/batch |
| --- | --- | --- | --- | --- |
| Hormel Eterna ™ Omegasource ™ Oil* (28% DHA/EPA) (non-polar active ingredient) | 425 | Oil | 21.25 | 68.0 |
| Kaneka Coenzyme Q10* (98%) (non-polar active ingredient) | 215.00 | Oil | 10.75 | 34.4000 |
| Novatol ADM Vitamin E Oil (5-67) (solvent) | 75 | Oil | 3.75 | 12.0 |
| Vitamin D3* (non-polar active ingredient) | 0.02 | Oil | 0.001 | 0.0034 |
| Tic Pretested ® TICAMULSION A-2010 (stabilizer) | 34.000 | Water | 1.70 | 5.4 |
| Sucrose Fatty Acid Ester (Ryoto Sugar Ester S-1670) ($1^{st}$ Fraction surfactant) | 110.8 | Water | 5.54 | 17.73 |
| Sucrose Fatty Acid Ester (Ryoto Sugar Ester S-1670) ($2^{nd}$ Fraction surfactant) | 63.9 | Water | 3.20 | 10.22 |
| Water | 988.46 | Water | 49.423 | 158.1536 |
| Benzyl Alcohol (Preservative) | 10.000 | Oil | 0.50 | 1.6 |
| Sucrose Fatty Acid Ester (Ryoto Sugar Ester S-1670) (surfactant) | 25.0 | Oil | 1.25 | 4.00 |

TABLE 5A-continued

Liquid Emulsion Concentrate with 10% CoQ10, 21.25% of a DHA-containing Non-Polar Compound (Fish Oil) and 10% SFAE Surfactant

| Ingredient | mg/2 mL serving | Phase | Percent (by weight) of concentrate | g/batch |
|---|---|---|---|---|
| Tic Pretested ® TICAMULSION A-2010 (stabilizer) | 10 | Oil | 0.5000 | 1.600 |
| Citric Acid (pH adjuster) | 42.83 | Emulsion | 2.1415 | 6.8528 |
| Totals | 2000.00 | | 100.000 | 320 |

*This ingredient was added at 5% overage to insure the final composition contained the stated amount of this ingredient.

Example 5B

Liquid Emulsion Concentrate with 10% CoQ10 and 10% SFAE Surfactant

Table 5B below, sets forth the ingredients to make a 320 g batch (2 mL serving size) of a liquid emulsion concentrate containing coenzyme Q10, vitamin E oil, oleic acid and vitamin D3, which was made according to the procedure set forth in Example 1. The resulting liquid emulsion concentrate was orange to white in color and contained 100 mg coenzyme Q10, 37.5 mg vitamin E, 212.5 mg oleic acid and 400 IU vitamin D3 per gram of the concentrate.

TABLE 5B

Liquid Emulsion Concentrate with 10% CoQ10 and 10% SFAE Surfactant

| Ingredient | mg/2 mL serving | Phase | Percent (by weight) of concentrate | g/batch |
|---|---|---|---|---|
| Oleic Acid (solvent) | 425 | Oil | 21.25 | 68.0 |
| Kaneka Coenzyme Q10* (98%) (non-polar active ingredient) | 215.00 | Oil | 10.75 | 34.4000 |
| Novatol ADM Vitamin E Oil (5-67) (solvent) | 75 | Oil | 3.75 | 12.0 |
| Vitamin D3* (non-polar active ingredient) | 0.02 | Oil | 0.001 | 0.0034 |
| Tic Pretested ® TICAMULSION A-2010 (stabilizer) | 34.000 | Water | 1.70 | 5.4 |
| Sucrose Fatty Acid Ester (Ryoto Sugar Ester S-1670) (1$^{st}$ Fraction surfactant) | 110.8 | Water | 5.54 | 17.73 |
| Sucrose Fatty Acid Ester (Ryoto Sugar Ester S-1670) (2$^{nd}$ Fraction surfactant) | 63.9 | Water | 3.20 | 10.22 |
| Water | 988.46 | Water | 49.423 | 158.1536 |
| Benzyl Alcohol (Preservative) | 10.000 | Oil | 0.50 | 1.6 |
| Sucrose Fatty Acid Ester (Ryoto Sugar Ester S-1670) (surfactant) | 25.0 | Oil | 1.25 | 4.00 |
| Tic Pretested ® TICAMULSION A-2010 (stabilizer) | 10 | Oil | 0.5000 | 1.600 |
| Citric Acid (pH adjuster) | 42.83 | Emulsion | 2.1415 | 6.8528 |
| Totals | 2000.00 | | 100.000 | 320 |

*This ingredient was added at 5% overage to insure the final composition contained the stated amount of this ingredient.

Example 6

Liquid Emulsion Concentrates with Micronutrient-Containing Non-Polar Compounds Examples 6A-6B, below, set forth the details of exemplary liquid emulsion concentrates containing non-polar compounds (non-polar active ingredients) containing alpha lipoic acid. The concentrates additionally contain one or more of polyunsaturated fatty acids (PUFAs), fatty acids and vitamins.

The alpha lipoic acid non-polar active ingredient containing 99% alpha lipoic acid (thioctic acid), was sold by Zhejiang Medicines & Health Products Import & Export Co., Ltd, Hangzhou, China. The alpha lipoic acid non-polar active ingredient was added at an amount of either 10.75% or 10.5%, by weight, of the final concentrate, whereby the concentrate contained at least 10% alpha lipoic acid.

The PUFA-containing non-polar active ingredient in the exemplified compositions was Fish oil, an omega-3 fatty acid, containing about 28% DHA/EPA (sold under the name Eterna™ Omegasource™ Oil by Hormel Foods Specialty Products Division, Austin, Minn.). The fish oil non-polar active ingredient was added at an amount of 25%, by weight of the final concentrate, whereby the concentrate contained 5.5% DHA+EPA.

The fatty acid-containing non-polar active ingredient in the exemplified compositions was oleic acid, an omega-9 fatty acid, which was Oleic Acid 70% Food Grade Kosher Vegetable-Based, 100% Natural, sold by KIC Chemicals, Inc., Armonk, N.Y.

The vitamin non-polar active ingredient exemplified in the compositions was vitamin D3, which was Vitamin D3 in corn oil, containing about 1 mIU/g, produced by DSM Nutritional Products, Inc., Belvidere, N.J., and distributed through Stauber Performance Ingredients, Inc., Fullerton, Calif. The vitamin D3 was added in an amount such that the emulsion concentrate contained 400 IU vitamin D3 per gram concentrate.

The liquid emulsion concentrates further contained one or more of the following additional ingredients:

An emulsion stabilizer, that was a modified gum acacia emulsion stabilizer, sold under the name Tic Pretested® Ticamulsion A-2010 Powder, by Tic Gums, Inc., Belcamp, Md.;

A preservative that was a natural (GRAS-certified) preservative, benzyl alcohol;

An antifoaming agent that was Tramfloc 1147, sold by Tramfloc Inc, Forney, Tex., that was added to the aqueous phase (approximately 1 drop per liter);

A surfactant that was a sucrose fatty acid ester (SFAE) surfactant (sold under the name Ryoto Sugar Ester S-1760, by Mitsubishi-Kagaku Foods Corporation, Tokyo, Japan); and Water, that was city water, which was purified prior to addition to the water phase vessel, by passage through using the following purifiers, sequentially in the following order: a carbon filter, an ion exchange purifier, a reverse osmosis purifier, a UV sterilizer and an end-point filter (a 100 micron end-point filter).

Tables 6A-6B set forth ingredients and other details of liquid emulsion concentrates, each containing at least one or more of the non-polar compounds described above, a polar solvent, and a sucrose fatty acid ester surfactant. The specific non-polar active ingredients are indicated in each table.

Each of the concentrates containing these non-polar active ingredients was made using the general procedure outlined in Example 1 above with the following details: the water phase was made by adding the purified water and heating to 60° C., followed by addition of the following water phase ingredients to the water phase vessel, sequentially, in the following order: 1) emulsion stabilizer; 2) antifoam; 3) $1^{st}$ fraction surfactant; and 4) $2^{nd}$ fraction surfactant, and mixing while heating to a temperature of 60° C., which was maintained until combining with the oil phase. The oil phase was generated by adding the following oil phase ingredients to the oil phase vessel, sequentially, in the following order: 1) preservative; 2) emulsion stabilizer; 3) vitamin non-polar active ingredient; heating to a temperature of 60° C., followed by the addition of 4) fish oil or oleic acid; 5) alpha lipoic acid; and 6) surfactant, and mixing and maintaining temperature of 60° C., until combining.

The pH of the emulsion was measured using a pH and temperature meter (Hanna Instruments, model HI 8314) and adjusted with the amount of citric acid indicated in the table until the emulsion reached a pH of between 2.0 and 3.0.

Example 6A

Liquid Emulsion Concentrate with 10% Alpha Lipoic Acid, 25% of a DHA-Containing Non-Polar Compound (Fish Oil) and 10% SFAE Surfactant Table 6A below, sets forth the ingredients to make a 320 g batch (2 mL serving size) of a liquid emulsion concentrate containing alpha lipoic acid, fish oil (e.g., DHA, EPA) and vitamin D3, which was made according to the procedure set forth in Example 1. The resulting liquid emulsion concentrate was yellow to white in color and contained 100 mg alpha lipoic acid, 60 mg DHA+EPA and 400 IU vitamin D3 per gram of the concentrate.

TABLE 6A

Liquid Emulsion Concentrate with 10% Alpha Lipoic Acid, 25% of a DHA-containing Non-Polar Compound (Fish Oil) and 10% SFAE Surfactant

| Ingredient | mg/2 mL serving | Phase | Percent (by weight) of concentrate | g/batch |
| --- | --- | --- | --- | --- |
| Hormel Eterna ™ Omegasource ™ Oil* (28% DHA/EPA) (non-polar active ingredient) | 500 | Oil | 25.00 | 80.0 |
| Alpha Lipoic Acid* (99%) (non-polar active ingredient) | 210.00 | Oil | 10.5 | 33.6000 |
| Vitamin D3* (non-polar active ingredient) | 0.02 | Oil | 0.001 | 0.0034 |
| Tic Pretested ® TICAMULSION A-2010 (stabilizer) | 34.000 | Water | 1.70 | 5.4 |
| Sucrose Fatty Acid Ester (Ryoto Sugar Ester S-1670) ($1^{st}$ Fraction surfactant) | 110.8 | Water | 5.54 | 17.73 |
| Sucrose Fatty Acid Ester (Ryoto Sugar Ester S-1670) ($2^{nd}$ Fraction surfactant) | 63.9 | Water | 3.20 | 10.22 |
| Water | 993.46 | Water | 49.673 | 158.9536 |
| Benzyl Alcohol (Preservative) | 10.000 | Oil | 0.50 | 1.6 |
| Sucrose Fatty Acid Ester (Ryoto Sugar Ester S-1670) (surfactant) | 25.0 | Oil | 1.25 | 4.00 |
| Tic Pretested ® TICAMULSION A-2010 (stabilizer) | 10 | Oil | 0.5000 | 1.600 |
| Citric Acid (pH adjuster) | 42.83 | Emulsion | 2.1415 | 6.8528 |
| Totals | 2000.00 | | 100.000 | 320 |

*This ingredient was added at 5% overage to insure the final composition contained the stated amount of this ingredient.

Example 6B

Liquid Emulsion Concentrate with 10% Alpha Lipoic Acid and 10% SFAE Surfactant

Table 6B below, sets forth the ingredients to make a 320 g batch (2 mL serving size) of a liquid emulsion concentrate containing alpha lipoic acid, oleic acid and vitamin D3, which was made according to the procedure set forth in Example 1. The resulting liquid emulsion concentrate was yellow to white in color and contained 100 mg alpha lipoic acid, 250 mg oleic acid and 400 IU vitamin D3 per gram of the concentrate.

TABLE 6B

Liquid Emulsion Concentrate with 10% Alpha Lipoic Acid and 10% SFAE Surfactant

| Ingredient | mg/2 mL serving | Phase | Percent (by weight) of concentrate | g/batch |
|---|---|---|---|---|
| Oleic Acid (solvent) | 500 | Oil | 25.00 | 80.0 |
| Alpha Lipoic Acid* (99%) (non-polar active ingredient) | 215.00 | Oil | 10.75 | 34.4000 |
| Vitamin D3* (non-polar active ingredient) | 0.02 | Oil | 0.001 | 0.0034 |
| Tic Pretested ® TICAMULSION A-2010 (stabilizer) | 34.000 | Water | 1.70 | 5.4 |
| Sucrose Fatty Acid Ester (Ryoto Sugar Ester S-1670) ($1^{st}$ Fraction surfactant) | 110.8 | Water | 5.54 | 17.73 |
| Sucrose Fatty Acid Ester (Ryoto Sugar Ester S-1670) ($2^{nd}$ Fraction surfactant) | 63.9 | Water | 3.20 | 10.22 |
| Water | 988.46 | Water | 49.423 | 158.1536 |
| Benzyl Alcohol (Preservative) | 10.000 | Oil | 0.50 | 1.6 |
| Sucrose Fatty Acid Ester (Ryoto Sugar Ester S-1670) (surfactant) | 25.0 | Oil | 1.25 | 4.00 |
| Tic Pretested ® TICAMULSION A-2010 (stabilizer) | 10 | Oil | 0.5000 | 1.600 |
| Citric Acid (pH adjuster) | 42.83 | Emulsion | 2.1415 | 6.8528 |
| Totals | 2000.00 | | 100.000 | 320 |

*This ingredient was added at 5% overage to insure the final composition contained the stated amount of this ingredient.

Example 7

Liquid Emulsion Concentrate with PUFA-Containing Non-Polar Compounds and a Mixture of SFAE and TPGS Surfactants Example 7A below sets forth the details of exemplary liquid emulsion concentrate containing non-polar compounds (non-polar active ingredients) containing polyunsaturated fatty acids (PUFAs) and vitamins. The PUFA-containing non-polar active ingredient was a conjugated fatty acid, namely a conjugated linoleic acid (CLA) oil, containing about 80% CLA (sold under the name Clarinol G-80, by Lipid Nutrition B.V., Channahon, Ill.). The CLA oil non-polar active ingredient was added at an amount of 21%, by weight of the final concentrate, whereby the concentrate contained 15% CLA. The vitamin non-polar active ingredients exemplified in the composition was Vitamin A Palmitate containing 1.7 mIU/g, produced by DSM Nutritional Products, Inc., Belvidere, N.J., and distributed through Stauber Performance Ingredients, Inc., Fullerton, Calif. The vitamin A palmitate was added in an amount such that the emulsion concentrate contained 400 micrograms (mcg) vitamin A per gram concentrate.

The liquid emulsion concentrate further contained one or more of the following additional ingredients:

A soluble fiber that was Oliggo-Fiber Instant Inulin (Fibruline® Instant), a chicory inulin, produced by Cosucra Groupe Warcoing, Belgium, and distributed through Gillco Products Inc., San Marcos, Calif.;

Emulsion stabilizers, including a modified gum acacia and an ester gum. The modified gum acacia emulsion stabilizer was Tic Pretested® Ticamulsion A-2010 Powder, by Tic Gums, Inc., Belcamp, Md. The ester gum emulsion stabilizer was Ester Gum 8BG by Pinova/Hercules, Brunswick, Ga.;

A preservative that was a natural (GRAS-certified) preservative, benzyl alcohol;

An antifoaming agent that was Tramfloc 1147, sold by Tramfloc Inc, Forney, Tex., that was added to the aqueous phase (approximately 1 drop per liter);

Surfactants, including a sucrose fatty acid ester (SFAE) surfactant and a TPGS surfactant. The sucrose fatty acid ester surfactant was Ryoto Sugar Ester S-1760, sold by Mitsubishi-Kagaku Foods Corporation, Tokyo, Japan. The TPGS surfactant was Vitamin E TPGS®, sold by Eastman Chemical Company; and Water, that was city water, which was purified prior to addition to the water phase vessel, by passage through using the following purifiers, sequentially in the following order: a carbon filter, an ion exchange purifier, a reverse osmosis purifier, a UV sterilizer and an end-point filter (a 100 micron end-point filter.

Table 7A sets forth the specific non-polar active ingredients. The concentrate was made using the general procedure outlined in Example 1 above with the following details: The water phase was made by adding the purified water and heating to 60° C., followed by addition of the following water phase ingredients to the water phase vessel, sequentially, in the following order: 1) Ticamulsion® stabilizer; 2) antifoam; 3) $1^{St}$ fraction surfactant; 4) $2^{nd}$ fraction surfactant; and 5) soluble fiber, and mixing while heating to a temperature of 60° C., which was maintained until combining with the oil phase. The oil phase was generated by adding the following oil phase ingredients to the oil phase vessel, sequentially, in the following order: 1) TPGS surfactant; 2) preservative; 3) ester gum emulsion stabilizer; 4) vitamin non-polar active ingredient; and heating to a temperature of 60° C., followed by the addition of 5) non-polar active ingredient; 6) SFAE surfactant; and 7) Ticamulsion® stabilizer and mixing and heating to a temperature of 60° C., which was maintained until combining.

The pH of the emulsion was measured using a pH and temperature meter (Hanna Instruments, model HI 8314) and adjusted with the amount of citric acid indicated in the table until the emulsion reached a pH of between 2.0 and 3.0.

Example 7A

Liquid Emulsion Concentrate with 21% of a CLA-Containing Non-Polar Compound and 19.56% of a Mixture of SFAE and TPGS Surfactants Table 7A, below, sets forth the ingredients to make a 320 g batch (2 mL serving size) of a liquid emulsion concentrate containing conjugated linoleic acid oil (e.g., CLA) and vitamin A, which was made according to the procedure set forth in Example 1. The resulting liquid emulsion concentrate was opaque to white in color and contained 150 mg CLA and 400 mcg vitamin A per gram of the concentrate.

Algal oil, containing about 40% DHA (sold under the name V Pure® DHA 40% Standard TAG Oil), which was derived from the microalgae. The algal oil non-polar active ingredient was added at an amount of 25%, by weight of the final concentrate, whereby the concentrate contained 7% DHA+EPA.

The liquid emulsion concentrates further contained one or more of the following additional ingredients:

A soluble fiber that was Oliggo-Fiber Instant Inulin (Fibruline® Instant), a chicory inulin, produced by Cosucra Groupe Warcoing, Belgium, and distributed through Gillco Products Inc., San Marcos, Calif.;

Emulsion stabilizers, including a modified gum acacia and an ester gum. The modified gum acacia emulsion stabilizer was Tic Pretested® Ticamulsion A-2010 Powder, by Tic Gums, Inc., Belcamp, Md. The ester gum emulsion stabilizer was Ester Gum 8BG by Pinova/Hercules, Brunswick, Ga.;

A preservative that was a natural (GRAS-certified) preservative, benzyl alcohol;

An antifoaming agent that was Tramfloc 1147, sold by Tramfloc Inc, Forney, Tex., that was added to the aqueous phase (approximately 1 drop per liter);

TABLE 7A

Liquid Emulsion Concentrate with 21% of a CLA-containing Non-Polar Compound and 19.56% of a mixture of SFAE and TPGS Surfactants

| Ingredient | mg/2 mL serving | Phase | Percent (by weight) of concentrate | g/batch |
|---|---|---|---|---|
| Clarinol ™ G-80 CLA Oil* (80% CLA) (non-polar active ingredient) | 420 | Oil | 21.00 | 67.2 |
| Vitamin A Palmitate* (non-polar active ingredient) | 0.84 | Oil | 0.04 | 0.1344 |
| Fibruline Instant ® (soluble fiber) | 40.5 | Water | 2.03 | 6.48 |
| Tic Pretested ® TICAMULSION A-2010 (stabilizer) | 20.000 | Water | 1.00 | 3.2 |
| Sucrose Fatty Acid Ester (Ryoto Sugar Ester S-1670) (1$^{st}$ Fraction surfactant) | 93.2 | Water | 4.66 | 14.91 |
| Sucrose Fatty Acid Ester (Ryoto Sugar Ester S-1670) (2$^{nd}$ Fraction surfactant) | 62.9 | Water | 3.15 | 10.06 |
| Water | 1042.71 | Water | 52.136 | 166.8336 |
| Benzyl Alcohol (Preservative) | 10.000 | Oil | 0.50 | 1.6 |
| Sucrose Fatty Acid Ester (Ryoto Sugar Ester S-1670) (surfactant) | 25.0 | Oil | 1.25 | 4.00 |
| Tocopherol Polyethylene Glycol Succinate (surfactant) | 210.0 | Oil | 10.50 | 33.60 |
| Ester Gum 8BG Pinova/Hercules (stabilizer) | 1.25 | Oil | 0.06 | 0.2 |
| Tic Pretested ® TICAMULSION A-2010 (stabilizer) | 10 | Oil | 0.5000 | 1.600 |
| Citric Acid (pH adjuster) | 63.60 | Emulsion | 3.18000 | 10.1760 |
| Totals | 2000.000 | | 100.0000 | 320 |

*This ingredient was added at 5% overage to insure the final composition contained the stated amount of this ingredient.

Example 8

Liquid Emulsion Concentrates with PUFA-Containing Non-Polar Compounds

Examples 8A-8B set forth the details of exemplary liquid emulsion concentrates containing omega-3 fatty acids, including:

Fish oil, containing about 30% DHA/EPA (sold under the name Omega 30 TG Food Grade (Non-GMO) MEG-3™ Fish Oil by Ocean Nutrition Canada Limited, Nova Scotia, Mass.). The fish oil non-polar active ingredient was added at an amount of 25%, by weight of the final concentrate, whereby the concentrate contained 6% DHA+EPA; and A surfactant that was a sucrose fatty acid ester (SFAE) surfactant (sold under the name Ryoto Sugar Ester S-1760, by Mitsubishi-Kagaku Foods Corporation, Tokyo, Japan); and Water, that was city water, which was purified prior to addition to the water phase vessel, by passage through using the following purifiers, sequentially in the following order: a carbon filter, an ion exchange purifier, a reverse osmosis purifier, a UV sterilizer and an end-point filter (a 100 micron end-point filter.

Tables 8A-8B set forth ingredients and other details of liquid emulsion concentrates, each containing at least one or more of the PUFA-containing non-polar compounds described above, a polar solvent, and a sucrose fatty acid ester surfactant. The specific non-polar active ingredients are indicated in each table.

Each of the concentrates containing these non-polar active ingredients was made using the general procedure outlined in Example 1 above with the following details: The water phase was made by adding the purified water and heating to 60° C., followed by addition of the following water phase ingredients to the water phase vessel, sequentially, in the following order: 1) Ticamulsion® stabilizer; 2) antifoam; 3) $1^{st}$ fraction surfactant; 4) $2^{nd}$ fraction surfactant; and 5) soluble fiber, and mixing while heating to a temperature of 60° C., which was maintained until combining with the oil phase. The oil phase was generated by adding the following oil phase ingredients to the oil phase vessel, sequentially, in the following order: 1) Ester Gum stabilizer; 2) preservative, and heating to a temperature of 60° C., followed by the addition of 3) non-polar active ingredient; 4) Ticamulsion® stabilizer; and 5) surfactant, and mixing and heating to a temperature of 60° C., which was maintained until combining.

The pH of the emulsion was measured using a pH and temperature meter (Hanna Instruments, model HI 8314) and adjusted with the amount of citric acid indicated in the table until the emulsion reached a pH of between 2.0 and 3.0.

Example 8A

Liquid Emulsion Concentrate with 25% of a DHA-Containing Non-Polar Compound (Fish Oil) and 9% SFAE Surfactant Table 2A(i), below, sets forth the ingredients to make a 500 g batch (2 mL serving size) of a liquid emulsion concentrate containing fish oil (e.g., DHA, EPA), which was made according to the procedure set forth in Example 1. The resulting liquid emulsion concentrate was opaque to white in color and contained 100 mg DHA+EPA per gram of the concentrate.

TABLE 8A

Liquid Emulsion Concentrate with 25% of a DHA-containing Non-Polar Compound (Fish Oil) and 9% SFAE Surfactant

| Ingredient | mg/2 mL serving | Phase | Percent (by weight) of concentrate | g/batch |
|---|---|---|---|---|
| Omega 30 TG Food Grade (Non-GM) MEG-3 ™ Fish Oil* (non-polar active ingredient) | 500 | Oil | 25 | 125.0 |
| Fibruline Instant ® (soluble fiber) | 40.5 | Water | 2.03 | 10.13 |
| Tic Pretested ® TICAMULSION A-2010 (stabilizer) | 34.000 | Water | 1.70 | 8.5 |
| Sucrose Fatty Acid Ester (Ryoto Sugar Ester S-1670) ($1^{st}$ Fraction surfactant) | 93.2 | Water | 4.66 | 23.30 |
| Sucrose Fatty Acid Ester (Ryoto Sugar Ester S-1670) ($2^{nd}$ Fraction surfactant) | 62.9 | Water | 3.15 | 15.73 |
| Water | 1180.32 | Water | 59.016 | 295.08 |
| Benzyl Alcohol (Preservative) | 10.000 | Oil | 0.50 | 2.5 |
| Sucrose Fatty Acid Ester (Ryoto Sugar Ester S-1670) (surfactant) | 25.0 | Oil | 1.25 | 6.25 |
| Ester Gum 8BG Pinova/Hercules (stabilizer) | 1.25 | Oil | 0.06 | 0.3 |
| Tic Pretested ® TICAMULSION A-2010 (stabilizer) | 10 | Oil | 0.5000 | 2.500 |
| Citric Acid (pH adjuster) | 42.83 | Emulsion | 2.1415 | 10.7075 |
| Totals | 2000.000 | | 100.0000 | 500 |

*This ingredient was added at 5% overage to insure the final composition contained the stated amount of this ingredient.

Example 8B

Liquid Emulsion Concentrate with 25% of a DHA-Containing Non-Polar Compound (Algal Oil) and 9% SFAE Surfactant Table 2A(i), below, sets forth the ingredients to make a 500 g batch (2 mL serving size) of a liquid emulsion concentrate containing algal oil (e.g., DHA, EPA), which was made according to the procedure set forth in Example 1. The resulting liquid emulsion concentrate was opaque to white in color and contained 100 mg DHA+EPA per gram of the concentrate.

TABLE 8B

Liquid Emulsion Concentrate with 25% of a DHA-containing Non-Polar Compound (Algal Oil) and 9% SFAE Surfactant

| Ingredient | mg/2 mL serving | Phase | Percent (by weight) of concentrate | g/batch |
|---|---|---|---|---|
| Algal Oil* (~40% DHA/EPA by area/~35% DHA/EPA by weight) (non-polar active ingredient) | 500 | Oil | 25 | 125.0 |
| Fibruline Instant ® (soluble fiber) | 40.5 | Water | 2.03 | 10.13 |
| Tic Pretested ® TICAMULSION A-2010 (stabilizer) | 34.000 | Water | 1.70 | 8.5 |
| Sucrose Fatty Acid Ester (Ryoto Sugar Ester S-1670) (1$^{st}$ Fraction surfactant) | 93.2 | Water | 4.66 | 23.30 |
| Sucrose Fatty Acid Ester (Ryoto Sugar Ester S-1670) (2$^{nd}$ Fraction surfactant) | 62.9 | Water | 3.15 | 15.73 |
| Water | 1180.32 | Water | 59.016 | 295.08 |
| Benzyl Alcohol (Preservative) | 10.000 | Oil | 0.50 | 2.5 |
| Sucrose Fatty Acid Ester (Ryoto Sugar Ester S-1670) (surfactant) | 25.0 | Oil | 1.25 | 6.25 |
| Ester Gum 8BG Pinova/Hercules (stabilizer) | 1.25 | Oil | 0.06 | 0.3 |
| Tic Pretested ® TICAMULSION A-2010 (stabilizer) | 10 | Oil | 0.5000 | 2.500 |
| Citric Acid (pH adjuster) | 42.83 | Emulsion | 2.1415 | 10.7075 |
| Totals | 2000.000 | | 100.0000 | 500 |

*This ingredient was added at 5% overage to insure the final composition contained the stated amount of this ingredient.

Example 9

Dilution of the Liquid Emulsion Concentrates and Evaluation of the Dilution Compositions For evaluation of stability, the liquid emulsion concentrate made in Example 2A(i) above, was diluted, according to the provided methods, into a variety of different food products, including nectar juice, orange juice, tomato-paste based products, salsa, salsa con queso, mayonnaise, fat free milk, fat free sour cream and ranch dressing to form dilution compositions.

The liquid emulsion concentrate containing 10% DHA/EPA Omega-3 with 400 mcg Vitamin A (made in Example 2A(i) above) was diluted into the food products resulting in final DHA/EPA loads of ≥16, 32 and/or 50 mg per serving, as set forth in Table 8 below. The resulting dilution compositions were evaluated for stability according to ICH (International Conference on Harmonisation of Technical Requirements for Registration of Pharmaceuticals for Human Use, www.ich.org) stability test guidelines (see Table 9 below). In general, the composition was maintained at a temperature of 25° C. with 65% relative humidity for a period of at least 12 months. At various time points, the stability of the composition was evaluated by examining physical, chemical, biological and microbiological properties. Alternatively, testing was accelerated by maintaining a temperature of 40° C. with 75% relative humidity for a period of at least 6 months. The environment chamber for accelerated testing was a testing chamber (Model PRA-1AP, Serial#2980 from Tabai Espec Corp.) maintained at 40±1° C. with 75±5% relative humidity. For refrigerated compositions, long term testing was carried out at 5° C. and accelerated testing was carried out at 25° C. with 60% relative humidity. The compositions were evaluated in finished containers for marketing. Juices were pasteurized at 85° C. for 30 seconds, hot filled and capped. Water based beverages had a pH of approximately 3.00 and typically were not pasteurized. At least 3 samples were tested per product and control samples that did not receive the emulsion concentrate were also evaluated.

TABLE 8

Dilution Compositions

| Food Product | Minimum load DHA/EPA (mg/serving) |
|---|---|
| Tinted Nutritional Beverages | 16, 32 & 50 mg |
| Nectar juice | 16, 32 & 50 mg |
| Tomato-paste based products | 32 & 50 mg |
| Mayonnaise | 32 & 50 mg |
| Fat Free Sour Cream | ≥32 mg |
| Fat Free Milk | 32 & 50 mg |
| Orange Juice | 50 mg |
| Salsa | ≥32 mg |
| Salsa Con Queso (Nacho Cheese) | ≥32 mg |
| Ranch Dressing | ≥32 mg |

TABLE 9

ICH Stability Testing Guidelines

| | Temperature (° C.) | Relative Humidity (%) | Time (minimum) | Testing Intervals |
|---|---|---|---|---|
| Long Term | 25 ± 2 | 65 ± 5 | 12 months | 0, 6, 12, 18, 24, 36 months |
| Accelerated | 40 ± 2 | 75 ± 5 | 6 months | 0, 1, 2, 4, 8, 12, 18, 24 weeks |

Shelf life of the dilution compositions was determined by 1) qualitative assessment of the physical appearance of the samples containing the concentrates compared to control samples that did not receive the Concentrate, and 2) sensory tasting tests. Qualitative assessment included evaluation of the appearance of the composition for the presence of undesirable characteristics, such as ringing, phase separation and formation of precipitates. For clear beverages, clarity and turbidity were evaluated. Sensory tasting tests included evaluation of aroma and flavor, i.e., smell and taste of the dilution compositions. In particular, compositions were evaluated for a 1) fishy smell; 2) metal/iron smell; 3) grass smell; 4) sharp/tingling smell; 5) fishy taste; 6) metal/iron taste; 7) grass taste; 8) sharp/tingling taste, and/or 9) oily taste. Sensory tasting tests were conducted by a minimum of 5 people as follows: taste sample A, eat an unsalted cracker and wait until the cracker is dissolved in the mouth, taste sample B, repeat cracker procedure, repeat sample tasting and cracker procedure until all samples are tasted, wait 2 minutes, repeat tasting in reverse sample order of first tasting.

The results are set forth in Table 10 below. None of the products exhibited a fishy smell or fishy taste. The orange juice samples had mild sharp/tingling smell that was also present in the control orange juice. None of the samples exhibited phase separation. Mild ringing (i.e., fine precipitate) was observed at the top of the bottle for the orange juice samples. Shelf life studies are ongoing, but in general, shelf life is at least as long as the shelf life of the application, i.e., the shelf life of the product not containing the liquid emulsion concentrate. Pasteurization of water based beverages did not affect stability.

TABLE 10

Shelf life of dilution compositions

| Food Product | Retail Storage Condition | Serving Size | Minimum Load DHA/EPA (mg/serving) | Shelf Life* |
|---|---|---|---|---|
| Tinted Nutritional Beverages | Shelf | 240 & 500 mL | 16, 32 & 50 mg | >6 months |
| Nectar juice | Shelf | ≤240 & 330 mL | 16 & ≥32 mg | >9 months |
| Tomato-paste based products | Shelf | Tomato sauce 62 g | 32 & 50 mg | >9 months |
| | Shelf | Tomato sauce 120 mL | 32 & 50 mg | >9 months |
| | Shelf | Vegetable Juice 240 mL | 32 & 50 mg | >9 months |
| Mayonnaise | Refrigerated open container | 14 g (1 tbsp) | 32 & 50 mg | >9 months |
| Fat free sour cream | Unopened refrigerated | 32 g (2 tbsp) | ≥32 mg | >4 months |
| | Opened refrigerated | 32 g (2 tbsp) | ≥32 mg | >2 months |
| Fat free milk | Unopened refrigerated | 240 mL (1 cup) | 32 & 50 mg | >4 months |
| | Opened refrigerated | 240 mL (1 cup) | 32 & 50 mg | >2 months |
| Orange juice (clear PET bottle) | Sealed container | 250 mL (8 ounces) | 50 mg | 8 months |
| Salsa | Shelf | 33 mg | ≥32 mg | >6 months |
| Salsa Con Queso (Nacho Cheese) | Shelf | 34 mg | ≥32 mg | >6 months |
| Ranch Dressing | Shelf | 30 mg | ≥32 mg | >6 months |

*shelf life is listed as > (greater than) due to the study being ongoing.

Since modifications will be apparent to those of skill in this art, it is intended that this invention be limited only by the scope of the appended claims.

The invention claimed is:

1. A liquid emulsion concentrate composition, comprising:
   an emulsion stabilizer that is a fatty acid-modified carbohydrate-based macromolecule in an amount between more than 1% and up to 5%, by weight, of the concentrate composition;
   one or more sucrose fatty acid ester surfactants, in addition to the emulsion stabilizer, in an amount between 3% and 16%, inclusive, by weight, of the concentrate;
   a polar solvent in an amount between 40% and 60%, by weight, of the composition; and
   one or more non-polar compounds that comprise non-polar active ingredients selected from among polyunsaturated fatty acids, omega-3 fatty acids, omega-6 fatty acids, omega-9 fatty acids, conjugated fatty acids, coenzyme Q-containing active ingredients, alpha lipoic acid, carotenoid-containing active ingredients and phytochemicals, wherein the one or more non-polar compounds is/are present in a total amount between 35% and 50%, inclusive, by weight, of the concentrate.

2. The liquid emulsion concentrate composition of claim 1, wherein the amount of emulsion stabilizer is more than 1% and up to 3%, by weight, of the concentrate composition.

3. The liquid emulsion concentrate composition of claim 1 that contains at least two different non-polar compounds.

4. The liquid emulsion concentrate of claim 1, wherein the fatty acid-modified carbohydrate-based macromolecule is a fatty acid modified gum, a fatty acid modified starch or a fatty acid modified cellulose.

5. The liquid emulsion concentrate of claim 4, wherein the fatty acid-modified carbohydrate-based macromolecule is a fatty acid modified gum that is an n-octenylsuccinic anhydride (OSAn-) modified gum acacia, or the fatty acid-modified carbohydrate-based macromolecule is a fatty acid modified starch that is an n-octenylsuccinic anhydride (OSAn-) modified corn starch.

6. The liquid emulsion concentrate composition of claim 1, wherein the emulsion stabilizer contains the reaction product of at least one hydrocolloid having a viscosity of at or about from 2 to 500 cP in 10% aqueous solution at 20° C. and at or about from 2 to 15%, by weight, based on the hydrocolloid, of at least one dicarboxylic acid anhydride selected from alkane- and alkene-substituted dicarboxylic acid anhydrides.

7. The liquid emulsion concentrate composition of claim 6, wherein:
the acid anhydride comprises at least one alkyl- or alkenyl-substituted dicarboxylic acid anhydride of the formula:

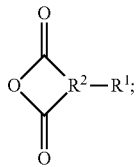

$R^1$ is an alkyl radical or ethylenically-unsaturated alkyl radical having 3-18 carbon atoms; and
$R^2$ is a divalent radical having 2-3 carbon atoms.

8. The liquid emulsion concentrate composition of claim 7, wherein $R^1$ has 6-10 carbon atoms.

9. The liquid emulsion concentrate composition of claim 7, wherein $R^2$ has 2 carbon atoms.

10. The liquid emulsion concentrate composition of claim 6, wherein the acid anhydride consists essentially of n-octenylsuccinic anhydride.

11. The liquid emulsion concentrate composition of claim 6, wherein the at least one hydrocolloid comprises at least or at least about 10%, by weight, of the hydrocolloid, of each of gum acacia and guar gum.

12. The liquid emulsion concentrate composition of claim 6, wherein the at least one hydrocolloid has a viscosity of about or at 2-250 cP, 2-100 cP, 50-100 cP, 50-200 cP or 2-150 cP in 10% aqueous solution at 20° C.

13. The liquid emulsion concentrate composition of claim 6, wherein the emulsion stabilizer further contains at least one carbohydrate bulking agent.

14. The liquid emulsion concentrate composition of claim 13, wherein the bulking agent is at least one selected from among hydrolyzed polysaccharides, oligosaccharides and monosaccharides.

15. The liquid emulsion concentrate composition of claim 14, wherein the bulking agent consists essentially of at least one dextrin.

16. The liquid emulsion concentrate composition of claim 14, wherein the bulking agent consists essentially of dextrose.

17. The liquid emulsion concentrate composition of claim 13, wherein the bulking agent is present in a quantity of up to 95%, by weight, of the total emulsion stabilizer solids.

18. The liquid emulsion concentrate of claim 1, wherein the surfactant is a mixture of sucrose fatty acid esters.

19. The liquid emulsion concentrate of claim 18, wherein the sucrose fatty acid ester mixture has an HLB value of between 12 and 20.

20. The liquid emulsion concentrate of claim 1, wherein the surfactant comprises a sucrose fatty acid ester mixture that contains a sucrose fatty acid monoester.

21. The liquid emulsion concentrate of claim 1, wherein the surfactant comprises a sucrose fatty acid ester mixture that contains any one or more of sucrose stearate, sucrose laurate, sucrose palmitate, sucrose oleate, sucrose caprylate, sucrose decanoate, sucrose myristate, sucrose pelargonate, sucrose undecanoate, sucrose tridecanoate, sucrose pentadeconoate and sucrose heptadecanoate, or homologs thereof.

22. The liquid emulsion concentrate of claim 1, wherein the surfactant comprises a sucrose fatty acid ester surfactant that contains any one or more of sucrose monostearate, sucrose monolaurate, sucrose monooleate and sucrose monopalmitate.

23. The liquid emulsion concentrate of claim 1, wherein the non-polar compound contains at least one polyunsaturated fatty acid selected from among omega-3 fatty acids, omega-6 fatty acids, omega-9 fatty acids and conjugated fatty acids.

24. The liquid emulsion concentrate of claim 1, wherein the non-polar compound contains a polyunsaturated fatty acid selected from among a docosahexaenoic acid (DHA), an eicosapentaenoic acid (EPA), a fish oil, an algal oil, a flaxseed oil, a borage oil, an alpha-linolenic acid (ALA), a gamma-linolenic acid (GLA), a conjugated linoleic acid (CLA), an oleic acid and a saw palmetto extract.

25. The liquid emulsion concentrate of claim 1, wherein the non-polar compound contains at least one phytochemical-containing active ingredient, carotenoid-containing active ingredient, coenzyme Q-containing active ingredient, oil soluble vitamin or lipoic acid.

26. The liquid emulsion concentrate of claim 25, wherein the non-polar compound:
contains a phytochemical-containing active ingredient selected from among phytosterols and resveratrol; and/or
contains a carotenoid-containing active ingredient selected from among lycopene, lutein, zeaxanthin and mixtures of lutein and zeaxanthin; and/or
contains coenzyme Q10 (CoQ10).

27. The liquid emulsion concentrate of claim 1, wherein the polar solvent is a polar protic solvent.

28. The liquid emulsion concentrate of claim 27, wherein the polar solvent is selected from among water, glycerin, propylene glycol, ethylene glycol, tetraethylene glycol, triethylene glycol and trimethylene glycol.

29. The liquid emulsion concentrate of claim 28, wherein the polar solvent is water.

30. The liquid emulsion concentrate of claim 1, further comprising a soluble fiber.

31. The liquid emulsion concentrate of claim 30, wherein the soluble fiber is a fructo-oligosaccharide or fructan.

32. The liquid emulsion concentrate of claim 31, wherein the soluble fiber is a fructo-oligosaccharide that comprises inulin.

33. The liquid emulsion concentrate of claim 30, wherein the amount of soluble fiber is between about 0.5% and about 10%, inclusive, by weight, of the concentrate.

34. The liquid emulsion concentrate of claim 1, comprising two or more surfactants.

35. A method of providing an oil-based additive in a food or beverage, comprising:
adding a liquid emulsion concentrate of claim 1 to a food or beverage in an amount, whereby:
the food or beverage contains an effective amount of the non-polar active ingredient for supplementation of the diet; and
the food or beverage containing the concentrate is as stable as the same food or beverage in the absence of the additive.

36. The method of claim 35, wherein the food or beverage is a water-based finished food or beverage selected from a tomato-paste based product, dairy-based product, sauce, dressing, cream, salsa, queso cheese, syrup, soup, juice, energy drink, sports drink, nutritional beverage, vitamin-fortified beverage, milk, tea, soda, flavored water or water.

37. The liquid emulsion concentrate of claim 1, wherein the amount of surfactant is between 8% and 11%.

38. The liquid emulsion concentrate of claim 37, wherein one surfactant is present.

39. The liquid emulsion concentrate of claim 37, wherein more than one surfactant is present.

40. A liquid emulsion concentrate composition, comprising:

an emulsion stabilizer that is a fatty acid-modified carbohydrate-based macromolecule in an amount between more than 1% and up to 5%, by weight, of the concentrate;

one or more sucrose fatty acid ester surfactants, in addition to the emulsion stabilizer, in an amount between 3% and 16%, inclusive, by weight, of the concentrate;

a polar solvent in an amount between 40% and 60%, by weight, of the concentrate; and one or more non-polar compounds, that comprise non-polar active ingredients selected from among polyunsaturated fatty acids, omega-3 fatty acids, omega-6 fatty acids, omega-9 fatty acids, conjugated fatty acids, coenzyme Q-containing active ingredients, alpha lipoic acid, carotenoid-containing active ingredients and phytochemicals, wherein the amount of the one or more non-polar compounds is between 25% and 45%, by weight, of the concentrate.

41. The liquid emulsion concentrate of claim 1, wherein the concentration of non-polar compounds is between 35% and 45%, by weight, of the concentrate.

42. The liquid emulsion concentrate of claim 1, wherein the surfactants are present in an amount between 6% and 14%, inclusive, by weight, of the concentrate.

43. The liquid emulsion concentrate of claim 1, wherein the amount of polar solvent is between 45% and 55%, by weight, of the concentrate.

44. The liquid emulsion concentrate of claim 1, wherein the sucrose fatty acid ester comprises a mixture of monoesters, diesters, triesters or polyesters.

45. The liquid emulsion concentrate of claim 40, wherein the amount of polar solvent is between 45% and 55%, by weight, of the concentrate.

* * * * *

UNITED STATES PATENT AND TRADEMARK OFFICE
CERTIFICATE OF CORRECTION

PATENT NO. : 8,741,373 B2
APPLICATION NO. : 13/134927
DATED : June 3, 2014
INVENTOR(S) : Bromley et al.

It is certified that error appears in the above-identified patent and that said Letters Patent is hereby corrected as shown below:

IN THE SPECIFICATION:

At column 6, line 50, please replace "Linoleic acid (18:2(06)" with —Linoleic acid (18:2ω6)—;

at column 6, line 67, please replace "Laurie acid" with —Lauric acid—;

at column 8, line 18, please replace "FT %" with —17 %—;

at column 68, line 40, please replace "Stearidonic acid (18:40)" with —Stearidonic acid (18:4ω3)—;

at column 71, line 17, please replace "(18:1 w 7)" with —(18:1 ω7)—;

at column 71, line 60, please replace "hill oils" with —krill oils—; and at column 74, line 28, please replace "(BPI-1)" with —(BPH)—.

Signed and Sealed this
Seventh Day of October, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,741,373 B2 | |
| APPLICATION NO. | : 13/134927 | |
| DATED | : June 3, 2014 | |
| INVENTOR(S) | : Bromley et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 44 days.

Signed and Sealed this
Twenty-eighth Day of July, 2015

Michelle K. Lee
*Director of the United States Patent and Trademark Office*